(12) United States Patent
Wang

(10) Patent No.: US 11,773,148 B2
(45) Date of Patent: Oct. 3, 2023

(54) TAU PEPTIDE IMMUNOGEN CONSTRUCTS

(71) Applicants: UNITED NEUROSCIENCE, Grand Cayman (KY); UNS IP HOLDINGS, LLC, Dallas, TX (US)

(72) Inventor: Chang Yi Wang, Cold Spring Harbor, NY (US)

(73) Assignees: UNITED NEUROSCIENCE, Grand Cayman (KY); UNS IP HOLDINGS, LLC, Dallas, TX (US)

( * ) Notice: Subject to any disclaimer, the term of this patent is extended or adjusted under 35 U.S.C. 154(b) by 310 days.

(21) Appl. No.: 16/759,584

(22) PCT Filed: Oct. 26, 2018

(86) PCT No.: PCT/US2018/057840
§ 371 (c)(1),
(2) Date: Apr. 27, 2020

(87) PCT Pub. No.: WO2019/084488
PCT Pub. Date: May 2, 2019

(65) Prior Publication Data
US 2021/0101948 A1    Apr. 8, 2021

Related U.S. Application Data

(60) Provisional application No. 62/578,124, filed on Oct. 27, 2017.

(51) Int. Cl.
| C07K 14/47 | (2006.01) |
| A61K 39/39 | (2006.01) |
| C07K 16/18 | (2006.01) |
| A61K 39/00 | (2006.01) |

(52) U.S. Cl.
CPC ...... *C07K 14/4711* (2013.01); *A61K 39/0007* (2013.01); *A61K 39/39* (2013.01); *C07K 16/18* (2013.01); *A61K 2039/55561* (2013.01); *A61K 2039/575* (2013.01); *C07K 2319/40* (2013.01)

(58) Field of Classification Search
CPC ............ C07K 14/4711; C07K 2319/40; A61K 2039/60; A61K 2039/627; A61K 39/0007
See application file for complete search history.

(56) References Cited

U.S. PATENT DOCUMENTS

| 7,951,909 B2 * | 5/2011 | Wang | ................. | C07K 14/4711 |
| | | | | 435/69.7 |
| 8,232,373 B2 | 7/2012 | Wang | | |
| 9,102,752 B2 | 8/2015 | Wang | | |
| 2008/0050383 A1 | 2/2008 | Sigurdsson et al. | | |
| 2012/0149365 A1 | 6/2012 | Ying et al. | | |
| 2017/0183400 A1 | 6/2017 | Sigurdsson | | |

FOREIGN PATENT DOCUMENTS

| JP | 2005506311 A | | 3/2005 |
| JP | 20080050383 A | | 3/2008 |
| JP | 2012530055 A | | 11/2012 |
| JP | 2013500326 A | | 1/2013 |
| JP | 2016513638 A | | 5/2016 |
| RU | 2518291 C2 | | 6/2014 |
| WO | 2010144711 A2 | | 12/2010 |
| WO | 2011013034 A1 | | 2/2011 |
| WO | 2012106363 A2 | | 8/2012 |
| WO | WO2012106363 | * | 8/2012 |
| WO | 2012149365 A2 | | 11/2012 |
| WO | 2018232369 A1 | | 12/2018 |

OTHER PUBLICATIONS

PCT International Search Report dated Mar. 27, 2019, issued during the prosecution of PCT International Patent Application No. PCT/US2018/057840.
Japanese Office Action dated Oct. 18, 2022, issued during the prosecution of Japanese Patent Application No. JP 2020-523430.
Extended European Search Report dated Feb. 4, 2022, issued during the proseciton of European Patent Application No. EP 18871080.0.
Partial European Search Report dated Aug. 2, 2021, issued during the prosecution of European Patent Application No. EP 18874080.0.
Kuznetsova E.A., Parentheses in the text of a legal document as a linguocognitive phenomenon, Vestnik MGOU, Series: Russian Philology, 2015, N3, pp. 37-43.
Russian Office Action of Aug. 25, 2022, issued during the prosecution of Russian Patent Application No. 2020117191.
Roit A., et al., Immunology, Moscow, Mir, 2000, pp. 110-111.
M. Singer et al., "Genes and Genomes", Moscow, "Mir", 1998, vol. 1, pp. 62-64.
J. Gu, et al., "Two Novel Tau Antibodies Targeting the 396/404 Region Are Primarily Taken Up by Neurons and Reduce Tau Protein Pathology", The Journal of Biological Chemistry, vol. 288, No. 46, pp. 33081-33095, Nov. 15, 2013.
A. Boutajangout, et al., "Immunotherapy Targeting Pathological Tau Prevents Cognitive Decline in a New Tangle Mouse Model", NIH Public Access, Author Manuscript, Jnl. Neuroscience, Dec. 8, 2010,, 30(49) pp. 16559-16566.
L. Larini, et al., "Initiation of Assembly of Tau (237-284) and its K280 Mutant: An Experimental and Computational Study", Phys. Chem. Chem Phys. 2013, 8916-8928.

(Continued)

*Primary Examiner* — Bao Q Li

(74) *Attorney, Agent, or Firm* — Locke Lord LLP; Peter N. Fill; Nicholas J. DiCeglie, Jr.

(57) ABSTRACT

The present disclosure is directed to individual peptide immunogen constructs targeting portions of the Tau protein for the treatment and/or prevention of tauopathies. The present disclosure is also directed to compositions containing the peptide immunogen constructs, methods of making and using the peptide immunogen constructs, and antibodies produced by the peptide immunogen constructs.

10 Claims, 11 Drawing Sheets
Specification includes a Sequence Listing.

(56) References Cited

OTHER PUBLICATIONS

T. Taniguchi et al., "Effects of Different Anti-Tau Antibodies on Tau Fibrillogenesis RTA-1 and RTA-2 Counteract Tau Aggregation", FEBS Letters 579, (2005) pp. 1399-1404.

C. L. Croft, "Novel Monoclonal Antibodies Targeting the Microtubule-Binding Domain of Human Tau", PLOS/one, 2018.

C. Y. Wang, et al., "Site-Specific UBITh® Amyloid-b Vaccine for Immunotherapy of Alzheimer's Disease", ScienceDirect, Vaccine 25, 2007, 3041-3052.

* cited by examiner

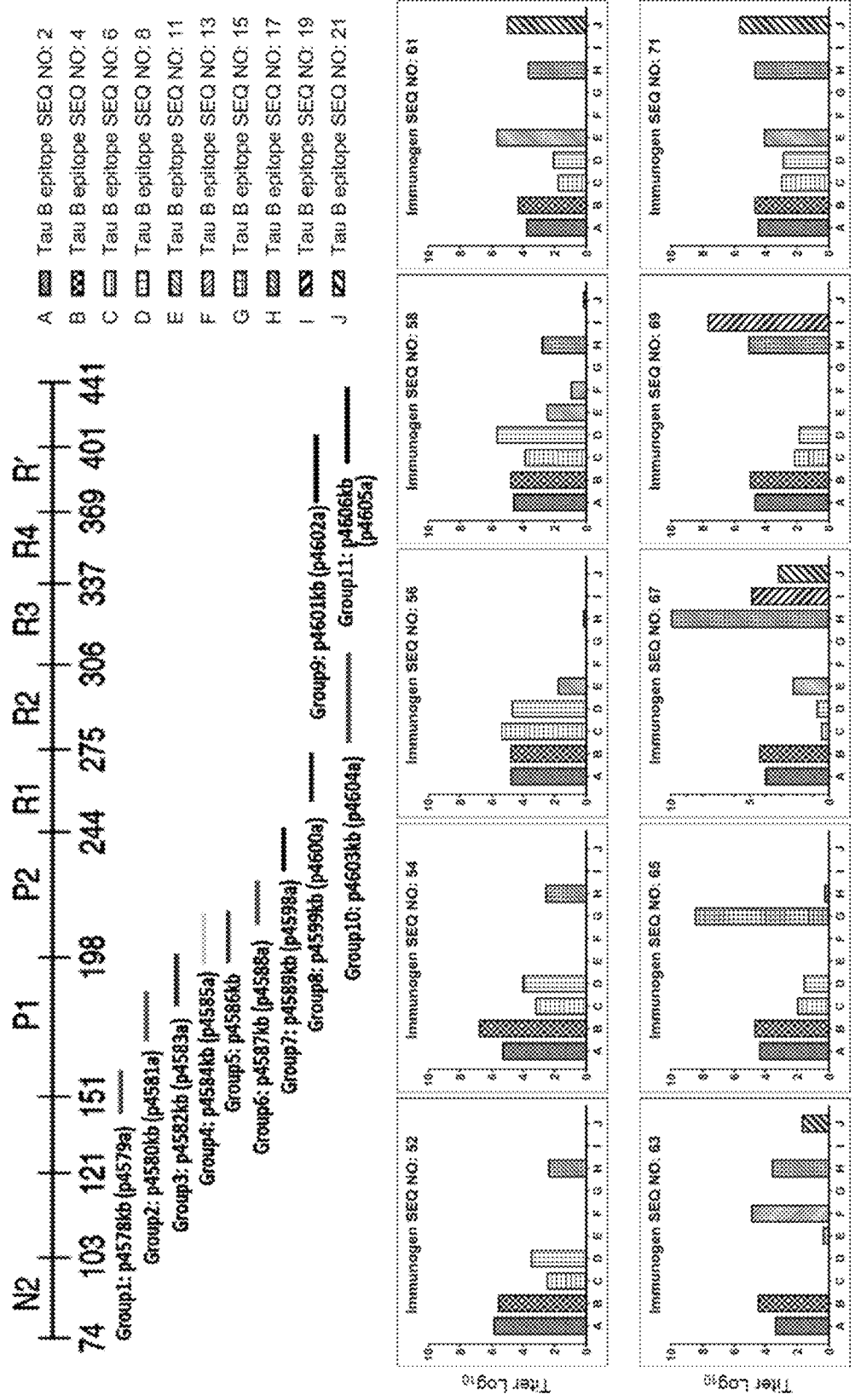

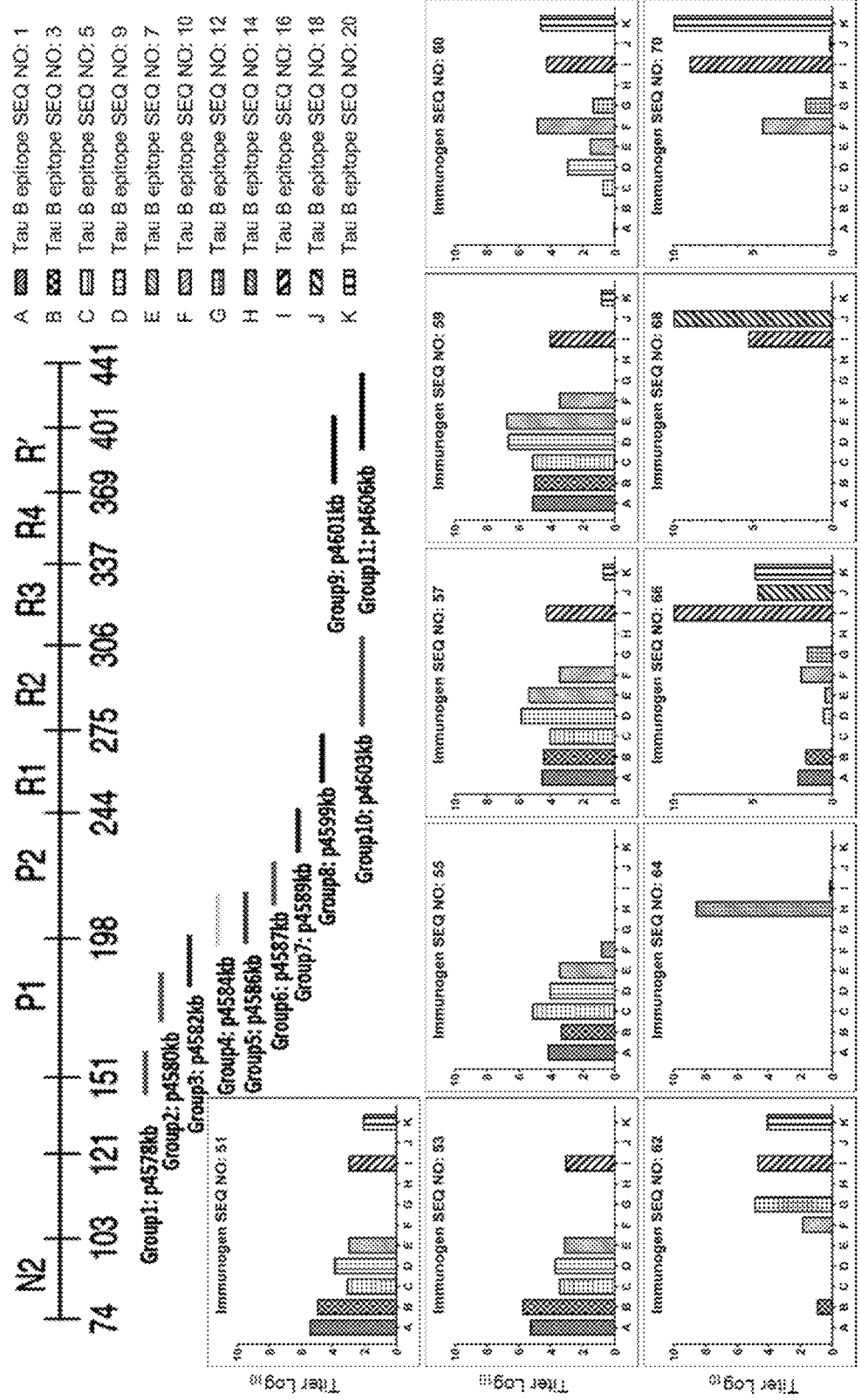

Western Blot Analysis of Cell Lysates containing monomers, dimers, trimers, oligomers and polymers of Tau

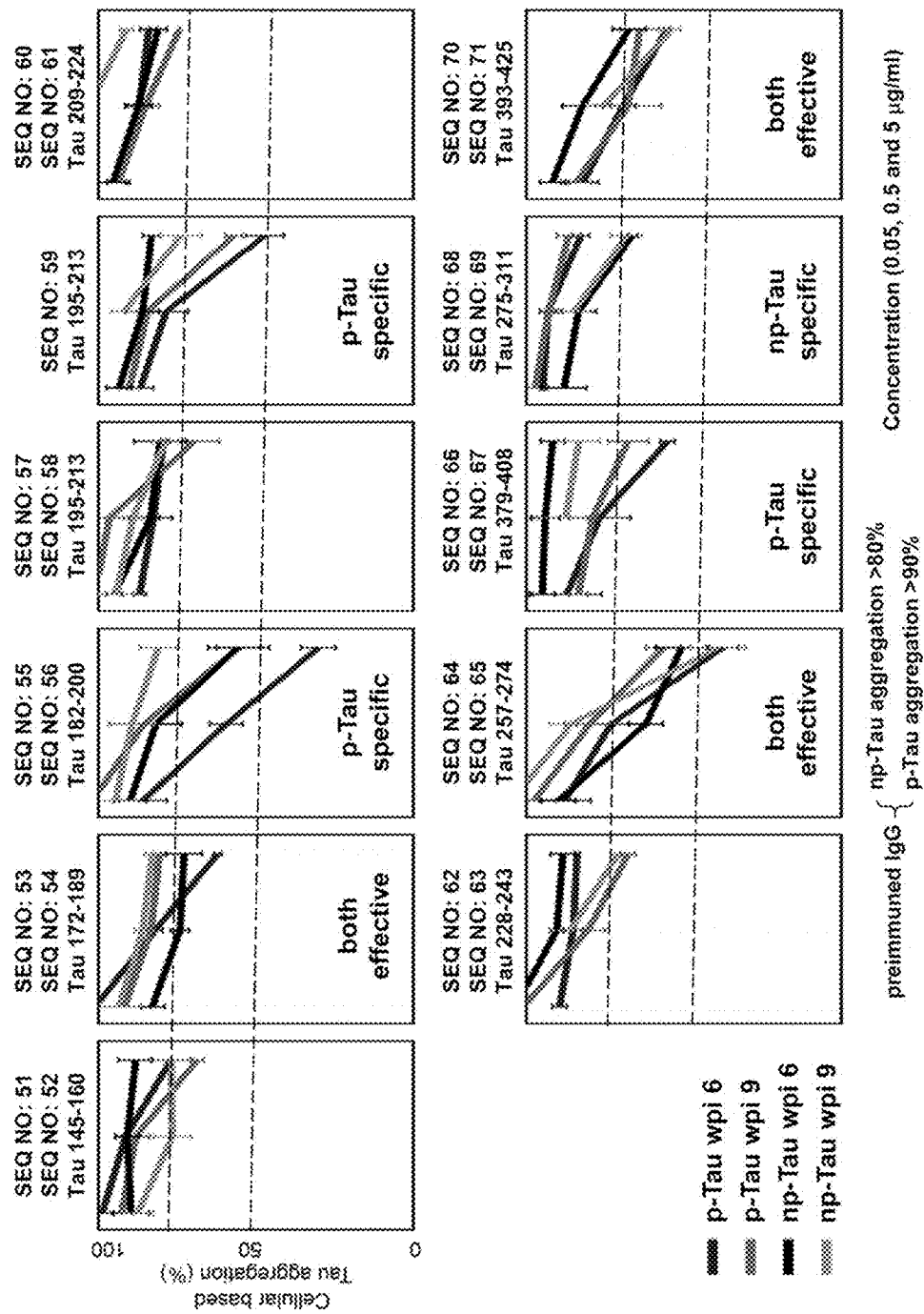

Dot Blot Analysis for Specific binding of non-denatured forms of Tau fibrils, oligomers and monomers by representative antibodies generated by both phosphor- and non-phospho Tau peptide immunogen constructs

Immunohistochemical Staining by representative antibodies generated by both phosphor- and non-phospho Tau peptide immunogen constructs Protection of neurons against fibril Tau by representative antibodies from phosphor- or non-phospho Tau peptide immunogen constructs Cell count was calculated by cell³ imager duos software (Miteklab)

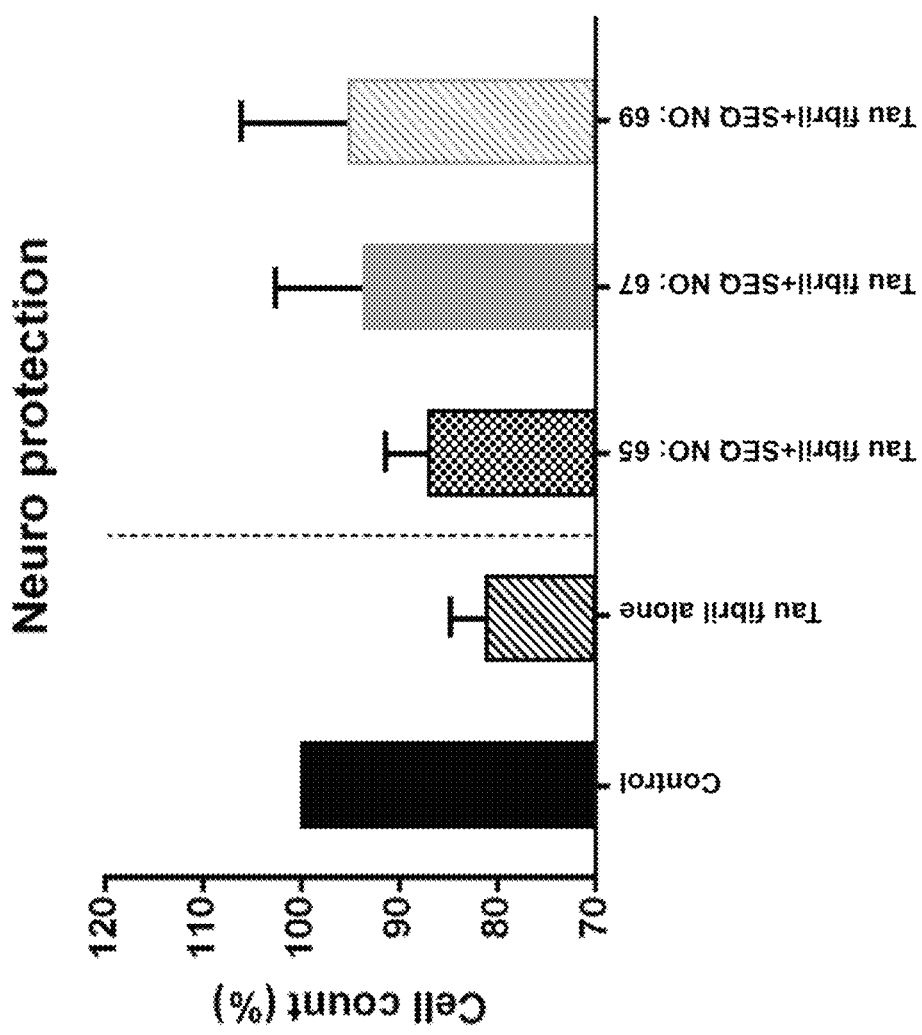

TAU PEPTIDE IMMUNOGEN CONSTRUCTS

The present application is a PCT International Application that claims the benefit of U.S. Provisional Application Ser. No. 62/578,124, filed Oct. 27, 2017, which is incorporated herein by reference in its entirety.

FIELD OF THE INVENTION

This disclosure relates to peptide immunogen constructs based on portions of the Tau protein and formulations thereof for the prevention and treatment of tauopathies

BACKGROUND OF THE INVENTION

Tau proteins (or τ proteins, after the Greek letter with that name) are proteins that stabilize microtubules (reviewed in website: en.wikipedia.org/wiki/Tau_protein). They are abundant in neurons of the central nervous system and are less common elsewhere, but are also expressed at very low levels in CNS astrocytes and oligodendrocytes. Pathologies and dementias of the nervous system such as Alzheimer's disease and Parkinson's disease are associated with Tau proteins that have become defective and no longer stabilize microtubules properly.

The Tau proteins are the product of alternative splicing from a single gene that in humans is designated MAPT (microtubule-associated protein Tau) and is located on chromosome 17. The Tau proteins were identified in 1975 as heat stable proteins essential for microtubule assembly and have since been characterized as an intrinsically disordered protein.

Tau protein is a highly soluble microtubule-associated protein (MAP). In humans, these proteins are found mostly in neurons compared to non-neuronal cells. One of Tau's main functions is to modulate the stability of axonal microtubules. Other nervous system MAPs may perform similar functions, as suggested by Tau knockout mice that did not show abnormalities in brain development—possibly because of compensation in Tau deficiency by other MAPs. Tau is not present in dendrites and is active primarily in the distal portions of axons where it provides microtubule stabilization but also flexibility as needed. This contrasts with MAP6(STOP) proteins in the proximal portions of axons, which, in essence, lock down the microtubules and MAP2 that stabilizes microtubules in dendrites.

Tau proteins interact with tubulin to stabilize microtubules and promote tubulin assembly into microtubules. Tau has two ways of controlling microtubule stability: isoforms and phosphorylation.

Six Tau isoforms ranging from 352 to 441 amino acids in length are expressed in the adult human brain; these are produced by alternative mRNA splicing of transcripts from MAPT (Fitzpatrick, et al., 2017; UniProtKB—P10636).

The isoforms are distinguished by their number of binding domains. Three isoforms have three binding domains and the other three have four binding domains. The binding domains are located in the carboxy-terminus of the protein and are positively charged (allowing it to bind to the negatively charged microtubule). The isoforms with four binding domains are better at stabilizing microtubules than those with three binding domains. The isoforms differ in the presence or absence of inserts of 29 or 58 amino acids in the N-terminal half, and the inclusion or absence of the 31-amino-acid microtubule-binding repeat, encoded by exon 10 of MAPT, in the C-terminal half. Inclusion of exon 10 results in the production of three Tau isoforms with four repeats each (4R), and its exclusion in a further three isoforms with three repeats each (3R). The four repeats (R1-R4) comprise residues 244-368 in the 441-amino-acid Tau isoform.

Tau is a phosphoprotein with 79 potential Serine (Ser) and Threonine (Thr) phosphorylation sites on the longest Tau isoform. Phosphorylation has been reported on approximately 30 of these sites in normal Tau proteins. Phosphorylation of Tau is regulated by a host of kinases, including PKN, a serine/threonine kinase. When PKN is activated, it phosphorylates Tau, resulting in disruption of microtubule organization. Phosphorylation of Tau is also developmentally regulated. For example, fetal Tau is more highly phosphorylated in the embryonic CNS than adult Tau. The degree of phosphorylation in all six isoforms decreases with age due to the activation of phosphatases. Like kinases, phosphatases too play a role in regulating the phosphorylation of Tau. For example, PP2A and PP2B are both present in human brain tissue and have the ability to dephosphorylate Ser396. The binding of these phosphatases to Tau affects Tau's association with MTs.

Hyperphosphorylation of the Tau protein (Tau inclusions, pTau) can result in the self-assembly of tangles of paired helical filaments and straight filaments, which are involved in the pathogenesis of Alzheimer's disease, frontotemporal dementia, and other tauopathies. All of the six Tau isoforms are present in an often hyperphosphorylated state in paired helical filaments from Alzheimer's disease brain. In other neurodegenerative diseases, the deposition of aggregates enriched in certain Tau isoforms has been reported. When misfolded, this otherwise very soluble protein can form extremely insoluble aggregates that contribute to a number of neurodegenerative diseases.

Recent research suggests that Tau may be released extracellularly by an exosome-based mechanism in Alzheimer's disease. Gender-specific Tau gene expression across different regions of the human brain has recently been implicated in gender differences in the manifestations and risk for tauopathies. Some aspects of how the disease functions also suggest that it has some similarities to prion proteins.

Neurodegenerative diseases with abundant filamentous Tau inclusions are referred to as tauopathies. Besides Alzheimer's disease, these diseases include tangle-only dementia, chronic traumatic encephalopathy (CTE), argyrophilic grain disease, progressive supranuclear palsy, corticobasal degeneration, globular glial tauopathy, and Pick's disease. Unlike Alzheimer's disease, these other diseases lack amyloid-β plaques. In Alzheimer's disease, tangle-only dementia and chronic traumatic encephalopathy, all six Tau isoforms (3R and 4R) are present in the disease filaments. In argyrophilic grain disease, progressive supranuclear palsy, corticobasal degeneration and globular glial tauopathy, only 4R Tau isoforms are found, whereas in Pick's disease only 3R Tau inclusions are present. The occurrence of human tauopathies with distinct filament morphologies has led to the idea that different molecular conformers of aggregated Tau exist. The occurrence of multiple molecular conformers might also explain why filaments from the brains of individuals with Alzheimer's are more effective than in vitro assembled filaments of recombinant protein in inducing Tau pathology in mouse brain.

Repetitive mild traumatic brain injury (TBI) is now recognized as a central component of brain injury in contact sports, especially American football, and the concussive force of military blasts. It can lead to chronic traumatic encephalopathy (CTE) that is characterized by fibrillar tangles of hyperphosphorylated Tau. High levels of Tau protein in fluid bathing the brain are linked to poor recovery after head trauma.

The Tau hypothesis states that excessive or abnormal phosphorylation of Tau results in the transformation of normal adult Tau into PHF-Tau (paired helical filament) and NFTs (neurofibrillary tangles). Tau protein is a highly soluble microtubule-associated protein (MAP). Through its isoforms and phosphorylation Tau protein interacts with tubulin to stabilize microtubule assembly. Tau proteins constitute a family of six isoforms with the range from 352-441 amino acids. The longest isoform in the CNS has four repeats (R1, R2, R3, and R4) and two inserts (441 amino acids total), whereas the shortest isoform has three repeats (R1, R3, and R4) and no insert (352 amino acids total). All of the six Tau isoforms are present in an often hyperphosphorylated state in paired helical filaments from AD.

Mutations that alter function and isoform expression of Tau lead to hyperphosphorylation. The process of Tau aggregation in the absence of mutations is not known but might result from increased phosphorylation, protease action or exposure to polyanions, such as glycosaminoglycans. Hyperphosphorylated Tau disassembles microtubules and sequesters normal Tau, MAP 1 (microtubule associated protein 1), MAP 2, and ubiquitin into tangles of PHFs. This insoluble structure damages cytoplasmic functions and interferes with axonal transport, which can lead to cell death.

As of this date, there is yet an unmet need to develop site-directed peptide immunogens and formulations thereof for cost effective treatment of patients suffering tauopathies.

REFERENCES

1. "Tau protein," Wikipedia, The Free Encyclopedia, (accessed Sep. 29, 2017).
2. Fitzpatrick, A W P, et al., "Cryo-EM structures of Tau filaments from Alzheimer's disease", *Nature*, 547(7662): 185-190 (2017).

SUMMARY OF THE INVENTION

The present disclosure is directed to individual peptide immunogen constructs targeting portions of the Tau protein for the treatment and/or prevention of tauopathies. The present disclosure is also directed to compositions containing the peptide immunogen constructs, methods of making and using the peptide immunogen constructs, and antibodies produced by the peptide immunogen constructs.

The disclosed peptide immunogen constructs contain about 15 or more amino acids. The peptide immunogen constructs contain a B cell epitope from portions of the longest isoform of the human Tau protein (GenBank: AGF19246.1) having the amino acid sequence of SEQ ID NO: 100 shown in Table 8. The B cell epitope can be linked to a heterologous T helper cell (Th) epitope derived from pathogen proteins through an optional heterologous spacer. The disclosed peptide immunogen constructs stimulate the generation of highly specific antibodies directed against Tau. The disclosed peptide immunogen constructs can be used as an immunotherapy for patients suffering from tauopathies.

The B cell epitope portion of the peptide immunogen constructs have amino acid sequences from the fill-length Tau protein (SEQ ID NO: 100). In some embodiments, the B cell epitope has a sequence containing any of SEQ ID NOs: 1-21 and 101-124 as shown in Table 1.

The peptide immunogen constructs of the present disclosure can contain a heterologous Th epitope amino acid sequence derived from a pathogenic protein (e.g., SEQ ID NOs: 22 to 50) as shown in Table 2. In certain embodiments, the heterologous Th epitope is derived from natural pathogens, such as Diphtheria Toxin (SEQ ID NO: 26), *Plasmodium Falciparum* (SEQ ID NO: 27), Cholera Toxin (SEQ ID NO: 29). In other embodiments, the heterologous Th epitope is an idealized artificial Th epitope derived from Measles Virus Fusion protein (MVF 1 to 5) or Hepatitis B Surface Antigen (HBsAg 1 to 3) in the form of either single sequence or combinatorial sequences (e.g., SEQ ID NOs: 33, 32, and 34).

In some embodiments, the peptide immunogen constructs contain a B cell epitope from Tau linked to a heterologous T helper cell (Th) epitope through an optional heterologous spacer. In certain embodiments, the peptide immunogen constructs contain a B cell antigenic site having the amino acid sequence from Tau (SEQ ID NOs: 1-21 and 101-124) linked to a heterologous Th epitope derived from a pathogenic protein (e.g., SEQ ID NOs: 22 to 50) through an optional heterologous spacer. In some embodiments, the optional heterologous spacer is a molecule or chemical structure capable of linking two amino acids and/or peptides together. In certain embodiments, the spacer is a naturally occurring amino acid, a non-naturally occurring amino acid, or a combination thereof. In specific embodiments, the peptide immunogen constructs have the amino acid sequence of SEQ ID NOs: 51-71 and 125-155 shown in Table 3.

The present disclosure is also directed to compositions containing a Tau peptide immunogen construct. In some embodiments, the disclosed compositions contain more than one Tau peptide immunogen constructs to cover multiple B epitopes from Tau. In certain embodiments, the compositions contain a mixture of Tau peptide immunogen constructs (e.g., any combination of SEQ ID NOs: 51-71 and 125-155) with more than one heterologous Th epitope derived from pathogenic proteins to cover a broad genetic background in patients. Compositions containing a mixture of peptide immunogen constructs can lead to a higher percentage in responder rate upon immunization for the treatment of tauopathies compared to compositions containing only a single Th peptide immunogen construct.

The present disclosure is also directed to pharmaceutical compositions for the treatment and/or prevention of tauopathies. In some embodiments, the pharmaceutical compositions contain the disclosed peptide immunogen constructs in the form of a stabilized immunostimulatory complex formed through electrostatic associations by mixing a CpG oligomer with a composition containing a peptide immunogen complex. Such stabilized immunostimulatory complexes are able to further enhance the immunogenicity of the peptide immunogen constructs. In some embodiments, the pharmaceutical compositions contain adjuvants such as mineral salts, including alum gel (ALHYDROGEL), aluminum phosphate (ADJUPHOS), or water-in-oil emulsions including MONTANIDE ISA 51 or 720.

The present disclosure is also directed to antibodies directed against the disclosed Tau peptide immunogen constructs. In particular, the peptide immunogen constructs of the present disclosure are able to stimulate the generation of highly specific antibodies that are cross-reactive with the Tau amino acid sequences (SEQ ID NOs: 1-21 and 101-124) when administered to a subject. The highly specific antibodies produced by the peptide immunogen constructs are cross reactive with recombinant Tau-containing proteins. The disclosed antibodies bind with high specificity to Tau without much, if any, directed to the heterologous Th epitopes employed for immunogenicity enhancement, which is in sharp contrast to the conventional protein or other biological carriers used for such peptide antigenicity enhancement.

The present disclosure also includes methods for treating and/or preventing tauopathies using the disclosed peptide immunogen constructs and/or antibodies directed against the peptide immunogen constructs. In some embodiments, the methods for treating and/or preventing tauopathies including administering to a host a composition containing a disclosed peptide immunogen construct. In certain embodiments, the compositions utilized in the methods contain a disclosed peptide immunogen construct in the form of a stable immunostimulatory complex with negatively charged oligonucleotides, such as CpG oligomers, through electrostatic association, which complexes are further supplemented, optionally, with mineral salts or oil as adjuvant, for administration to patients with tauopathies. The disclosed methods also include dosing regimens, dosage forms, and routes for administering the peptide immunogen constructs to a host at risk for, or with, tauopathies.

BRIEF DESCRIPTION OF THE DRAWINGS

FIG. 1A—ELISA results expressed in $Log_{10}$ Titers for immune ae obtained from multiple Tau immunogen constructs at 6 weeks post initial injection (wpi) against non-phosphorylated Tau peptides when analyzed on antigenic regions of Tau.

FIG. 1B—ELSA results expressed in $Log_{10}$ Titers for immune sera obtained from multiple Tau immunogen constructs at 6 weeks post initial injection (wpi) against phosphorylated au peptides when analyzed on antigenic regions of Tau.

FIG. 4—Graphs showing the level of Tau aggregation after exposure to antibodies directed against either the phospho or non-phospho Tau peptide immunogens, as indicated above each graph. The level of Tau aggregation was measured by Thioflavin-T (ThT) staining of the aggregates. Varying degree of inhibition was found for antibodies directed against either phospho- or non-phospho Tau immunogens.

FIG. 8B—Graph quantifying the protection of neurons against fibril Tau by representative antibodies generated by both phospho- and non-phospho-Tau peptide immunogens of the present disclosure.

DETAILED DESCRIPTION OF THE INVENTION

Figure 2:
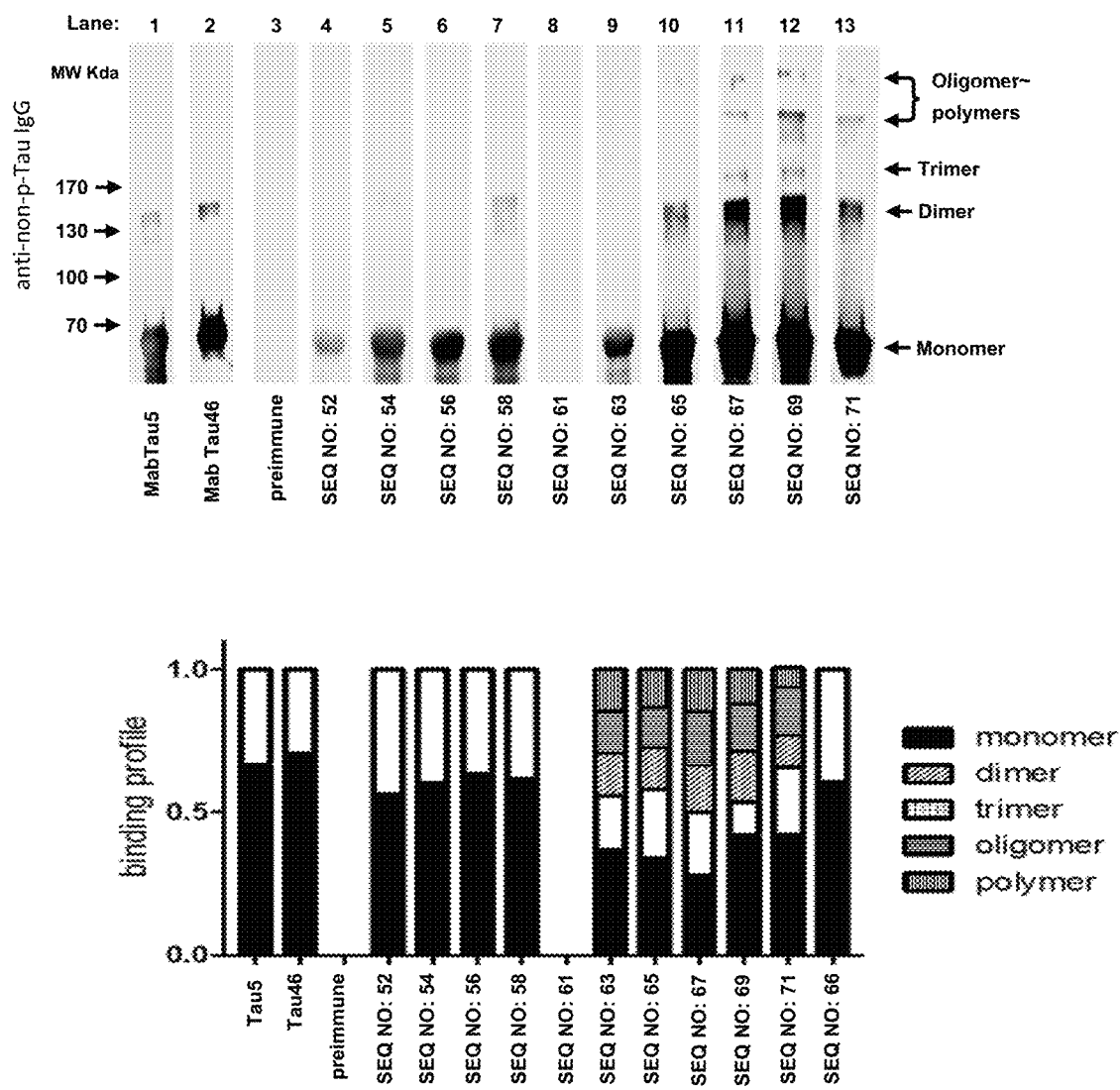
FIG. 2—Western blot analysis of cell lysates containing monomers, dimers, trimers, and oligomers of the Tau protein. The various lanes indicate IgG antibodies elicited by the non-phosphorylated Tau peptide immunogen constructs shown above each lane (left side). These peptide immunogen constructs correspond to the constructs shown in Table 3. The binding profiles for each antibody was analyzed and summarized in the bar graph (right side). Representative immune sera to Tau immunogen constructs demonstrated binding reactivities to multispecies of Tau (monomers, dimer, trimers, oligomers and polymers).

The present disclosure is directed to individual peptide immunogen constructs targeting portions of the Tau protein for the treatment and/or prevention of Alzheimer's disease and/or tauopathies. The present disclosure is also directed to compositions containing the peptide immunogen constructs, methods of making and using the peptide immunogen constructs, and antibodies produced by the peptide immunogen constructs.

The disclosed peptide immunogen constructs contain about 15 or more amino acids. The peptide immunogen constructs contain a B cell epitope from portions of the longest isoform of the human Tau protein (GenBank: AGF19246.1) having the amino acid sequence of SEQ ID NO: 100 shown in Table 8. The B cell epitope can be linked to a heterologous T helper cell (Th) epitope derived from pathogen proteins through an optional heterologous spacer. The disclosed peptide immunogen constructs stimulate the generation of highly specific antibodies directed against Tau. The disclosed peptide immunogen constructs can be used as an immunotherapy for patients suffering from Alzheimer's disease and/or tauopathies.

The B cell epitope portion of the peptide immunogen constructs have amino acid sequences from the full-length Tau protein (SEQ ID NO: 100). In some embodiments, the B cell epitope has a sequence containing any of SEQ ID NOs: 1-21 and 101-124 as shown in Table 1.

The peptide immunogen constructs of the present disclosure can contain a heterologous Th epitope amino acid sequence derived from a pathogenic protein (e.g., SEQ ID NOs: 22 to 50) as shown in Table 2. In certain embodiments, the heterologous Th epitope is derived from natural pathogens, such as Diphtheria Toxin (SEQ ID NO: 26), *Plasmodium Falciparum (SEQ ID NO: 27), Cholera Toxin (SEQ ID NO: 29). In other embodiments, the heterologous Th epitope is an idealized artificial Th epitope derived from Measles Virus Fusion protein (MVF 1 to 5) or Hepatitis B Surface Antigen (HBsAg 1 to 3) in the form of either single sequence or combinatorial sequences (e.g., SEQ ID NOs: 33, 32, and 34).

In some embodiments, the peptide immunogen constructs contain a B cell epitope from Tau linked to a heterologous T helper cell (Th) epitope through an optional heterologous spacer. In certain embodiments, the peptide immunogen constructs contain a B cell antigenic site having the amino acid sequence from Tau (SEQ ID NOs: 1-21 and 101-124) linked to a heterologous Th epitope derived from a pathogenic protein (e.g., SEQ ID NOs: 22 to 50) through an optional heterologous spacer. In some embodiments, the optional heterologous spacer is a molecule or chemical structure capable of linking two amino acids and/or peptides together. In certain embodiments, the spacer is a naturally occurring amino acid, a non-naturally occurring amino acid, or a combination thereof. In specific embodiments, the peptide immunogen constructs have the amino acid sequence of SEQ ID NOs: 51-71 and 125-155 shown in Table 4.

The present disclosure is also directed to compositions containing a Tau peptide immunogen construct. In some embodiments, the disclosed compositions contain more than one Tau peptide immunogen constructs to cover multiple B epitopes from Tau. In certain embodiments, the compositions contain a mixture of Tau peptide immunogen constructs (e.g., any combination of SEQ ID NOs: 51-71 and 125-155) with more than one heterologous Th epitope derived from pathogenic protein to cover a broad genetic background in patients. Compositions containing a mixture of peptide immunogen constructs can lead to a higher percentage in responder rate upon immunization for the treatment of Alzheimer's disease and/or tauopathies compared to compositions containing only a single peptide immunogen construct.

The present disclosure is also directed to pharmaceutical compositions for the treatment and/or prevention of Alzheimer's disease and/or tauopathies. In some embodiments, the pharmaceutical compositions contain the disclosed peptide immunogen constructs in the form of a stabilized immunostimulatory complex formed through electrostatic associations by mixing a CpG oligomer with a composition containing a peptide immunogen complex. Such stabilized immunostimulatory complexes are able to further enhance the immunogenicity of the peptide immunogen constructs. In some embodiments, the pharmaceutical compositions contain adjuvants such as mineral salts, including alum gel (ALHYDROGEL), aluminum phosphate (ADJUPHOS), or water-in-oil emulsions including MONTANIDE ISA 51 or 720.

The present disclosure is also directed to antibodies directed against the disclosed Tau peptide immunogen constructs. In particular, the peptide immunogen constructs of the present disclosure are able to stimulate the generation of highly specific antibodies that are cross-reactive with the Tau amino acid sequences (SEQ ID NOs: 1-21 and 101-124) when administered to a subject. The highly specific antibodies produced by the peptide immunogen constructs are cross reactive with recombinant Tau-containing proteins. The disclosed antibodies bind with high specificity to Tau without much, if any, directed to the heterologous Th epitopes employed for immunogenicity enhancement, which is in sharp contrast to the conventional protein or other biological carriers used for such peptide antigenicity enhancement.

The present disclosure also includes methods for treating and/or preventing Alzheimer's disease and/or tauopathies using the disclosed peptide immunogen constructs and/or antibodies directed against the peptide immunogen constructs. In some embodiments, the methods for treating and/or preventing Alzheimer's disease and/or tauopathies including administering to a host a composition containing a disclosed peptide immunogen construct. In certain embodiments, the compositions utilized in the methods contain a disclosed peptide immunogen construct in the form of a stable immunostimulatory complex with negatively charged oligonucleotides, such as CpG oligomers, through electrostatic association, which complexes are further supplemented, optionally, with mineral salts or oil as adjuvant, for administration to patients with Alzheimer's disease and/or tauopathies. The disclosed methods also include dosing regimens, dosage forms, and routes for administering the peptide immunogen constructs to a host at risk for, or with, Alzheimer's disease and/or tauopathies.

The section headings used herein we for organizational purposes only and are not to be construed as limiting the subject matter described. All references or portions of references cited in this application are expressly incorporated by reference herein in their entirety for any purpose.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all amino acid sizes, and all molecular weight or molecular mass values, given for polypeptides are approximate, and are provided for description. Although methods and materials similar or equivalent to those described herein can be used in the practice or testing of the disclosed method, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Tau Peptide Immunogen Construct

The present disclosure provides peptide immunogen constructs containing a B cell epitope with an amino acid sequence from Tau covalently linked to a heterologous T helper cell (Th) epitope directly or through an optional heterologous spacer.

The phrase "Tau peptide immunogen construct" or "peptide immunogen construct", as used herein, refers to a peptide containing (a) a B cell epitope having about 15 or more amino acid residues from the full-length sequence of the longest Tau isoform (SEQ ID NO: 100); (b) a heterologous Th epitope; and (c) an optional heterologous spacer.

In certain embodiments, the Tau peptide immunogen construct can be represented by the formulae:

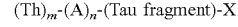

(Th)$_m$-(A)$_n$-(Tau fragment)-X or

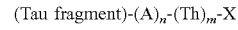

(Tau fragment)-(A)$_n$-(Th)$_m$-X wherein

Th is a heterologous T helper epitope;

A is a heterologous spacer;

(Tau fragment) is a B cell epitope having about 15 to about 40 amino acid residues from SEQ ID NO: 100;

X is an α-COOH or α-CONH$_2$ of an amino acid;

m is from 1 to about 4; and n is from 0 to about 10.

The various components of the disclosed Tau peptide immunogen construct are described below.

a. Tau Fragments

The disclosed peptide immunogen constructs contain about 15 or more amino acids. The peptide immunogen constructs contain a B cell epitope from portions of the longest isoform of the human Tau protein (GenBank: AGF19246.1) having the amino acid sequence of SEQ ID NO: 100 shown in Table g. The B cell epitope can be linked to a heterologous T helper cell (Th) epitope derived from pathogen proteins through an optional heterologous spacer. The disclosed peptide immunogen constructs stimulate the generation of highly specific antibodies directed against Tau. The disclosed peptide immunogen constructs can be used as an immunotherapy for patients suffering from Alzheimer's disease and/or tauopathies.

The B cell epitope portion of the peptide immunogen constructs have amino acid sequences from the full-length Tau protein (SEQ ID NO: 100). In some embodiments, the B cell epitope has a sequence containing any of SEQ ID NOs: 1-21 and 101-124 as shown in Table 1.

In some embodiments, the Tau fragments contain non-phosphorylated amino acids (e.g., SEQ ID NOs: 2, 4, 6, 8, 11, 13, 15, 17, 19, and 21), as shown in Table 1. In other embodiments, the Tau fragments contain phosphorylated serine and/or threonine amino acids (e.g., SEQ ID NOs: 1, 3, 5, 7, 9, 10, 12, 14, 16, 18, and 20), as shown in Table 1. The Tau fragments as well as the phosphorylation sites shown in the peptides of Table 1 are exemplary and the present disclosure includes any other fragment and/or phosphorylation site of the full-length Tau protein of SEQ ID NO: 100.

b. Heterologous T Helper Cell Epitopes (Th Epitopes)

The present disclosure provides peptide immunogen constructs containing a B cell epitope from Tau covalently linked to a heterologous T helper cell (Th) epitope directly or through an optional heterologous spacer.

The heterologous Th epitope in the Tau peptide immunogen construct enhances the immunogenicity of the Tau fragments, which facilitates the production of specific high titer antibodies directed against the optimized target B cell epitope (i.e., the Tau fragment) through rational design.

The term "heterologous", as used herein, refers to an amino acid sequence that is derived from an amino acid sequence that is not part of, or homologous with, the wild-type sequence of Tau. Taus, a heterologous Th epitope is a Th epitope derived from an amino acid sequence that is not naturally found in Tau (i.e., the Th epitope is not autologous to Tau). Since the Th epitope is heterologous to Tau, the natural amino acid sequence of Tau is not extended in either the N-terminal or C-terminal directions when the heterologous Th epitope is covalently linked to the Tau fragment.

The heterologous Th epitope of the present disclosure can be any Th epitope that does not have an amino acid sequence naturally found in Tau. The Th epitope can have an amino acid sequence derived from any species (e.g., human, pig, cattle, dog, rat, mouse, guinea pigs, etc.). The Th epitope can also have promiscuous binding motifs to MHC class II molecules of multiple species. In certain embodiments, the Th epitope comprises multiple promiscuous MHC class II binding motifs to allow maximal activation of T helper cells leading to initiation and regulation of immune responses. The Th epitope is preferably immunosilent on its own, i.e., little, if any, of the antibodies generated by the Tau peptide immunogen constructs will be directed towards the Tb epitope, thus allowing a very focused immune response directed to the targeted B cell epitope of the Tau fragment.

Th epitopes of the present disclosure include, but are not limited to, amino acid sequences derived from foreign pathogens, as exemplified in Table 2 (SEQ ID NOs: 22 to 50). Further, Th epitopes include idealized artificial Th epitopes and combinatorial idealized artificial Th epitopes (e.g., SEQ ID NOs: 23 and 30-36). The heterologous Tb epitope peptides presented as a combinatorial sequence (e.g., SEQ ID NOs: 31-34), contain a mixture of amino acid residues represented at specific positions within the peptide framework based on the variable residues of homologues for that particular peptide. An assembly of combinatorial peptides can be synthesized in one process by adding a mixture of the designated protected amino acids, instead of one particular amino acid, at a specified position during the synthesis process. Such combinatorial heterologous Tb epitope peptides assemblies can allow broad Th epitope coverage for animals having a diverse genetic background. Representative combinatorial sequences of heterologous Th epitope peptides include SEQ ID NOs: 31-34 which are shown in Table 2. Tb epitope peptides of the present invention provide broad reactivity and immunogenicity to animals and patients from genetically diverse populations.

Tau peptide immunogen constructs comprising Tb epitopes are produced simultaneously in a single solid-phase peptide synthesis in tandem with the Tau fragment. Th epitopes also include immunological analogues of Th epitopes. Immunological Th analogues include immune-enhancing analogs, cross-reactive analogues and segments of any of these Th epitopes that are sufficient to enhance or stimulate an immune response to the Tau fragments.

Functional immunologically analogues of the Th epitope peptides are also effective and included as part of the present invention. Functional immunological Th analogues can include conservative substitutions, additions, deletions and insertions of from one to about five amino acid residues in the Th epitope which do not essentially modify the Th-stimulating function of the Th epitope. The conservative substitutions, additions, and insertions can be accomplished with natural or non-natural amino acids, as described above for the Tau fragments. Table 2 identifies another variation of a functional analogue for Th epitope peptide. In particular, SEQ ID NOs: 23 and 30 of MvF1 and MvF2 Th are functional analogues of SEQ ID NOs: 33 and 35 of MvF4 and MvF5 in that they differ in the amino acid frame by the deletion (SEQ ID NOs: 23 and 30) or the inclusion (SEQ ID NOs: 33 and 35) of two amino acids each at the N- and C-termini. The differences between these two series of analogous sequences would not affect the function of the Th epitopes contained within these sequences. Therefore, functional immunological Th analogues include several versions of the Th epitope derived from Measles Virus Fusion protein MvF1-4 Th (SEQ ID NOs: 23, 30, 31, 33, and 35) and from Hepatitis Surface protein HBsAg 1-3 Ths (SEQ ID NOs: 32, 34, and 36).

The Th epitope in the Tau peptide immunogen construct can be covalently linked at either N- or C-terminal end of the Tau peptide. In some embodiments, the Th epitope is covalently linked to the N-terminal end of the Tau peptide. In other embodiments, the Th epitope is covalently linked to the C-terminal end of the Tau peptide. In certain embodiments, more than one Th epitope is covalently linked to the Tau fragment. When more than one Th epitope is linked to the Tau fragment, each Th epitope can have the same amino acid sequence or different amino acid sequences. In addition, when more than one Th epitope is linked to the Tau fragment, the Th epitopes can be arranged in any order. For example, the Th epitopes can be consecutively linked to the N-terminal end of the Tau fragment, or consecutively linked to the C-terminal end of the Tau fragment, or a Th epitope can be covalently linked to the N-terminal end of the Tau fragment while a separate Th epitope is covalently linked to the C-terminal end of the Tau fragment. There is no limitation in the arrangement of the Th epitopes in relation to the Tau fragment.

In some embodiments, the Th epitope is covalently linked to the Tau fragment directly. In other embodiments, the Th epitope is covalently linked to the Tau fragment through a heterologous spacer described in further detail below.

c. Heterologous Spacer

The disclosed Tau peptide immunogen constructs optionally contain a heterologous spacer that covalently links the B cell epitope from Tau to the heterologous T helper cell (Th) epitope.

As discussed above, the term "heterologous", refers to an amino acid sequence that is derived from an amino acid sequence that is not part of, or homologous with, the wild-type sequence of Tau. Taus, the natural amino acid sequence of Tau is not extended in either the N-terminal or C-terminal directions when the heterologous spacer is covalently linked to the B cell epitope from Tau because the spacer is heterologous to the Tau sequence.

The spacer is any molecule or chemical structure capable of linking two amino acids and/or peptides together. The spacer can vary in length or polarity depending on the application. The spacer attachment can be through an amide- or carboxyl-linkage but other functionalities are possible as well. The spacer can include a chemical compound, a naturally occurring amino acid, or a non-naturally occurring amino acid.

The spacer can provide structural features to the Tau peptide immunogen construct. Structurally, the spacer provides a physical separation of the Th epitope from the B cell epitope of the Tau fragment. The physical separation by the spacer can disrupt any artificial secondary structures created by joining the Th epitope to the B cell epitope. Additionally, the physical separation of the epitopes by the spacer can eliminate interference between the Th cell and/or B cell responses. Furthermore, the spacer can be designed to create or modify a secondary structure of the peptide immunogen construct. For example, a spacer can be designed to act as a flexible hinge to enhance the separation of the Th epitope and B cell epitope. A flexible hinge spacer can also permit more efficient interactions between the presented peptide immunogen and the appropriate Th cells and B cells to enhance the immune responses to the Th epitope and B cell epitope. Examples of sequences encoding flexible hinges are found in the immunoglobulin heavy chain hinge region, which are often proline rich. One particularly useful flexible hinge that can be used as a spacer is provided by the sequence Pro-Pro-Xaa-Pro-Xaa-Pro (SEQ ID NO: 101), where Xaa is any amino acid, and preferably aspartic acid.

The spacer can also provide functional features to the Tau peptide immunogen construct. For example, the spacer can be designed to change the overall charge of the Tau peptide immunogen construct, which can affect the solubility of the peptide immunogen construct. Additionally, changing the overall charge of the Tau peptide immunogen construct can affect the ability of the peptide immunogen construct to associate with other compounds and reagents. As discussed in further detail below, the Tau peptide immunogen construct can be formed into a stable immunostimulatory complex with a highly charged oligonucleotide, such as CpG oligomers through electrostatic association. The overall charge of the Tau peptide immunogen construct is important for the formation of these stable immunostimulatory complexes.

Chemical compounds that can be used as a spacer include, but are not limited to, (2-aminoethoxy) acetic acid (AEA), 5-aminovaleric acid (AVA), 6-aminocaproic acid (Ahx), 8-amino-3,6-dioxaoctanoic acid (AEEA, mini-PEG1), 12-amino-4,7,10-trioxadodecanoic acid (mini-PEG2), 15-amino-4,7,10,13-tetraoxapenta decanoic acid (mini-PEG3), trioxatridecan-succinamic acid (Ttds), 12-amino-dodecanoic acid, Fmoc-5-amino-3-oxapentanoic acid (O1Pen), and the like.

Naturally-occurring amino acids include alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

Non-naturally occurring amino acids include, but are not limited to, ε-N Lysine, β-alanine, ornithine, norleucine, norvaline, hydroxyproline, thyroxine, γ-amino butyric acid, homoserine, citrulline, aminobenzoic acid,6-aminocaproic acid (Aca; 6-Aminohexanoic acid), hydroxyproline, mercaptopropionic acid (MPA), 3-nitro-tyrosine, pyroglutamic acid, and the like.

The spacer in the Tau peptide immunogen construct can be covalently linked at either N- or C-terminal end of the Th epitope and the Tau peptide. In some embodiments, the spacer is covalently linked to the C-terminal end of the Th epitope and to the N-terminal end of the Tau peptide. In other embodiments, the spacer is covalently linked to the C-terminal end of the Tau peptide and to the N-terminal end of the Th epitope. In certain embodiments, more than one spacer can be used, for example, when more than one Th epitope is present in the peptide immunogen construct. When more than one spacer is used, each spacer can be the same as each other or different. Additionally, when more than one Th epitope is present in the peptide immunogen construct, the Th epitopes can be separated with a spacer, which can be the same as, or different from, the spacer used to separate the Th epitope from the B cell epitope. There is no limitation in the arrangement of the spacer in relation to the Th epitope or the Tau fragment.

In certain embodiments, the heterologous spacer is a naturally occurring amino acid or a non-naturally occurring amino acid. In other embodiments, the spacer contains more than one naturally occurring or non-naturally occurring amino acid. In specific embodiments, the spacer is Lys-, Gly-, Lys-Lys-Lys-, (α, ε-N)Lys, or ε-N-Lys-Lys-Lys-Lys (SEQ ID NO: 102).

d. Specific Embodiments of the Tau Peptide Immunogen Construct

The Tau peptide immunogen construct can be represented by the formulae:

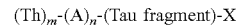

$(Th)_m\text{-}(A)_n\text{-}(Tau\ fragment)\text{-}X$ or

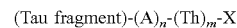

$(Tau\ fragment)\text{-}(A)_n\text{-}(Th)_m\text{-}X$ wherein

Th is a heterologous T helper epitope;

A is a heterologous spacer, (Tau fragment) is a B cell epitope having about 15 to about 40 amino acid residues from the full-length Tau protein of SEQ ID NO: 100;

X is an α-COOH or α-CONH$_2$ of an amino acid;

m is from 1 to about 4; and n is from 0 to about 10.

In certain embodiments, the heterologous Th epitope in the Tau peptide immunogen construct has an amino acid sequence selected from any of SEQ ID NOs: 51-71 and 125-155 and combinations thereof, shown in Table 3. In specific embodiments, the Th epitope has an amino acid sequence selected from any of SEQ ID NOs: 30-36. In certain embodiments, the Tau peptide immunogen construct contains more than one Th epitope.

In certain embodiments, the optional heterologous spacer is selected from any of Lys-, Gly-, Lys-Lys-Lys-, (α, ε-N) Lys, ε-N-Lys-Lys-Lys-Lys (SEQ ID NO: 102), and combinations thereof. In specific embodiments, the heterologous spacer is ε-N-Lys-Lys-Lys-Lys (SEQ ID NO: 102).

In certain embodiments, the Tau fragment has about 15 to about 40 amino acid residues from the full-length Tau protein of SEQ ID NO: 100. In specific embodiments, the Tau fragment has an amino acid sequence represented by SEQ ID NOs: 1-21 and 101-124, as shown in Table 1.

In certain embodiments, the Tau peptide immunogen construct has an amino acid sequence selected from any of SEQ ID NOs: 51-71 and 125-155, as shown in Table 3.

a. Variants, Homologues, and Functional Analogues

Variants and analogs of the above immunogenic peptides that induce and/or cross-react with antibodies to the preferred epitopes of Tau protein can also be used. Analogs, including allelic, species, and induced variants, typically differ from naturally occurring peptides at one, two, or a few positions, often by virtue of conservative substitutions. Analogs typically exhibit at least 80 or 90% sequence identity with natural peptides. Some analogs also include unnatural amino acids or modifications of N- or C-terminal amino acids at one, two, or a few positions.

Variants that are functional analogues can have a conservative substitution in an amino acid position; a change in overall charge; a covalent attachment to another moiety; or amino acid additions, insertions, or deletions; and/or any combination thereof.

Conservative substitutions are when one amino acid residue is substituted for another amino acid residue with similar chemical properties. For example, the nonpolar (hydrophobic) amino acids include alanine, leucine, isoleucine, valine, proline, phenylalanine, tryptophan and methionine; the polar neutral amino acids include glycine, serine, threonine, cysteine, tyrosine, asparagine, and glutamine; the positively charged (basic) amino acids include arginine, lysine and histidine; and the negatively charged (acidic) amino acids include aspartic acid and glutamic acid.

In a particular embodiment, the functional analogue has at least 50% identity to the original amino acid sequence. In another embodiment, the functional analogue has at least 80% identity to the original amino acid sequence. In yet another embodiment, the functional analogue has at least 85% identity to the original amino acid sequence. In still another embodiment, the functional analogue has at least 90% identity to the original amino acid sequence.

Variants also include variations to the phosphorylated residues. For example, variants can include different residues within the peptides that are phosphorylated. Variant immunogenic Tau peptides can also include pseudo-phosphorylated peptides. The pseudo-phosphorylated peptides are generated by substituting one or more of the phosphorylated serine, threonine, and tyrosine residues of the Tau peptides with acidic amino acid residues such as glutamic acid and aspartic acid.

Compostions

The present disclosure also provides compositions comprising the disclosed Tau immunogen construct.

a. Peptide Compositions

Compositions containing a disclosed Tau peptide immunogen construct can be in liquid or solid form. Liquid compositions can include water, buffers, solvents, salts, and/or any other acceptable reagent that does not alter the structural or functional properties of the Tau peptide immunogen construct. Peptide compositions can contain one or more of the disclosed Tau peptide immunogen constructs.

b. Pharmaceutical Compostions

The present disclosure is also directed to pharmaceutical compositions containing the disclosed Tau peptide immunogen construct.

Pharmaceutical compositions can contain carriers and/or other additives in a pharmaceutically acceptable delivery system. Accordingly, pharmaceutical compositions can contain a pharmaceutically effective amount of an Tau peptide immunogen construct together with pharmaceutically-acceptable carrier, adjuvant, and/or other excipients such as diluents, additives, stabilizing agents, preservatives, solubilizing agents, buffers, and the like.

Pharmaceutical compositions can contain one or more adjuvant that act(s) to accelerate, prolong, or enhance the immune response to the Tau peptide immunogen construct without having any specific antigenic effect itself. Adjuvants used in the pharmaceutical composition can include oils, aluminum salts, virosomes, aluminum phosphate (e.g., ADJU-PHOS®), aluminum hydroxide (e.g., ALHYDROGEL®), liposyn, saponin, squalene, L121, Emulsigen®, monophosphoryl lipid A (MPL), QS21, ISA35, ISA 206, ISA50V, ISA51, ISA 720, as well as the other adjuvants and emulsifiers.

In some embodiments, the pharmaceutical composition contains MONTANIDE™ ISA 51 (an oil adjuvant composition comprised of vegetable oil and mannide oleate for production of water-in-oil emulsions), Tween® 80 (also known s: Polysorbate 80 or Polyoxyethylene (20) sorbitan monooleate), a CpG oligonucleotide, and/or any combination thereof. In other embodiments, the pharmaceutical composition is a water-in-oil-in-water (i.e., w/o/w) emulsion with Emulsigen or Emulsigen D as the adjuvant.

Pharmaceutical compositions can be formulated as immediate release or for sustained release formulations. Additionally the pharmaceutical compositions can be formulated for induction of systemic, or localized mucosal, immunity through immunogen entrapment and co-administration with microparticles. Such delivery systems are readily determined by one of ordinary skill in the art.

Pharmaceutical compositions can be prepared as injectables, either as liquid solutions or suspensions. Liquid vehicles containing the Tau peptide immunogen construct can also be prepared prior to injection. The pharmaceutical composition can be administered by any suitable mode of application, for example, i.d., i.v., i.p., i.m., intranasally, orally, subcutaneously, etc. and in any suitable delivery device. In certain embodiments, the pharmaceutical composition is formulated for intravenous, subcutaneous, intradermal, or intramuscular administration. Pharmaceutical compositions suitable for other modes of administration can also be prepared, including oral and intranasal applications.

Pharmaceutical compositions can be formulated as immediate release or for sustained release formulations. Additionally the pharmaceutical compositions can be formulated for induction of systemic, or localized mucosal, immunity through immunogen entrapment and co-administration with microparticles. Such delivery systems are readily determined by one of ordinary skill in the art.

Pharmaceutical compositions can also formulated in a suitable dosage unit form. In some embodiments, the pharmaceutical composition contains from about 0.5 µg to about 1 mg of the Tau peptide immunogen construct per kg body weight. Effective doses of the pharmaceutical compositions vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. When delivered in multiple doses, the pharmaceutical compositions may be conveniently divided into an appropriate amount per dosage unit form. The administered dosage will depend on the age, weight and general health of the subject as is well known in the therapeutic arts.

In some embodiments, the pharmaceutical composition contains more than one Tau peptide immunogen construct. A pharmaceutical composition containing a mixture of more than one Tau peptide immunogen construct to allow for synergistic enhancement of the immunoefficacy of the constructs. Pharmaceutical compositions containing more than one Tau peptide immunogen construct can be more effective in a larger genetic population due to a broad MHC class II coverage thus provide an improved immune response to the Tau peptide immunogen constructs.

In some embodiments, the pharmaceutical composition contains an Tau peptide immunogen construct selected from SEQ ID NOs: 51-71 and 125-155, as well as homologues, analogues and/or combinations thereof. In specific embodiments, pharmaceutical compositions contain an Tau peptide immunogen construct selected from SEQ ID NOs: 51-71 and 125-155, and any combination thereof.

Pharmaceutical compositions containing an Tau peptide immunogen construct can be used to elicit an immune response and produce antibodies in a host upon administration.

c. Immunostimulatory Complexes

The present disclosure is also directed to pharmaceutical compositions containing an Tau peptide immunogen construct in the form of an immunostimulatory complex with a CpG oligonucleotide. Such immunostimulatory complexes are specifically adapted to act as an adjuvant and as a peptide immunogen stabilizer. The immunostimulatory complexes are in the form of a particulate, which can efficiently present the Tau peptide immunogen to the cells of the immune system to produce an immune response. The immunostimulatory complexes may be formulated as a suspension for parenteral administration. The immunostimulatory complexes may also be formulated in the form of w/o emulsions, as a suspension in combination with a mineral salt or with an in-situ gelling polymer for the efficient delivery of the Tau peptide immunogen to the cells of the immune system of a host following parenteral administration.

The stabilized immunostimulatory complex can be formed by complexing a Tau peptide immunogen construct with an anionic molecule, oligonucleotide, polynucleotide, or combinations thereof via electrostatic association. The stabilized immunostimulatory complex may be incorporated into a pharmaceutical composition as an immunogen delivery system.

In certain embodiments, the Mau peptide immunogen construct is designed to contain a cationic portion that is positively charged at a pH in the range of 5.0 to 8.0. The net charge on the cationic portion of the Tau peptide immunogen construct, or mixture of constructs, is calculated by assigning a +1 charge for each lysine (K), arginine (R) or histidine (H), a −1 charge for each aspartic acid (D) or glutamic acid (E) and a charge of 0 for the other amino acid within the sequence. The charges are summed within the cationic portion of the Tau peptide immunogen construct and expressed as the net average charge. A suitable peptide immunogen has a cationic portion with a net average positive charge of +1. Preferably, the peptide immunogen has a net positive charge in the range that is larger than +2. In some embodiments, the cationic portion of the Tau peptide immunogen construct is the heterologous spacer. In certain embodiments, the cationic portion of the Tau peptide immunogen construct has a charge of +4 when the spacer sequence is (α, ε-N)Lys, ε-N-Lys-Lys-Lys-Lys (SEQ ID NO: 102).

An "anionic molecule" as described herein refers to any molecule that is negatively charged at a pH in the range of 5.0-8.0. In certain embodiments, the anionic molecule is an oligomer or polymer. The net negative charge on the oligomer or polymer is calculated by assigning a −1 charge for each phosphodiester or phosphorothioate group in the oligomer. A suitable anionic oligonucleotide is a single-stranded DNA molecule with 8 to 64 nucleotide bases, with the number of repeats of the CpG motif in the range of 1 to 10. Preferably, the CpG immunostimulatory single-stranded DNA molecules contain 18-48 nucleotide bases, with the number of repeats of CpG motif in the range of 3 to 8.

More preferably the anionic oligonucleotide is represented by the formula: 5'$X^1$CG$X^2$ 3' wherein C and G are unmethylated; and $X^1$ is selected from the group consisting of A (adenine), G (guanine) and T (thymine); and $X^2$ is C (cytosine) or T (thymine). Or, the anionic oligonucleotide is represented by the formula: 5' (X)CG($X^4$)$_2$ 3' wherein C and G are unmethylated; and $X^3$ is selected from the group consisting of A, T or G; and $X^4$ is C or T.

The resulting immunostimulatory complex is in the form of particles with a size typically in the range from 1-50 microns and is a function of many factors including the relative charge stoichiometry and molecular weight of the interacting species. The particulated immunostimulatory complex has the advantage of providing adjuvantation and upregulation of specific immune responses in vivo. Additionally, the stabilized immunostimulatory complex is suitable for preparing pharmaceutical compositions by various processes including water-in-oil emulsions, mineral salt suspensions and polymeric gels.

Antibodies

The present disclosure also provides antibodies elicited by the Tau peptide immunogen construct.

The disclosed Tau peptide immunogen constructs, comprising a Tau fragment, heterologous Th epitope, and optional heterologous spacer, are capable of eliciting an immune response and the production of antibodies when administered to a host. The design of the Tau peptide immunogen constructs can break tolerance to self Tau and elicit the production of site-specific antibodies that recognize conformational, not linear, epitopes.

The antibodies produced by the Tau peptide immunogen constructs recognize and bind to Tau in the forms of monomers, dimers, trimers, and oligomers.

Antibodies elicited by the Tau peptide immunogen constructs surprisingly can prevent aggregation of Tau (anti-aggregation activity) and can disassociate preformed Tau aggregates (disaggregation activity).

The resulting immune responses from animals immunized with Tau peptide immunogen constructs of the present invention demonstrated the ability of the constructs to produce potent site-directed antibodies that are reactive with n in the forms of monomers, dimers, trimers, and oligomers.

Methods

The present disclosure is also directed to methods for making and using the Tau peptide immunogen constructs, compositions, and pharmaceutical compositions.

a. Methods for Manufacturing the Tau Peptide Immunogen Construct

The Tau peptide immunogen constructs of this disclosure can be made by chemical synthesis methods well known to the ordinarily skilled artisan (see, e.g., Fields et al., Chapter 3 in Synthetic Peptides: A User's Guide, ed. Grant, W. H. Freeman & Co., New York, N.Y., 1992, p. 77).

The Tau peptide immunogen constructs can be synthesized using the automated Merrifield techniques of solid phase synthesis with the $\alpha$-$NH_2$ protected by either t-Boc or F-moc chemistry using side chain protected amino acids on, for example, an Applied Biosystems Peptide Synthesizer Model 430A or 431. Preparation of Tau peptide immunogen constructs comprising combinatorial library peptides for Th epitopes can be accomplished by providing a mixture of alternative amino acids for coupling at a given variable position.

After complete assembly of the desired Tau peptide immunogen construct, the resin can be treated according to standard procedures to cleave the peptide from the resin and the functional groups on the amino acid side chains can be deblocked. The free peptide can be purified by HPLC and characterized biochemically, for example, by amino acid analysis or by sequencing.

Purification and characterization methods for peptides are well known to one of ordinary skill in the art.

The quality of peptides produced by this chemical process can be controlled and defined and, as a result, reproducibility of Tau peptide immunogen constructs, immunogenicity, and yield can be assured. Detailed description of the manufacturing of the Tau peptide immunogen construct through solid phase peptide synthesis is shown in Example 1.

The range in structural variability that allows for retention of an intended immunological activity has been found to be far more accommodating than the range in structural variability allowed for retention of a specific drug activity by a small molecule drug or the desired activities and undesired toxicities found in large molecules that are co-produced with biologically-derived drugs. Taus, peptide analogues, either intentionally designed or inevitably produced by errors of the synthetic process as a mixture of deletion sequence byproducts that have chromatographic and immunologic properties similar to the intended peptide, are frequently as effective as a purified preparation of the desired peptide. Designed analogues and unintended analogue mixtures are effective as long as a discerning QC procedure is developed to monitor both the manufacturing process and the product evaluation process so as to guarantee the reproducibility and efficacy of the final product employing these peptides.

The Tau peptide immunogen constructs can also be made using recombinant DNA technology including nucleic acid molecules, vectors, and/or host cells. As such, nucleic acid molecules encoding the Tau peptide immunogen construct and immunologically functional analogues thereof are also encompassed by the present disclosure as part of the present invention. Similarly, vectors, including expression vectors, comprising nucleic acid molecules as well as host cells containing the vectors are also encompassed by the present disclosure as part of the present invention.

Various exemplary embodiments also encompass methods of producing the Tau peptide immunogen construct and immunologically functional analogues thereof. For example, methods can include a step of incubating a host cell containing an expression vector containing a nucleic acid molecule encoding an Tau peptide immunogen construct and/or immunologically functional analogue thereof under such conditions where the peptide and/or analogue is expressed. The longer synthetic peptide immunogens can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

b. Methods for the Manufacturing of Immunostimulatory Complexes

Various exemplary embodiments also encompass methods of producing the Immunostimulatory complexes comprising Tau peptide immunogen constructs and CpG oligodeoxynucleotide (ODN) molecule. Stabilized immunostimulatory complexes (ISC) are derived from a cationic portion of the Tau peptide immunogen construct and a polyanionic CpG ODN molecule. The self-assembling system is driven by electrostatic neutralization of charge. Stoichiometry of the molar charge ratio of cationic portion of the Tau peptide immunogen construct to anionic oligomer determines extent of association. The non-covalent electrostatic association of Tau peptide immunogen construct and CpG ODN is a completely reproducible process. The peptide/CpG ODN immunostimulatory complex aggregates, which facilitate presentation to the "professional" antigen-presenting cells (APC) of the immune system thus further enhancing of the immunogenicity of the complexes. These complexes ae easily characterized for quality control during manufacturing. The peptide/CpG ISC are well tolerated in vivo. This novel particulate system comprising CpG ODN and Tau fragment derived peptide immunogen constructs was designed to take advantage of the generalized B cell mitogenicity associated with CpG ODN use, yet promote balanced Th-1/Th-2 type responses.

The CpG ODN in the disclosed pharmaceutical compositions is 100% bound to immunogen in a process mediated by electrostatic neutralization of opposing charge, resulting in the formation of micron-sized particulates. The particulate form allows for a significantly reduced dosage of CpG from the conventional use of CpG adjuvants, less potential for adverse innate immune responses, and facilitates alternative immunogen processing pathways including antigen-presenting cells (APC). Consequently, such formulations are novel conceptually and offer potential advantages by promoting the stimulation of immune responses by alternative mechanism.

c. Methods for the Manufacturing of Pharmaceutical Compositions

Various exemplary embodiments also encompass pharmaceutical compositions containing Tau peptide immunogen constructs. In certain embodiments, the pharmaceutical compositions employ water in oil emulsions and in suspension with mineral salts.

In order for a pharmaceutical composition to be used by a large population and with prevention of Tau aggregation also being part of the goal for administration, safety becomes another important factor for consideration. Despite the use of water-in-oil emulsions in humans for many formulations in clinical trials, Alum remains the major adjuvant for use in formulations due to its safety. Alum or its mineral salts Aluminum phosphate (ADJUPHOS) are, therefore, frequently used as adjuvants in preparation for clinical applications.

Other adjuvants and immunostimulating agents include 3 De-O-acylated monophosphoryl lipid A (MPL) or 3-DMP, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-glycero-3-hydroxyphosphoryloxy)-ethylamine (MTP-PE), N-acetylglucsaminyl-N-acetylmuramyl-L-A1-D-isoglu-L-Ala-dipalmitoxy propylamide (DTP-DPP) Theramide™), or other bacterial cell wall components. Oil-in-water emulsions include MF59 (see WO 90/14837 to Van Nest et al., which is hereby incorporated by reference in its entirety), containing 5% Squalene, 0.5% Tween 80, and 0.5% Span 85 (optionally containing various amounts of MTP-PE) formulated into submicron particles using a microfluidizer, SAF, containing 10% Squalene, 0.4% Tween 80, 5% pluronic-blocked polymer L121, and thr-MDP, either microfluidized into a submicron emulsion or vortexed to generate a larger particle size emulsion; and the Ribi™ adjuvant system (RAS) (Ribi ImmunoChem, Hamilton, Mont.) containing 2% squalene, 0.2% Tween 80, and one or more bacterial cell wall components selected from the group consisting of monophosphoryllipid A (MPL), trehalose dimycolate (TDM), and cell wall skeleton (CWS), preferably MPL+CWS (Detox™). Other adjuvants include Complete Freund's Adjuvant (CFA), Incomplete Freund's Adjuvant (IFA), and cytokines, such as interleukins (IL-1, IL-2, and IL-12), granulocyte-macrophage colony stimulating factor (GM-CSF), and tumor necrosis factor (TNF).

The choice of an adjuvant depends on the stability of the immunogenic formulation containing the adjuvant, the route of administration, the dosing schedule, the efficacy of the adjuvant for the species being vaccinated, and, in human, a pharmaceutically acceptable adjuvant is one that has been approved or is approvable for human administration by pertinent regulatory bodies. For example, alum, MPL or Incomplete Freund's adjuvant (Chang et al., Advanced Drug Delivery Reviews 32:173-186 (1998), which is hereby incorporated by reference in its entirety) alone or optionally all combinations thereof are suitable for human administration.

The compositions can include pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, non-immunogenic stabilizers, and the like.

Pharmaceutical compositions can also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes). Additionally, these carriers can function as immunostimulating agents (i.e., adjuvants).

The pharmaceutical compositions of the present invention can further include a suitable delivery vehicle. Suitable delivery vehicles include, but are not limited to viruses, bacteria, biodegradable microspheres, microparticles, nanoparticles, liposomes, collagen minipellets, and cochleates.

d. Methods Using Pharmaceutical Compositions

The present disclosure also includes methods of using pharmaceutical compositions containing Tau peptide immunogen constructs.

In certain embodiments, the pharmaceutical compositions containing Tau peptide immunogen constructs can be used for:

(a) inhibiting Tau aggregation in a host;
(b) inducing disaggregate of preformed Tau aggregates in a host;
(c) reducing neurodegeneration triggered by exogeneous Tau aggregates in a host;
(d) reducing neurodegeneration in Tau overexpressing cells;
(e) reducing serum Tau levels in a host;
(f) reducing oligomeric Tau level in the brain of a host;
(g) reducing neuropathology and recovery of motor activities in a host; and the like.

The above methods comprise administering a pharmaceutical composition comprising a pharmacologically effective amount of a Tau peptide immunogen construct to a host in need thereof.

As used herein a "tauopathy" encompasses any neurodegenerative disease that involves the pathological aggregation of the microtubule protein Tau within the brain. Accordingly, in addition to both familial and sporadic Alzheimer's disease, other tauopathies that can be treated using the methods of the present invention include, without limitation, frontotemporal dementia, parkinsonism linked to chromosome 17 (FTDP-17), progressive supranuclear palsy, corticobasal degeneration, Pick's disease, progressive subcortical gliosis, tangle only dementia, diffuse neurofibrillary tangles with calcification, argyrophilic grain dementia, amyotrophic lateral sclerosis parkinsonism-dementia complex, dementia pugilistica, Down syndrome, Gerstmann-Straussler-Scheinker disease, Hallerworden-Spatz disease, inclusion body myositis, Creutzfeld-Jakob disease, multiple system atropy, Niemann-Pick disease type C, prion protein cerebral amyloid angiopathy, subacute sclerosing panencephalitis, myotonic dystrophy, non-guanamian motor neuron disease with neurofibrillary tangles, postencephalitic parkinsonism, and chronic traumatic encephalopathy.

Another aspect of the present disclosure is directed to a method of promoting clearance of Tau aggregates from the brain of a subject. This method involves administering, to the subject, any one or more immunogenic Tau peptides having an amino acid sequence selected from the group consisting of SEQ ID NOs: 1-21 and 101-124, or one or more antibodies recognizing an immunogenic Tau epitope comprising an amino acid sequence selected from the group consisting of SEQ ID NOs: 1-21 and 101-124 and 51-71 and 125-155 under conditions effective to promote clearance of Tau aggregates from the brain of the subject.

The clearance of Tau aggregates includes clearance of neurofibrillary tangles and/or the pathological Tau precursors to neurofibrillary tangles. Neurofibrillary tangles are often associated with neurodegenerative diseases including, for example, sporadic and familial Alzheimer's disease, amyotrophic lateral sclerosis, argyrophilic grain dementia, dementia pugilistica, chronic traumatic encephalopathy, diffuse neurofibrillary tangles with calcification, Down syndrome, Gerstmann-Straussler-Scheinker disease, Hallervorden-Spatz disease, hereditary frontotemporal dementia, parkinsonism linked to chromosome 17 (FTDP-17), inclusion body myositis, Creutzfeld-Jakob disease, multiple system atrophy, Niemann-Pick disease type C, Pick's disease, prion protein cerebral amyloid angiopathy, sporadic corticobasal degeneration, progressive supranuclear palsy, subacute sclerosing panencephalitis, myotonic dystrophy, motor neuron disease with neurofibrillary tangles, tangle only dementia, and progressive subcortical gliosis.

Another aspect of the present disclosure is directed to a method of slowing the progression of a Tau-pathology related behavioral phenotype in a subject. This method involves administering, to the subject, any one or more immunogenic Tau peptides comprising an amino acid sequence selected from the group consisting of SEQ ID NOs: 1-21 and 101-124 and 51-71 and 125-155, or one or more antibodies recognizing an immunogenic Tau epitope comprising an amino acid sequence selected from the group consisting of SEQ ID NOs: 1-21 and 101-124 and 51-71 and 125-155, under conditions effective to slow the Tau-pathology related behavioral phenotype in the subject.

As used herein, a Tau-pathology related behavioral phenotype includes, without limitation, cognitive impairments, early personality change and disinhibition, apathy, abulia, mutism, apraxia, perseveration, stereotyped movements/behaviors, hyperorality, disorganization, inability to plan or organize sequential tasks, selfishness/callousness, antisocial traits, a lack of empathy, halting, agrammatic speech with frequent paraphasic errors but relatively preserved comprehension, impaired comprehension and word-finding deficits, slowly progressive gait instability, retropulsions, freezing, frequent falls, non-levodopa responsive axial rigidity, supranuclear gaze palsy, square wave jerks, slow vertical saccades, pseudobulbar palsy, limb apraxia, dystonia, cortical sensory loss, and tremor.

In accordance with the methods of the present disclosure, in one embodiment, an immunogenic Tau peptide or a combination of immunogenic Tau peptides are administered to a subject in need. Suitable immunogenic Tau peptide fragments of the Tau protein contain one or more antigenic epitopes that mimic the pathological form of the Tau protein. Exemplary immunogenic Tau epitopes are phosphorylated at one or more amino acids that are phosphorylated in the pathological form of Tau, but not phosphorylated in the normal or non-pathological form of Tau.

In some embodiments, administration of an immunogenic Tau peptide induces an active immune response in the subject to the immunogenic Tau peptide and to the pathological form of Tau, thereby facilitating the clearance of related Tau aggregates, slowing the progression of Tau-pathology related behavior and treating the underlying tauopathy. In accordance with this aspect of the present invention, an immune response involves the development of a beneficial humoral (antibody mediated) and/or a cellular (mediated by antigen-specific T cells or their secretion products) response directed against the immunogenic Tau peptide.

The presence of a humoral immunological response can be determined and monitored by testing a biological sample (e.g., blood, plasma, serum, urine, saliva feces, CSF or lymph fluid) from the subject for the presence of antibodies directed to the immunogenic Tau peptide. Methods for detecting antibodies in a biological sample are well known in the art, e.g., ELISA, Dot blots, SDS-PAGE gels or ELISPOT. The presence of a cell-mediated immunological response can be determined by proliferation assays (CD4+ T cells) or CTL (cytotoxic T lymphocyte) assays which are readily known in the art.

Isolated immunogenic Tau peptides of the present invention include any one of the amino acid sequences of SEQ ID NOs: 1-21 and 101-124 and 51-71 and 125-155 shown in Tables 1 and 3 below. Amino acid residues of each sequence which are phosphorylated am shown in bold and underline. The names of the peptides in Table 1 correspond to the amino acid position of these peptides within the longest isoform of the human Tau protein having the amino acid sequence of SEQ ID NO:100 as shown in Table 8.

Specific Embodiments (1) A Tau peptide immunogen construct can be represented by the formulae:

$$(Th)_m\text{-}(A)_n\text{-}(Tau\ fragment)\text{-}X$$

or $$(Tau\ fragment)\text{-}(A)_n\text{-}(Th)_m\text{-}X$$

wherein

Th is a heterologous T helper epitope;

A is a heterologous spacer;

(Tau fragment) is a B cell epitope having about 15 to about 40 amino acid residues from the full-length Tau protein of SEQ ID NO: 100;

X is an α-COOH or α-CONH$_2$ of an amino acid;

m is from 1 to about 4; and n is from 0 to about 10.

(2) The Tau peptide immunogen construct according to (1), wherein the Tau fragment is selected from the group consisting of SEQ ID NOs: 1-21 and 101-124.

(3) The Tau peptide immunogen construct according to any of (1) or (2), wherein the Th epitope is selected from the group consisting of SEQ ID NOs: 22-50.

(4) The Tau peptide immunogen construct according to (1), wherein the peptide immunogen construct is selected from the group consisting of SEQ ID NOs: 51-71 and 125-155.

(5) An Tau peptide immunogen construct comprising:

a B cell epitope comprising about 15 to about 40 amino acid residues from the full-length Tau protein sequence of SEQ ID NO: 100;

a T helper epitope comprising an amino acid sequence selected from the group consisting of SEQ ID NOs: 22-50; and an optional heterologous spacer selected from the group consisting of an amino acid, Lys-, Gly-, Lys-Lys-Lys-, (α, ε-N)Lys, and ε-N-Lys-Lys-Lys-Lys (SEQ ID NO: 102), wherein the B cell epitope is covalently linked to the T helper epitope directly or through the optional heterologous spacer.

(6) The Tau peptide immunogen construct of (5), wherein the B cell epitope is selected from the group consisting of SEQ ID NOs: 1-21 and 101-124.
(7) The Tau peptide immunogen construct of (5), wherein the T helper epitope is selected from the group consisting of SEQ ID NOs: 22-50.
(8) The Tau peptide immunogen construct of (5), wherein the optional heterologous spacer is (α, ε-N)Lys or ε-N-Lys-Lys-Lys-Lys (SEQ ID NO: 102).
(9) The Tau peptide immunogen construct of (5), wherein the T helper epitope is covalently linked to the amino terminus of the B cell epitope.
(10) The Tau peptide immunogen construct of (5), wherein the T helper epitope is covalently linked to the amino terminus of the B cell epitope through the optional heterologous spacer.
(11) A composition comprising a peptide immunogen construction according to any of (1) to (4).
(12) A pharmaceutical composition comprising:
  a. a peptide immunogen construct according to any of (1) to (4); and
  b. and a pharmaceutically acceptable delivery vehicle and/or adjuvant.
(13) The pharmaceutical composition of (12), wherein
  a. the Tau peptide immunogen construct is selected from the group consisting of SEQ ID NOs: 51-71 and 125-155; and
  b. the Tau peptide immunogen construct is mixed with an CpG oligodeoxynucleotide (ODN) to form a stabilized immunostimulatory complex.
(14) An isolated antibody or epitope-binding fragment thereof that specifically binds to the B cell epitope of the Tau peptide immunogen construct according to any of (1) to (10).
(15) The isolated antibody or epitope-binding fragment thereof according to (14) bound to the Tau peptide immunogen construct.
(16) An isolated antibody or epitope-biding fragment thereof that specifically binds to the B cell epitope of the Tau peptide immunogen construct according to any of (1) to (10).
(17) A composition comprising the isolated antibody or epitope-binding fragment thereof according to any of claims (14) to (16).

Example 1

Antibodies Elicited by Non-Phosphorylated Tau Peptide Immunogen Constructs and Binding Profiles a. Synthesis of Tau Fragments and Immunizations Methods for synthesizing designer Tau fragments that were included in the development effort of non-phosphorylated and phosphorylated Tau peptide immunogen constructs we described in the Detailed Description. In general, the peptides were synthesized in small-scale for serological assays, laboratory pilot-scale for field or clinical studies, as well as largo-scale (kilogram) for industrial/commercial production of pharmaceutical compositions. A large repertoire of Tau related antigenic B cell epitope peptides having sequences with lengths ranging from approximately 10 to approximately 40 amino acids were designed for extensive serological screening and selection as the candidate B cell epitope for incorporation in the design of Tau peptide immunogen constructs for immunogenicity and functional testing for use in a Tau vaccine formulation.

Full-length Tau (Table 8), used as a recombinant protein in these serological studies, was purchased from rPeptide Company (Tau-441, T-1001-2). Tau peptide segments employed for epitope mapping in various serological assays are identified in Table 1 (SEQ ID NOs: 1 to 21 and 101-124). Selected Tau peptide segments were made into Tau peptide immunogen constructs by synthetically linking the Tau peptides to a carefully designed helper T cell (Th) epitope derived from pathogen proteins including Measles Virus Fusion protein (MVF), Hepatitis B Surface Antigen protein (HBsAg) influenza, *Clostridium tetani*, and Epstein-Barr virus (EBV). The designed Th epitopes are shown in Table 2 (SEQ ID NOs: 22 to 50).

Formulations employing water-in-oil emulsions and in suspension with mineral salts were prepared as described in the Detailed Description. In designing an appropriate pharmaceutical composition to be used by a large population for the purpose of preventing disease, it is important to consider the safety of the composition. Despite the use of water-in-oil emulsions in humans for many pharmaceutical compositions in clinical trials, alum remains the major adjuvant for use in pharmaceutical composition due to its safety. Alum or its mineral salts, such as ADJUPHOS (aluminum phosphate), are frequently used as adjuvants in preparation for clinical applications. The non-phosphorylated Tau peptide immunogen constructs were prepared (i) in a water-in-oil emulsion with Seppic MONTANIDE™ ISA 51 as the approved oil for human use, or (ii) mixed with mineral salts ADJUPHOS (aluminum phosphate) or ALHYDROGEL (alum), at varying amounts of peptide constructs, as specified. Compositions were typically prepared by dissolving the Tau peptide immunogen constructs in water at about 400 μg/mL and formulated with MONTANIDE™ ISA 51 into water-in-oil emulsions (1:1 in volume) or with mineral salts (1:1 in volume). The compositions were kept at room temperature for about 30 min and mixed by vortex for about 10 to 15 seconds prior to immunization. Some animals were immunized with more than one dose of a specific composition, which were administered at time 0 (prime) and 3 week post initial immunization (wpi) (booster), and optionally at 6 wpi for a second boost by intramuscular route. These immunized animals were then tested with selected B cell epitope peptide(s) to evaluate the immunogenicity of the various Tau peptide immunogen constructs present in the formulation as well as their cross-reactivity with related target peptides or proteins. Those Tau peptide immunogen constructs with potent immunogenicity in the initial screening in guinea pigs were then farther tested in both water-in-oil emulsion, mineral salts, and alum-based formulations in primates for dosing regimens over a specified period as dictated by the immunizations protocols.

Non-phosphorylated Tau peptide immunogen constructs (SEQ ID NOs: 52, 54, 56, 58, 61, 63, 65, 67, 69, and 71) dissolved in solvent (ISA 51 VG, CpG3 50 μg/mL, 0.2% TWEEN-80) were injected into guinea pigs at specified schedule with immune sera collected for extensive serological analyses.

b. ELISA Assays and Results

Serum from the immunized animals was collected at various time points post-initial immunization and the binding profiles were initially analyzed by ELISA to determine the immunogenicity of the corresponding construct against its own B cell epitope target. Assessment of serological cross-reactivities amongst Tau peptides from other functional regions was assessed extensively by ELISA with plates coated with different peptides selected from those shown in Tables 9a-9e.

ELISA protocols were developed to evaluate immune serum samples and are described in the following Examples. Briefly, the wells of 96-well plates were coated individually for 1 hour at 37° C. with 100 µL of target peptide Tau fragments A145-P160, P172-P189, P182-P200, S195-P213, R209-L224, V228-L243, K257-K274, R379-L408, V275-K311, and V393-LA25 peptide (SEQ ID NOs: 2, 4, 6, 8, 11, 13, 15, 17, 19, and 21, respectively) at 2 µg/mL (unless noted otherwise), in 10 mM NaHCO$_3$ buffer, pH 9.5 (unless noted otherwise). The peptide-coated wells were incubated with 250 µL of 3% by weight of gelatin in PBS in 37° C. for 1 hour to block non-specific protein binding sites, followed by three washes with PBS containing 0.05% by volume of TWEEN® 20 and then dried. Sera to be analyzed were diluted 1:20 (unless noted otherwise) with PBS containing 20% by volume normal goat serum, 1% by weight gelatin and 0.05% by volume TWEEN® 20. One hundred microliters (100 µL) of the diluted specimens (e.g., serum, plasma) were added to each of the wells and allowed to react for 60 minutes at 37° C. The wells were then washed six times with 0.05% by volume TWEEN® 20 in PBS in order to remove unbound antibodies. Horseradish peroxidase (HRP)-conjugated species (e.g., mouse, guinea pig, or human) specific goat anti-IgG, was used as a labeled tracer to bind with the antibody/peptide antigen complex formed in positive wells. One hundred microliters (100 µL) of the peroxidase-labeled goat anti-IgG, at a pre-titered optimal dilution and in 1% by volume normal goat serum with 0.05% by volume TWEEN® 20 in PBS, was added to each well and incubated at 37° C. for another 30 minutes. The wells were washed six times with 0.05% by volume TWEEN® 20 in PBS to remove unbound antibody and reacted with 100 µL of the substrate mixture containing 0.04% by weight 3', 3', 5', 5'-Tetramethylbenzidine (TMB) and 0.12% by volume hydrogen peroxide in sodium citrate buffer for another 15 minutes. This substrate mixture was used to detect the peroxidase label by forming a colored product. Reactions were stopped by the addition of 100 µL of 1.0 M H$_2$SO$_4$ and absorbance at 450 nm (A$_{450}$) determined. For the determination of antibody titers of the immunized animals that received the various Tau derived peptide immunogens, 10-fold serial dilutions of sera from 1:100 to 1:10,000 were tested, and the titer of a tested serum, expressed as Log$_{10}$, was calculated by linear regression analysis of the A$_{450}$ with the cutoff A$_{450}$ set at 0.5. The ELISA results shown in Tables 9a-9e were further analyzed by plotting on bar graphs as shown in FIG. 1A.

In general, high immunogenicity was found to be associated with each of the selected Tau peptide constructs when tested against its own B cell epitope (Tables 9a-9e and FIG. 1A). High cross-reactivity was found with antibodies elicited by the peptide immunogen constructs of SEQ ID Nos: 52, 54, 56, 58, and 61 (see FIG. 1A).

Interestingly, SEQ ID NO: 65, which contains the B cell epitope K257-K274 (SEQ ID NO: 15), was found to be a highly immunogenic sequence among the Tau peptide constructs designed, yet the antibodies elicited from this construct were the most specific without much cross-reactivity to any of the other B cell epitopes (see FIG. 1A). On the contrary, the Tau peptide immunogen construct of SEQ ID NO: 67, which contains the B cell epitope R379-L408 (SEQ ID NO: 17) was the most immunogenic, having high reactivity with its own B epitope, but also has a reasonable cross-reactivity to other Tau B cell epitopes (see FIG. 1A).

Example 2

Antibodies Elicited by Phosphorylated Tau Peptide Immunogen Constructs and Binding Profiles Antibodies generated against the phosphorylated Tau peptide immunogen constructs were evaluated for their ability to bind to their phosphorylated B cell epitopes by ELISA at 6 weeks post initial immunization (wpi).

a. Immunizations

Phosphorylated Tau peptide immunogens (SEQ ID NOs: 51, 53, 55, 57, 59, 60, 62, 64, 66, 68, and 70) were formulated and administered to guinea pigs under the same conditions discussed in Example 1 for the non-phosphorylated Tau peptide immunogens. Formulations containing the phosphorylated Tau peptide immunogens were administered at 0, 3, and 6 wpi.

b. ELISA Assays and Results

The wells of 96-well plates were coated individually for 1 hour at 37° C. with 100 µL of phosphorylated Tau target peptide fragments A145-P160, P172-P189, P182-P200, S195-P213, R209-L224, V228-L243, K257-K274, R379-L408, V275-K311 and V393-L425 peptide (SEQ ID NOs: 1, 3, 5, 7, 9, 10, 12, 14, 16, 18, and 20, respectively) at 2 µg/mL (unless noted otherwise), in 10 mM NaHCO$_3$ buffer, pH 9.5 (unless noted otherwise). The peptide-costed wells were incubated with 250 µL of 3% by weight of gelatin in PBS in 37° C. for 1 hour to block non-specific protein binding sites, followed by three washes with PBS containing 0.05% by volume of TWEEN® 20 and then dried. Sera to be analyzed were diluted 1:20 (unless noted otherwise) with PBS containing 20% by volume normal goat serum, 1% by weight gelatin and 0.05% by volume TWEEN® 20. One hundred microliters (100 µL) of the diluted specimens (e.g., serum, plasma) were added to each of the wells and allowed to react for 60 minutes at 37° C. The wells were then washed six times with 0.05% by volume TWEEN® 20 in PBS in order to remove unbound antibodies. Horseradish peroxidase (HRP)-conjugated species (e.g., mouse, guinea pig, or human) specific goat anti-IgG, was used as a labeled tracer to bind with the antibody/peptide antigen complex formed in positive wells. One hundred microliters (100 µL) of the peroxidase-labeled goat anti-IgG, at a pre-titered optimal dilution and in 1% by volume normal goat serum with 0.05% by volume TWEEN® 20 in PBS, was added to each well and incubated at 37° C. for another 30 minutes. The wells were washed six times with 0.05% by volume TWEEN® 20 in PBS to remove unbound antibody and reacted with 100 µL of the substrate mixture containing 0.04% by weight 3', 3', 5', 5'-Tetramethylbenzidine (TMB) and 0.12% by volume hydrogen peroxide in sodium citrate buffer for another 15 minutes. This substrate mixture was used to detect the peroxidase label by forming a colored product. Reactions were stopped by the addition of 100 µL of 1.0M H$_2$SO$_4$ and absorbance at 450 nm (A$_{450}$) determined. For the determination of antibody titers of the immunized animals that received the various Tau derived peptide immunogens, 10-fold serial dilutions of sera from 1:100 to 1:10,000 were tested, and the titer of a tested serum, expressed as Log$_{10}$, was calculated by linear regression analysis of the A$_{450}$ with the cutoff A$_{450}$ set at 0.5. Serum from the immunized animals was collected at various time points post-injection and the binding profiles were analyzed by ELISA. ELISA plates were coated with various Tau fragments and the results are shown in Tables 10a-10d.

The ELISA results shown in Tables 10a-10d were further analyzed by plotting on bar graphs as shown in FIG. 1B.

Similar immunogenicity and serological profiles including cross-reactivities amongst the B cell epitopes were found when phosphorylated Tau peptide constructs were used as immunogens.

Example 3

Antibodies Elicited by Phosphorylated Tau Peptide Immunogen Constructs and Binding Profiles Against their Non-Phosphorylated Peptide Counterparts Antibodies generated against the phosphorylated Tau peptides were evaluated for their ability to bind to their corresponding non-phosphorylated counterpart peptide by ELISA at 6 weeks post injection (wpi) as described in further detail below.

a. Immunizations

Phosphorylated Tau peptide immunogens (SEQ ID NOs: 51, 53, 55, 57, 59, 60, 62, 64, 66, 68, and 70) were formulated and administered to guinea pigs under the conditions described in Example 1 for the non-phosphorylated Mu peptide immunogens.

b. ELISA assays and results

The wells of 96-well plates were coated individually for 1 hour at 37° C. with 100 µL of target peptide Tau fragments A145-P160, P172-P189, P182-P200, S195-P213, R209-L224, V228-L243, K257-K274, R379-L408, V275-K311 and V393-L425 peptide (SEQ ID NOs: 2, 4, 6, 8, 11, 13, 15, 17, 19, and 21, respectively) at 2 µg/mL (unless noted otherwise), in 10 mM $NaHCO_3$ buffer, pH 9.5 (unless noted otherwise). The peptide-coated wells were incubated with 250 µL of 3% by weight of gelatin in PBS in 37° C. for 1 hour to block non-specific protein binding sites, followed by three washes with PBS containing 0.05% by volume of TWEEN® 20 and dried. Sera to be analyzed were diluted 1:20 (unless noted otherwise) with PBS containing 20% by volume normal goat serum, 1% by weight gelatin and 0.05% by volume TWEEN® 20. One hundred microliters (100 µL) of the diluted specimens (e.g., serum, plasma) were added to each of the wells and allowed to react for 60 minutes at 37° C. The wells were then washed six times with 0.05% by volume TWEEN® 20 in PBS in order to remove unbound antibodies. Horseradish peroxidase (HRP)-conjugated species (e.g., mouse, guinea pig, or human) specific goat anti-IgG, was used as a labeled tracer to bind with the antibody/peptide antigen complex formed in positive wells. One hundred microliters (100 µL) of the peroxidase-labeled goat anti-IgG, at a pre-titered optimal dilution and in 1% by volume normal goat serum with 0.05% by volume TWEEN® 20 in PBS, was added to each well and incubated at 37° C. for another 30 minutes. The wells were washed six times with 0.05% by volume TWEEN® 20 in PBS to remove unbound antibody and reacted with 100 µL of the substrate mixture containing 0.04% by weight 3', 3', 5', 5'-Tetramethylbenzidine (TMB) and 0.12% by volume hydrogen peroxide in sodium citrate buffer for another 15 minutes. This substrate mixture was used to detect the peroxidase label by forming a colored product. Reactions were stopped by the addition of 100 µL of 1.0M $H_2SO_4$ and absorbance at 450 nm ($A_{450}$) determined. For the determination of antibody titers of the immunized animals that received the various Tau derived peptide immunogens, 10-fold serial dilutions of sera from 1:100 to 1:10,000 were tested, and the titer of a tested serum, expressed as $Log_{10}$, was calculated by linear regression analysis of the $A_{450}$ with the cutoff $A_{450}$ set at 0.5. Serum from the immunized animals was collected at various time points post-injection and the binding profiles were analyzed by ELISA.

ELISA plates were coated with various non-phosphorylated Tau fragments and the results are shown in Tables 11a-11e. Similar serological binding profiles were obtained for all antibodies generated against phosphorylated Tau peptide constructs when the immune sera were tested on corresponding non-phosphorylated Tau B cell epitope peptides. From the extensive immunogenicity and serological studies conducted in Examples 1, 2, and 3, it is clear that the antibodies elicited by the Tau peptide immunogen constructs exhibit similar properties. Most of these properties can be attributed to the amino acid sequences. The conformation assessment using cross-reactivity studies indicate that there were only subtle differences caused by the phosphorylation of the peptides, suggesting that there would be similar functional properties of these immune sera raised by their corresponding phosphorylated vs non-phosphorylated peptide immunogen constructs.

Example 4

Binding Profiles of Antibodies Directed Against Non-Phosphorylated Tau Peptide Immunogens a. Specificity of Anti-Non-Phosphorylated Tau Antibodies Purified from Guinea Pig and Antisera Immunized with Different Tau Peptide Immunogen Constructs of Different Sizes Guinea pigs were immunized with non-phosphorylated Tau peptide immunogen constructs as described in Example 1. Western blot was used to screen anti-non-phosphorylated Tau antibodies (anti-non-p-Tau antibodies) purified from guinea pig antisera immunized with different Tau peptide immunogen constructs for the binding specificity to Tau molecular complex of different sizes. Various forms (monomers, dimers, trimers, oligomers, and polymers) of Tau (20 µM) were separated on 12% Tris-glycine SDS-PAGE and transferred to nitrocellulose (NC) membrane before photo-induced cross-linking (PICUP) treatment. The membrane was incubated with anti-non-p-Tau antibodies purified from guinea pigs antisera at 1 µg/mL, and then incubated with donkey anti-guinea pig antibody conjugated HRP (706-035-148, Jackson). The blot was visualized with chemiluminescence reagent Western Lightning ECL Pro (PerkinElmer).

b. Results

Western blot analysis of lysates containing monomers, dimers, trimers, and oligomers of Tau are shown in FIG. 2 (left panel). Monomeric Nu appeared around 60 kDa and the dimer, trimer, as well as oligomers appeared at their corresponding molecular weights. The commercial monoclonal antibody Mab Tau 5 and Mab Tau 46 were able to detect the monomeric and, to a minor extent, the dimer form of Tau (FIG. 2, lanes 1 and 2). Mab Tau5 was employed as a total Tau marker and Tau46 is a marker for Tau 404-441.

IgG antibodies elicited by non-phosphorylated peptide immunogen constructs (SEQ ID NOs: 52, 54, 56, 58, 61, 63, 65, 67, 69, and 71) detected Tau monomers, dimers, trimers, and oligomers at different efficiencies (FIG. 2, lanes 4-13). The binding profiles for each antibody was analyzed and summarized quantitatively in the bar graph (FIG. 2, right panel). In general, antibodies derived from Tau peptide immunogen constructs from the C-terminal region were capable of eliciting antibodies with higher preferential binding profiles to those from the N-terminal region (data not shown).

Example 5

Antibodies Directed Against Non-Phosphorylated Tau Peptide Immunogens Inhibit Tau Aggregation a. Immunization and Exposure to Tau Animals were immunized with either non-phosphorylated Tau immunogen constructs (SEQ ID NOs: 52, 54, 56, 58, 61, 63, 65, 67, 69, and 71) as described in Example 1, or phosphorylated Tau immunogen constructs (SEQ ID NOs: 51, 53, 55, 57, 60, 62, 64, 66, 68, and 70) as described in Example 2.

The antibodies generated from the immunizations were then exposed to samples containing commercial full-length Tau441 recombinant protein under conditions that promote Tau aggregation. Tau441 β-sheet fibrils were generated using 60 μg of Tau aggregated in 100 μL 1×PBS with 10 unit/mL heparin at 37° C. for 7 days and then transferred onto 300 kDa cut-off filters (Pall) at 4° C. to isolate the β-sheet fibrils. These aggregations were verified by Thioflavin-T (ThT, Sigma) fluorescence.

Tau was aggregated in 200 μL PBS buffer with heparin at concentration of 5 μM for 3 days with or without IgG antibodies elicited from the Tau peptide immunogen constructs. After centrifugation (13,000×g, 4° C., 30 mins), Tau aggregates were harvested and confirmed with the TT assays.

b. Results

Figure 3A:
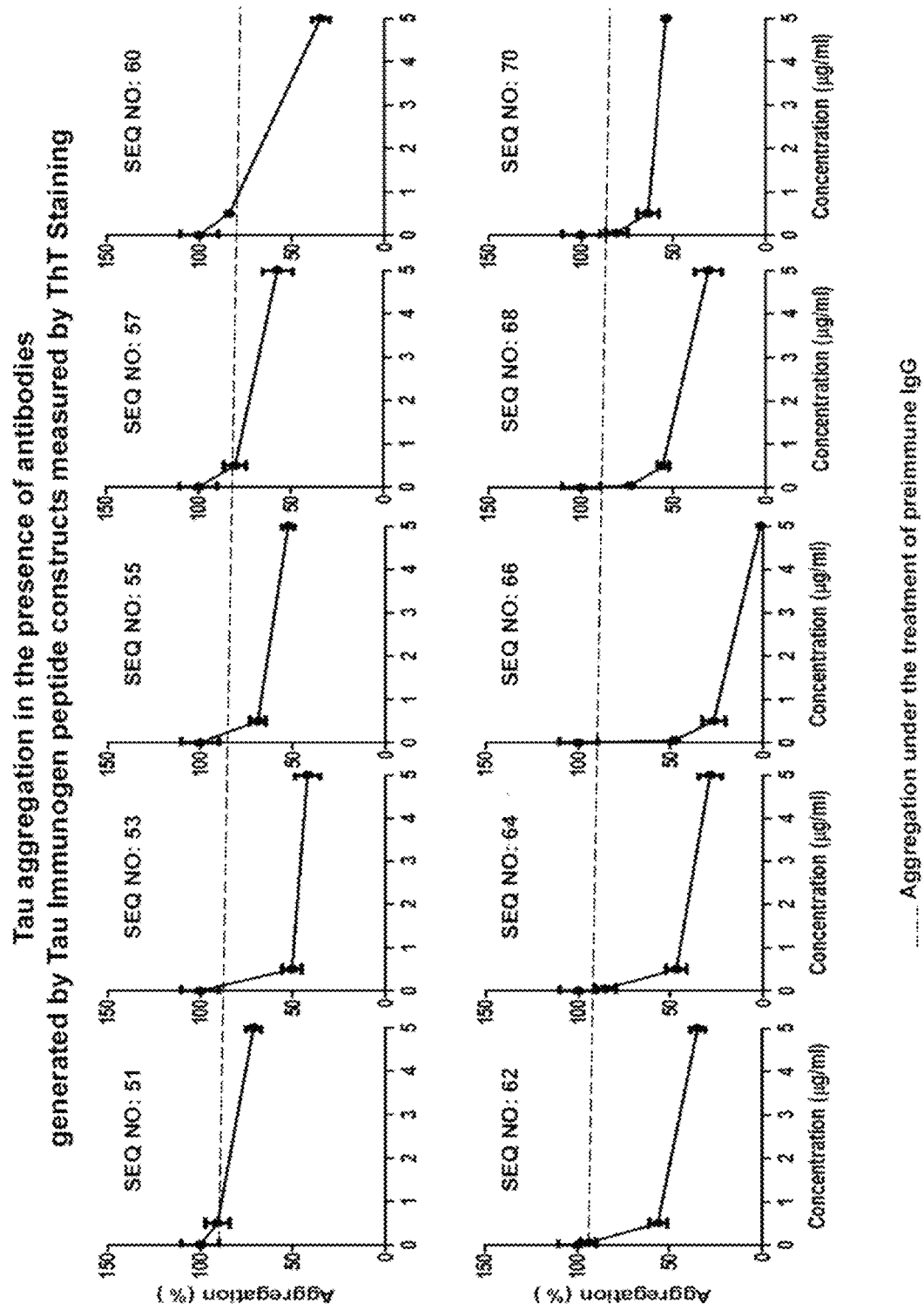
FIG. 3A—Graphs showing the level of full-length Tau (Tau441 amino acids) aggregation after exposure to various antibodies directed against phosphorylated Tau peptide immunogens at concentrations ranging from 0 to 5 sg/mL shown above each graph in comparison to antibodies from the preimmune sera. The level of Tau aggregation was measured by Thioflavin-T (ThT) staining of the aggregates.

FIG. 3A contains graphs showing the level of full-length Tau (Tau441) aggregation in the presence of antibodies directed against the phosphorylated Tau peptide immunogen constructs shown above each graph. The dashed line shown in FIG. 3A represents the control sample that evaluated Tau aggregation using pro-immune IgG. The results show that all of the antibodies directed against the phosphorylated Tau peptide immunogens inhibited Tau aggregation compared to the pre-immune serum control sample. The antibodies were able to inhibit Tau aggregation at different rates.

Figure 3B:
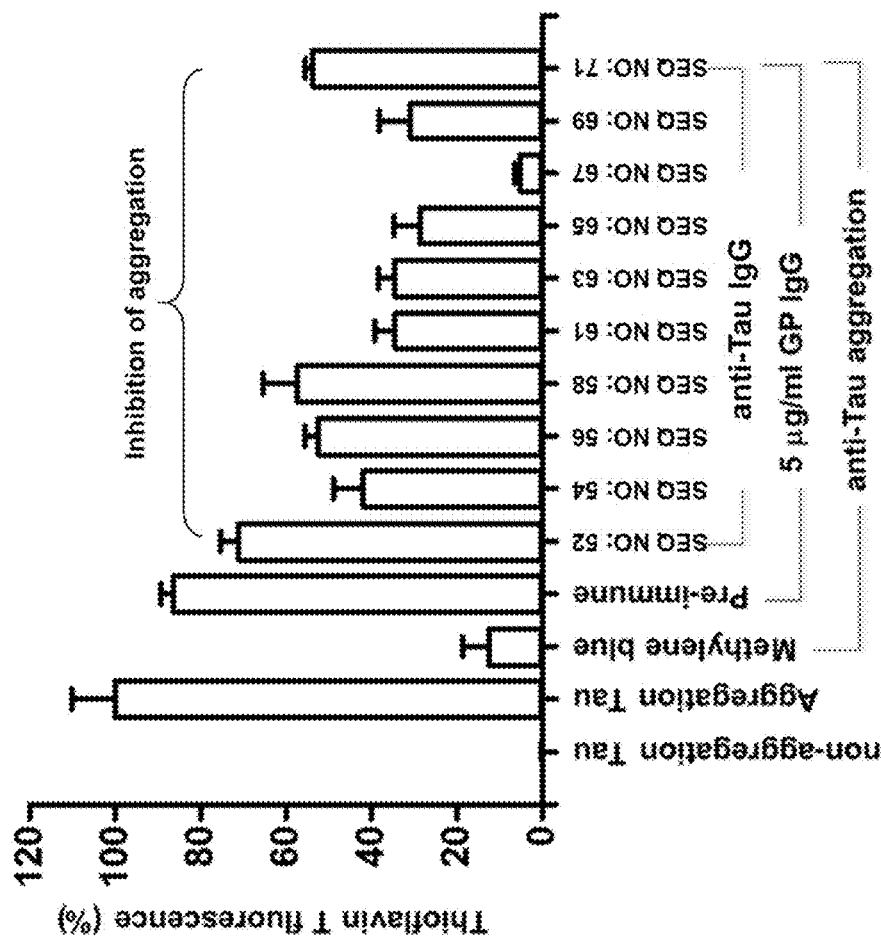
FIG. 3B—Bar graphs showing the level of in vitro Tau aggregation in the presence 5 μg/mL of antibodies directed against the phosphorylated Tau peptide immunogen constructs and methylene glue, which is known to disaggregate Tau in vitro, used as a positive control.

FIG. 3B quantifies the level of full-length Tau (Tau441) aggregation by ThT staining of the aggregates in the presence of antibodies directed against the non-phosphorylated Tau peptide immunogen constructs shown below the bar graph. The results show that the antibodies directed against the non-phosphorylated Tau peptide immunogens inhibited Tau aggregation compared to the pre-immune serum control sample. The antibodies were able to inhibit Tau aggregation at different rates.

The results suggest that there is greater anti-aggregation ability on Tau polymerization when using Tau peptide immunogen constructs having B cell epitopes closer to the C-terminal region of Tau.

Example 6

Antibodies Directed Against Tau Peptide Immunogens Inhibit Tau Aggregation a. Immunization and Exposure to Tau Animals were immunized with non-phosphorylated Tau immunogen constructs as described in Example 1. Animals were also immunized with phosphorylated Tau immunogen constructs as described in Example 2.

The antibodies generated from the immunizations were then exposed to cell lysates from (a) okadaic acid (OKA) treated neuronal cells (SH-SY5Y cells) as hyperphosphorylated Tau or (b) OKA-free neuronal calls as non-phosphorylated Tau. OKA was added into the media to a final concentration of 100 nM for three hours in the presence of anti-sera at wpi 6 and 9 to determine the doe-dependent effects of the effect of anti-sera in inhibiting on the Tau-aggregation.

b. Results

FIG. 4 contains graphs showing the level of Tau aggregation of the various lysates after exposure to antibodies directed against the Tau peptide immunogens shown above each graph. The level of Tau aggregation was measured by ThT staining of the aggregates. Again, antibodies from both phosphorylated- or non-phosphorylated-Tau peptide immunogen constructs were able to inhibit Tau aggregation which is consistent with the serological analyses described in the previous Examples.

The results suggest that there is greater anti-aggregation ability on Tau polymerization with Tau epitopes derived from the central and the C-terminal regions of Tau.

Example 7

Disaggregation of Preformed Tau Aggregates after Exposure to Antibodies Directed Against Tau Peptide Immunogens a. Immunization and Exposure to Preformed Tau Aggregates Animals were immunized with non-phosphorylated Tau immunogen constructs as described in Example 1. Animals were also immunized with phosphorylated Tau immunogen constructs as described in Example 2.

The antibodies generated from the immunizations were then exposed to preformed Tau fibrils. The pre-formed Tau aggregates were then incubated with or without either anti-p-Tau antibodies or anti-non-p-Tau antibodies purified from guinea pigs antisera for 2 and 4 days. After incubation, the aggregates were collected after centrifugation of 13,000×g at 4° C. for 30 minutes and then quantified with the ThT assay.

b. Results

Figure 5:
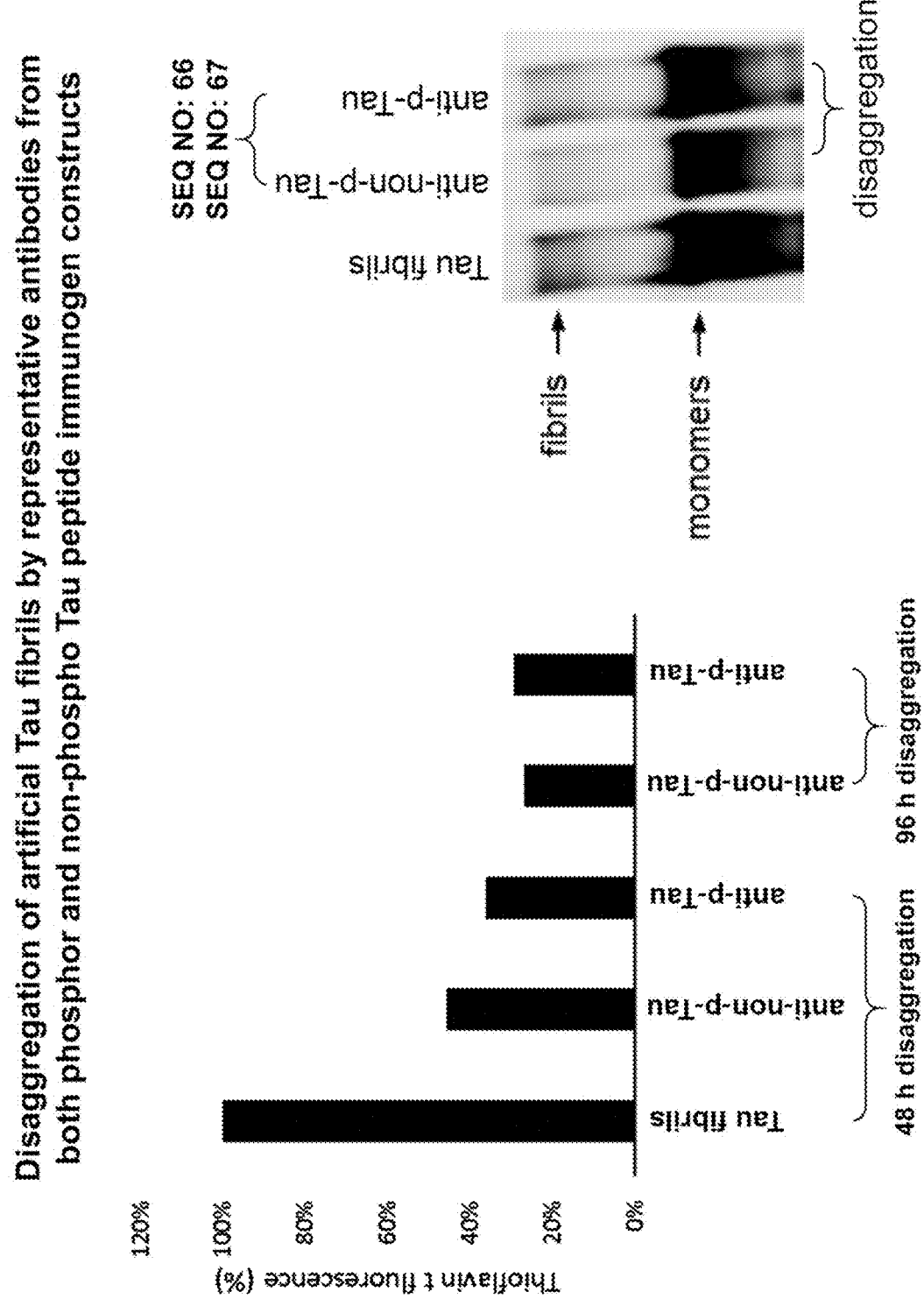
FIG. 5—Graphs showing the level of Tau disaggregation of preformed artificial Tau fibrils upon exposure to antibodies directed against representative Tau peptide immunogens, either phospho or non-phospho, as shown below each graph. The level of Tau aggregation was measured by Thioflavin-T (ThT) staining of the aggregates. Disaggregation to varying extent was found with antibodies from immune sera derived from representative phospho or non-phospho Tau immunogens.

FIG. 5 contains graphs showing the level of Tau disaggregation after exposure to antibodies directed against the Tau peptide immunogens (representative peptide constructs of SEQ ID NOs: 66 and 67), as shown above FIG. 5 (right panel). The level of Tau aggregation was measured by ThT staining and Western blot.

The data from both the Western blot and ThT assay show that anti-non-p/p-Tau 379-408 IgGs, elicited by SEQ ID NOs: 67 and 66, respectively, have the ability to disrupt the aggregation of the recombinant Tau fibrils.

Example 8

Dot Blot Analysis for Specific Binding of Non-Denatured Forms of Tau Fibrils, Oligomers, and Monomers by Representative Antibodies Generated by Both Phosphorylated Tau and Non-Phosphorylated Tau Peptide Immunogen Constructs a. Immunization, Western Blot and Dot Blot Analysis of Binding Profiles of Anti-Tau Antibodies Animals were immunized with non-phosphorylated Tau immunogen constructs as described in Example 1. Animals were also immunized with phosphorylated Tau immunogen constructs as described in Example 2.

Different species of Tau protein (i.e., the α-helix monomers, β-sheet monomers, β-sheet oligomers and β-sheet fibrils) were prepared as described in Example 5. Western blot and dot blot assays with the different species of Tau protein were carried out using anti-p-Tau or anti-non-p-Tau antibodies purified from guinea pig antisera immunized with different Tau peptide immunogen constructs as primary antibodies. Various forms of β-sheet fibrils, oligomers, monomers, α-helical monomers, and other control reagents were dotted on the blot for tight specific control. Detailed procedures for preparation of these reagents for serological testing and assessment are described further in Example 11.

b. Results

Figure 6:
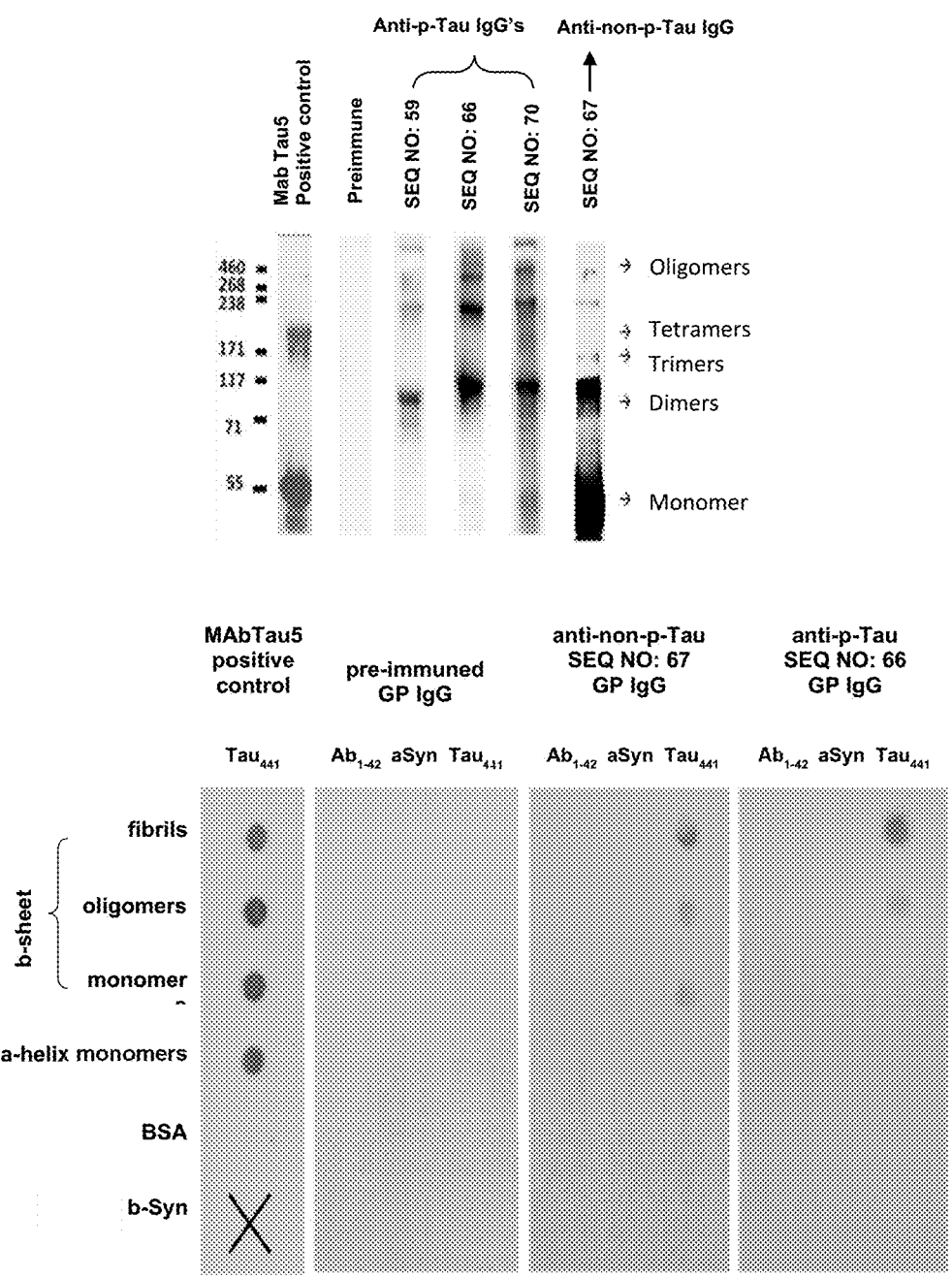
FIG. 6—Western blot analysis (under denaturing conditions) of anti-phospho-Tau and anti-non-phospho-Tau IgGs produced by the Tau peptide immunogens of the present disclosure, as shown on the left. Dot blot analysis (under non-denaturing conditions) of anti-phospho-Tau and anti-non-phospho-Tau IgGs produced by the representative Tau peptide immunogens of the present disclosure as shown on the right panel. Antibodies elicited by phospho-Tau peptide immunogens showed preferential binding to fibrils and oligomers of Tau.

FIG. 6 (left panel) contains Western blot analysis (under denaturing conditions) of anti-p-Tau IgG produced by the Tau peptide immunogens (SEQ ID NOs: 59, 66, and 70) and anti-non-p-Tau IgG produced by the Tau peptide immunogen (SEQ ID NO: 67). The Western blot results show that anti-p-Tau IgGs directed against the C-terminal end of Tau specifically recognize high molecular weight Tau aggregate, but not the Tau monomer.

FIG. 6 (right panel) contains dot blot analysis (under non-denaturing conditions) of anti-p-Tau and anti-non-p-Tau IgGs produced by the Tau peptide immunogens of SEQ ID NOs: 66 and 67, respectively. The results show that both anti-non-p-/p-Tau379-408 IgGs have specific binding to various forms of Tau but not to other amyloidogenic proteins (i.e., API-42 and alpha-Synuclein). Also, when compared to the monoclonal antibody Mab Tau 5 and another IgGs against non-C-terminal region of Tau, anti-p-/anti-non-p-Tau379-408 IgGs derived from this invention (SEQ ID NOs: 66 and 67, respectively) have higher affinity to the fibrils and oligomers rather than monomers. Additionally, the anti-p-Tau379-408 IgG does not bind to β-sheet monomers.

Example 9

Tissue Binding Profiles of Antibodies Directed Against Tau Peptide Immunogens a. Immunization and Tissue Staining Animals were immunized with non-phosphorylated Tau immunogen constructs as described in Example 1. Animals were also immunized with phosphorylated Tau immunogen constructs as described in Example 2.

The antibodies generated from the immunizations were then used to stain tissues from healthy (normal) brains and Alzheimer's disease (AD) brains. The panel of human tissues (Pantomics) was deparaffinized with xylene, rehydrated in ethanol, and then treated with 0.25% trypsin solution with 0.5% $CaCl_2$) in PBS for 30 min and incubated in 1% hydrogen peroxide in methanol to block endogenous peroxidase activity followed by incubation with 10% Block Ace (Sigma) in PBS, before applying either anti-Tau 349-408 (SEQ ID NOs: 66 or 67) or pre-immune sera to the tissues. The sections were developed with 3-3'diaminobenzidine (DAB) and were counter-stained with hematoxylin before being examined microscopically.

b. Results

Figure 7:
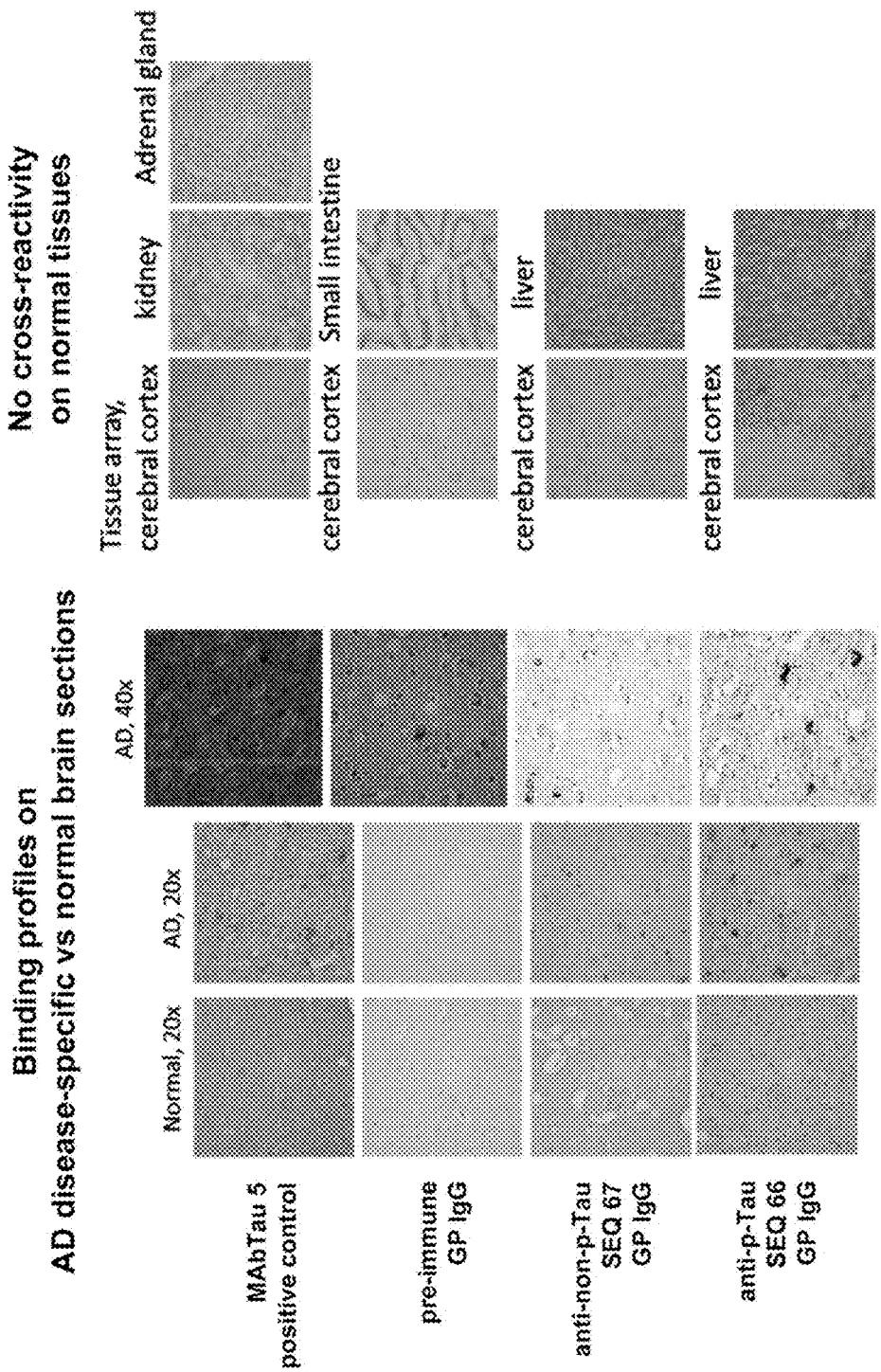
FIG. 7—Immunohistochemical staining by representative antibodies generated by both phospho- and non-phospho-Tau peptide immunogens of the present disclosure. The left panel shows binding profiles on Alzheimer's disease-specific vs normal brain sections; whereas the right panel shows that there is no cross-reactivity on normal tissues.

FIG. 7 shows the staining images from this experiment. Antibodies directed against non-phosphorylated Tau 379-408 (SEQ ID NO: 67) and phosphorylated Tau 379-408 (SEQ ID NO: 66) had no cross-reactivity with sections from normal tissue, but were cross-reactive to Alzheimer's disease brain tissues. The antibody directed against the phosphorylated peptide (SEQ ID NO: 66) showed stronger binding on hippocampus region of the AD brain.

Example 10

Antibodies Elicited by Tau Peptide Immunogen Constructs and Formulations Thereof: Neuroprotective Effect on Reduction of Neurodegeneration Triggered by Exogenous Tau Fibrils In order to assess the neuroprotective effects of anti-Tau antibodies purified from guinea pig antisera immunized with different Tau peptide immunogen constructs, an in vitro neurodegeneration model with exogenous, pre-formed Tau aggregates on NGF-treated, neuronal-differentiated PC12 cells was adopted.

PC12 cells were treated with NGF (100 ng/mL) for 6 days to induce neuronal differentiation. The morphology of the neuronal-differentiated cells were confirmed and analyzed by cell$^3$ iMager duos high-throughput imaging system (Screen). Fluorescein dye was used to label cell death and the cells were counted using a cell count software. Antibodies elicited by the Tau peptide immunogen constructs were able to enter cells and bind to Tau aggregates (data not shown). The neurotrophic effects of NGF reflected on neurite outgrowth and the number of neuronal-differentiated cells were quantified. The levels of neurite outgrowth and the number of neuronal-differentiated cells were shown in percentages (mean±SEM) after normalization. Th neurite length of PC12 cells with and without NGF treatment were taken as 100% and 0%, respectively. The number of neuronal-differentiated PCl2 cells upon 6 days of NGF treatment was normalized to 100%.

Neurodegeneration was observed by adding exogenous, pre-formed Tau aggregates treated by heparin for one week at 37° C. onto the neuronal-differentiated PC12 cells. In the presence of pre-formed Tau aggregates, the neurite length was shortened and the number of cells was decreased in the neuronal-differentiated PCl2 cells. This Tau fibrils-driven neurodegeneration was proportional to the amount of exogenous Tau aggregates added in a concentration dependent manner. The commercially available anti-Tau antibodies (e.g., Mab Tau and Mab Tau46), but not the antibodies purified from naïve guinea pigs, attenuated the Tau-fibrils-driven neurodegeneration. This model was adopted as a screening platform to identify which anti-Tau antibodies purified from guinea pig antisera immunized with different Tau peptide immunogen constructs possessed the neuroprotective effects in restoring the neuronal survival in a concentration-dependent manner (FIGS. 8A and B).

As a result, the anti-Tau antibodies purified from guinea pig antisera immunized with more than half of the different Tau peptide immunogen constructs restored the neurite growth. Tau fibril was provided at 5 ug/mL, a concentration previously optimized to cause lesion (FIG. 8A). The anti-Tau antibodies purified from guinea pig antisera immunized with phosphorylated- or non-phosphorylated-Tau peptide constructs protected neuronal-differentiated PCl2 cells from Tau fibril triggered neuronal death. FIG. 8B shows the data from anti-non-p-Tau antibodies obtained from immunizations with SEQ ID NOs: 65, 67 and 69.

Figure 8A:
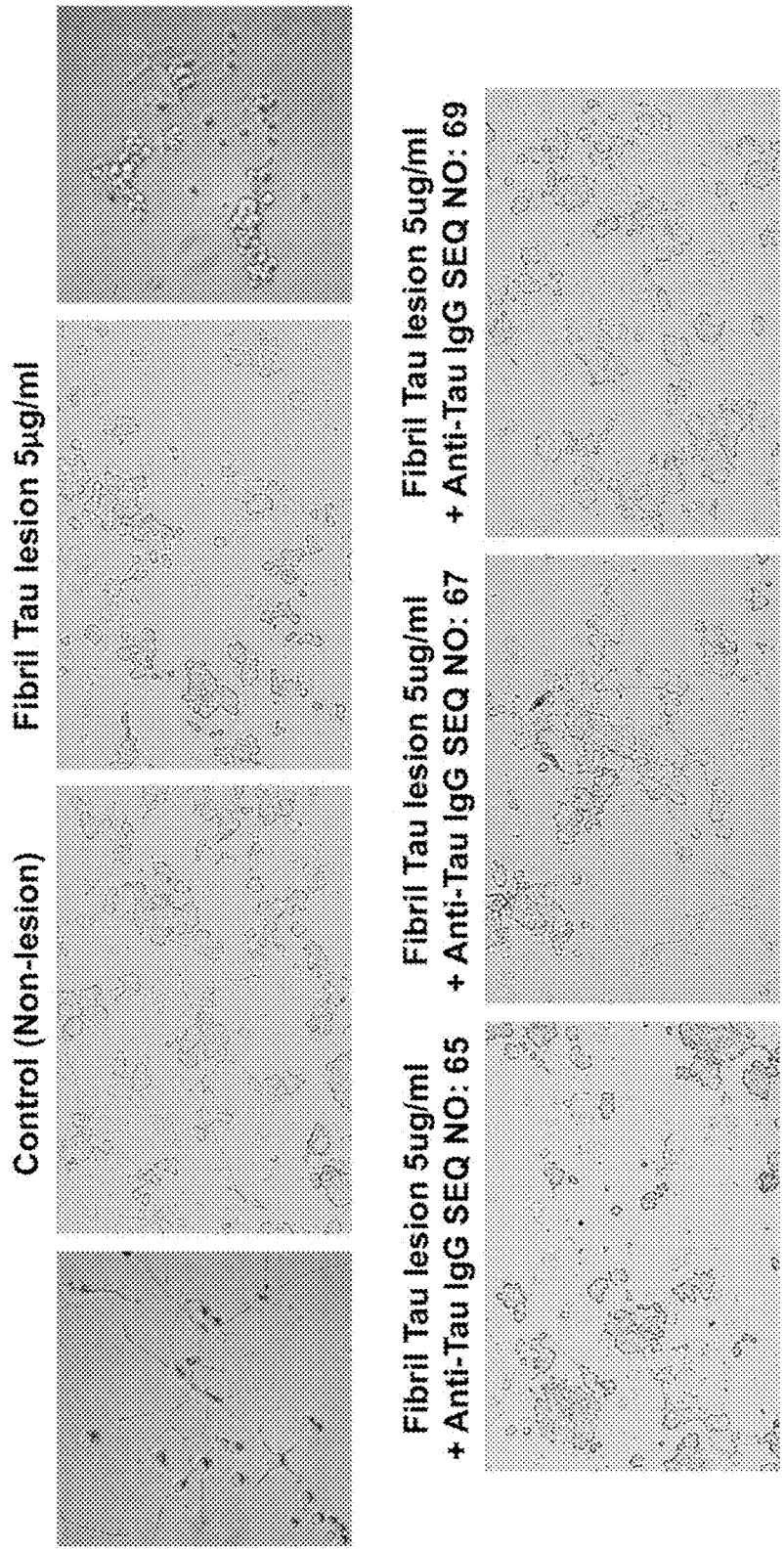
FIG. 8A—Tissue staining showing the protection of neurons against fibril Tau by representative antibodies generated by both phospho- and non-phospho-Tau peptide immunogens of the present disclosure.

The results from FIGS. 8A and 8B demonstrate that anti-Tau antibodies (e.g., SEQ ID NOs: 65, 67, and 69) are capable of protecting neurons against the neurotoxicity of Tau fibrils. The anti-neurodegenerative effects of the anti-Tau antibodies elicited by Tau peptide immunogen constructs (SEQ ID Nos: 65, 67, and 69) were observed and quantified through calculation by Cell³ Imager duos software (Miteklab) for the number of cells survived in the culture.

Regarding neuroprotection by anti-Tau antibodies through in vitro functional assay assessment, it has been shown that in vitro Tau aggregation seeding could markedly decrease pathology and improve cognition in vivo, as reported by Yanamandra, K, et al. (*Neuron* 80:402-414, 2013). Tau monomer has been considered to be natively unstructured and may not have much of a functional role in Tau aggregation and related cell cytotoxicity. Recent findings show that initiation of pathological aggregation could begin with conversion of nu monomer from an inert to a seed-competent form (Mirbaha, H., et al., *eLife* 2018; 7:e36584; doi: 10.7554/eLife.36584). Based on these findings, we tested the anti-Tau antibodies elicited by the Tau peptide immunogen constructs for their ability to reduce seeding activities. Specifically, anti-Tau antibodies directed against the Tau peptide immunogen constructs were incubated with brain homogenates from Alzheimer's Disease (AD) patients and found these antibodies have the ability to reduce such seeding activities (data not shown). Our extensive Tau immunogen design, immunogenicity and serological analyses have facilitated the development of a neuroprotective intervention as vaccines at both the molecular and serological levels for the treatment of the devastating tauopathies.

Example 11

Additional Serological Assays and Reagents

Serological assays and reagents for evaluating functional immunogenicity of the synthetic peptide constructs and formulations thereof are described in details below.

a. Fine Specificity Analysis and Epitope Mapping to Tau Fragments by B Cell Epitope Cluster Peptide-Based ELISA Test Fine specificity analyses of anti-Tau antibodies in immunized hosts were determined by epitope mapping. Briefly, the wells of 96-well plates were coated with individual Tau fragment peptides (SEQ ID NOs: 115 and 156-171) from the Tau 275-311 region (SEQ ID NO: 19) to be mapped, at 0.5 µg per 0.1 mL per well and then 100 µL serum samples (1:100 dilution in PBS) were incubated in plate wells in duplicate following the steps of the antibody ELISA method described above. The B cell epitope of the Tau peptide immunogen construct and related fine specificity analyses of immune sera's anti-Tau antibodies in immunized hosts were also tested with corresponding Tau peptides (e.g. SEQ ID NOs: 1-21, 101-124 as shown in Table 1, SEQ ID NOs: 72-99 as shown in Tables 4 to 7, and SEQ ID NO: 100 as shown in Table 8) without the spacer and Th sequences, for additional reactivity and specificity confirmation.

b. Immunogenicity Evaluation

Preimmune and immune serum samples from animals were collected according to experimental immunization protocols and heated at 56° C. for 30 minutes to inactivate serum complement factors. Following the administration of the Tau peptide immunogen constructs, blood samples were obtained according to protocols and their immunogenicity against specific target site(s) evaluated. Serially diluted sera were tested and positive titers were expressed as $Log_{10}$ of the reciprocal dilution. Immunogenicity of a particular Tau peptide immunogen construct was assessed by its ability to elicit high titer B cell antibody response directed against the desired epitope specificity within the target antigen while maintaining a low to negligible antibody reactivity towards the "Helper T cell epitopes" employed to provide enhancement of the desired B cell responses.

c. Preparation of Tau Aggregates (Dimers, Trimers, Oligomers, and Fibrils) with Recombinant Tau Protein To prepare aggregated Tau, purified recombinant Tau protein (0.1 µg/µL) in 100 µL PBS/KCl aggregation buffer (2.5 mM $MgCl_2$, 50 mM HEPES and 150 mM KCl in 1×PBS, pH 7.4) was incubated at 37° C. in 1.5 mL Eppendorf tubes for 7 days in a Thermomixer (Eppendorf) without shaking. Aggregated Tau was immediately frozen at −80° C. for later use.

d. Purification of Anti-Tau Antibodies

Anti-Tau antibodies were purified from sea collected at 3 to 15 weeks post-initial immunization (wpi) of guinea pigs immunized with Tau peptide immunogen constructs containing peptides of different sequences (SEQ ID NOs: 51-71 and 125-155) by using an affinity column (Thermo Scientific, Rockford). Briefly, after buffer (0.1 M phosphate and 0.15 M sodium chloride, pH 7.2) equilibration, 400 µL of serum was added into the Nab Protein G Spin column followed by end-over-end mixing for 10 min and centrifugation at 5,800×g for 1 min. The column was washed with binding buffer (400 µL) for three times. Subsequently, elution buffer (400 µL, 0.1 M glycine pH 2.0) was added into the spin column to elute the antibodies after centrifuging at 5,800×g for 1 min. The eluted antibodies were mixed with neutralization buffer (400 µL, 0.1 M Tis pH 8.0) and the concentrations of these purified antibodies were measured by using Nan-Drop at $OD_{280}$, with BSA (bovine serum albumin) as the standard.

e. Specificity of Anti-Tau Antibodies Purified from Guinea Pig Antisera Immunized with Different Tau Peptide Immunogen Constructs of Different Sizes Western blot was used to screen anti-Tau antibodies purified from guinea pig antisera immunized with different Tau peptide immunogen constructs for the binding specificity to Tau molecular complex of different sizes. Various forms of Tau (20 µM) were separated on 12% Tris-glycine SDS-PAGE and transferred to nitrocellulose (NC) membrane before photo-induced cross-linking (PICUP) treatment. The membrane was incubated with anti-Tau antibodies purified from guinea pigs antisera at 1 µg/mL, and then incubated with donkey anti-guinea pig antibody conjugated HRP (706-035-148, Jackson). The blot was visualized with chemiluminescence reagent Western Lightning ECL Pro (PerkinElmer). The monomeric Tau blotted around the size of 60 kDa, while dimer, trimer, or oligomers had their respective molecular weights several folds greater than the monomeric Tau. The commercial antibody which is able to detect various oligomeric species such as dimers, trimers, and larger oligomers, e.g., Mab Tau 5 or Mab Tau 46 was employed as a positive control.

f. Dot Blot Assay with Different Species of Amyloidogenic Proteins

Preparation of α-helix monomers, β-sheet monomers, β-sheet oligomers, and β-sheet fibrils of $Aβ_{1-42}$, Tau, and α-Syn are described as follows.

1. $Aβ_{1-42}$ α-helix monomers: 20 µg of $Aβ_{1-42}$ β-sheet monomers (50 µL) was added in 1×PBS containing with 20% trifluoroacetic acid and 20% hexafluoroisopropanol (10 µL) and incubated at 4° C. for 24 hrs to form the α-helix monomers.
2. $Aβ_{1-42}$ β-sheet monomers: 60 µg of $Aβ_{1-42}$ in 120 µL 1×PBS containing 5% TFA aggregated at 37° C. for 24 hrs was transferred onto a 10 kDa cut-off filter (Millipore) to recover the β-sheet monomers.

3. Aβ$_{1-42}$ β-sheet oligomers: 60 μg of Aβ$_{1-42}$ in 120 μL 1×PBS aggregated at 37° C. for 3 days was sonicated on ice and transferred onto 10 and 30 kDa cut-off filters (Millipore) to recover the β-sheet oligomeric fibrils of less than 35 kDa.
4. Aβ$_{1-42}$ β-sheet fibrils: 60 μg of Aβ$_{1-42}$ in 120 μL 1×PBS aggregated at 37° C. for 3 days was sonicated on ice and transferred onto 30 kDa cut-off filters (Millipore) to isolate the β-sheet fibrils.
5. α-Syn α-helix monomers: 40 μg of freshly prepared α-Syn was dissolved in cold 100 μL 1×PBS at 4° C. and immediately transferred onto a 10 kDa cut-off filter (Millipore) to recover the α-helix monomer.
6. α-Syn β-sheet monomers: 40 μg of α-Syn incubated in 100 μL PBS/KCl buffer at 37° C. for 24 hrs was transferred onto a 10 kDa cut-off filter (Millipore) to recover the β-sheet monomers.
7. α-Syn β-sheet oligomers: 40 μg of α-Syn aggregated in 100 μL PBS/KCl buffer at 37° C. for 8 days was sonicated on ice and then transferred onto 30 and 100 kDa cut-off filters to recover the β-sheet oligomers.
8. α-Syn β-sheet fibrils: 40 μg of α-Syn aggregated in 100 μL PBS/KCl buffer at 37° C. for 8 days was sonicated on ice and then transferred onto 30 and 100 kDa cut-off filters to isolate the β-sheet fibrils.
9. Tau441 α-helix monomers: 60 μg of Tau prepared in 100 μL 1×PBS at 4° C. was transferred onto a 100 kDa cut-off to recover the α-helix monomers.
10. Tau441 β-sheet monomers: 60 μg of Tau aggregated in 100 μL 1×PBS with 10 unit/mL heparin at 25° C. for 48 hrs was transferred onto a 100 kDa cut-off filter at 4° C. to recover the β-sheet monomers.
11. Tau441 β-sheet oligomers: 60 μg of Tau aggregated in 100 μL 1×PBS with 10 unit/mL heparin at 37° C. for 48 hrs was transferred onto 100 and 300 kDa cut-off filters (Pall) at 4° C. to recover the β-sheet oligomers.
12. Tau441 β-sheet fibrils: 60 μg of Tau aggregated in 100 μL 1×PBS with 10 unit/mL heparin at 37° C. for 6 days was transferred onto 300 kDa cut-off filters (Pall) at 4° C. to isolate the β-sheet fibrils.

These monomers and oligomers were verified by Thioflavin-T (ThT, Sigma) fluorescence or PAGE (polyacrylamide gel electrophoresis). The concentrations of the amyloidogenic proteins were measured by Nano-Drop with commercial amyloidogenic Aβ$_{1-42}$ stock as the standard. These monomers and oligomers were spotted individually onto PVDF membranes with the amount of 3 μg for Aβ$_{1-42}$, 4 μg for α-Syn, and 7 μg for Tau. The membranes were incubated with the anti-Tau antibodies purified from guinea pigs antisera (1:1,000 dilution) as primary antibody, followed by hybridization with the anti-guinea pig HRP-conjugated secondary antibody (1:5,000; Vector Laboratories). The membranes were treated with Luminata Western HRP Substrates (Bio-Rad, Hercules, Calif., USA) and the signals were detected with a ChemiDoc-It 810 digital image system (UVP Inc., Upland, Calif., USA).

Example 12

Animals Used in Immunogenicity and Efficacy Studies a. Guinea Pigs:

Immunogenicity studies were conducted in mature, naïve, adult male and female Duncan-Hartley guinea pigs (300-350 g/BW). The experiments utilized at least 3 Guinea pigs per group. Protocols involving Duncan-Hartley guinea pigs (8-12 weeks of age; Covance Research Laboratories, Denver, Pa., USA), were performed under approved IACUC applications at the contracted animal facility as well as at United Biomedical, Inc. (UBI), as sponsor.

Example 13

Identification of Focused Antibody Response Elicited by Tau Peptide Immunogen Constructs to the Targeted B Cell Epitope: A Representative Study In a representative fine epitope mapping study (Table 16) to determine the antibody binding site(s) to specific residues elicited by a Tau peptide immunogen construct directed at its Tau 275-311 region (SEQ ID NO: 19), overlapping peptides with increasing lengths from this region (SEQ ID NOs: 115 and 156-171) were synthesized and individually coated onto 96-well microtiter plate wells as solid-phase immunoabsorbents. The peptides (0.5 μg per 0.1 mL per well) were coated onto the plates and then 100 μL serum samples (1:100 dilution in PBS) were incubated in plate wells in duplicate following the steps of the antibody ELISA method described above.

Pooled 6 wpi guinea pig antisera directed against Tau peptide immunogen construct of SEQ ID NO: 68 were added at 1:100 dilution in specimen diluent buffer to the plate wells coated with Tau overlapping peptides from this region at 2.0 μg/mL and then incubated for one hour at 37° C. After washing the plate wells with wash buffer, the horseradish peroxidase-conjugated Protein A/G is added and incubated for 30 min. After washing with PBS again, the substrate is added to the wells for measurement of absorbance at 450 nm by ELISA plate reader, which the samples were analyzed in duplicate. The binding of antisera with the corresponding long Tau peptide of the B epitope immunogen construct represents the maximal binding.

As shown in Table 16, the pooled 6 wpi guinea pig immune sera demonstrated a high precision binding profile where two Tau peptides with SEQ ID NOs 164 and 115 having only two amino acids different in length yet the longer peptide SEQ ID NO:115 was able to present a strong Tau epitope from this hyperphosphorylation and aggregation region. However, the pooled immune sera were not able to recognize peptide SEQ ID NO: 164 due to deletion of two N-terminal amino acids (I297 and K298), indicating that these two amino acids are critical in presenting this region as an immunodominant epitope.

This region was subject to further careful design of Tau peptide constructs for immunogenicity studies as shown in Tables 12,13a, 13b, and 15 including peptide immunogen constructs incorporating a trans conformation of Proline at position 301 for immunogenicity assessment. In general, high immunogenicity was found with the carefully designed Tau immunogen peptide constructs of SEQ ID NOs: 126-132, 135, 136, 140 and 141 with the exception of SEQ ID NO: 128 in this hyper-phosphorylation and aggregation region.

Additional Tau peptide immunogen construct designs were used for the "fuzzy coat" region of Tau which is located at the N-terminal region that is frequently deleted from the Tau isomers. Tau peptide immunogen constructs from this region (SEQ ID Nos: 137-139) as shown in Table 3 were also designed and assessed for their corresponding immunogenicity.

Table 14 shows that the Tau peptide immunogen constructs from the fuzzy-coat region were highly immunogenic. These results suggest that Tau peptide immunogen constructs from the N-terminal fuzzy-coat region may be useful for incorporation in a composition to elicit antibodies for the prevention of Tau aggregation in addition to the potential reduction in initiation of monomeric Tau seeding leading Tau aggregation.

TABLE 1

Amino Acid Sequences of Tau and phospho-Tau (pTau) Fragments

| SEQ ID | Code | Description | Sequence[1] |
|---|---|---|---|
| 1 | p4578 | pTau-aa145-160 (pT149/pT153) | ADGKTKIATPRGAAPP |
| 2 | p4579 | Tau-aa145-160 | ADGKTKIATPRGAAPP |
| 3 | p4580 | pTau-aa172-189 (pT175/pT181/pS185) | PAKTPPAPKTPPSSGEPP |
| 4 | p4581 | Tau-aa172-189 | PAKTPPAPKTPPSSGEPP |
| 5 | p4582 | pTau-aa182-200 pS184/pY197) | PPSSGEPPKSGDRSGYSSP |
| 6 | p4583 | Tau-aa182-200 | PPSSGEPPKSGDRSGYSSP |
| 7 | p4586 | pTau-aa195-213 (pS198/pS208/pS210) | SGYSSPGSPGTPGSRSRTP |
| 8 | p4585 | Tau-aa195-213 | SGYSSPGSPGTPGSRSRTP |
| 9 | p4584 | pTau-aa195-213 (pS199/pS202/pT205) | SGYSSPGSPGTPGSRSRTP |
| 10 | p4587 | pTau-aa209-224 (pT212/pS214/pT217) | RSRTPSLPTPPTREPK |
| 11 | p4588 | Tau-aa209-224 | RSRTPSLPTPPTREPK |
| 12 | p4589 | pTau-aa228-243 (pT231/pS235/pS238) | VVRTPPKSPSSAKSRL |
| 13 | p4598 | Tau-aa228-243 | VVRTPPKSPSSAKSRL |
| 14 | p4599 | pTau-aa257-274 (pS262) | KSKIGSTENLKHQPGGGK |
| 15 | p4600 | Tau-aa257-274 | KSKIGSTENLKHQPGGGK |
| 16 | p4601 | pTau-aa379-408 (pS396/pS404) | RENAKAKTDHGAEIVYKSPVVSGDTSPRHL |
| 17 | p4602 | Tau-aa379-408 | RENAKAKTDHGAEIVYKSPVVSGDTSPRHL |
| 18 | p4603 | pTau-aa275-311 *P301->S (pS293/pS301) | VQIINKKLDLSNVQSKCGSKDNIKHVSGGGSVQIVYK |
| 19 | p4604 | Tau-aa275-311 | VQIINKKLDLSNVQSKCGSKDNIKHVPGGGSVQIVYK |
| 20 | p4606 | pTau-aa275-311 (pS396/pS404/pS422) | VYKSPVVSGDTSPRHLSNVSSTGSIDMVDSPQL |
| 101 | p4605 | Tau-aa393-425 | VYKSPVVSGDTSPRHLSNVSSTGSIDMVDSPQL |
| 102 | p5031a | Tau-aa131-141 | SKDGTGSDDKK |
| 103 | p5032a | Tau-aa241-257 | SRLQTAPVPMPDLKNVK |
| 104 | p5033a | Tau-aa242-259 | VQIINKK |
| 105 | p5135a | Tau-aa281-294 | KLDLSNVQSKCGSK |
| 106 | p5236a | Tau-aa275-294 | VQIINKKLDLSNVQSKCGSK |
| 107 | p5137a | Tau-aa294-311 | KDNIKHVPGGGSVQIVYK |
| 108 | p5138a | Tau-aa294-311, P301-S301 | KDNIKHVSGGGSVQIVYK |
| 109 | p5158a | Tau-aa294-311, p301 trans | KDNIKHVPGGGSVQIVYK |

TABLE 1-continued

Amino Acid Sequences of Tau and phospho-Tau (pTau) Fragments

| SEQ ID | Code | Description | Sequence[1] |
|---|---|---|---|
| 110 | p5159a | Tau-aa275-311, p301 trans | VQIINKKLDLSNVQSKCGSKDNIKHVPGGGSVQIVYK |
| 111 | p5183a | Tau-aa297-311, p301 trans | IKHVPGGGSVQIVYK |
| 112 | p5160a | Tau-aa22-34 | DRKDQGGYTMHQD |
| 113 | p5161a | Tau-aa18-34 | YGLGDRKDQGGYTMHQD |
| 114 | p5162a | Tau-aa22-38 | DRKDQGGYTMHQDQEGD |
| 115 | p5186a | Tau-aa297-311 | IKHVPGGGSVQIVYK |
| 116 | p5404a | Tau-aa359-370 | NITHVPGGNKK |
| 117 | p5405a | Tau-aa349-370 | RVQSKIGSLDNITHVPGGNKK |
| 118 | p5406a | Tau-aa339-370 | VKSEKLDFKDRVQSKIGSLDNITHVPGGNKK |
| 119 | p5407a | Tau-aa329-370 | HHKPGGGQVEVKSEKLDFKDRVQSKIGSLDNITHVPGGNKK |
| 120 | p5408a | Tau-aa329-349 | HHKPGGGQVEVKSEKLDFKDR |
| 121 | p5456a | Tau-aa1-40 | MAEPPQEFEVMEDHAGTYGLGDRKDQGGYTMHQDQEGDTD |
| 122 | p5457a | Tau-aa11-50 | MEDHAGTYGLGDRKDQGGYTMHQDQEGDTDAGLKESPLQT |
| 123 | p5458a | Tau-aa1-34 | MAEPRQEFEVMEDHAGTYGLGDRKDQGGYTMHQD |
| 124 | p5459a | Tau-aa1-22 | MAEPRQEFEVMEDHAGTYGLGD |

[1]Phosphorylated residues are bolded and underlined

TABLE 2

Amino Acid Sequences of Pathogen Protein Derived Th Epitopes Including Idealized Artificial Th Epitopes for Employment in the Design of Tau Peptide Immunogen Constructs

| Description | Sequence | SEQ ID NO |
|---|---|---|
| *Clostridium tetani*1 Th | KKQYIKANSKFIGITEL | 22 |
| MvF1 Th | LSEIKGVIVHRLEGV | 23 |
| *Bordetella pertussis* Th | GAYARCPNGTRALTVAELRGNAEL | 24 |
| *Clodstrdium tetani*2 Th | WVRDIIDDFTNESSQKT | 25 |
| *Diptheria* Th | DSETADNLEKTVAALSILPGHGC | 26 |
| *Plasmodium falciparum* Th | DHEKKHAKMEKASSVFNVVNS | 27 |
| *Schistosoma mansoni* Th | KWFKTNAPNGVDEKHRH | 28 |
| Cholera Toxin Th | ALNIWDRFDVFCTLGATTGYLKGNS | 29 |
| MvF2 Th | ISEIKGVIVHKIEGI | 30 |
| KKKMvF3 Th | KKKISISEIKGVIVHKIEGILF<br>     T  RT    TR  T | 31 |
| HBsAg1 Th | KKKLFLLTKLLTLPQSLD<br>RRRIKII RII I L IR<br>  VRVV  VV V I V<br>  F FF   FF F V F<br>                F | 32 |
| MvF4 Th (UBITh ®3) | ISISEIKGVIVHKIETILF<br>  T  RT    TR | 33 |

TABLE 2-continued

Amino Acid Sequences of Pathogen Protein Derived Th Epitopes Including Idealized Artificial Th Epitopes for Employment in the Design of Tau Peptide Immunogen Constructs

| Description | Sequence | SEQ ID NO |
|---|---|---|
| HBsAg2 Th | KKKIITITRIITIPQSLD<br>   FFLL    L   ITTI | 34 |
| MvF5 Th (UBITh ®1) | ISITEIKGVIVHRIETILF | 35 |
| HBsAg3 Th (UBITh ®2) | KKKIITITRIITIITTID | 36 |
| Influenza MP1_1 Th | FVFTLTVPSER | 37 |
| Influenza MP1_2 Th | SGPLKAEIAQRLEDV | 38 |
| Influenza NSP1 Th | DRLRRDQKS | 39 |
| EBV BHRF1 Th | AGLTLSLLVICSYLFISRG | 40 |
| *Clostridium tetani* TT1 Th | QYIKANSKFIGITEL | 41 |
| EBV EBNA-1 Th | PGPLRESIVCYFMVFLQTHI | 42 |
| *Clostridium tetani* TT2 Th | FNNFTVSFWLRVPKVSASHLE | 43 |
| *Clostridium tetani* TT3 Th | KFIIKRYTPNNEIDSF | 44 |
| *Clostridium tetani* TT4 Th | VSIDKFRIFCKALNPK | 45 |
| EBV CP Th | VPGLYSPCRAFFNKEELL | 46 |
| MCMV IE1 Th | DKREMWVACIKELH | 47 |
| EBV GP340 Th | TGHGARTSTEPTTDY | 48 |
| EBV BPLF1 Th | KELKRQYEKKLRQ | 49 |
| EBV EBNA-2 Th | TVFYNIPPMPL | 50 |

TABLE 3

Tau Peptide Immunogen Constructs

| SEQ Code | Description | Sequence[1] |
|---|---|---|
| 51 | p4578 kbpTau construct (pT149/pT153) UBITh1-εk-kkk-(A145-P160) | UBITh1-εk-kkk-ADGKTKIATPRGAAPP |
| 52 | p4579 kbTau construct UBITh1-εk-kkk-(A145-P160) | UBITh1-εk-kkk-ADGKTKIATPRGAAPP |
| 53 | p4580 kbpTau construct (pT175/pT181/pS185) UBITh1-εk-kkk-(P172-P189) | UBITh1-εk-kkk-PAKTPPAPKTPPSSGEPP |
| 54 | p4581 kb Tau construct UBITh1-εk-kkk-(P172-P189) | UBITh1-εk-kkk-PAKTPPAPKTPPSSGEPP |
| 55 | p4582 kbpTau construct (pS184/pY197) UBITh1-εk-kkk-(P182-P200) | UBITh1-εk-kkk-PPSSGEPPKSGDRSGYSSP |
| 56 | p4583 kb Tau construct UBITh1-εk-kkk-(P182-P200) | UBITh1-εk-kkk-PPSSGEPPKSGDRSGYSSP |
| 57 | p4584 kbpTau construct (pS199/pS201/pT206) UBITh1-εk-kkk-(S195-P213) | UBITh1-εk-kkk-SGYSSPGSPGTPGSRSRTP |
| 58 | p4585 kb Tau construct UBITh1-εk-kkk-(S195-P213) | UBITh1-εk-kkk-SGYSSPGSPGTPGSRSRTP |

TABLE 3-continued

Tau Peptide Immunogen Constructs

| SEQ Code | Description | Sequence[1] |
|---|---|---|
| 59 | p4586 kb pTau construct (pS198/pS208/pS210) UBITh1-εk-kkk-(S195-P213) | UBITh1-εk-kkk-SGYSSPGSPGTPGSRSRTP |
| 60 | p4587 kb pTau construct (pT212/pS214/pT217) UBITh1-εk-kkk-(R209-L224) | UBITh1-εk-kkk-RSRTPTPGSRSRTPSL |
| 61 | p4588 kb Tau construct UBITh1-εk-kkk-(R209-L224) | UBITh1-εk-kkk-RSRTPTPGSRSRTPSL |
| 62 | p4589 kb pTau construct (T231/pS235/pS238) UBITh1-εk-kkk-(V228-L243) | UBITh1-εk-kkk-VVRTPPKSPSSAKSRL |
| 63 | p4598 kb Tau construct UBITh1-εk-kkk-(V228-L243) | UBITh1-εk-kkk-VVRTPPKSPSSAKSRL |
| 64 | p4599 kb pTau construct (pS262) UBITh1-εk-kkk-(R257-K274) | UBITh1-εk-kkk-KSKIGSTENLKHQPGGGK |
| 65 | p4600 kb Tau construct UBITh1-εk-kkk-(K257-K274) | UBITh1-εk-kkk-KSKIGSTENLKHQPGGGK |
| 66 | p4601 kb pTau construct (pS396/pS404) UBITh1-εk-kkk-(R379-L408) | UBITh1-εk-kkk-RENAKAKTDHGAEIVYKSPVVSGDTSPRHL |
| 67 | p4602 kb Tau construct UBITh1-εk-kkk-(R379-L408) | UBITh1-εk-kkk-RENAKAKTDHGAEIVYKSPVVSGDTSPRHL |
| 68 | p4603 kb pTau construct (pS293/pS301) UBITh1-εk-kkk-(V275-K311; *P301->S301) | UBITh1-εk-kkk-VQIINKKLDLSNVQSKCGSKDNIKHVSGGGSVQIVYK |
| 69 | p4604 kb Tau construct UBITh1-εk-kkk-(V275-K311) | UBITh1-εk-kkk-VQIINKKLDLSNVQSKCGSKDNIKHVPGGGSVQIVYK |
| 70 | p4606 kb pTau construct (pS396/pS404/pS422) UBITh1-εk-kkk-(V393-L425) | UBITh1-εk-kkk-VYKSPVVSGDTSPRHLSNVSSTGSIDMVDSPQL |
| 71 | p4605 kb Tau construct UBITh1-εk-kkk-(V393-L425) | UBITh1-εk-kkk-VYKSPVVSGDTSPRHLSNVSSTGSIDMVDSPQL |
| 125 | p5031 kb UBITh1-εk-kkk-S131-K141 | UBITh1-εk-kkk-SKDGTGSDDKK |
| 126 | p5032 kb UBITh1-εk-kkk-S241-K257 | UBITh1-εk-kkk-SRLQTAPVPMPDLKNVK |
| 127 | p5033 kb UBITh1-εk-kkk-L243-K259 | UBITh1-εk-kkk-LQTAPVPMPDLKNVKSK |
| 128 | p5134 kb UBITh1-εK-KKK-V275-K281 | UBITh1-εK-KKK-VQIINKK |
| 129 | p5135 kb UBITh1-εK-KKK-K281-K294 | UBITh1-εk-kkk-KLDLSNVQSKCGSK |
| 130 | p5136 kb UBITh1-εK-KKK-V275-K294 | UBITh1-εk-kkk-VQIINKKLDLSNVQSKCGSK |
| 131 | p5137 kb UBITh1-εK-KKK-K294-K311 | UBITh1-εk-kkk-KDNIKHVPGGGSVQIVYK |
| 132 | p5139 kb UBITh1-εK-KKK-K294-K311, P301-S301 | UBITh1-εK-KKK-KDNIKHVSGGGSVQIVYK |
| 133 | p5142 kb UBITh1-εK-KKK-K257-K274 | UBITh1-εK-KKK-KSKIGSTENLKHQPGGGK |
| 134 | p5143 kb UBITh1-εK-KKK-R379-L408 | UBITh1-εK-KKK-RENAKAKTDHGAEIVYKSPVVSGDTSPRHL |
| 135 | p5184 kb UBITh1-εK-KKK-K294-K311, p301 trans | UBITh1-εK-KKK-KDNIKHVPGGGSVQIVYK |

TABLE 3-continued

Tau Peptide Immunogen Constructs

| SEQ | Code | Description | Sequence[1] |
|---|---|---|---|
| 136 | p5159 | kb UBITh1-εK-KKK-V275-K311, p301 trans | UBITh1-εK-KKK-VQIINKKLDLSNVQSKCGSKDNIKHVPGGGSVQIVYK |
| 137 | p5160 | kb UBITh1-εK-KKK-D22-D34 | UBITh1-εK-KKK-DRKDQGGYTMHQD |
| 138 | p5161 | kb UBITh1-εK-KKK-Y18-D34 | UBITh1-εK-KKK-YGLGDRKDQGGYTMHQD |
| 139 | p5162 | kb UBITh1-εK-KKK-D22-D38 | UBITh1-εK-KKK-DRKDQGGYTMHQDQEGD |
| 140 | p5183 | kb UBITh1-εK-KKK-I297-K311, p301 trans | UBITh1-εK-KKK-IKHVPGGGSVQIVYK |
| 141 | p5184 | kb I297-K311, p301 trans-KKK-εK-UBITh1 | IKHVPGGGSVQIVYK-KKK-εK-UBITh1 |
| 142 | p5185 | kb UBITh1-εK-K294-K311 | UBITh1-εK-KDNIKHVPGGGSVQIVYK |
| 143 | p5186 | kb UBITh1-εK-I297-K311 | UBITh1-εK-IKHVPGGGSVQIVYK |
| 144 | p5187 | kb UBITh1-εK-KKK-I297-K311 | UBITh1-εK-KKK-IKHVPGGGSVQIVYK |
| 145 | p5200 | kb UBITh1-εK-KKK-A145-P160 | UBITh1-εK-KKK-ADGKTKIATPRGAAPP |
| 146 | p5201 | kb UBITh1-εK-KKK-V275-K311 | UBITh1-εK-KKK-VQIINKKLDLSNVQSKCGSKDNIKHVPGGGSVQIVYK |
| 147 | p5404 | kb UBITh1-εK-KKK-N359-K370 | UBITh1-εK-KKK-HITHVPGGNKK |
| 148 | p5405 | kb UBITh1-εK-KKK-R349-K370 | UBITh1-εK-KKK-RVQSKIGSLDNITHVPGGNKK |
| 149 | p5406 | kb UBITh1-εK-KKK-V339-K370 | UBITh1-εK-KKK-VKSEKLDFKDRVQSKIGSLDNITHVPGGNKK |
| 150 | p5407 | kb UBITh1-εK-KKK-H329-K370 | UBITh1-εK-KKK-HHKPGGGQVEVKSEKLDFKDRVQSKIGSLDNITHVPGGNKK |
| 151 | p5408 | kb UBITh1-εK-KKK-H329-R349 | UBITh1-εK-KKK-HHKPGGGQVEVKSEKLDFKDR |
| 152 | p5456 | kb Tau M1-D40-KKK-εK-UBITh1 | MAEPRQEFEVMEDHAGTYGLGDRKDQGGYTMHQDQEGDTD-KKK-εK-UBITh1 |
| 153 | p5457 | kb Tau M11-T50-KKK-εK-UBITh1 | MEDHAGTYGLGDRKDQGGYTMHQDQEGDTDAGLKESPLQT-KKK-εK-UBITh1 |
| 154 | p5458 | kb Tau M1-D34-KKK-εK-UBITh1 | MAEPRQEFEVMEDHAGTYGLGDRKDQGGYTMHQD-KKK-εK-UBITh1 |
| 155 | p5459 | kb Tau M1-D22-KKK-εK-UBITh1 | MAEPRQEFEVMEDHAGTYGLGD-KKK-εK-UBITh1 |

[1]UBITh1 = SEQ ID NO: 35; UBITh3 = SEQ ID NO: 33; Phosphorylated residues are bolded and underlined

TABLE 4 p4607X: Analysis of Antigenic Regions within Tau Protein (R115-V226)
(based on GenBank: AGF19246.1)

| SEQ | Code | Description | Sequence |
|---|---|---|---|
| 72 | p4607a | Tau peptide, L215-V226 | LPTPPTREPKKV |
| 73 | p4607b | Tau peptide, T205-V226 | TPGSRSRTPSLPTPPTREPKKV |
| 74 | p4607c | Tau peptide, S195-V226 | SGYSSPGSPGTPGSRSRTPSLPTPPTREPKKV |
| 75 | p4607d | Tau peptide, S185-V226 | SGEPPKSGDRSGYSSPGSPGTPGSRSRTPSLPTPPTREPKKV |
| 76 | p4607e | Tau peptide, T175-V226 | TPPAPKTPPSSGEPPKSGDRSGYSSPGSPGTPGSRSRTPSLPTPPTREPKKV |

TABLE 4-continued p4607X: Analysis of Antigenic Regions within Tau Protein (R115-V226)
(based on GenBank: AGF19246.1)

| SEQ | Code | Description | Sequence |
|---|---|---|---|
| 77 | p4607f | Tau peptide, Q165-V226 | QANATRIPAKTPPAPKTPPSSGEPPKSGDRSGYSSPGSPGTPGSRSRTPSLPTPPTREPKKV |
| 78 | p4607g | Tau peptide; R155-V226 | RGAAPPGQKGQANATRIPAKTPPAPKTPPSSGEPPKSGDRSGYSSPGSPGTPGSRSRTPSLPTPPTREPKKV |

TABLE 5

P4608X: Analysis of Antigenic Regions within Tau Protein (A227-K298)
(based on GenBank: AGF19246.1)

| SEQ | Code | Description | Sequence |
|---|---|---|---|
| 79 | p4608a | Tau peptide, V287-K298 | VQSKCGSKDNIK |
| 80 | p4608b | Tau peptide, I277-K298 | IINKKLDLSNVQSKCGSKDNIK |
| 81 | p4608c | Tau peptide, K267-K298 | KHQPGGGKVQIINKKLDLSNVQSKCGSKDNIK |
| 82 | p4608d | Tau peptide, K257-K298 | KSKIGSTENLKHQPGGGKVQIINKKLDLSNVQSKCGSKDNIK |
| 83 | p4608e | Tau peptide, P247-K298 | PVPMPDLKNVKSKIGSTENLKHQPGGGKVQIINKKLDLSNVQSKCGSKDNIK |
| 84 | p4608f | Tau peptide, S237-K298 | SSAKSRLQTAPVPMPDLKNVKSKIGSTENLKHQPGGGKVQIINKKLDLSNVQSKCGSKDNIK |
| 85 | p4608g | Tau peptide, A227-K298 | AVVRTPPKSPSSAKSRLQTAPVPMPDLKNVKSKIGSTENLKHQPGGGKVQIINKKLDLSNVQSKCGSKDNIK |

TABLE 6 p469X: Analysis of Antigenic Regions within Tau Protein (H299-K370)
(based on GenBank: AGF190246.1)

| SEQ | Code | Description | Sequence |
|---|---|---|---|
| 86 | p4609a | Tau peptide, N359-K370 | NITHVPGGGNKK |
| 87 | p4609b | Tau peptide, R349-K370 | PVQSKIGSLDNITHVPGGGNKK |
| 88 | p4609c | Tau peptide, V339-K370 | VKSEKLDFKDRVQSKIGSLDNITHVPGGGNKK |
| 89 | p4609d | Tau peptide, H329-K370 | HHKPGGGQVEVKSEKLDFKDRVQSKIGSLDNITHVPGGGNKK |
| 90 | p4609e | Tau peptide, T319-K370 | TSKCGSLGNIHRKPGGGQVEVKSEKLDFKDRVQSKIGSLDNITHVPGGGNKK |
| 91 | p4609f | Tau peptide, V309-K370 | VYKPVDLSKVTSKCGSLGNIHHKPGGGQVEVKSEKLDFKDRVQSKIGSLDNITHVPGGGNKK |
| 92 | p4609g | Tau peptide, H299-K370 | HVPGGGSVQIVYKPVDLSKVTSKCGSLGNIHHKPGGGQVEVKSEKLDFKDRVQSKIGSLDNITHVPGGGNKK |

TABLE 7 p4610X: Anaylsis of Antigenic Regions within Tau Protein (I371-L441)
(based on GenBan: AGF19246.1)

| SEQ | Code | Description | Sequence |
|---|---|---|---|
| 93 | p4609a | Tau peptide, E431-L441 | EVSASLAKQGL |
| 94 | p4609b | Tau peptide, D421-L441 | DSPQLATLADEVSASLAKQGL |
| 95 | p4609c | Tau peptide, V411-L441 | VSSTGSIDMVDSPQLATLADEVSASLAKQGL |
| 96 | p4609d | Tau peptide, G401-L441 | GDTSPRHLSNVSSTGSIDMVDSPQLATLADEVSASLAKQGL |
| 97 | p4609e | Tau peptide, E391-L441 | EIVYKSPVVSGDTSPRHLSNVSSTGSIDMVDSPQLATLADEVSASLAKQGL |
| 96 | p4609f | Tau peptide, N381-L441 | NAKAKTDHGAEIVYKSPVVSGDTSPRHLSNVSSTGSIDMVDSPQLATLADEVSASLAKQGL |
| 99 | p4609g | Tau peptide, I371-L441 | IETHKLTFRENAKAKTDHGAEIVYKSPVVSGDTSPRHLSNVSSTGSIDMVDSPQLATLADEVSASLAKQGL |

TABLE 8

Tau protein sequence, full length (441 aa) isoform with 4R and 2N
(GenBank: AGF19246.1)

Sequence (SEQ ID NO: 100)

MAEPRQEFEVMEDHAGTYGLGDRKDQGGYTMHQDQEGDTDAGLKESPLQTPTELGSEEPGSETSDAKSTP 70

TAEDVTAPLVDEGAPGKQAAAQPHTEIPEGTTAEEAGIGDTPSLEDEAAGHVTQARMVSKSKDGTGSDDK 140

KAKGADGKTKIATPRGAAPPGQKGQANATRIPAKTPPAPKTPPSSGEPPKSGDRSGYSSPGSPGTPGSPS 210

RTPSLPTPPTREPKKVAVVRTPPKSPSSAKSRLQTAPVPMPDLKNVSKIGSTENLKHQPGGGKVQIINK 280

KLDLSNVQSKCGSKDNIKHVPGGGSVQIVYKPVDLSKVTSKCGSLGNIHHKPGGGQVEVKSEKLDFKDRV 350

QSKIGSLDNITHVPGGGNKKIETHKLTFRENAKAKTDHGAEIVYKSPVVSGDTSPRHLSNVSSTGSIDMV 420

DSPQALTLADEVSASLAKQGL

TABLE 9a

Immunogenicity analysis of Tau peptide constructs
(Data corresponds to Figure 1A)
Adjuvant: ISA 51VG; CpG3 50 µg/ml; 0.2% tween 80
Immunogen dose: Prime: 400 µg/1.0 ml/dose/IM (four injection sites, 0.25 ml/site);
Boosts: 100 µg/0.25 ml/dose/IM Vaccination schedule: 0, 3 and 6wpi

| | | | Anti-p4579a (P145-P160) ELISA $Log_{10}$ Titer (SEQ ID NO: 2) | | | | Anti-p4581a (P172-P189) ELISA $Log_{10}$ Titer (SEQ ID NO: 4) | | | |
|---|---|---|---|---|---|---|---|---|---|---|
| Grp # | Immunogen | GP# | 0wpi | 3wpi | 6wpi | 9wpi | 0wpi | 3wpi | 6wpi | 9wpi |
| 1 | p4579kb: Tau construct, UBITh1-εk-kkk-(A145-P160) SEQ ID NO: 52 | 5811 | 0.15 | 5.07 | 5.12 | 5.42 | 0.11 | 8.05 | 6.70 | 6.03 |
| | | 5812 | 0.11 | 5.11 | 5.05 | 5.15 | 0.08 | 4.81 | 4.76 | 4.99 |
| | | 5813 | 0.11 | 9.40 | 7.49 | 5.58 | 0.08 | 5.06 | 5.33 | 5.24 |
| | | AVG | 0.12 | 6.52 | 5.89 | 5.38 | 0.09 | 5.97 | 5.60 | 5.42 |
| 2 | p4581kb: Tau construct, UBITh1-εk-kkk-(P172-P189) SEQ ID NO: 55 | 5814 | 0.11 | 5.89 | 5.46 | 5.26 | 0.08 | 12.54 | 9.44 | 6.81 |
| | | 5815 | 0.09 | 4.52 | 4.96 | 5.05 | 0.07 | 4.99 | 5.89 | 5.45 |
| | | 5816 | 0.11 | 5.18 | 5.33 | 5.12 | 0.08 | 4.51 | 5.07 | 5.17 |
| | | AVG | 0.10 | 5.20 | 5.25 | 5.14 | 0.08 | 7.35 | 6.80 | 5.81 |

TABLE 9a-continued

Immunogenicity analysis of Tau peptide constructs
(Data corresponds to Figure 1A)
Adjuvant: ISA 51VG; CpG3 50 μg/ml; 0.2% tween 80
Immunogen dose: Prime: 400 μg/1.0 ml/dose/IM (four injection sites, 0.25 ml/site);
Boosts: 100 μg/0.25 ml/dose/IM Vaccination schedule: 0, 3 and 6wpi

| Grp # | Immunogen | GP# | Anti-p4579a (P145-P160) ELISA Log$_{10}$ Titer (SEQ ID NO: 2) | | | | Anti-p4581a (P172-P189) ELISA Log$_{10}$ Titer (SEQ ID NO: 4) | | | |
|---|---|---|---|---|---|---|---|---|---|---|
| | | | 0wpi | 3wpi | 6wpi | 9wpi | 0wpi | 3wpi | 6wpi | 9wpi |
| 3 | p4583kb: Tau construct, UBITh1-εk-kkk-(P182-P200) SEQ ID NO: 56 | 5817 | 0.11 | 4.60 | 4.97 | 5.36 | 0.08 | 4.40 | 4.52 | 4.72 |
| | | 5818 | 0.12 | 4.57 | 4.67 | 4.95 | 0.10 | 4.55 | 4.86 | 5.06 |
| | | 5819 | 0.11 | 4.76 | 4.85 | 4.82 | 0.11 | 4.72 | 4.91 | 4.94 |
| | | AVG | 0.11 | 4.64 | 4.83 | 5.04 | 0.10 | 4.56 | 4.76 | 4.91 |
| 4 | p4585kb: Tau construct, UBITh1-εk-kkk-(S195-P213) SEQ ID NO: 58 | 5820 | 0.09 | 3.09 | 4.33 | 4.20 | 0.09 | 3.32 | 4.67 | 4.66 |
| | | 5821 | 0.10 | 4.21 | 4.95 | 4.92 | 0.09 | 4.51 | 5.05 | 4.93 |
| | | 5822 | 0.09 | 4.81 | 4.64 | 4.85 | 0.08 | 4.79 | 4.54 | 4.58 |
| | | AVG | 0.09 | 4.04 | 4.64 | 4.66 | 0.08 | 4.21 | 4.75 | 4.72 |
| 5 | p4588kb: Tau construct, UBITh1-εk-kkk-(R209-L224) SEQ ID NO: 61 | 5823 | 0.08 | 2.66 | 4.42 | 4.63 | 0.08 | 2.96 | 4.78 | 4.90 |
| | | 5824 | 0.09 | 2.81 | 3.81 | 4.35 | 0.08 | 3.29 | 4.56 | 4.83 |
| | | 5845 | 0.09 | 3.03 | 3.10 | 3.85 | 0.08 | 2.93 | 3.59 | 4.50 |
| | | AVG | 0.09 | 2.83 | 3.78 | 4.28 | 0.08 | 3.06 | 4.31 | 4.74 |
| 6 | p4598kb: Tau construct, UBITh1-εk-kkk-(V228-L243) SEQ ID NO: 63 | 5826 | 0.10 | 1.67 | 2.99 | 3.30 | 0.12 | 2.66 | 4.31 | 4.37 |
| | | 5827 | 0.11 | 1.86 | 3.18 | 3.66 | 0.12 | 2.95 | 4.62 | 4.52 |
| | | 5828 | 0.09 | 3.31 | 4.06 | 4.38 | 0.08 | 3.87 | 4.61 | 4.77 |
| | | AVG | 0.10 | 2.28 | 3.41 | 3.78 | 0.11 | 3.16 | 4.51 | 4.55 |
| 7 | p4600kb: Tau construct, UBITh1-εk-kkk-(K257-K274) SEQ ID NO: 65 | 5829 | 0.08 | 3.02 | 4.39 | 4.72 | 0.08 | 2.99 | 4.60 | 4.77 |
| | | 5830 | 0.08 | 3.93 | 4.83 | 4.75 | 0.08 | 4.46 | 5.03 | 4.93 |
| | | 5831 | 0.08 | 3.02 | 4.02 | 3.86 | 0.07 | 3.64 | 4.52 | 3.41 |
| | | AVG | 0.08 | 3.32 | 4.42 | 4.44 | 0.08 | 3.70 | 4.72 | 4.37 |
| 8 | p4602kb: Tau construct, UBITh1-εk-kkk-(R379-L408) SEQ ID NO: 67 | 5832 | 0.08 | 3.08 | 4.27 | 4.29 | 0.08 | 3.26 | 4.62 | 4.64 |
| | | 5833 | 0.08 | 2.99 | 4.04 | 3.54 | 0.08 | 3.15 | 4.37 | 4.28 |
| | | 5834 | 0.10 | 2.86 | 3.63 | 4.29 | 0.10 | 2.87 | 4.10 | 4.45 |
| | | AVG | 0.09 | 2.96 | 3.98 | 4.04 | 0.09 | 3.09 | 4.36 | 4.46 |
| 9 | p4604kb: Tau construct, UBITh1-εk-kkk-(V275-K311) SEQ ID NO: 69 | 5835 | 0.12 | 3.85 | 4.55 | 4.33 | 0.12 | 4.87 | 5.08 | 4.90 |
| | | 5836 | 0.08 | 3.98 | 4.64 | 4.44 | 0.09 | 4.26 | 4.95 | 4.77 |
| | | 5837 | 0.10 | 4.83 | 4.83 | 4.85 | 0.08 | 4.44 | 4.85 | 4.89 |
| | | AVG | 0.10 | 4.22 | 4.67 | 4.54 | 0.09 | 4.52 | 4.96 | 4.85 |
| 10 | p4605kb: Tau construct, UBITh1-εk-kkk-(V393-L425) SEQ ID NO: 71 | 5838 | 0.08 | 3.05 | 4.36 | 4.37 | 0.08 | 3.75 | 4.62 | 4.63 |
| | | 5839 | 0.08 | 3.18 | 4.52 | 4.56 | 0.08 | 3.40 | 4.71 | 4.78 |
| | | 5840 | 0.10 | 3.16 | 4.52 | 4.59 | 0.09 | 3.76 | 4.85 | 4.90 |
| | | AVG | 0.09 | 3.13 | 4.46 | 4.51 | 0.08 | 3.64 | 4.73 | 4.78 |

TABLE 9b

Immunogenicity analysis of Tau peptide constructs
(Data corresponds to Figure 1A)
Adjuvant: ISA 51VG; CpG3 50 μg/ml; 0.2% tween 80
Immunogen dose: Prime: 400 μg/1.0 ml/dose/IM (four injection sites, 0.25 ml/site);
Boosts: 100 μg/0.25 ml/dose/IM Vaccination schedule: 0, 3 and 6wpi

| Grp # | Immunogen | GP# | Anti-p4538a (P182-P200) ELISA Log$_{10}$ Titer (SEQ ID NO: 6) | | | | Anti-p4585a (S195-P213) ELISA Log$_{10}$ Titer (SEQ ID NO: 8) | | | |
|---|---|---|---|---|---|---|---|---|---|---|
| | | | 0wpi | 3wpi | 6wpi | 9wpi | 0wpi | 3wpi | 6wpi | 9wpi |
| 1 | p4579kb: Tau construct, UBITh1-εk-kkk-(A145-P160) SEQ ID NO: 52 | 5811 | 0.12 | 3.15 | 3.59 | 4.62 | 0.12 | 3.02 | 3.29 | 4.72 |
| | | 5812 | 0.09 | 1.20 | 0.66 | 2.91 | 0.12 | 2.06 | 2.96 | 4.24 |
| | | 5813 | 0.08 | 3.10 | 3.28 | 3.76 | 0.10 | 3.65 | 4.23 | 4.38 |
| | | AVG | 0.10 | 2.48 | 2.51 | 3.76 | 0.11 | 2.91 | 3.49 | 4.45 |
| 2 | p4581kb: Tau construct, UBITh1-εk-kkk-(P172-P189) SEQ ID NO: 55 | 5814 | 0.08 | 4.65 | 4.83 | 4.65 | 0.10 | 4.42 | 4.78 | 4.53 |
| | | 5815 | 0.08 | 2.36 | 4.25 | 4.52 | 0.10 | 2.23 | 4.31 | 4.52 |
| | | 5816 | 0.09 | 0.00 | 0.65 | 1.75 | 0.09 | 2.64 | 3.05 | 2.90 |
| | | AVG | 0.08 | 2.34 | 3.24 | 3.64 | 0.10 | 3.09 | 4.05 | 3.98 |
| 3 | p4583kb: Tau construct, UBITh1-εk-kkk-(P182-P200) SEQ ID NO: 56 | 5817 | 0.09 | 4.83 | 5.53 | 6.59 | 0.08 | 3.08 | 4.40 | 4.60 |
| | | 5818 | 0.11 | 4.69 | 5.19 | 5.57 | 0.09 | 3.87 | 4.83 | 5.02 |
| | | 5819 | 0.12 | 5.04 | 5.59 | 5.34 | 0.10 | 3.81 | 4.90 | 4.93 |
| | | AVG | 0.10 | 4.85 | 5.44 | 5.83 | 0.09 | 3.58 | 4.71 | 4.85 |
| 4 | p4585kb: Tau construct, UBITh1-εk-kkk-(S195-P213) SEQ ID NO: 58 | 5820 | 0.09 | 2.15 | 2.82 | 3.11 | 0.10 | 4.02 | 4.91 | 4.93 |
| | | 5821 | 0.08 | 3.12 | 4.60 | 4.69 | 0.09 | 4.88 | 5.17 | 5.08 |
| | | 5822 | 0.08 | 4.31 | 4.29 | 4.36 | 0.08 | 5.80 | 7.07 | 5.62 |
| | | AVG | 0.08 | 3.20 | 3.90 | 4.05 | 0.09 | 4.90 | 5.71 | 5.21 |

TABLE 9b-continued

Immunogenicity analysis of Tau peptide constructs
(Data corresponds to Figure 1A)
Adjuvant: 1SA 51VG; CpG3 50 μg/ml; 0.2% tween 80
Immunogen dose: Prime: 400 μg/1.0 ml/dose/IM (four injection sites, 0.25 ml/site);
Boosts: 100 μg/0.25 ml/dose/IM Vaccination schedule: 0, 3 and 6wpi

| Grp # | Immunogen | GP# | Anti-p4538a (P182-P200) ELISA $Log_{10}$ Titer (SEQ ID NO: 6) | | | | Anti-p4585a (S195-P213) ELISA $Log_{10}$ Titer (SEQ ID NO: 8) | | | |
|---|---|---|---|---|---|---|---|---|---|---|
| | | | 0wpi | 3wpi | 6wpi | 9wpi | 0wpi | 3wpi | 6wpi | 9wpi |
| 5 | p4588kb: Tau construct, UBITh1-εk-kkk-(R209-L224) SEQ ID NO: 61 | 5823 | 0.08 | 0.00 | 3.13 | 3.06 | 0.08 | 0.21 | 3.26 | 3.10 |
| | | 5824 | 0.08 | 0.00 | 2.14 | 2.92 | 0.07 | 0.00 | 1.74 | 2.79 |
| | | 5845 | 0.09 | 0.00 | 0.00 | 0.00 | 0.08 | 0.00 | 1.39 | 2.62 |
| | | AVG | 0.08 | 0.00 | 1.76 | 1.99 | 0.08 | 0.07 | 2.13 | 2.84 |
| 6 | p4598kb: Tau construct, UBITh1-εk-kkk-(V228-L243) SEQ ID NO: 63 | 5826 | 0.10 | 0.00 | 0.00 | 0.00 | 0.09 | 0.00 | 0.00 | 0.85 |
| | | 5827 | 0.12 | 0.00 | 0.00 | 0.00 | 0.10 | 0.00 | 0.00 | 0.00 |
| | | 5828 | 0.09 | 0.00 | 0.00 | 0.52 | 0.09 | 0.00 | 0.00 | 0.39 |
| | | AVG | 0.10 | 0.00 | 0.00 | 0.17 | 0.09 | 0.00 | 0.00 | 0.41 |
| 7 | p4600kb: Tau construct, UBITh1-εk-kkk-(K257-K274) SEQ ID NO: 65 | 5829 | 0.08 | 0.00 | 2.68 | 3.14 | 0.08 | 0.00 | 2.52 | 3.13 |
| | | 5830 | 0.08 | 0.00 | 2.93 | 2.70 | 0.07 | 0.00 | 2.37 | 1.96 |
| | | 5831 | 0.08 | 0.00 | 0.28 | 0.00 | 0.07 | 0.00 | 0.00 | 0.00 |
| | | AVG | 0.08 | 0.00 | 1.96 | 1.95 | 0.07 | 0.00 | 1.63 | 1.70 |
| 8 | p4602kb: Tau construct, UBITh1-εk-kkk-(R379-L408) SEQ ID NO: 67 | 5832 | 0.09 | 0.00 | 0.24 | 1.24 | 0.07 | 0.00 | 0.00 | 0.35 |
| | | 5833 | 0.09 | 0.00 | 1.35 | 0.00 | 0.07 | 0.78 | 2.53 | 0.33 |
| | | 5834 | 0.10 | 0.00 | 0.00 | 0.00 | 0.08 | 1.52 | 0.00 | 0.00 |
| | | AVG | 0.09 | 0.00 | 0.53 | 0.41 | 0.07 | 0.77 | 0.84 | 0.23 |
| 9 | p4604kb: Tau construct, UBITh1-εk-kkk-(V275-K311) SEQ ID NO: 69 | 5835 | 0.11 | 0.00 | 0.73 | 0.00 | 0.10 | 1.00 | 3.03 | 2.28 |
| | | 5836 | 0.08 | 2.57 | 2.97 | 2.59 | 0.09 | 0.47 | 0.00 | 0.00 |
| | | 5837 | 0.08 | 1.78 | 2.99 | 2.79 | 0.08 | 1.02 | 2.58 | 1.94 |
| | | AVG | 0.09 | 1.45 | 2.23 | 1.79 | 0.09 | 0.83 | 1.87 | 1.41 |
| 10 | p4605kb: Tau construct, UBITh1-εk-kkk-(V393-L425) SEQ ID NO: 71 | 5838 | 0.08 | 0.00 | 3.08 | 2.91 | 0.08 | 0.00 | 3.02 | 2.66 |
| | | 5839 | 0.08 | 0.00 | 3.00 | 3.12 | 0.07 | 0.00 | 2.75 | 2.96 |
| | | 5840 | 0.09 | 0.66 | 3.04 | 3.18 | 0.08 | 0.00 | 2.92 | 3.10 |
| | | AVG | 0.08 | 0.22 | 3.04 | 3.07 | 0.08 | 0.00 | 2.90 | 2.90 |

TABLE 9c

Immunogenicity analysis of Tau peptide constructs
(Data corresponds to Figure 1A)
Adjuvant: 1SA 51VG; CpG3 50 μg/ml; 0.2% tween 80
Immunogen dose: Prime: 400 μg/1.0 ml/dose/IM (four injection sites, 0.25 ml/site);
Boosts: 100 μg/0.25 ml/dose/IM Vaccination schedule: 0, 3 and 6wpi

| Grp # | Immunogen | GP# | Anti-p4538a (R209-L224) ELISA $Log_{10}$ Titer (SEQ ID NO: 11) | | | | Anti-p4585a (V228-L243) ELISA $Log_{10}$ Titer (SEQ ID NO: 13) | | | |
|---|---|---|---|---|---|---|---|---|---|---|
| | | | 0wpi | 3wpi | 6wpi | 9wpi | 0wpi | 3wpi | 6wpi | 9wpi |
| 1 | p4579kb: Tau construct, UBITh1-εk-kkk-(A145-P160) SEQ ID NO: 52 | 5811 | 0.105 | 0.000 | 0.000 | 0.000 | 0.093 | 0.000 | 0.000 | 0.000 |
| | | 5812 | 0.095 | 0.000 | 0.000 | 0.000 | 0.081 | 0.000 | 0.000 | 0.000 |
| | | 5813 | 0.074 | 0.752 | 0.000 | 0.000 | 0.078 | 0.000 | 0.000 | 0.000 |
| | | AVG | 0.091 | 0.251 | 0.000 | 0.000 | 0.084 | 0.000 | 0.000 | 0.000 |
| 2 | p4581kb: Tau construct, UBITh1-εk-kkk-(P172-P189) SEQ ID NO: 55 | 5814 | 0.071 | 0.000 | 0.000 | 0.000 | 0.074 | 0.000 | 0.000 | 0.000 |
| | | 5815 | 0.070 | 0.000 | 0.000 | 0.000 | 0.075 | 0.000 | 0.000 | 0.000 |
| | | 5816 | 0.067 | 0.000 | 0.000 | 0.000 | 0.076 | 0.000 | 0.000 | 0.000 |
| | | AVG | 0.069 | 0.000 | 0.000 | 0.000 | 0.075 | 0.000 | 0.000 | 0.000 |
| 3 | p4583kb: Tau construct, UBITh1-εk-kkk-(P182-P200) SEQ ID NO: 56 | 5817 | 0.080 | 2.922 | 2.659 | 1.231 | 0.084 | 0.000 | 0.000 | 0.000 |
| | | 5818 | 0.084 | 0.843 | 0.689 | 0.000 | 0.084 | 0.000 | 0.000 | 0.000 |
| | | 5819 | 0.092 | 2.483 | 1.984 | 0.033 | 0.097 | 0.000 | 0.000 | 0.000 |
| | | AVG | 0.085 | 2.083 | 1.777 | 0.421 | 0.088 | 0.000 | 0.000 | 0.000 |
| 4 | p4585kb: Tau construct, UBITh1-εk-kkk-(S195-P213) SEQ ID NO: 58 | 5820 | 0.077 | 3.288 | 3.340 | 3.061 | 0.077 | 0.000 | 2.956 | 0.000 |
| | | 5821 | 0.076 | 1.958 | 0.627 | 0.000 | 0.088 | 0.000 | 0.000 | 0.000 |
| | | 5822 | 0.073 | 3.106 | 3.455 | 3.144 | 0.074 | 0.000 | 0.000 | 0.000 |
| | | AVG | 0.075 | 2.784 | 2.474 | 2.068 | 0.080 | 0.000 | 0.985 | 0.000 |
| 5 | p4588kb: Tau construct, UBITh1-εk-kkk-(R209-L224) SEQ ID NO: 61 | 5823 | 0.09 | 6.026 | 6.512 | 6.387 | 0.080 | 0.000 | 0.000 | 0.000 |
| | | 5824 | 0.070 | 4.858 | 5.132 | 5.159 | 0.081 | 0.000 | 0.000 | 0.000 |
| | | 5845 | 0.142 | 5.287 | 5.314 | 7.040 | 0.082 | 0.000 | 0.000 | 0.000 |
| | | AVG | 0.107 | 5.390 | 5.653 | 6.195 | 0.081 | 0.000 | 0.000 | 0.000 |
| 6 | p4598kb: Tau construct, UBITh1-εk-kkk-(V228-L243) SEQ ID NO: 63 | 5826 | 0.083 | 0.000 | 1.053 | 1.759 | 0.086 | 4.514 | 4.778 | 4.929 |
| | | 5827 | 0.094 | 0.000 | 0.218 | 2.044 | 0.098 | 4.966 | 5.146 | 5.138 |
| | | 5828 | 0.080 | 0.000 | 0.000 | 0.736 | 0.100 | 4.563 | 4.660 | 4.962 |
| | | AVG | 0.086 | 0.000 | 0.424 | 1.513 | 0.095 | 4.681 | 4.861 | 5.010 |

TABLE 9c-continued

Immunogenicity analysis of Tau peptide constructs
(Data corresponds to Figure 1A)
Adjuvant: ISA 51VG; CpG3 50 μg/ml; 0.2% tween 80
Immunogen dose: Prime: 400 μg/1.0 ml/dose/IM (four injection sites, 0.25 ml/site);
Boosts: 100 μg/0.25 ml/dose/IM Vaccination schedule: 0, 3 and 6wpi

| Grp # | Immunogen | GP# | Anti-p4538a (R209-L224) ELISA Log$_{10}$ Titer (SEQ ID NO: 11) | | | | Anti-p4585a (V228-L243) ELISA Log$_{10}$ Titer (SEQ ID NO: 13) | | | |
|---|---|---|---|---|---|---|---|---|---|---|
| | | | 0wpi | 3wpi | 6wpi | 9wpi | 0wpi | 3wpi | 6wpi | 9wpi |
| 7 | p4600kb: Tau construct, UBITh1-εk-kkk-(K257-K274) SEQ ID NO: 65 | 5829 | 0.089 | 0.000 | 0.000 | 0.000 | 0.084 | 0.000 | 0.000 | 0.000 |
| | | 5830 | 0.076 | 0.000 | 0.000 | 0.000 | 0.082 | 0.000 | 0.000 | 0.000 |
| | | 5831 | 0.073 | 0.000 | 0.000 | 0.000 | 0.082 | 0.000 | 0.000 | 0.000 |
| | | AVG | 0.079 | 0.000 | 0.000 | 0.000 | 0.083 | 0.000 | 0.000 | 0.000 |
| 8 | p4602kb: Tau construct, UBITh1-εk-kkk-(R379-L408) SEQ ID NO: 67 | 5832 | 0.069 | 2.468 | 2.504 | 1.654 | 0.079 | 0.000 | 0.000 | 0.000 |
| | | 5833 | 0.093 | 1.952 | 2.677 | 2.274 | 0.083 | 0.000 | 0.000 | 0.000 |
| | | 5834 | 0.083 | 2.847 | 1.839 | 0.648 | 0.091 | 0.000 | 0.000 | 0.000 |
| | | AVG | 0.082 | 2.422 | 2.340 | 1.525 | 0.084 | 0.000 | 0.000 | 0.000 |
| 9 | p4604kb: Tau construct, UBITh1-εk-kkk-(V275-K311) SEQ ID NO: 69 | 5835 | 0.099 | 0.000 | 0.000 | 0.000 | 0.089 | 0.000 | 0.000 | 0.000 |
| | | 5836 | 0.086 | 0.000 | 0.000 | 0.000 | 0.077 | 0.000 | 0.000 | 0.000 |
| | | 5837 | 0.080 | 0.000 | 0.000 | 0.000 | 0.082 | 0.000 | 0.000 | 0.000 |
| | | AVG | 0.088 | 0.000 | 0.000 | 0.000 | 0.083 | 0.000 | 0.000 | 0.000 |
| 10 | p4605kb: Tau construct, UBITh1-εk-kkk-(V393-L425) SEQ ID NO: 71 | 5838 | 0.077 | 2.752 | 3.484 | 4.146 | 0.076 | 0.000 | 0.000 | 0.000 |
| | | 5839 | 0.070 | 2.538 | 4.371 | 4.716 | 0.079 | 0.000 | 0.000 | 0.000 |
| | | 5840 | 0.075 | 2.951 | 4.301 | 4.570 | 0.080 | 0.000 | 0.000 | 0.000 |
| | | AVG | 0.074 | 2.747 | 4.052 | 4.477 | 0.078 | 0.000 | 0.000 | 0.000 |

TABLE 9d

Immunogenicity analysis of Tau peptide constructs
(Data corresponds to Figure 1A)
Adjuvant: ISA 51VG; CpG3 50 μg/ml; 0.2% tween 80
Immunogen dose: Prime: 400 μg/1.0 ml/dose/IM (four injection sites, 0.25 ml/site);
Boosts: 100 μg/0.25 ml/dose/IM Vaccination schedule: 0, 3 and 6wpi

| Grp # | Immunogen | GP# | Anti-p4600a (K257-K274) ELISA Log10 Titer (SEQ ID NO: 15) | | | | Anti-p4602a (R379-L408) ELISA Log10 Titer (SEQ ID NO: 17) | | | |
|---|---|---|---|---|---|---|---|---|---|---|
| | | | 0wpi | 3wpi | 6wpi | 9wpi | 0wpi | 3wpi | 6wpi | 9wpi |
| 1 | p4579kb: Tau construct, UBITh1-εk-kkk-(A145-P160) SEQ ID NO: 52 | 5811 | 0.102 | 0.000 | 0.000 | 0.000 | 0.076 | 3.314 | 2.855 | 2.809 |
| | | 5812 | 0.102 | 0.000 | 0.000 | 0.000 | 0.065 | 2.881 | 1.857 | 1.207 |
| | | 5813 | 0.083 | 0.000 | 0.000 | 0.000 | 0.064 | 3.113 | 2.407 | 2.778 |
| | | AVG | 0.096 | 0.000 | 0.000 | 0.000 | 0.068 | 3.103 | 2.373 | 2.265 |
| 2 | p4581kb: Tau construct, UBITh1-εk-kkk-(P172-P189) SEQ ID NO: 55 | 5814 | 0.093 | 0.000 | 0.000 | 0.000 | 0.069 | 3.036 | 2.075 | 0.330 |
| | | 5815 | 0.086 | 0.000 | 0.000 | 0.000 | 0.068 | 3.020 | 2.942 | 2.471 |
| | | 5816 | 0.103 | 0.000 | 0.000 | 0.000 | 0.073 | 2.791 | 2.711 | 2.393 |
| | | AVG | 0.094 | 0.000 | 0.000 | 0.000 | 0.070 | 2.949 | 2.576 | 1.731 |
| 3 | p4583kb: Tau construct, UBITh1-εk-kkk-(P182-P200) SEQ ID NO: 56 | 5817 | 0.090 | 0.000 | 0.000 | 0.000 | 0.074 | 0.000 | 0.000 | 0.679 |
| | | 5818 | 0.087 | 0.000 | 0.000 | 0.000 | 0.083 | 0.000 | 0.000 | 0.000 |
| | | 5819 | 0.083 | 0.000 | 0.000 | 0.000 | 0.080 | 0.000 | 0.642 | 2.602 |
| | | AVG | 0.087 | 0.000 | 0.000 | 0.000 | 0.079 | 0.000 | 0.214 | 1.094 |
| 4 | p4585kb: Tau construct, UBITh1-εk-kkk-(S195-P213) SEQ ID NO: 58 | 5820 | 0.078 | 0.000 | 0.000 | 0.000 | 0.073 | 1.094 | 2.307 | 2.171 |
| | | 5821 | 0.076 | 0.000 | 0.000 | 0.000 | 0.073 | 2.935 | 2.798 | 2.205 |
| | | 5822 | 0.080 | 0.000 | 0.000 | 0.000 | 0.071 | 3.865 | 3.386 | 3.227 |
| | | AVG | 0.078 | 0.000 | 0.000 | 0.000 | 0.072 | 2.631 | 2.830 | 2.534 |
| 5 | p4588kb: Tau construct, UBITh1-εk-kkk-(R209-L224) SEQ ID NO: 61 | 5823 | 0.083 | 0.000 | 0.000 | 0.000 | 0.069 | 3.035 | 4.551 | 4.580 |
| | | 5824 | 0.084 | 0.000 | 0.000 | 0.000 | 0.079 | 3.032 | 2.980 | 3.100 |
| | | 5845 | 0.076 | 0.000 | 0.000 | 0.000 | 0.074 | 2.846 | 3.654 | 4.357 |
| | | AVG | 0.081 | 0.000 | 0.000 | 0.000 | 0.074 | 2.971 | 3.728 | 4.012 |
| 6 | p4598kb: Tau construct, UBITh1-εk-kkk-(V228-L243) SEQ ID NO: 63 | 5826 | 0.091 | 0.000 | 0.000 | 0.000 | 0.082 | 3.187 | 3.971 | 4.583 |
| | | 5827 | 0.074 | 0.000 | 0.000 | 0.000 | 0.085 | 3.224 | 4.256 | 4.648 |
| | | 5828 | 0.073 | 0.000 | 0.000 | 0.000 | 0.075 | 1.762 | 2.510 | 3.068 |
| | | AVG | 0.079 | 0.000 | 0.000 | 0.000 | 0.081 | 2.724 | 3.579 | 4.100 |
| 7 | p4600kb: Tau construct, UBITh1-εk-kkk-(K257-K274) SEQ ID NO: 65 | 5829 | 0.063 | 4.619 | 5.104 | 5.879 | 0.065 | 0.000 | 0.877 | 2.010 |
| | | 5830 | 0.067 | 5.125 | 9.486 | 8.478 | 0.069 | 0.000 | 0.000 | 0.000 |
| | | 5831 | 0.067 | 5.454 | 10.840 | 14.170 | 0.066 | 0.000 | 0.000 | 0.185 |
| | | AVG | 0.066 | 5.066 | 8.477 | 9.509 | 0.067 | 0.000 | 0.292 | 0.732 |
| 8 | p4602kb: Tau construct, UBITh1-εk-kkk-(R379-L408) SEQ ID NO: 67 | 5832 | 0.071 | 0.000 | 0.000 | 1.879 | 0.205 | 8.520 | 8.112 | 6.557 |
| | | 5833 | 0.076 | 0.000 | 0.000 | 0.160 | 0.074 | 12.920 | 11.790 | 11.200 |
| | | 5834 | 0.080 | 0.000 | 0.000 | 2.851 | 0.085 | 9.382 | 10.350 | 8.024 |
| | | AVG | 0.076 | 0.000 | 0.000 | 1.630 | 0.121 | 10.274 | 10.084 | 8.594 |

TABLE 9d-continued

Immunogenicity analysis of Tau peptide constructs
(Data corresponds to Figure 1A)
Adjuvant: 1SA 51VG; CpG3 50 µg/ml; 0.2% tween 80
Immunogen dose: Prime: 400 µg/1.0 ml/dose/IM (four injection sites, 0.25 ml/site);
Boosts: 100 µg/0.25 ml/dose/IM Vaccination schedule: 0, 3 and 6wpi

| | | | Anti-p4600a (K257-K274) ELISA Log10 Titer (SEQ ID NO: 15) | | | | Anti-p4602a (R379-L408) ELISA Log10 Titer (SEQ ID NO: 17) | | | |
|---|---|---|---|---|---|---|---|---|---|---|
| Grp # | Immunogen | GP# | 0wpi | 3wpi | 6wpi | 9wpi | 0wpi | 3wpi | 6wpi | 9wpi |
| 9 | p4604kb: Tau construct, UBITh1-εk-kkk-(V275-K311) SEQ ID NO: 69 | 5835 | 0.086 | 0.000 | 0.000 | 0.000 | 0.083 | 4.050 | 5.398 | 4.995 |
| | | 5836 | 0.076 | 0.000 | 0.000 | 0.000 | 0.067 | 4.503 | 4.974 | 4.876 |
| | | 5837 | 0.074 | 0.000 | 0.000 | 0.000 | 0.068 | 5.233 | 4.940 | 4.574 |
| | | AVG | 0.079 | 0.000 | 0.000 | 0.000 | 0.073 | 4.595 | 5.104 | 4.815 |
| 10 | p4605kb: Tau construct, UBITh1-εk-kkk-(V393-L425) SEQ ID NO: 71 | 5838 | 0.075 | 0.000 | 0.000 | 0.000 | 0.069 | 4.676 | 4.511 | 4.574 |
| | | 5839 | 0.070 | 0.000 | 0.000 | 0.000 | 0.064 | 4.722 | 4.686 | 4.868 |
| | | 5840 | 0.077 | 0.000 | 0.000 | 0.000 | 0.070 | 5.202 | 4.954 | 4.846 |
| | | AVG | 0.074 | 0.000 | 0.000 | 0.000 | 0.068 | 4.867 | 4.717 | 4.763 |

TABLE 9e

Immunogenicity analysis of Tau peptide constructs
(Data corresponds to FIG. 1A)
Adjuvant: ISA 51VG; CpG3 50 µg/ml; 0.2% tween 80
Immunogen dose: Prime: 400 µg/1.0 ml/dose/IM
(four injection sites, 0.25 ml/site);
Boosts: 100 µg/0.25 ml/dose/IM
Vaccination schedule: 0, 3 and 6 wpi

| | | | Anti-p4604a (V275-K311) ELISA Log10 Titer (SEQ ID NO: 19) | | | | Anti-p4605a (V393-L425) ELISA Log10 Titer (SEQ ID NO: 21) | | | |
|---|---|---|---|---|---|---|---|---|---|---|
| Grp # | Immunogen | GP# | 0 wpi | 3 wpi | 6 wpi | 9 wpi | 0 wpi | 3 wpi | 6 wpi | 9 wpi |
| 1 | p4579kb: Tau construct, UBITh1-εk-kkk-(A145-P160) SEQ ID NO: 52 | 5811 | 0.084 | 0.000 | 0.000 | 0.000 | 0.088 | 0.000 | 0.000 | 0.000 |
| | | 5812 | 0.072 | 0.000 | 0.000 | 0.000 | 0.088 | 0.000 | 0.000 | 0.000 |
| | | 5813 | 0.075 | 0.000 | 0.000 | 0.000 | 0.083 | 0.000 | 0.000 | 0.000 |
| | | AVG | 0.077 | 0.000 | 0.000 | 0.000 | 0.086 | 0.000 | 0.000 | 0.000 |
| 2 | p4581kb: Tau construct, UBITh1-εk-kkk-(P172-P189) SEQ ID NO: 55 | 5814 | 0.075 | 0.000 | 0.000 | 0.000 | 0.078 | 0.000 | 0.000 | 0.000 |
| | | 5815 | 0.072 | 0.000 | 0.000 | 1.342 | 0.070 | 0.000 | 0.000 | 0.000 |
| | | 5816 | 0.078 | 0.000 | 0.000 | 0.000 | 0.075 | 0.000 | 0.000 | 0.234 |
| | | AVG | 0.075 | 0.000 | 0.000 | 0.447 | 0.074 | 0.000 | 0.000 | 0.078 |
| 3 | p4583kb: Tau construct, UBITh1-εk-kkk-(P182-P200) SEQ ID NO: 56 | 5817 | 0.090 | 0.000 | 0.000 | 0.000 | 0.083 | 0.000 | 0.000 | 0.000 |
| | | 5818 | 0.088 | 0.000 | 0.000 | 0.000 | 0.101 | 0.000 | 0.000 | 0.000 |
| | | 5819 | 0.086 | 0.000 | 0.000 | 0.000 | 0.090 | 0.000 | 0.000 | 0.301 |
| | | AVG | 0.088 | 0.000 | 0.000 | 0.000 | 0.091 | 0.000 | 0.000 | 0.100 |
| 4 | p4585kb: Tau construct, UBITh1-εk-kkk-(S195-P213) SEQ ID NO: 58 | 5820 | 0.077 | 0.000 | 0.000 | 0.000 | 0.084 | 0.000 | 0.000 | 0.000 |
| | | 5821 | 0.074 | 0.000 | 0.000 | 0.000 | 0.080 | 0.000 | 0.578 | 0.182 |
| | | 5822 | 0.075 | 0.000 | 0.000 | 0.000 | 0.072 | 0.000 | 0.000 | 1.969 |
| | | AVG | 0.075 | 0.000 | 0.000 | 0.000 | 0.079 | 0.000 | 0.193 | 0.717 |
| 5 | p4588kb: Tau construct, UBITh1-εk-kkk-(R209-L224) SEQ ID NO: 61 | 5823 | 0.074 | 0.000 | 0.000 | 0.000 | 0.074 | 4.755 | 5.129 | 5.495 |
| | | 5824 | 0.076 | 0.000 | 0.000 | 0.000 | 0.068 | 4.658 | 4.882 | 5.120 |
| | | 5825 | 0.081 | 0.000 | 0.000 | 0.000 | 0.082 | 4.583 | 4.943 | 5.727 |
| | | AVG | 0.077 | 0.000 | 0.000 | 0.000 | 0.075 | 4.665 | 4.985 | 5.447 |
| 6 | p4598kb: Tau construct, UBITh1-εk-kkk-(V228-L243) SEQ ID NO: 63 | 5826 | 0.120 | 0.000 | 0.000 | 0.000 | 0.112 | 2.883 | 2.688 | 1.790 |
| | | 5827 | 0.097 | 0.000 | 0.000 | 0.000 | 0.090 | 2.910 | 2.322 | 1.864 |
| | | 5828 | 0.080 | 0.000 | 0.000 | 0.000 | 0.085 | 0.000 | 0.000 | 0.000 |
| | | AVG | 0.099 | 0.000 | 0.000 | 0.000 | 0.096 | 1.931 | 1.670 | 1.218 |
| 7 | p4600kb: Tau construct, UBITh1-εk-kkk-(K257-K274) SEQ ID NO: 65 | 5829 | 0.082 | 0.000 | 0.000 | 0.000 | 0.078 | 0.000 | 0.000 | 0.000 |
| | | 5830 | 0.084 | 0.000 | 0.000 | 0.000 | 0.079 | 0.000 | 0.000 | 0.000 |
| | | 5831 | 0.084 | 0.000 | 0.000 | 0.000 | 0.069 | 0.000 | 0.000 | 0.000 |
| | | AVG | 0.083 | 0.000 | 0.000 | 0.000 | 0.075 | 0.000 | 0.000 | 0.000 |
| 8 | p4602kb: Tau construct, UBITh1-εk-kkk-(R379-L408) SEQ ID NO: 67 | 5832 | 0.085 | 5.034 | 4.818 | 4.554 | 0.071 | 2.955 | 2.752 | 2.808 |
| | | 5833 | 0.095 | 5.333 | 4.969 | 4.957 | 0.083 | 3.885 | 4.090 | 4.557 |
| | | 5834 | 0.104 | 5.102 | 4.827 | 4.607 | 0.095 | 2.931 | 2.880 | 3.032 |
| | | AVG | 0.095 | 5.156 | 4.871 | 4.706 | 0.083 | 3.257 | 3.241 | 3.466 |
| 9 | p4604kb: Tau construct, UBITh1-εk-kkk-(V275-K311) SEQ ID NO: 69 | 5835 | 0.085 | 4.967 | 10.060 | 7.244 | 0.100 | 0.000 | 0.000 | 0.000 |
| | | 5836 | 0.079 | 4.896 | 7.084 | 6.091 | 0.090 | 0.000 | 0.000 | 0.000 |
| | | 5837 | 0.073 | 5.492 | 5.930 | 5.425 | 0.086 | 0.000 | 0.000 | 1.137 |
| | | AVG | 0.079 | 5.118 | 7.691 | 6.253 | 0.092 | 0.000 | 0.000 | 0.379 |

TABLE 9e-continued

Immunogenicity analysis of Tau peptide constructs
(Data corresponds to FIG. 1A)
Adjuvant: ISA 51VG; CpG3 50 μg/ml; 0.2% tween 80
Immunogen dose: Prime: 400 μg/1.0 ml/dose/IM
(four injection sites, 0.25 ml/site);
Boosts: 100 μg/0.25 ml/dose/IM
Vaccination schedule: 0, 3 and 6 wpi

| | | | Anti-p4604a (V275-K311) ELISA Log10 Titer (SEQ ID NO: 19) | | | | Anti-p4605a (V393-L425) ELISA Log10 Titer (SEQ ID NO: 21) | | | |
|---|---|---|---|---|---|---|---|---|---|---|
| Grp # | Immunogen | GP# | 0 wpi | 3 wpi | 6 wpi | 9 wpi | 0 wpi | 3 wpi | 6 wpi | 9 wpi |
| 10 | p4605kb: Tau construct, UBITh1-εk-kkk-(V393-L425) SEQ ID NO: 71 | 5838 | 0.079 | 0.000 | 0.000 | 0.000 | 0.090 | 5.709 | 5.234 | 5.387 |
| | | 5839 | 0.086 | 0.000 | 0.000 | 0.000 | 0.069 | 7.296 | 6.288 | 6.562 |
| | | 5840 | 0.084 | 0.000 | 0.000 | 0.000 | 0.113 | 5.513 | 5.446 | 5.673 |
| | | AVG | 0.083 | 0.000 | 0.000 | 0.000 | 0.091 | 6.173 | 5.656 | 5.874 |

TABLE 10a

Immunogenicity Analysis of phosphorylated Tau peptide constructs
(Data corresponds to FIG. 1B)
Adjuvant: ISA 51VG; CpG3 50 μg/ml; 0.2% tween 80
Immunogen dose: Prime: 400 μg/1.0 ml/dose/IM
(four injection sites, 0.25 ml/site);
Boosts: 100 μg/0.25 ml/dose/IM
Vaccination schedule: 0, 3 and 6 wpi

| | | | Anti-p4578a (A145-P160) ELISA Log$_{10}$ Titer (SEQ ID NO: 1) | | | Anti-p4580a (P172-P189) ELISA Log$_{10}$ Titer (SEQ ID NO: 3) | | | Anti-p4582a (P182-P200) ELISA Log$_{10}$ Titer (SEQ ID NO: 5) | | |
|---|---|---|---|---|---|---|---|---|---|---|---|
| Grp # | Immunogen | GP# | 0 wpi | 3 wpi | 6 wpi | 0 wpi | 3 wpi | 6 wpi | 0 wpi | 3 wpi | 6 wpi |
| 1 | p4578kb: pTau construct, UBITh1-εk-kkk-(A145-P160) SEQ ID NO: 51 | 5778 | 0.110 | 5.936 | 5.193 | 0.087 | 4.949 | 4.856 | 0.083 | 3.147 | 3.229 |
| | | 5779 | 0.089 | 6.520 | 5.659 | 0.090 | 5.069 | 5.189 | 0.080 | 3.141 | 3.043 |
| | | 5780 | 0.096 | 6.844 | 5.642 | 0.083 | 4.920 | 5.013 | 0.065 | 2.887 | 2.904 |
| | | AVG | 0.098 | 6.433 | 5.465 | 0.087 | 4.979 | 5.019 | 0.076 | 3.058 | 3.059 |
| 2 | p4580kb: pTau construct, UBITh1-εk-kkk-(P172-P189) SEQ ID NO: 53 | 5781 | 0.092 | 5.127 | 5.277 | 0.063 | 5.430 | 5.732 | 0.082 | 3.292 | 3.754 |
| | | 5782 | 0.097 | 5.035 | 5.003 | 0.083 | 5.401 | 5.331 | 0.088 | 4.421 | 4.394 |
| | | 5783 | 0.086 | 5.293 | 5.694 | 0.070 | 5.782 | 6.406 | 0.076 | 1.897 | 2.395 |
| | | AVG | 0.092 | 5.152 | 5.291 | 0.072 | 5.538 | 5.823 | 0.082 | 3.203 | 3.514 |
| 3 | p4582kb: pTau construct, UBITh1-εk-kkk-(P182-P200) SEQ ID NO: 55 | 5784 | 0.164 | 4.056 | 4.521 | 0.095 | 3.932 | 4.344 | 0.089 | 4.650 | 4.929 |
| | | 5785 | 0.094 | 3.135 | 3.108 | 0.076 | 0.725 | 1.047 | 0.090 | 4.817 | 4.900 |
| | | 5786 | 0.089 | 5.049 | 4.981 | 0.090 | 4.988 | 4.920 | 0.083 | 5.512 | 5.843 |
| | | AVG | 0.116 | 4.080 | 4.203 | 0.087 | 3.215 | 3.437 | 0.087 | 4.993 | 5.224 |
| 4 | p4584kb: pTau construct, UBITh1-εk-kkk-(S195-P213) SEQ ID NO: 57 | 5787 | 0.081 | 4.938 | 4.758 | 0.089 | 4.736 | 4.644 | 0.071 | 3.614 | 4.508 |
| | | 5788 | 0.091 | 4.694 | 4.414 | 0.085 | 4.071 | 4.276 | 0.067 | 3.009 | 3.446 |
| | | 5789 | 0.074 | 4.958 | 4.729 | 0.091 | 4.659 | 4.557 | 0.089 | 3.985 | 4.383 |
| | | AVG | 0.082 | 4.863 | 4.634 | 0.088 | 4.489 | 4.492 | 0.076 | 3.536 | 4.112 |
| 5 | p4586kb: pTau construct, UBITh1-εk-kkk-(S195-P213) SEQ ID NO: 59 | 5790 | 0.085 | 4.670 | 4.442 | 0.092 | 4.714 | 4.382 | 0.084 | 4.350 | 4.064 |
| | | 5791 | 0.078 | 4.956 | 4.876 | 0.077 | 4.908 | 4.803 | 0.088 | 4.813 | 4.816 |
| | | 5792 | 0.078 | 5.534 | 6.162 | 0.095 | 5.489 | 6.171 | 0.083 | 5.139 | 6.607 |
| | | AVG | 0.080 | 5.053 | 5.160 | 0.088 | 5.037 | 5.119 | 0.085 | 4.767 | 5.162 |
| 6 | p4587kb: pTau construct, UBITh1-εk-kkk-(R209-L224) SEQ ID NO: 60 | 5793 | 0.090 | 0.000 | 0.000 | 0.090 | 0.000 | 0.000 | 0.093 | 0.000 | 0.998 |
| | | 5794 | 0.090 | 0.000 | 0.000 | 0.087 | 0.000 | 0.000 | 0.098 | 2.279 | 1.536 |
| | | 5795 | 0.096 | 0.939 | 0.165 | 0.095 | 0.000 | 0.000 | 0.094 | 0.000 | 0.000 |
| | | AVG | 0.092 | 0.313 | 0.055 | 0.091 | 0.000 | 0.000 | 0.095 | 0.760 | 0.845 |
| 7 | p4589kb: pTau construct, UBITh1-εk-kkk-(V228-L243) SEQ ID NO: 62 | 5796 | 0.102 | 0.000 | 0.000 | 0.092 | 0.000 | 0.000 | 0.086 | 0.000 | 0.000 |
| | | 5797 | 0.076 | 0.000 | 0.000 | 0.078 | 0.000 | 0.000 | 0.083 | 0.000 | 0.000 |
| | | 5798 | 0.082 | 0.000 | 0.000 | 0.081 | 0.000 | 3.108 | 0.080 | 0.000 | 0.000 |
| | | AVG | 0.087 | 0.000 | 0.000 | 0.084 | 0.000 | 1.036 | 0.083 | 0.000 | 0.000 |
| 8 | p4599kb: pTau construct, UBITh1-εk-kkk-(K257-K274) SEQ ID NO: 64 | 5799 | 0.078 | 0.000 | 0.000 | 0.080 | 0.000 | 0.000 | 0.075 | 0.000 | 0.000 |
| | | 5800 | 0.080 | 0.000 | 0.000 | 0.084 | 0.000 | 0.000 | 0.095 | 0.000 | 0.000 |
| | | 5801 | 0.092 | 0.000 | 0.000 | 0.079 | 0.000 | 0.000 | 0.096 | 0.000 | 0.000 |
| | | AVG | 0.083 | 0.000 | 0.000 | 0.081 | 0.000 | 0.000 | 0.089 | 0.000 | 0.000 |
| 9 | p4601kb: pTau construct, UBITh1-εk-kkk-(R379-L408) SEQ ID NO: 66 | 5802 | 0.086 | 2.493 | 1.345 | 0.087 | 2.680 | 1.766 | 0.093 | 0.000 | 0.000 |
| | | 5803 | 0.102 | 3.097 | 2.330 | 0.099 | 3.699 | 2.294 | 0.080 | 0.000 | 0.000 |
| | | 5804 | 0.089 | 3.213 | 2.922 | 0.085 | 2.930 | 1.135 | 0.076 | 0.000 | 0.000 |
| | | AVG | 0.092 | 2.934 | 2.199 | 0.090 | 3.103 | 1.732 | 0.083 | 0.000 | 0.000 |
| 10 | p4603kb: pTau construct, UBITh1-εk-kkk-(V275-K311, P301→S301 SEQ ID NO: 68 | 5805 | 0.075 | 0.000 | 0.000 | 0.087 | 0.000 | 0.000 | 0.085 | 0.000 | 0.000 |
| | | 5806 | 0.085 | 0.000 | 0.000 | 0.084 | 0.000 | 0.000 | 0.081 | 0.000 | 0.000 |
| | | 5807 | 0.074 | 0.000 | 0.000 | 0.084 | 0.000 | 0.000 | 0.088 | 0.000 | 0.000 |
| | | AVG | 0.078 | 0.000 | 0.000 | 0.085 | 0.000 | 0.000 | 0.085 | 0.000 | 0.000 |

TABLE 10a-continued

Immunogenicity Analysis of phosphorylated Tau peptide constructs
(Data corresponds to FIG. 1B)
Adjuvant: ISA 51VG; CpG3 50 μg/ml; 0.2% tween 80
Immunogen dose: Prime: 400 μg/1.0 ml/dose/IM
(four injection sites, 0.25 ml/site);
Boosts: 100 μg/0.25 ml/dose/IM
Vaccination schedule: 0, 3 and 6 wpi

| | | | Anti-p4578a (A145-P160) ELISA Log$_{10}$ Titer (SEQ ID NO: 1) | | | Anti-p4580a (P172-P189) ELISA Log$_{10}$ Titer (SEQ ID NO: 3) | | | Anti-p4582a (P182-P200) ELISA Log$_{10}$ Titer (SEQ ID NO: 5) | | |
|---|---|---|---|---|---|---|---|---|---|---|---|
| Grp # | Immunogen | GP# | 0 wpi | 3 wpi | 6 wpi | 0 wpi | 3 wpi | 6 wpi | 0 wpi | 3 wpi | 6 wpi |
| 11 | p4606kb: pTau construct, UBITh1-εk-kkk-(V393-L425) SEQ ID NO: 70 | 5808 | 0.080 | 0.000 | 0.000 | 0.092 | 0.000 | 0.000 | 0.103 | 0.000 | 0.000 |
| | | 5809 | 0.089 | 0.000 | 0.000 | 0.081 | 0.000 | 0.000 | 0.109 | 0.000 | 0.000 |
| | | 5810 | 0.081 | 0.000 | 0.000 | 0.069 | 0.000 | 0.000 | 0.096 | 0.000 | 0.000 |
| | | AVG | 0.083 | 0.000 | 0.000 | 0.081 | 0.000 | 0.000 | 0.103 | 0.000 | 0.000 |

TABLE 10b

Immunogenicity Analysis of phosphorylated Tau peptide constructs
(Data corresponds to FIG. 1B)
Adjuvant: ISA 51VG; CpG3 50 μg/ml; 0.2% tween 80
Immunogen dose: Prime: 400 μg/1.0 ml/dose/IM
(four injection sites, 0.25 ml/site);
Boosts: 100 μg/0.25 ml/dose/IM
Vaccination schedule: 0, 3 and 6 wpi

| | | | Anti-p4584a (S195-P213) ELISA Log10 Titer (SEQ ID NO: 9) | | | Anti-p4586a (S195-P213) ELISA Log10 Titer (SEQ ID NO: 7) | | | Anti-p4587a (R209-L224) ELISA Log10 Titer (SEQ ID NO: 10) | | |
|---|---|---|---|---|---|---|---|---|---|---|---|
| Grp # | Immunogen | GP# | 0 wpi | 3 wpi | 6 wpi | 0 wpi | 3 wpi | 6 wpi | 0 wpi | 3 wpi | 6 wpi |
| 1 | p4578kb: pTau construct, UBITh1-εk-kkk-(A145-P160) SEQ ID NO: 51 | 5778 | 0.075 | 4.442 | 4.006 | 0.070 | 2.921 | 3.053 | 0.069 | 0.000 | 0.000 |
| | | 5779 | 0.079 | 3.820 | 3.724 | 0.069 | 2.993 | 2.826 | 0.074 | 0.000 | 0.000 |
| | | 5780 | 0.094 | 4.014 | 4.077 | 0.066 | 2.961 | 3.050 | 0.066 | 0.000 | 0.000 |
| | | AVG | 0.083 | 4.092 | 3.936 | 0.068 | 2.958 | 2.976 | 0.070 | 0.000 | 0.000 |
| 2 | p4580kb: pTau construct, UBITh1-εk-kkk-(P172-P189) SEQ ID NO: 53 | 5781 | 0.087 | 4.063 | 4.016 | 0.073 | 3.106 | 4.017 | 0.078 | 0.000 | 0.000 |
| | | 5782 | 0.085 | 4.398 | 4.372 | 0.072 | 4.221 | 4.168 | 0.075 | 0.000 | 0.000 |
| | | 5783 | 0.084 | 3.091 | 3.087 | 0.068 | 0.793 | 1.362 | 0.080 | 0.000 | 0.000 |
| | | AVG | 0.085 | 3.851 | 3.825 | 0.071 | 2.707 | 3.182 | 0.078 | 0.000 | 0.000 |
| 3 | p4582kb: pTau construct, UBITh1-εk-kkk-(P182-P200) SEQ ID NO: 55 | 5784 | 0.069 | 3.216 | 4.245 | 0.063 | 2.992 | 3.818 | 0.086 | 0.000 | 0.000 |
| | | 5785 | 0.073 | 2.995 | 2.808 | 0.069 | 0.642 | 1.791 | 0.074 | 1.030 | 0.000 |
| | | 5786 | 0.076 | 4.758 | 5.304 | 0.078 | 4.538 | 5.010 | 0.081 | 2.568 | 2.820 |
| | | AVG | 0.073 | 3.656 | 4.119 | 0.070 | 2.724 | 3.540 | 0.080 | 1.199 | 0.940 |
| 4 | p4584kb: pTau construct, UBITh1-εk-kkk-(S195-P213) SEQ ID NO: 57 | 5787 | 0.069 | 5.280 | 5.320 | 0.071 | 4.890 | 5.056 | 0.085 | 2.979 | 3.035 |
| | | 5788 | 0.071 | 6.587 | 7.196 | 0.069 | 5.232 | 6.139 | 0.073 | 4.435 | 4.492 |
| | | 5789 | 0.071 | 5.045 | 5.312 | 0.075 | 4.744 | 5.013 | 0.083 | 2.925 | 2.940 |
| | | AVG | 0.070 | 5.637 | 5.943 | 0.072 | 4.955 | 5.403 | 0.080 | 3.446 | 3.489 |
| 5 | p4586kb: pTau construct, UBITh1-εk-kkk-(S195-P213) SEQ ID NO: 59 | 5790 | 0.076 | 5.185 | 5.545 | 0.083 | 5.475 | 5.314 | 0.086 | 3.082 | 2.865 |
| | | 5791 | 0.075 | 5.345 | 5.635 | 0.079 | 5.163 | 5.357 | 0.079 | 3.249 | 3.093 |
| | | 5792 | 0.066 | 5.701 | 8.875 | 0.073 | 5.547 | 9.583 | 0.091 | 4.832 | 4.670 |
| | | AVG | 0.072 | 5.410 | 6.685 | 0.078 | 5.395 | 6.751 | 0.085 | 3.721 | 3.543 |
| 6 | p4587kb: pTau construct, UBITh1-εk-kkk-(R209-L224) SEQ ID NO: 60 | 5793 | 0.069 | 2.902 | 2.787 | 0.075 | 0.000 | 0.000 | 0.087 | 4.763 | 4.857 |
| | | 5794 | 0.078 | 2.983 | 3.088 | 0.069 | 2.326 | 2.836 | 0.074 | 4.725 | 4.864 |
| | | 5795 | 0.069 | 3.108 | 2.993 | 0.065 | 2.637 | 2.079 | 0.074 | 5.050 | 4.968 |
| | | AVG | 0.072 | 2.998 | 2.956 | 0.070 | 1.654 | 1.638 | 0.078 | 4.846 | 4.896 |
| 7 | p4589kb: pTau construct, UBITh1-εk-kkk-(V228-L243) SEQ ID NO: 62 | 5796 | 0.082 | 0.000 | 0.000 | 0.071 | 0.000 | 0.000 | 0.078 | 0.685 | 3.032 |
| | | 5797 | 0.074 | 0.000 | 0.000 | 0.068 | 0.000 | 0.000 | 0.076 | 2.436 | 2.700 |
| | | 5798 | 0.080 | 0.000 | 0.000 | 0.066 | 0.000 | 0.000 | 0.081 | 0.000 | 0.000 |
| | | AVG | 0.079 | 0.000 | 0.000 | 0.068 | 0.000 | 0.000 | 0.078 | 1.040 | 1.911 |
| 8 | p4599kb: pTau construct, UBITh1-εk-kkk-(K257-K274) SEQ ID NO: 64 | 5799 | 0.069 | 0.000 | 0.000 | 0.068 | 0.000 | 0.000 | 0.081 | 0.000 | 0.000 |
| | | 5800 | 0.071 | 0.000 | 0.000 | 0.081 | 0.000 | 0.000 | 0.086 | 0.000 | 0.000 |
| | | 5801 | 0.071 | 0.000 | 0.000 | 0.073 | 0.000 | 0.000 | 0.082 | 0.000 | 0.000 |
| | | AVG | 0.070 | 0.000 | 0.000 | 0.074 | 0.000 | 0.000 | 0.083 | 0.000 | 0.000 |
| 9 | p4601kb: pTau construct, UBITh1-εk-kkk-(R379-L408) SEQ ID NO: 66 | 5802 | 0.068 | 0.000 | 0.000 | 0.071 | 0.424 | 0.000 | 0.088 | 0.764 | 2.819 |
| | | 5803 | 0.062 | 0.000 | 0.000 | 0.070 | 0.000 | 0.000 | 0.096 | 3.152 | 2.660 |
| | | 5804 | 0.058 | 2.905 | 1.915 | 0.066 | 2.973 | 1.427 | 0.104 | 2.802 | 0.621 |
| | | AVG | 0.063 | 0.968 | 0.638 | 0.069 | 1.132 | 0.476 | 0.096 | 2.239 | 2.033 |
| 10 | p4603kb: pTau construct, UBITh1-εk-kkk-(V275-K311, P301→S301) SED ID NO: 68 | 5805 | 0.062 | 0.000 | 0.000 | 0.073 | 0.000 | 0.000 | 0.103 | 0.000 | 0.000 |
| | | 5806 | 0.061 | 0.000 | 0.000 | 0.068 | 0.000 | 0.000 | 0.104 | 0.000 | 0.000 |
| | | 5807 | 0.062 | 0.000 | 0.000 | 0.078 | 0.000 | 0.000 | 0.096 | 0.000 | 0.000 |
| | | AVG | 0.062 | 0.000 | 0.000 | 0.073 | 0.000 | 0.000 | 0.103 | 0.000 | 0.000 |

TABLE 10b-continued

Immunogenicity Analysis of phosphorylated Tau peptide constructs
(Data corresponds to FIG. 1B)
Adjuvant: ISA 51VG; CpG3 50 μg/ml; 0.2% tween 80
Immunogen dose: Prime: 400 μg/1.0 ml/dose/IM
(four injection sites, 0.25 ml/site);
Boosts: 100 μg/0.25 ml/dose/IM
Vaccination schedule: 0, 3 and 6 wpi

| Grp # | Immunogen | GP# | Anti-p4584a (S195-P213) ELISA Log10 Titer (SEQ ID NO: 9) | | | Anti-p4586a (S195-P213) ELISA Log10 Titer (SEQ ID NO: 7) | | | Anti-p4587a (R209-L224) ELISA Log10 Titer (SEQ ID NO: 10) | | |
|---|---|---|---|---|---|---|---|---|---|---|---|
| | | | 0 wpi | 3 wpi | 6 wpi | 0 wpi | 3 wpi | 6 wpi | 0 wpi | 3 wpi | 6 wpi |
| 11 | p4606kb: pTau construct, UBITh1-ϵk-kkk-(V393-L425) SED ID NO: 70 | 5808 | 0.074 | 0.000 | 0.000 | 0.102 | 0.000 | 0.000 | 0.111 | 3.418 | 4.861 |
| | | 5809 | 0.064 | 0.000 | 0.000 | 0.079 | 0.000 | 0.000 | 0.106 | 3.321 | 4.861 |
| | | 5810 | 0.061 | 0.000 | 0.000 | 0.079 | 0.000 | 0.000 | 0.071 | 3.925 | 3.423 |
| | | AVG | 0.066 | 0.000 | 0.000 | 0.087 | 0.000 | 0.000 | 0.096 | 3.555 | 4.382 |

TABLE 10c

Immunogenicity Analysis of phosphorylated Tau peptide constructs
(Data corresponds to FIG. 1B)
Adjuvant: ISA 51VG; CpG3 50 μg/ml; 0.2% tween 80
Immunogen dose: Prime: 400 μg/1.0 ml/dose/IM
(four injection sites, 0.25 ml/site);
Boosts: 100 μg/0.25 ml/dose/IM
Vaccination schedule: 0, 3 and 6 wpi

| Grp # | Immunogen | GP# | Anti-p4589a (V228-L243) ELISA $\text{Log}_{10}$ Titer (SEQ ID NO: 12) | | | Anti-p4599a (K257-K274) ELISA $\text{Log}_{10}$ Titer (SEQ ID NO: 14) | | | Anti-p4601a (R379-L408) ELISA $\text{Log}_{10}$ Titer (SEQ ID NO: 16) | | |
|---|---|---|---|---|---|---|---|---|---|---|---|
| | | | 0 wpi | 3 wpi | 6 wpi | 0 wpi | 3 wpi | 6 wpi | 0 wpi | 3 wpi | 6 wpi |
| 1 | p4578kb: pTau construct, UBITh1-ϵk-kkk-(A145-P160) SEQ ID NO: 51 | 5778 | 0.078 | 0.000 | 0.000 | 0.066 | 0.000 | 0.000 | 0.074 | 3.717 | 3.152 |
| | | 5779 | 0.100 | 0.000 | 0.000 | 0.071 | 0.000 | 0.000 | 0.077 | 3.186 | 3.033 |
| | | 5780 | 0.107 | 0.000 | 0.000 | 0.074 | 0.000 | 0.000 | 0.086 | 3.242 | 2.855 |
| | | AVG | 0.095 | 0.000 | 0.000 | 0.070 | 0.000 | 0.000 | 0.079 | 3.382 | 3.013 |
| 2 | p4580kb: pTau construct, UBITh1-ϵk-kkk-(P172-P189) SEQ ID NO: 53 | 5781 | 0.102 | 0.000 | 0.000 | 0.069 | 0.000 | 0.000 | 0.078 | 3.139 | 3.211 |
| | | 5782 | 0.083 | 0.000 | 0.000 | 0.070 | 0.000 | 0.000 | 0.076 | 2.869 | 2.760 |
| | | 5783 | 0.093 | 0.000 | 0.000 | 0.067 | 0.000 | 0.000 | 0.082 | 2.823 | 3.188 |
| | | AVG | 0.093 | 0.000 | 0.000 | 0.069 | 0.000 | 0.000 | 0.079 | 2.944 | 3.053 |
| 3 | p4582kb: pTau construct, UBITh1-ϵk-kkk-(P182-P200) SEQ ID NO: 55 | 5784 | 0.092 | 0.000 | 0.000 | 0.096 | 0.000 | 0.000 | 0.122 | 0.000 | 0.000 |
| | | 5785 | 0.097 | 0.000 | 0.000 | 0.082 | 0.000 | 0.000 | 0.118 | 0.000 | 0.000 |
| | | 5786 | 0.070 | 0.000 | 0.000 | 0.080 | 0.000 | 0.000 | 0.073 | 0.000 | 0.000 |
| | | AVG | 0.086 | 0.000 | 0.000 | 0.086 | 0.000 | 0.000 | 0.104 | 0.000 | 0.000 |
| 4 | p4584kb: pTau construct, UBITh1-ϵk-kkk-(S195-P213) SEQ ID NO: 57 | 5787 | 0.090 | 0.000 | 0.000 | 0.084 | 0.000 | 0.000 | 0.071 | 4.639 | 4.505 |
| | | 5788 | 0.079 | 0.000 | 0.000 | 0.090 | 0.000 | 0.000 | 0.080 | 4.220 | 4.681 |
| | | 5789 | 0.079 | 0.000 | 0.000 | 0.085 | 0.000 | 0.000 | 0.076 | 3.268 | 3.687 |
| | | AVG | 0.083 | 0.000 | 0.000 | 0.086 | 0.000 | 0.000 | 0.076 | 4.042 | 4.291 |
| 5 | p4586kb: pTau construct, UBITh1-ϵk-kkk-(S195-P213) SEQ ID NO: 59 | 5790 | 0.078 | 0.000 | 0.000 | 0.080 | 0.000 | 0.000 | 0.077 | 4.890 | 4.715 |
| | | 5791 | 0.078 | 0.000 | 0.000 | 0.079 | 0.000 | 0.000 | 0.078 | 4.375 | 4.300 |
| | | 5792 | 0.085 | 0.000 | 0.000 | 0.080 | 0.000 | 0.000 | 0.078 | 4.236 | 3.342 |
| | | AVG | 0.080 | 0.000 | 0.000 | 0.080 | 0.000 | 0.000 | 0.078 | 4.500 | 4.119 |
| 6 | p4587kb: pTau construct, UBITh1-ϵk-kkk-(R209-L224) SEQ ID NO: 60 | 5793 | 0.095 | 3.155 | 1.806 | 0.115 | 0.000 | 0.000 | 0.108 | 4.500 | 4.740 |
| | | 5794 | 0.062 | 0.639 | 0.000 | 0.072 | 0.000 | 0.000 | 0.075 | 3.827 | 3.816 |
| | | 5795 | 0.062 | 2.892 | 2.388 | 0.070 | 0.000 | 0.000 | 0.079 | 4.045 | 4.326 |
| | | AVG | 0.073 | 2.229 | 1.398 | 0.086 | 0.000 | 0.000 | 0.087 | 4.124 | 4.294 |
| 7 | p4589kb: pTau construct, UBITh1-ϵk-kkk-(V228-L243) SEQ ID NO: 62 | 5796 | 0.077 | 4.738 | 5.004 | 0.089 | 0.000 | 0.000 | 0.096 | 4.608 | 4.879 |
| | | 5797 | 0.063 | 4.970 | 5.077 | 0.073 | 0.000 | 0.000 | 0.076 | 4.752 | 4.739 |
| | | 5798 | 0.067 | 4.341 | 4.684 | 0.071 | 0.000 | 0.000 | 0.072 | 3.476 | 4.450 |
| | | AVG | 0.069 | 4.683 | 4.922 | 0.078 | 0.000 | 0.000 | 0.081 | 4.279 | 4.689 |
| 8 | p4599kb: pTau construct, UBITh1-ϵk-kkk-(K257-K274) SEQ ID NO: 64 | 5799 | 0.083 | 0.000 | 0.000 | 0.073 | 10.440 | >10 | 0.078 | 0.000 | 0.539 |
| | | 5800 | 0.242 | 0.000 | 0.000 | 0.095 | 6.378 | 5.732 | 0.085 | 0.000 | 0.000 |
| | | 5801 | 0.085 | 0.000 | 0.000 | 0.090 | 7.182 | >10 | 0.097 | 0.000 | 0.000 |
| | | AVG | 0.137 | 0.000 | 0.000 | 0.086 | 8.000 | 5.732 | 0.087 | 0.000 | 0.180 |
| 9 | p4601kb: pTau construct, UBITh1-ϵk-kkk-(R379-L408) SEQ ID NO: 66 | 5802 | 0.060 | 0.000 | 0.000 | 0.098 | 0.000 | 0.000 | 0.097 | 9.906 | >10 |
| | | 5803 | 0.069 | 2.844 | 2.839 | 0.082 | 0.000 | 0.000 | 0.121 | >10 | >10 |
| | | 5804 | 0.071 | 2.693 | 2.027 | 0.098 | 0.000 | 0.000 | 0.100 | >10 | >10 |
| | | AVG | 0.067 | 1.846 | 1.622 | 0.093 | 0.000 | 0.000 | 0.106 | 9.906 | >10 |
| 10 | p4603kb: pTau construct, UBITh1-ϵk-kkk-(V275-K311, P301→S301) SEQ ID NO: 68 | 5805 | 0.068 | 0.000 | 0.000 | 0.081 | 0.000 | 0.000 | 0.094 | 4.664 | 5.271 |
| | | 5806 | 0.068 | 0.000 | 0.000 | 0.074 | 0.000 | 0.000 | 0.096 | 4.452 | 5.467 |
| | | 5807 | 0.069 | 0.000 | 0.000 | 0.082 | 0.000 | 0.000 | 0.092 | 4.758 | 5.015 |
| | | AVG | 0.068 | 0.000 | 0.000 | 0.079 | 0.000 | 0.000 | 0.094 | 4.625 | 5.251 |

TABLE 10c-continued

Immunogenicity Analysis of phosphorylated Tau peptide constructs
(Data corresponds to FIG. 1B)
Adjuvant: ISA 51VG; CpG3 50 μg/ml; 0.2% tween 80
Immunogen dose: Prime: 400 μg/1.0 ml/dose/IM
(four injection sites, 0.25 ml/site);
Boosts: 100 μg/0.25 ml/dose/IM
Vaccination schedule: 0, 3 and 6 wpi

| Grp # | Immunogen | GP# | Anti-p4589a (V228-L243) ELISA $Log_{10}$ Titer (SEQ ID NO: 12) | | | Anti-p4599a (K257-K274) ELISA $Log_{10}$ Titer (SEQ ID NO: 14) | | | Anti-p4601a (R379-L408) ELISA $Log_{10}$ Titer (SEQ ID NO: 16) | | |
|---|---|---|---|---|---|---|---|---|---|---|---|
| | | | 0 wpi | 3 wpi | 6 wpi | 0 wpi | 3 wpi | 6 wpi | 0 wpi | 3 wpi | 6 wpi |
| 11 | p4606kb: pTau construct, UBITh1-εk-kkk-(V393-L425) SEQ ID NO: 70 | 5808 | 0.089 | 2.308 | 0.000 | 0.098 | 0.000 | 0.000 | 0.084 | 6.308 | 11.990 |
| | | 5809 | 0.094 | 4.224 | 3.237 | 0.107 | 0.000 | 0.000 | 0.115 | 8.761 | 9.667 |
| | | 5810 | 0.089 | 2.392 | 1.767 | 0.100 | 0.000 | 0.000 | 0.093 | 4.950 | 5.308 |
| | | AVG | 0.091 | 2.975 | 1.668 | 0.102 | 0.000 | 0.000 | 0.097 | 6.673 | 8.988 |

TABLE 10d

Immunogenicity Analysis of phosphorylated Tau peptide constructs
(Data corresponds to FIG. 1B)
Adjuvant: ISA 51VG; CpG3 50 μg/ml; 0.2% tween 80
Immunogen dose: Prime: 400 μg/1.0 ml/dose/IM
(four injection sites, 0.25 ml/site);
Boosts: 100 μg/0.25 ml/dose/IM
Vaccination schedule: 0, 3 and 6 wpi

| Grp # | Immunogen | GP# | Anti-p4603a (V275-K311) ELISA Log10 Titer (SEQ ID NO: 18) | | | Anti-p4606a (V393-L425) ELISA Log10 Titer (SEQ ID NO: 20) | | |
|---|---|---|---|---|---|---|---|---|
| | | | 0 wpi | 3 wpi | 6 wpi | 0 wpi | 3 wpi | 6 wpi |
| 1 | p4578kb: pTau construct, UBITh1-εk-kkk-(A145-P160) SEQ ID NO: 51 | 5778 | 0.116 | 0.000 | 0.000 | 0.069 | 0.000 | 1.797 |
| | | 5779 | 0.111 | 0.000 | 0.000 | 0.070 | 0.000 | 2.797 |
| | | 5780 | 0.105 | 0.000 | 0.000 | 0.057 | 0.000 | 1.854 |
| | | AVG | 0.111 | 0.000 | 0.000 | 0.065 | 0.000 | 2.149 |
| 2 | p4580kb: pTau construct, UBITh1-εk-kkk-(P172-P189) SEQ ID NO: 53 | 5781 | 0.107 | 0.000 | 0.000 | 0.055 | 0.000 | 0.000 |
| | | 5782 | 0.089 | 0.000 | 0.000 | 0.064 | 0.000 | 0.000 |
| | | 5783 | 0.090 | 0.000 | 0.000 | 0.066 | 0.000 | 0.000 |
| | | AVG | 0.095 | 0.000 | 0.000 | 0.062 | 0.000 | 0.000 |
| 3 | p4582kb: pTau construct, UBITh1-εk-kkk-(P182-P200) SEQ ID NO: 55 | 5784 | 0.096 | 0.000 | 0.000 | 0.085 | 0.000 | 0.000 |
| | | 5785 | 0.275 | 0.000 | 0.000 | 0.065 | 0.000 | 0.000 |
| | | 5786 | 0.084 | 0.000 | 0.000 | 0.075 | 0.000 | 0.000 |
| | | AVG | 0.152 | 0.000 | 0.000 | 0.075 | 0.000 | 0.000 |
| 4 | p4584kb: pTau construct, UBITh1-εk-kkk-(S195-P213) SEQ ID NO: ID 57 | 5787 | 0.087 | 0.000 | 0.000 | 0.070 | 0.000 | 0.000 |
| | | 5788 | 0.082 | 0.159 | 0.000 | 0.061 | 0.000 | 2.433 |
| | | 5789 | 0.079 | 0.000 | 0.000 | 0.058 | 0.000 | 0.000 |
| | | AVG | 0.083 | 0.053 | 0.000 | 0.063 | 0.000 | 0.811 |
| 5 | p4586kb: pTau construct, UBITh1-εk-kkk-(S195-P213) SEQ ID NO: 59 | 5790 | 0.075 | 0.000 | 0.000 | 0.065 | 0.000 | 0.000 |
| | | 5791 | 0.082 | 0.000 | 0.000 | 0.072 | 0.000 | 0.000 |
| | | 5792 | 0.092 | 0.000 | 0.000 | 0.085 | 0.000 | 2.807 |
| | | AVG | 0.083 | 0.000 | 0.000 | 0.074 | 0.000 | 0.936 |
| 6 | p4587kb: pTau construct, UBITh1-εk-kkk-(R209-L224) SEQ ID NO: 60 | 5793 | 0.076 | 0.000 | 0.000 | 0.075 | 0.000 | 4.829 |
| | | 5794 | 0.085 | 0.000 | 0.000 | 0.077 | 0.000 | 4.545 |
| | | 5795 | 0.083 | 0.000 | 0.000 | 0.077 | 0.000 | 4.818 |
| | | AVG | 0.081 | 0.000 | 0.000 | 0.076 | 0.000 | 4.731 |
| 7 | p4589kb: pTau construct, UBITh1-εk-kkk-(V228-L243) SEQ ID NO: 62 | 5796 | 0.090 | 0.000 | 0.000 | 0.067 | 0.000 | 4.675 |
| | | 5797 | 0.072 | 0.000 | 0.000 | 0.226 | 0.000 | 4.394 |
| | | 5798 | 0.076 | 0.000 | 0.000 | 0.072 | 0.000 | 3.176 |
| | | AVG | 0.079 | 0.000 | 0.000 | 0.122 | 0.000 | 4.082 |
| 8 | p4599kb: pTau construct, UBITh1-εk-kkk-(K257-K274) SEQ ID NO: 64 | 5799 | 0.078 | 0.000 | 0.000 | 0.075 | 0.000 | 0.000 |
| | | 5800 | 0.096 | 0.000 | 0.000 | 0.096 | 0.000 | 0.000 |
| | | 5801 | 0.080 | 0.000 | 0.000 | 0.087 | 0.000 | 0.000 |
| | | AVG | 0.085 | 0.000 | 0.000 | 0.086 | 0.000 | 0.000 |
| 9 | p4601kb: pTau construct, UBITh1-εk-kkk-(R379-L408) SEQ ID NO: 66 | 5802 | 0.082 | 4.683 | 4.463 | 0.070 | 4.947 | 4.788 |
| | | 5803 | 0.084 | 5.542 | 5.047 | 0.079 | 4.993 | 4.910 |
| | | 5804 | 0.076 | 4.827 | 4.520 | 0.065 | 4.965 | 4.938 |
| | | AVG | 0.081 | 5.017 | 4.677 | 0.071 | 4.968 | 4.879 |

TABLE 10d-continued

Immunogenicity Analysis of phosphorylated Tau peptide constructs
(Data corresponds to FIG. 1B)
Adjuvant: ISA 51VG; CpG3 50 μg/ml; 0.2% tween 80
Immunogen dose: Prime: 400 μg/1.0 ml/dose/IM
(four injection sites, 0.25 ml/site);
Boosts: 100 μg/0.25 ml/dose/IM
Vaccination schedule: 0, 3 and 6 wpi

| Grp # | Immunogen | GP# | Anti-p4603a (V275-K311) ELISA Log10 Titer (SEQ ID NO: 18) | | | Anti-p4606a (V393-L425) ELISA Log10 Titer (SEQ ID NO: 20) | | |
|---|---|---|---|---|---|---|---|---|
| | | | 0 wpi | 3 wpi | 6 wpi | 0 wpi | 3 wpi | 6 wpi |
| 10 | p4603kb: pTau construct, UBITh1-ɛk-kkk-(V275-K311, P301→S301) SEQ ID NO: 68 | 5805 | 0.071 | 5.080 | >10 | 0.061 | 0.000 | 0.000 |
| | | 5806 | 0.074 | 4.898 | >10 | 0.069 | 0.000 | 0.000 |
| | | 5807 | 0.078 | 4.942 | 10.260 | 0.072 | 0.000 | 0.000 |
| | | AVG | 0.074 | 4.973 | 10.260 | 0.067 | 0.000 | 0.000 |
| 11 | p4606kb: pTau construct, UBITh1-ɛk-kkk-(V393-L425) SEQ ID NO: 70 | 5808 | 0.111 | 0.000 | 0.678 | 0.091 | >10 | >10 |
| | | 5809 | 0.080 | 0.000 | 0.000 | 0.389 | >10 | >10 |
| | | 5810 | 0.095 | 0.000 | 0.000 | 0.089 | 7.200 | 8.246 |
| | | AVG | 0.095 | 0.000 | 0.226 | 0.090 | 7.200 | 8.246 |

TABLE 11a

Immunogenicity Analysis of phosphorylated Tau peptide constructs
Adjuvant: ISA 51VG; CpG3 50 μg/ml; 0.2% tween 80
Immunogen dose: Prime: 400 μg/1.0 ml/dose/IM
(four injection sites, 0.25 ml/site);
Boosts: 100 μg/0.25 ml/dose/IM
Vaccination schedule: 0, 3 and 6 wpi

| Grp # | Immunogen | GP# | Anti-p4583a (P182-P200) ELISA Log$_{10}$ Titer (SEQ ID NO: 2) | | | Anti-p4585a (S195-P213) ELISA Log$_{10}$ Titer (SEQ ID NO: 4) | | |
|---|---|---|---|---|---|---|---|---|
| | | | 0 wpi | 3 wpi | 6 wpi | 0 wpi | 3 wpi | 6 wpi |
| 1 | p4578kb: pTau construct, UBITh1-ɛk-kkk-(A145-P160) SEQ ID NO: 51 | 5778 | 0.17 | 5.61 | 5.20 | 0.14 | 4.88 | 4.87 |
| | | 5779 | 0.14 | 5.70 | 5.73 | 0.10 | 4.88 | 5.05 |
| | | 5780 | 0.11 | 6.26 | 5.81 | 0.09 | 4.76 | 4.95 |
| | | AVG | 0.14 | 5.86 | 5.58 | 0.11 | 4.84 | 4.96 |
| 2 | p4580kb: pTau construct, UBITh1-ɛk-kkk-(P172-P189) SEQ ID NO: 53 | 5781 | 0.11 | 5.01 | 5.15 | 0.11 | 5.28 | 5.94 |
| | | 5782 | 0.11 | 4.94 | 4.97 | 0.09 | 5.25 | 5.33 |
| | | 5783 | 0.11 | 5.18 | 5.18 | 0.09 | 5.79 | 6.06 |
| | | AVG | 0.11 | 5.04 | 5.10 | 0.10 | 5.44 | 5.78 |
| 3 | p4582kb: pTau construct, UBITh1-ɛk-kkk-(P182-P200) SEQ ID NO: 55 | 5784 | 0.14 | 3.73 | 4.34 | 0.09 | 3.67 | 4.16 |
| | | 5785 | 0.12 | 2.95 | 2.85 | 0.10 | 0.00 | 0.00 |
| | | 5786 | 0.13 | 5.00 | 4.87 | 0.12 | 4.96 | 4.81 |
| | | AVG | 0.13 | 3.89 | 4.02 | 0.10 | 2.88 | 2.99 |
| 4 | p4584kb: pTau construct, UBITh1-ɛk-kkk-(S195-P213) SEQ ID NO: 57 | 5787 | 0.11 | 4.71 | 4.64 | 0.09 | 4.57 | 4.60 |
| | | 5788 | 0.10 | 4.65 | 4.30 | 0.08 | 3.46 | 3.66 |
| | | 5789 | 0.16 | 4.65 | 4.42 | 0.08 | 4.54 | 4.38 |
| | | AVG | 0.12 | 4.67 | 4.45 | 0.08 | 4.19 | 4.21 |
| 5 | p4586kb: pTau construct, UBITh1-ɛk-kkk-(S195-P213) SEQ ID NO: 59 | 5790 | 0.09 | 4.44 | 3.89 | 0.08 | 4.70 | 4.20 |
| | | 5791 | 0.10 | 4.71 | 4.61 | 0.09 | 4.83 | 4.69 |
| | | 5792 | 0.10 | 5.04 | 5.33 | 0.10 | 5.31 | 5.57 |
| | | AVG | 0.10 | 4.73 | 4.61 | 0.09 | 4.95 | 4.82 |
| 6 | p4587kb: pTau construct, UBITh1-ɛk-kkk-(R209-L224) SEQ ID NO: 60 | 5793 | 0.11 | 0.00 | 0.00 | 0.10 | 0.00 | 0.00 |
| | | 5794 | 0.14 | 0.00 | 0.00 | 0.12 | 0.00 | 0.00 |
| | | 5795 | 0.11 | 0.14 | 0.00 | 0.10 | 0.00 | 0.00 |
| | | AVG | 0.12 | 0.05 | 0.00 | 0.11 | 0.00 | 0.00 |
| 7 | p4589kb: pTau construct, UBITh1-ɛk-kkk-(V228-L243) SEQ ID NO: 62 | 5796 | 0.10 | 0.00 | 0.00 | 0.09 | 0.00 | 0.00 |
| | | 5797 | 0.09 | 0.00 | 0.00 | 0.08 | 0.00 | 0.00 |
| | | 5798 | 0.09 | 0.00 | 0.00 | 0.08 | 0.00 | 0.00 |
| | | AVG | 0.09 | 0.00 | 0.00 | 0.08 | 0.00 | 0.00 |
| 8 | p4599kb: pTau construct, UBITh1-ɛk-kkk-(K257-K274) SEQ ID NO: 64 | 5799 | 0.09 | 0.00 | 0.00 | 0.09 | 0.00 | 0.00 |
| | | 5800 | 0.10 | 0.00 | 0.00 | 0.09 | 0.00 | 0.00 |
| | | 5801 | 0.10 | 0.00 | 0.00 | 0.10 | 0.00 | 0.00 |
| | | AVG | 0.10 | 0.00 | 0.00 | 0.09 | 0.00 | 0.00 |
| 9 | p4601kb: pTau construct, UBITh1-ɛk-kkk-(R379-L408) SEQ ID NO: 66 | 5802 | 0.12 | 2.12 | 0.00 | 0.10 | 2.69 | 0.97 |
| | | 5803 | 0.10 | 3.05 | 1.36 | 0.08 | 2.36 | 0.00 |
| | | 5804 | 0.09 | 3.08 | 2.43 | 0.09 | 2.89 | 0.53 |
| | | AVG | 0.10 | 2.75 | 1.26 | 0.09 | 2.65 | 0.50 |

TABLE 11a-continued

Immunogenicity Analysis of phosphorylated Tau peptide constructs
Adjuvant: ISA 51VG; CpG3 50 µg/ml; 0.2% tween 80
Immunogen dose: Prime: 400 µg/1.0 ml/dose/IM
(four injection sites, 0.25 ml/site);
Boosts: 100 µg/0.25 ml/dose/IM
Vaccination schedule: 0, 3 and 6 wpi

| | | | Anti-p4583a (P182-P200) ELISA $Log_{10}$ Titer (SEQ ID NO: 2) | | | Anti-p4585a (S195-P213) ELISA $Log_{10}$ Titer (SEQ ID NO: 4) | | |
|---|---|---|---|---|---|---|---|---|
| Grp # | Immunogen | GP# | 0 wpi | 3 wpi | 6 wpi | 0 wpi | 3 wpi | 6 wpi |
| 10 | p4603kb: pTau construct, UBITh1-ek-kkk-(V275-K311, P301→S301) SEQ ID NO: 68 | 5805 | 0.08 | 0.00 | 0.00 | 0.08 | 0.00 | 0.00 |
| | | 5806 | 0.09 | 0.00 | 0.00 | 0.09 | 0.00 | 0.00 |
| | | 5807 | 0.09 | 0.00 | 0.00 | 0.09 | 0.00 | 0.00 |
| | | AVG | 0.09 | 0.00 | 0.00 | 0.09 | 0.00 | 0.00 |
| 11 | p4606kb: pTau construct, UBITh1-ek-kkk-(V393-L425) SEQ ID NO: 70 | 5808 | 0.09 | 0.00 | 0.00 | 0.09 | 0.00 | 0.00 |
| | | 5809 | 0.10 | 0.00 | 0.00 | 0.10 | 0.00 | 0.00 |
| | | 5810 | 0.10 | 0.00 | 0.00 | 0.08 | 0.00 | 0.00 |
| | | AVG | 0.10 | 0.00 | 0.00 | 0.09 | 0.00 | 0.00 |

TABLE 11b

Immunogenicity Analysis of phosphorylated Tau peptide constructs
Adjuvant: ISA 51VG; CpG3 50 µg/ml; 0.2% tween 80
Immunogen dose: Prime: 400 µg/1.0 ml/dose/IM
(four injection sites, 0.25 ml/site);
Boosts: 100 µg/0.25 ml/dose/IM
Vaccination schedule: 0, 3, 6 wpi

| | | | Anti-p4583a (P182-P200) ELISA $Log_{10}$ Titer (SEQ ID NO: 6) | | | Anti-p4585a (S195-P213) ELISA $Log_{10}$ Titer (SEQ ID NO: 8) | | |
|---|---|---|---|---|---|---|---|---|
| Grp # | Immunogen | GP# | 0 wpi | 3 wpi | 6 wpi | 0 wpi | 3 wpi | 6 wpi |
| 1 | p4578kb: pTau construct, UBITh1-ek-kkk-(A145-P160) SEQ ID NO: 51 | 5778 | 0.11 | 2.70 | 3.06 | 0.13 | 2.96 | 3.16 |
| | | 5779 | 0.09 | 2.29 | 2.70 | 0.11 | 2.69 | 2.94 |
| | | 5780 | 0.09 | 2.56 | 2.53 | 0.11 | 3.02 | 3.29 |
| | | AVG | 0.10 | 2.52 | 2.76 | 0.12 | 2.89 | 3.13 |
| 2 | p4580kb: pTau construct, UBITh1-ek-kkk-(P172-P189) SEQ ID NO: 53 | 5781 | 0.09 | 2.45 | 3.32 | 0.12 | 2.78 | 3.09 |
| | | 5782 | 0.09 | 3.41 | 3.72 | 0.11 | 3.28 | 3.59 |
| | | 5783 | 0.10 | 0.97 | 1.11 | 0.11 | 0.72 | 0.30 |
| | | AVG | 0.09 | 2.28 | 2.72 | 0.11 | 2.26 | 2.33 |
| 3 | p4582kb: pTau construct, UBITh1-ek-kkk-(P182-P200) SEQ ID NO: 55 | 5784 | 0.10 | 3.23 | 4.60 | 0.09 | 2.78 | 3.64 |
| | | 5785 | 0.10 | 2.74 | 4.31 | 0.13 | 1.24 | 0.87 |
| | | 5786 | 0.11 | 4.84 | 5.56 | 0.10 | 4.47 | 4.94 |
| | | AVG | 0.10 | 3.60 | 4.82 | 0.11 | 2.83 | 3.15 |
| 4 | p4584kb: pTau construct, UBITh1-ek-kkk-(S195-P213) SEQ ID NO: 57 | 5787 | 0.09 | 3.00 | 4.41 | 0.10 | 5.06 | 5.43 |
| | | 5788 | 0.09 | 2.54 | 3.54 | 0.09 | 5.53 | 9.14 |
| | | 5789 | 0.09 | 3.08 | 3.84 | 0.10 | 4.78 | 5.14 |
| | | AVG | 0.09 | 2.87 | 3.93 | 0.10 | 5.12 | 6.57 |
| 5 | p4586kb: pTau construct, UBITh1-ek-kkk-(S195-P213) SEQ ID NO: 59 | 5790 | 0.09 | 3.26 | 3.53 | 0.10 | 4.84 | 5.02 |
| | | 5791 | 0.09 | 4.38 | 4.73 | 0.09 | 4.82 | 5.10 |
| | | 5792 | 0.10 | 4.85 | 6.71 | 0.08 | 5.18 | 8.62 |
| | | AVG | 0.09 | 4.16 | 4.99 | 0.09 | 4.95 | 6.25 |
| 6 | p4587kb: pTau construct, UBITh1-ek-kkk-(R209-L224) SEQ ID NO: 60 | 5793 | 0.11 | 0.00 | 0.00 | 0.10 | 2.59 | 2.12 |
| | | 5794 | 0.10 | 0.00 | 0.00 | 0.10 | 3.04 | 3.03 |
| | | 5795 | 0.09 | 0.00 | 0.00 | 0.10 | 2.82 | 2.49 |
| | | AVG | 0.10 | 0.00 | 0.00 | 0.10 | 2.82 | 2.55 |
| 7 | p4589kb: pTau construct, UBITh1-ek-kkk-(V228-L243) SEQ ID NO: 62 | 5796 | 0.09 | 0.00 | 0.00 | 0.10 | 0.00 | 0.00 |
| | | 5797 | 0.08 | 0.00 | 0.00 | 0.09 | 0.00 | 0.00 |
| | | 5798 | 0.08 | 0.00 | 0.00 | 0.09 | 0.00 | 0.00 |
| | | AVG | 0.08 | 0.00 | 0.00 | 0.09 | 0.00 | 0.00 |
| 8 | p4599kb: pTau construct, UBITh1-ek-kkk-(K257-K274) SEQ ID NO: 64 | 5799 | 0.09 | 0.00 | 0.00 | 0.08 | 0.00 | 0.00 |
| | | 5800 | 0.10 | 0.00 | 0.00 | 0.09 | 0.00 | 0.00 |
| | | 5801 | 0.11 | 0.00 | 0.00 | 0.10 | 0.00 | 0.00 |
| | | AVG | 0.10 | 0.00 | 0.00 | 0.09 | 0.00 | 0.00 |
| 9 | p4601kb: pTau construct, UBITh1-ek-kkk-(R379-L408) SEQ ID NO: 66 | 5802 | 0.11 | 0.00 | 0.00 | 0.11 | 0.00 | 0.00 |
| | | 5803 | 0.10 | 0.00 | 0.00 | 0.09 | 0.00 | 0.00 |
| | | 5804 | 0.09 | 0.00 | 0.00 | 0.09 | 2.90 | 1.43 |
| | | AVG | 0.10 | 0.00 | 0.00 | 0.10 | 0.97 | 0.48 |

TABLE 11b-continued

Immunogenicity Analysis of phosphorylated Tau peptide constructs
Adjuvant: ISA 51VG; CpG3 50 μg/ml; 0.2% tween 80
Immunogen dose: Prime: 400 μg/1.0 ml/dose/IM
(four injection sites, 0.25 ml/site);
Boosts: 100 μg/0.25 ml/dose/IM
Vaccination schedule: 0, 3, 6 wpi

| | | | Anti-p4583a (P182-P200) ELISA Log$_{10}$ Titer (SEQ ID NO: 6) | | | Anti-p4585a (S195-P213) ELISA Log$_{10}$ Titer (SEQ ID NO: 8) | | |
|---|---|---|---|---|---|---|---|---|
| Grp # | Immunogen | GP# | 0 wpi | 3 wpi | 6 wpi | 0 wpi | 3 wpi | 6 wpi |
| 10 | p4603kb: pTau construct, UBITh1-ϵk-kkk-(V275-K311, P301→S301) SEQ ID NO: 68 | 5805 | 0.08 | 0.00 | 0.00 | 0.09 | 0.00 | 0.00 |
| | | 5806 | 0.09 | 0.00 | 0.00 | 0.08 | 0.00 | 0.00 |
| | | 5807 | 0.09 | 0.00 | 0.00 | 0.08 | 0.00 | 0.00 |
| | | AVG | 0.09 | 0.00 | 0.00 | 0.08 | 0.00 | 0.00 |
| 11 | p4606kb: pTau construct, UBITh1-ϵk-kkk-(V393-L425) SEQ ID NO: 70 | 5808 | 0.15 | 0.00 | 0.00 | 0.08 | 0.00 | 0.00 |
| | | 5809 | 0.11 | 0.00 | 0.00 | 0.10 | 0.00 | 0.00 |
| | | 5810 | 0.12 | 0.00 | 0.00 | 0.11 | 0.00 | 0.00 |
| | | AVG | 0.13 | 0.00 | 0.00 | 0.10 | 0.00 | 0.00 |

TABLE 11c

Immunogenicity Analysis of phosphorylated Tau peptide constructs
Adjuvant: ISA 51VG; CpG3 50 μg/ml; 0.2% tween 80
Immunogen dose: Prime: 400 μg/1.0 ml/dose/IM
(four injection sites, 0.25 ml/site);
Boosts: 100 μg/0.25 ml/dose/IM
Vaccination schedule: 0, 3, 6 wpi

| | | | Anti-p4588a (R209-L224) ELISA Log$_{10}$ Titer (SEQ ID NO: 11) | | | Anti-p4598a (V228-L243) ELISA Log$_{10}$ Titer (SEQ ID NO: 13) | | |
|---|---|---|---|---|---|---|---|---|
| Grp # | Immunogen | GP# | 0 wpi | 3 wpi | 6 wpi | 0 wpi | 3 wpi | 6 wpi |
| 1 | p4578kb: pTau construct, UBITh1-ϵk-kkk-(A145-P160) SEQ ID NO: 51 | 5778 | 0.10 | 0.00 | 0.00 | 0.20 | 0.00 | 0.00 |
| | | 5779 | 0.09 | 0.00 | 0.00 | 0.11 | 0.00 | 0.00 |
| | | 5780 | 0.09 | 0.00 | 0.00 | 0.10 | 0.00 | 0.00 |
| | | AVG | 0.09 | 0.00 | 0.00 | 0.14 | 0.00 | 0.00 |
| 2 | p4580kb: pTau construct, UBITh1-ϵk-kkk-(P172-P189) SEQ ID NO: 53 | 5781 | 0.10 | 0.00 | 0.00 | 0.10 | 0.00 | 0.00 |
| | | 5782 | 0.08 | 0.00 | 0.00 | 0.10 | 0.00 | 0.00 |
| | | 5783 | 0.08 | 0.00 | 0.00 | 0.11 | 0.00 | 0.00 |
| | | AVG | 0.09 | 0.00 | 0.00 | 0.10 | 0.00 | 0.00 |
| 3 | p4582kb: pTau construct, UBITh1-ϵk-kkk-(P182-P200) SEQ ID NO: 55 | 5784 | 0.08 | 0.00 | 0.00 | 0.10 | 0.00 | 0.00 |
| | | 5785 | 0.10 | 0.18 | 0.00 | 0.11 | 0.00 | 0.00 |
| | | 5786 | 0.11 | 2.01 | 2.67 | 0.19 | 0.00 | 0.00 |
| | | AVG | 0.10 | 0.73 | 0.89 | 0.13 | 0.00 | 0.00 |
| 4 | p4584kb: pTau construct, UBITh1-ϵk-kkk-(S195-P213) SEQ ID NO: 57 | 5787 | 0.10 | 3.13 | 2.83 | 0.10 | 0.00 | 0.00 |
| | | 5788 | 0.09 | 4.76 | 4.39 | 0.08 | 0.00 | 0.00 |
| | | 5789 | 0.10 | 1.33 | 2.51 | 0.09 | 0.00 | 0.00 |
| | | AVG | 0.10 | 3.07 | 3.24 | 0.09 | 0.00 | 0.00 |
| 5 | p4586kb: pTau construct, UBITh1-ϵk-kkk-(S195-P213) SEQ ID NO: 59 | 5790 | 0.09 | 2.35 | 2.55 | 0.09 | 0.00 | 0.00 |
| | | 5791 | 0.08 | 3.33 | 3.26 | 0.09 | 0.00 | 0.00 |
| | | 5792 | 0.08 | 4.82 | 4.82 | 0.09 | 0.00 | 0.00 |
| | | AVG | 0.08 | 3.50 | 3.54 | 0.09 | 0.00 | 0.00 |
| 6 | p4587kb: pTau construct, UBITh1-ϵk-kkk-(R209-L224) SEQ ID NO: 60 | 5793 | 0.10 | 5.01 | 5.11 | 0.09 | 0.00 | 0.00 |
| | | 5794 | 0.10 | 4.98 | 5.05 | 0.19 | 0.00 | 0.00 |
| | | 5795 | 0.09 | 5.27 | 5.22 | 0.09 | 2.62 | 1.56 |
| | | AVG | 0.10 | 5.09 | 5.13 | 0.12 | 0.87 | 0.52 |
| 7 | p4589kb: pTau construct, UBITh1-ϵk-kkk-(V228-L243) SEQ ID NO: 62 | 5796 | 0.09 | 0.00 | 2.74 | 0.08 | 4.40 | 4.98 |
| | | 5797 | 0.09 | 0.65 | 1.98 | 0.09 | 4.77 | 5.16 |
| | | 5798 | 0.08 | 0.00 | 0.00 | 0.09 | 3.75 | 4.68 |
| | | AVG | 0.09 | 0.22 | 1.57 | 0.09 | 4.31 | 4.94 |
| 8 | p4599kb: pTau construct, UBITh1-ϵk-kkk-(K257-K274) SEQ ID NO: 64 | 5799 | 0.08 | 0.00 | 0.00 | 0.08 | 0.00 | 0.00 |
| | | 5800 | 0.08 | 0.00 | 0.00 | 0.10 | 0.00 | 0.00 |
| | | 5801 | 0.10 | 0.00 | 0.00 | 0.10 | 0.00 | 0.00 |
| | | AVG | 0.09 | 0.00 | 0.00 | 0.09 | 0.00 | 0.00 |
| 9 | p4601kb: pTau construct, UBITh1-ϵk-kkk-(R379-L408) SEQ ID NO: 66 | 5802 | 0.09 | 0.00 | 2.28 | 0.18 | 0.00 | 0.00 |
| | | 5803 | 0.08 | 2.95 | 1.69 | 0.09 | 0.00 | 1.47 |
| | | 5804 | 0.08 | 2.26 | 0.00 | 0.08 | 0.00 | 0.83 |
| | | AVG | 0.08 | 1.74 | 1.32 | 0.12 | 0.00 | 0.77 |

TABLE 11c-continued

Immunogenicity Analysis of phosphorylated Tau peptide constructs
Adjuvant: ISA 51VG; CpG3 50 µg/ml; 0.2% tween 80
Immunogen dose: Prime: 400 µg/1.0 ml/dose/IM
(four injection sites, 0.25 ml/site);
Boosts: 100 µg/0.25 ml/dose/IM
Vaccination schedule: 0, 3, 6 wpi

| | | | Anti-p4588a (R209-L224) ELISA Log$_{10}$ Titer (SEQ ID NO: 11) | | | Anti-p4598a (V228-L243) ELISA Log$_{10}$ Titer (SEQ ID NO: 13) | | |
|---|---|---|---|---|---|---|---|---|
| Grp # | Immunogen | GP# | 0 wpi | 3 wpi | 6 wpi | 0 wpi | 3 wpi | 6 wpi |
| 10 | p4603kb: pTau construct, UBITh1-ϵk-kkk-(V275-K311, P301→S301) SEQ ID NO: 68 | 5805 | 0.09 | 0.00 | 0.00 | 0.08 | 0.00 | 0.00 |
| | | 5806 | 0.08 | 0.00 | 0.00 | 0.09 | 0.00 | 0.00 |
| | | 5307 | 0.09 | 0.00 | 0.00 | 0.09 | 0.00 | 0.00 |
| | | AVG | 0.09 | 0.00 | 0.00 | 0.09 | 0.00 | 0.00 |
| 11 | p4606kb: pTau construct, UBITh1-ϵk-kkk-(V393-L425) SEQ ID NO: 70 | 5808 | 0.08 | 3.29 | 4.85 | 0.09 | 0.00 | 0.00 |
| | | 5309 | 0.11 | 3.24 | 4.90 | 0.10 | 2.60 | 0.35 |
| | | 5510 | 0.09 | 3.16 | 3.17 | 0.10 | 0.00 | 0.00 |
| | | AVG | 0.09 | 3.23 | 4.31 | 0.10 | 0.87 | 0.28 |

TABLE 11d

Immunogenicity Analysis of phosphorylated Tau peptide constructs
Adjuvant: ISA 51VG; CpG3 50 µg/ml; 0.2% tween 80
Immunogen dose: Prime: 400 µg/1.0 ml/dose/IM
(four injection sites, 0.25 ml/site);
Boosts: 100 µg/0.25 ml/dose/IM
Vaccination schedule: 0, 3, 6 wpi

| | | | Anti-p4600a (K257-K274) ELISA Log10 Titer (SEQ ID NO: 15) | | | Anti-p4602a (R379-L408) ELISA Log10 Titer (SEQ ID NO: 17) | | |
|---|---|---|---|---|---|---|---|---|
| Grp # | Immunogen | GP# | 0 wpi | 3 wpi | 6 wpi | 0 wpi | 3 wpi | 6 wpi |
| 1 | p4578kb: pTau construct, UBITh1-ϵk-kkk-(A145-P160) SEQ ID NO: 51 | 5778 | 0.17 | 0.00 | 0.00 | 0.20 | 3.48 | 2.87 |
| | | 5779 | 0.09 | 0.00 | 0.00 | 0.10 | 3.10 | 2.93 |
| | | 5780 | 0.08 | 0.00 | 0.00 | 0.08 | 3.23 | 2.62 |
| | | AVG | 0.11 | 0.00 | 0.00 | 0.13 | 3.27 | 2.81 |
| 2 | p4580kb: pTau construct, UBITh1-ϵk-kkk-(P172-P189) SEQ ID NO: 53 | 5781 | 0.08 | 0.00 | 0.00 | 0.08 | 2.88 | 2.67 |
| | | 5782 | 0.08 | 0.00 | 0.00 | 0.08 | 0.32 | 0.00 |
| | | 5783 | 0.08 | 0.00 | 0.00 | 0.08 | 2.23 | 2.04 |
| | | AVG | 0.08 | 0.00 | 0.00 | 0.08 | 1.81 | 1.57 |
| 3 | p4582kb: pTau construct, UBITh1-ϵk-kkk-(P182-P200) SEQ ID NO: 55 | 5784 | 0.12 | 0.00 | 0.00 | 0.08 | 0.00 | 0.00 |
| | | 5785 | 0.10 | 0.00 | 0.00 | 0.09 | 0.00 | 0.00 |
| | | 5786 | 0.18 | 0.00 | 0.00 | 0.19 | 0.00 | 0.00 |
| | | AVG | 0.13 | 0.00 | 0.00 | 0.12 | 0.00 | 0.00 |
| 4 | p4584kb: pTau construct, UBITh1-ϵk-kkk-(S195-P213) SEQ ID NO: 57 | 5787 | 0.09 | 0.00 | 0.00 | 0.09 | 2.91 | 2.84 |
| | | 5788 | 0.08 | 0.00 | 0.00 | 0.09 | 2.86 | 3.42 |
| | | 5789 | 0.08 | 0.00 | 0.00 | 0.08 | 1.88 | 0.93 |
| | | AVG | 0.08 | 0.00 | 0.00 | 0.09 | 2.55 | 2.40 |
| 5 | p4586kb: pTau construct, UBITh1-ϵk-kkk-(S195-P213) SEQ ID NO: 59 | 5790 | 0.09 | 0.00 | 0.00 | 0.08 | 2.99 | 2.83 |
| | | 5791 | 0.08 | 0.00 | 0.00 | 0.08 | 4.20 | 4.03 |
| | | 5792 | 0.09 | 0.00 | 0.00 | 0.09 | 3.23 | 2.98 |
| | | AVG | 0.09 | 0.00 | 0.00 | 0.08 | 3.47 | 3.28 |
| 6 | p4587kb: pTau construct, UBITh1-ϵk-kkk-(R209-L224) SEQ ID NO: 60 | 5793 | 0.10 | 0.00 | 0.00 | 0.10 | 3.52 | 4.45 |
| | | 5794 | 0.18 | 0.00 | 0.00 | 0.15 | 2.71 | 2.85 |
| | | 5795 | 0.09 | 0.00 | 0.00 | 0.08 | 3.08 | 3.43 |
| | | AVG | 0.12 | 0.00 | 0.00 | 0.11 | 3.10 | 3.58 |
| 7 | p4589kb: pTau construct, UBITh1-ϵk-kkk-(V228-L243) SEQ ID NO: 62 | 5796 | 0.10 | 0.00 | 0.00 | 0.08 | 3.62 | 4.56 |
| | | 5797 | 0.08 | 0.00 | 0.00 | 0.09 | 4.48 | 4.34 |
| | | 5798 | 0.08 | 0.00 | 0.00 | 0.07 | 3.11 | 3.76 |
| | | AVG | 0.09 | 0.00 | 0.00 | 0.08 | 3.74 | 4.22 |
| 8 | p4599kb: pTau construct, UBITh1-ϵk-kkk-(K257-K274) SEQ ID NO: 64 | 5799 | 0.09 | 5.62 | 14.11 | 0.07 | 0.00 | 0.00 |
| | | 5800 | 0.10 | 5.84 | 9.55 | 0.09 | 0.00 | 0.00 |
| | | 5801 | 0.10 | 5.51 | 11.39 | 0.09 | 0.00 | 0.00 |
| | | AVG | 0.10 | 5.66 | 11.68 | 0.08 | 0.00 | 0.00 |
| 9 | p4601kb: pTau construct, UBITh1-ϵk-kkk-(R379-L408) SEQ ID NO: 66 | 5802 | 0.18 | 0.00 | 0.00 | 0.15 | 7.75 | 6.71 |
| | | 5803 | 0.10 | 0.00 | 0.00 | 0.09 | 13.34 | 12.63 |
| | | 5804 | 0.08 | 0.00 | 0.00 | 0.09 | 9.08 | 9.59 |
| | | AVG | 0.12 | 0.00 | 0.00 | 0.11 | 10.06 | 9.64 |
| 10 | p4603kb: pTau construct, UBITh1-ϵk-kkk-(V275-K311, P301→S301) SEQ ID NO: 68 | 5805 | 0.08 | 0.00 | 0.00 | 0.09 | 4.71 | 5.55 |
| | | 5806 | 0.08 | 0.00 | 0.00 | 0.08 | 4.53 | 5.34 |
| | | 5807 | 0.09 | 0.00 | 0.00 | 0.09 | 4.60 | 4.91 |
| | | AVG | 0.08 | 0.00 | 0.00 | 0.09 | 4.61 | 5.27 |

TABLE 11d-continued

Immunogenicity Analysis of phosphorylated Tau peptide constructs
Adjuvant: ISA 51VG; CpG3 50 µg/ml; 0.2% tween 80
Immunogen dose: Prime: 400 µg/1.0 ml/dose/IM
(four injection sites, 0.25 ml/site);
Boosts: 100 µg/0.25 ml/dose/IM
Vaccination schedule: 0, 3, 6 wpi

| | | | Anti-p4600a (K257-K274) ELISA Log10 Titer (SEQ ID NO: 15) | | | Anti-p4602a (R379-L408) ELISA Log10 Titer (SEQ ID NO: 17) | | |
|---|---|---|---|---|---|---|---|---|
| Grp # | Immunogen | GP# | 0 wpi | 3 wpi | 6 wpi | 0 wpi | 3 wpi | 6 wpi |
| 11 | p4606kb: pTau construct, UBITh1-ϵk-kkk-(V393-L425) SEQ ID NO: 70 | 5808 | 0.09 | 0.00 | 0.00 | 0.10 | 3.94 | 4.40 |
| | | 5809 | 0.10 | 0.00 | 0.00 | 0.10 | 2.81 | 3.41 |
| | | 5810 | 0.11 | 0.00 | 0.00 | 0.09 | 3.36 | 3.44 |
| | | AVG | 0.10 | 0.00 | 0.00 | 0.10 | 3.37 | 3.75 |

TABLE 11e

Immunogenicity Analysis of phosphorylated Tau peptide constructs
Adjuvant: ISA 51VG; CpG3 50 µg/ml; 0.2% tween 80
Immunogen dose: Prime: 400 µg/1.0 ml/dose/IM
(four injection sites, 0.25 ml/site);
Boosts: 100 µg/0.25 ml/dose/IM
Vaccination schedule: 0, 3, 6 wpi

| | | | Anti-p604a (V275-K311) ELISA Log10 Titer (SEQ ID NO: 19) | | | Anti-p4605a (V393-L425) ELISA Log10 Titer (SEQ ID NO: 21) | | |
|---|---|---|---|---|---|---|---|---|
| Grp # | Immunogen | GP# | 0 wpi | 3 wpi | 6 wpi | 0 wpi | 3 wpi | 6 wpi |
| 1 | p4578kb: pTau construct, UBITh1-ϵk-kkk-(A145-P160) SEQ ID NO: 51 | 5778 | 0.10 | 0.00 | 0.00 | 0.16 | 0.00 | 0.31 |
| | | 5779 | 0.09 | 0.00 | 0.00 | 0.09 | 0.00 | 0.00 |
| | | 5780 | 0.08 | 0.00 | 0.00 | 0.09 | 0.00 | 1.89 |
| | | AVG | 0.09 | 0.00 | 0.00 | 0.11 | 0.00 | 0.73 |
| 2 | p4580kb: pTau construct, UBITh1-ϵk-kkk-(P172-P189) SEQ ID NO: 53 | 5781 | 0.09 | 0.00 | 0.00 | 0.10 | 0.00 | 0.00 |
| | | 5782 | 0.08 | 0.00 | 0.00 | 0.09 | 0.00 | 0.00 |
| | | 5783 | 0.10 | 0.00 | 0.00 | 0.09 | 0.00 | 0.00 |
| | | AVG | 0.09 | 0.00 | 0.00 | 0.09 | 0.00 | 0.00 |
| 3 | p4582kb: pTau construct, UBITh1-ϵk-kkk-(P182-P200) SEQ ID NO: 55 | 5784 | 0.09 | 0.00 | 0.00 | 0.11 | 0.00 | 0.00 |
| | | 5785 | 0.11 | 0.00 | 0.00 | 0.10 | 0.00 | 0.00 |
| | | 5786 | 0.10 | 0.00 | 0.00 | 0.09 | 0.00 | 0.00 |
| | | AVG | 0.10 | 0.00 | 0.00 | 0.10 | 0.00 | 0.00 |
| 4 | p4584kb: pTau construct, UBITh1-ϵk-kkk-(S195-P213) SEQ ID NO: 57 | 5787 | 0.09 | 0.00 | 0.00 | 0.09 | 0.00 | 0.00 |
| | | 5788 | 0.08 | 0.00 | 0.00 | 0.10 | 0.00 | 0.00 |
| | | 5789 | 0.09 | 0.00 | 0.00 | 0.10 | 0.00 | 0.00 |
| | | AVG | 0.09 | 0.00 | 0.00 | 0.10 | 0.00 | 0.00 |
| 5 | p4586: pTau construct, UBITh1-ϵk-kkk-(S195-P213) SEQ ID NO: 59 | 5790 | 0.09 | 0.00 | 0.00 | 0.10 | 0.00 | 0.00 |
| | | 5791 | 0.09 | 0.00 | 0.00 | 0.11 | 0.00 | 0.00 |
| | | 5792 | 0.09 | 0.00 | 0.00 | 0.13 | 0.13 | 2.11 |
| | | AVG | 0.09 | 0.00 | 0.00 | 0.11 | 0.04 | 0.70 |
| 6 | p4587kb: pTau construct, UBITh1-ϵk-kkk-(R209-L224) SEQ ID NO: 60 | 5793 | 0.11 | 0.00 | 0.00 | 0.12 | 4.38 | 4.78 |
| | | 5794 | 0.10 | 0.00 | 0.00 | 0.12 | 4.38 | 4.47 |
| | | 5765 | 0.08 | 0.00 | 0.00 | 0.10 | 4.38 | 4.76 |
| | | AVG | 0.10 | 0.00 | 0.00 | 0.11 | 4.38 | 4.67 |
| 7 | p4589kb: pTau construct, UBITh1-ϵk-kkk-(V228-L243) SEQ ID NO: 62 | 5796 | 0.08 | 0.00 | 0.00 | 0.11 | 4.37 | 4.23 |
| | | 5797 | 0.09 | 0.00 | 0.00 | 0.10 | 4.33 | 4.51 |
| | | 5798 | 0.09 | 0.00 | 0.00 | 0.09 | 2.58 | 1.70 |
| | | AVG | 0.09 | 0.00 | 0.00 | 0.10 | 3.76 | 3.48 |
| 8 | p4599kb: pTau construct, UBITh1-ϵk-kkk-(K257-K274) SEQ ID NO: 64 | 5799 | 0.09 | 0.00 | 0.00 | 0.10 | 0.00 | 0.00 |
| | | 5800 | 0.10 | 0.00 | 0.00 | 0.11 | 0.00 | 0.00 |
| | | 5801 | 0.11 | 1.57 | 0.00 | 0.11 | 0.00 | 0.00 |
| | | AVG | 0.10 | 0.52 | 0.00 | 0.11 | 0.00 | 0.00 |
| 9 | p4601kb: pTau construct, UBITh1-ϵk-kkk-(R379-L408) SEQ ID NO: 66 | 5802 | 0.10 | 4.40 | 4.00 | 0.08 | 1.48 | 2.92 |
| | | 5803 | 0.09 | 5.10 | 4.90 | 0.09 | 3.03 | 3.17 |
| | | 5804 | 0.09 | 4.60 | 4.20 | 0.09 | 2.96 | 3.00 |
| | | AVG | 0.09 | 4.70 | 4.37 | 0.09 | 2.49 | 3.03 |
| 10 | p4603kb: pTau construct, UBITh1-ϵk-kkk-(V275-K311, P301→S301) SEQ ID NO: 68 | 5805 | 0.10 | 4.90 | 12.50 | 0.10 | 0.00 | 0.00 |
| | | 5806 | 0.10 | 4.80 | 13.10 | 0.09 | 0.00 | 0.00 |
| | | 5807 | 0.10 | 4.80 | 7.40 | 0.10 | 0.00 | 0.00 |
| | | AVG | 0.10 | 4.83 | 11.00 | 0.10 | 0.00 | 0.00 |

TABLE 11e-continued

Immunogenicity Analysis of phosphorylated Tau peptide constructs
Adjuvant: ISA 51VG; CpG3 50 μg/ml; 0.2% tween 80
Immunogen dose: Prime: 400 μg/1.0 ml/dose/IM
(four injection sites, 0.25 ml/site);
Boosts: 100 μg/0.25 ml/dose/IM
Vaccination schedule: 0, 3, 6 wpi

| | | | Anti-p604a (V275-K311) ELISA Log10 Titer (SEQ ID NO: 19) | | | Anti-p4605a (V393-L425) ELISA Log10 Titer (SEQ ID NO: 21) | | |
|---|---|---|---|---|---|---|---|---|
| Grp # | Immunogen | GP# | 0 wpi | 3 wpi | 6 wpi | 0 wpi | 3 wpi | 6 wpi |
| 11 | p4606kb: pTau construct, UBITh1-ϵk-kkk-(V393-L425) SEQ ID NO: 70 | 5508 | 0.10 | 0.00 | 0.00 | 0.11 | 10.14 | 13.15 |
| | | 5809 | 0.13 | 0.00 | 0.00 | 0.12 | 10.14 | 12.89 |
| | | 5810 | 0.09 | 0.00 | 0.00 | 0.09 | 5.87 | 6.92 |
| | | AVG | 0.11 | 0.00 | 0.00 | 0.11 | 8.72 | 10.99 |

TABLE 12

Immunogenicity Analysis of Tau peptide constructs containing B
epitope from the Tau hyperphosphorylation and aggregation site
Adjuvant: ISA 51VG; CpG3: 50 μg/ml; 0.2% tween 80
Immunogen dose: Prime: 400 μg/1.0 ml/dose/IM
four injection sites, 0.25 ml/site;
Boosts: 100 μg/0.25 ml/dose/IM
Vaccination schedule: 0, 3, 6 wpi

| | | | Anti-p5031a (131-141) ELISA Log10 Titer SEQ ID NO: 101 | | | Anti-p5032a (241-257) ELISA Log10 Titer SEQ ID NO: 102 | | | Anti-p5033a (243-259) ELISA Log10 Titer SEQ ID NO: 103 | | |
|---|---|---|---|---|---|---|---|---|---|---|---|
| Grp # | Immunogen | GP# | 0 wpi | 3 wpi | 6 wpi | 0 wpi | 3 wpi | 6 wpi | 0 wpi | 3 wpi | 6 wpi |
| 1 | p5031kb UBITh1-ϵk-kkk- Tau 131-141 SEQ ID NO: 125 | 6670 | 0.245 | 3.110 | 4.985 | 0.072 | 0.000 | 3.373 | 0.073 | 0.000 | 0.000 |
| | | 6671 | 0.291 | 4.538 | 5.765 | 0.083 | 2.309 | 4.448 | 0.069 | 0.988 | 3.366 |
| | | 6672 | 0.420 | 3.094 | 4.640 | 0.079 | 0.728 | 3.971 | 0.068 | 1.741 | 4.446 |
| | | Avg. | 0.319 | 3.581 | 5.130 | 0.078 | 1.012 | 3.931 | 0.070 | 0.910 | 2.604 |
| 2 | p5032kb UBITh1-ϵk-kkk- Tau 241-257 SEQ ID NO: 126 | 6673 | 0.565 | 2.622 | 0.000 | 0.089 | 4.960 | 5.276 | 0.091 | 4.415 | 4.737 |
| | | 6674 | 0.336 | 2.691 | 0.000 | 0.084 | >10 | 10.66 | 0.104 | 5.228 | 4.904 |
| | | 6675 | 0.174 | 2.595 | 0.000 | 0.076 | >10 | >10 | 0.071 | 5.488 | 5.266 |
| | | Avg. | 0.358 | 2.636 | 0.000 | 0.083 | 4.960 | 7.966 | 0.089 | 5.044 | 4.969 |
| 3 | p5033kb UBITh1-ϵk-kkk- Tau 243-259 SEQ ID NO: 127 | 6676 | 0.162 | 0.095 | 0.000 | 0.065 | 5.063 | 5.085 | 0.060 | 4.979 | 5.225 |
| | | 6677 | 0.202 | 1.374 | 0.000 | 0.065 | 4.694 | 4.784 | 0.065 | 4.644 | 4.893 |
| | | 6678 | 0.306 | 2.219 | 0.000 | 0.075 | 5.088 | 5.055 | 0.063 | 5.557 | 5.968 |
| | | Avg. | 0.223 | 1.229 | 0.000 | 0.068 | 4.948 | 4.975 | 0.063 | 5.060 | 5.362 |

TABLE 13a

Immunogenicity Analysis of Tau peptide constructs derived from B epitope
from Tau 275-311 region
Adjuvant: ISA 51VG; CpG3: 50 μg/ml; 0.2% tween 80
Immunogen dose: Prime: 400 μg/1.0 ml/dose/IM
four injection sites, 0.25 ml/site;
Boosts: 100 μg/0.25 ml/dose/IM
Vaccination schedule: 0, 3, 6 wpi

| | | | Anti-p5134a (275-281) ELISA Log10 Titer SEQ ID NO: 104 | | | Anti-p5135a (281-294) ELISA Log10 Titer SEQ ID NO: 105 | | | Anti-p5136a (275-294) ELISA Log10 Titer SEQ ID NO: 106 | | |
|---|---|---|---|---|---|---|---|---|---|---|---|
| Grp # | Immunogen | GP# | 0 wpi | 3 wpi | 6 wpi | 0 wpi | 3 wpi | 6 wpi | 0 wpi | 3 wpi | 6 wpi |
| 1 | p5134kb UBITh1-ϵk-kkk- Tau 275-281 SEQ ID NO: 128 | 6742 | 0.193 | 0.000 | 2.847 | 0.113 | 0.113 | 0.000 | 0.113 | 0.000 | 2.973 |
| | | 6743 | 0.192 | 0.284 | 3.255 | 0.102 | 0.102 | 1.240 | 0.102 | 0.648 | 3.160 |
| | | 6744 | 0.181 | 1.133 | 2.164 | 0.109 | 0.109 | 5.208 | 0.109 | 4.416 | 5.134 |
| | | Avg. | 0.189 | 0.472 | 2.755 | 0.108 | 0.108 | 2.149 | 0.108 | 1.688 | 3.756 |

TABLE 13a-continued

Immunogenicity Analysis of Tau peptide constructs derived from B epitope
from Tau 275-311 region
Adjuvant: ISA 51VG; CpG3: 50 μg/ml; 0.2% tween 80
Immunogen dose: Prime: 400 μg/1.0 ml/dose/IM
four injection sites, 0.25 ml/site;
Boosts: 100 μg/0.25 ml/dose/IM
Vaccination schedule: 0, 3, 6 wpi

| Grp # | Immunogen | GP# | Anti-p5134a (275-281) ELISA Log10 Titer SEQ ID NO: 104 | | | Anti-p5135a (281-294) ELISA Log10 Titer SEQ ID NO: 105 | | | Anti-p5136a (275-294) ELISA Log10 Titer SEQ ID NO: 106 | | |
|---|---|---|---|---|---|---|---|---|---|---|---|
| | | | 0 wpi | 3 wpi | 6 wpi | 0 wpi | 3 wpi | 6 wpi | 0 wpi | 3 wpi | 6 wpi |
| 2 | p5135kb | 6745 | 0.160 | 1.466 | 1.327 | 0.110 | 0.110 | 7.273 | 0.110 | 10.235 | 7.100 |
| | UBITh1-ϵk-kkk- | 6746 | 0.587 | 1.100 | 2.755 | 0.150 | 0.150 | 5.29 | 0.150 | 5.086 | 5.397 |
| | Tau 281-294 | 6747 | 0.269 | 1.509 | 3.056 | 0.103 | 0.103 | 7.733 | 0.103 | 9.398 | 8.508 |
| | SEQ ID NO: 129 | Avg. | 0.339 | 1.358 | 2.379 | 0.121 | 0.121 | 6.765 | 0.121 | 8.240 | 7.002 |
| 3 | p5136kb | 6748 | 0.485 | 0.000 | 1.848 | 0.126 | 0.126 | 6.723 | 0.126 | 5.107 | >10 |
| | UBITh1-ϵk-kkk- | 6749 | 0.232 | 1.555 | 1.048 | 0.149 | 0.149 | 7.746 | 0.149 | 6.862 | >10 |
| | Tau 275-294 | 6750 | 0.144 | 0.000 | 2.797 | 0.101 | 0.101 | 5.182 | 0.101 | 5.134 | 5.488 |
| | SEQ ID NO: 130 | Avg. | 0.287 | 0.518 | 1.898 | 0.125 | 0.125 | 6.550 | 0.125 | 5.701 | 5.488 |
| 4 | p5137kb | 6751 | 0.339 | 2.714 | 2.356 | 0.125 | 0.125 | 0.377 | 0.125 | 3.116 | 2.954 |
| | UBITh1-ϵk-kkk- | 6752 | 0.213 | 2.800 | 2.552 | 0.122 | 0.122 | 1.243 | 0.122 | 0.509 | 2.442 |
| | Tau 294-311 | 6753 | 0.201 | 2.701 | 2.709 | 0.101 | 0.101 | 0.000 | 0.101 | 3.522 | 3.743 |
| | SEQ ID NO: 131 | Avg. | 0.251 | 2.738 | 2.539 | 0.116 | 0.116 | 0.540 | 0.116 | 2.382 | 3.046 |
| 5 | p5138kb | 6754 | 0.222 | 2.829 | 2.985 | 0.154 | 0.154 | 2.201 | 0.154 | 1.348 | 2.159 |
| | UBITh1-ϵk-kkk- | 6755 | 0.378 | 2.971 | 3.121 | 0.106 | 0.106 | 1.361 | 0.106 | 0.000 | 0.000 |
| | Tau 294-311, P301→S301 | 6756 | 0.454 | 3.012 | 2.823 | 0.127 | 0.127 | 1.513 | 0.127 | 3.343 | 3.065 |
| | SEQ ID NO: 139 | Avg. | 0.351 | 2.937 | 2.976 | 0.129 | 0.129 | 1.692 | 0.129 | 1.564 | 1.741 |

TABLE 13b

| Grp # | Immunogen | GP# | Anti-p5137a (294-311) ELISA Log10 Titer SEQ ID NO: 107 | | | Anti-p5138a (294-311, P301→S301) ELISA Log10 Titer SEQ ID NO: 108 | | |
|---|---|---|---|---|---|---|---|---|
| | | | 0 wpi | 3 wpi | 6 wpi | 0 wpi | 3 wpi | 6 wpi |
| 1 | p5134kb | 6742 | 0.120 | 0.000 | 0.000 | 0.124 | 0.000 | 0.000 |
| | UBITh1-ϵk-kkk- | 6743 | 0.104 | 0.000 | 0.000 | 0.125 | 0.000 | 0.000 |
| | Tau 275-281 | 6744 | 0.114 | 1.075 | 4.557 | 0.096 | 0.804 | 4.514 |
| | SEQ ID NO: 128 | Avg. | 0.113 | 0.353 | 1.519 | 0.115 | 0.268 | 1.505 |
| 2 | p5135kb | 6745 | 0.092 | 0.000 | 0.000 | 0.095 | 0.000 | 0.000 |
| | UBITh1-ϵk-kkk- | 6746 | 0.068 | 0.000 | 0.000 | 0.097 | 0.000 | 0.000 |
| | Tau 281-294 | 6747 | 0.102 | 0.000 | 0.000 | 0.146 | 0.000 | 0.000 |
| | SEQ ID NO: 129 | Avg. | 0.087 | 0.000 | 0.000 | 0.113 | 0.000 | 0.000 |
| 3 | p5136kb | 6748 | 0.085 | 0.000 | 0.805 | 0.117 | 0.000 | 0.712 |
| | UBITh1-ϵk-kkk- | 6749 | 0.086 | 2.787 | 2.896 | 0.096 | 2.892 | 2.715 |
| | Tau 275-294 | 6750 | 0.105 | 0.000 | 2.448 | 0.110 | 0.000 | 2.466 |
| | SEQ ID NO: 130 | Avg. | 0.092 | 0.929 | 2.050 | 0.108 | 0.964 | 1.964 |
| 4 | p5137kb | 6751 | 0.097 | 4.910 | 5.151 | 0.130 | 4.927 | 5.122 |
| | UBITh1-ϵk-kkk- | 6752 | 0.112 | 5.015 | 5.130 | 0.099 | 5.035 | 5.136 |
| | Tau 294-311 | 6753 | 0.111 | 4.999 | 5.236 | 0.088 | 5.001 | 5.199 |
| | SEQ ID NO: 131 | Avg. | 0.107 | 4.975 | 5.172 | 0.105 | 4.988 | 5.152 |
| 5 | p5138kb | 6754 | 0.086 | 4.851 | 5.185 | 0.103 | 4.896 | 5.405 |
| | UBITh1-ϵk-kkk- | 6755 | 0.077 | 4.997 | 11.375 | 0.125 | 5.078 | 11.562 |
| | Tau 294-311, P301→S301 | 6756 | 0.080 | 4.945 | 4.957 | 0.108 | 4.960 | 5.034 |
| | SEQ ID NO: 132 | Avg. | 0.081 | 4.931 | 7.172 | 0.112 | 4.978 | 7.334 |

TABLE 14

Immunogenicity Analysis of Tau peptide constructs from Tau N-terminal 'fuzzy coat'
Adjuvant: ISA 51VG; CpG3: 50 µg/ml; 0.2% tween 80
Immunogen dose: Prime: 400 µg/1.0 ml/dose/IM
four injection sites, 0.25 ml/site;
Boosts: 100 µg/0.25 ml/dose/IM
Vaccination schedule: 0, 3, 6 wpi

| | | | Anti-p5160a (D22-D34) ELISA $Log_{10}$ Titer SEQ ID NO: 112 | | | Anti-p5161a (Y18-D34) ELISA $Log_{10}$ Titer SEQ ID NO: 113 | | | Anti-p5162a (D22-D38) ELISA $Log_{10}$ Titer SEQ ID NO: 114 | | |
|---|---|---|---|---|---|---|---|---|---|---|---|
| Grp # | Immunogen | GP# | 0 wpi | 3 wpi | 6 wpi | 0 wpi | 3 wpi | 6 wpi | 0 wpi | 3 wpi | 6 wpi |
| 1 | p5160kb | 6898 | 0.190 | 4.913 | 5.564 | 0.080 | 5.943 | 9.261 | 0.075 | 3.303 | 4.186 |
| | UBITh1-εK-KKK- | 6899 | 0.205 | 4.786 | 5.002 | 0.071 | 5.356 | 5.206 | 0.084 | 3.316 | 4.188 |
| | Tau D22-D34 | 6900 | 0.205 | 4.844 | 5.016 | 0.073 | 5.047 | 5.343 | 0.070 | 0.000 | 3.392 |
| | SEQ ID NO: 137 | Avg. | 0.200 | 4.848 | 5.194 | 0.075 | 5.449 | 6.603 | 0.076 | 2.206 | 3.922 |
| 2 | p5161kb | 6901 | 0.327 | 5.017 | 7.534 | 0.079 | 6.650 | 10.454 | 0.064 | 3.264 | 4.380 |
| | UBITh1-εK-KKK- | 6902 | 0.135 | 3.461 | 4.870 | 0.057 | 4.783 | 5.189 | 0.056 | 2.164 | 3.982 |
| | Tau Y18-D34 | 6903 | 0.310 | 3.643 | 5.048 | 0.070 | 4.887 | 5.339 | 0.059 | 1.919 | 3.472 |
| | SEQ ID NO: 133 | Avg. | 0.257 | 4.040 | 5.817 | 0.069 | 5.440 | 6.994 | 0.060 | 2.449 | 3.945 |
| 3 | p5162kb | 6904 | 0.159 | 3.471 | 4.139 | 0.062 | 4.883 | 4.862 | 0.055 | 4.600 | 5.408 |
| | UBITh1-εK-KKK- | 6905 | 0.264 | 3.092 | 3.683 | 0.076 | 4.663 | 4.696 | 0.071 | 4.694 | 5.228 |
| | Tau D22-D38 | 6906 | 0.117 | 3.316 | 4.505 | 0.051 | 4.826 | 5.004 | 0.063 | 3.726 | 5.091 |
| | SEQ ID NO: 139 | Avg. | 0.150 | 3.293 | 4.109 | 0.073 | 4.791 | 4.854 | 0.063 | 4.340 | 5.242 |

TABLE 15

Immunogenicity Analysis of Tau peptide constructs
containing P301 trans from Tau aggregation-prone location
Adjuvant: ISA 51VG; CpG3: 50 µg/ml; 0.2% tween 80
Immunogen dose: Prime: 400 µg/1.0 ml/dose/IM
four injection sites, 0.25 ml/site;
Boosts: 100 µg/0.25 ml/dose/IM
Vaccination schedule: 0, 3, 6 wpi

| | | | Anti-p5159a (275-311, P301 trans) ELISA $Log_{10}$ Titer SEQ ID NO: 110 | | | Anti-p5193a (297-311, P301 trans) ELISA $Log_{10}$ Titer SEQ ID NO: 111 | | | Anti-p5137a (294-311) ELISA $Log_{10}$ Titer SEQ ID NO: 107 | | | Anti-p4604a (275-311) ELISA $Log_{10}$ Titer SEQ ID NO: 19 | | |
|---|---|---|---|---|---|---|---|---|---|---|---|---|---|---|
| Grp # | Immunogen | GP# | 0 wpi | 3 wpi | 6 wpi | 0 wpi | 3 wpi | 6 wpi | 0 wpi | 3 wpi | 6 wpi | 0 wpi | 3 wpi | 6 wpi |
| 1 | p5158kb | 6919 | 0.094 | 5.080 | 5.866 | 0.064 | 2.813 | 4.759 | 0.075 | 3.727 | 5.083 | 0 wpi | 3 wpi | 6 wpi |
| | UBITh1-εK-KKK-K294- | 6920 | 0.078 | >10 | 13.839 | 0.086 | 4.850 | 4.913 | 0.095 | 5.533 | 5.217 | 0.069 | 5.069 | 6.126 |
| | K311, P301 trans | 6921 | 2.312 | 5.113 | 6.209 | 0.078 | 2.227 | 4.753 | 0.093 | 3.991 | 5.033 | 0.101 | >10 | 11.667 |
| | SEQ ID NO: 135 | Avg. | 0.828 | 5.097 | 8.638 | 0.076 | 3.297 | 4.808 | 0.088 | 4.417 | 5.111 | 0.073 | 5.209 | 6.836 |
| 2 | p5159kb | 6922 | 0.097 | 5.532 | 5.772 | 0.090 | 4.683 | 4.774 | 0.080 | 4.911 | 5.006 | 0.081 | 5.139 | 8.210 |
| | UBITh1-εK-KKK-V275- | 6923 | 0.084 | 7.204 | >10 | 0.099 | 4.687 | 5.000 | 0.086 | 4.975 | 5.540 | 0.075 | 5.604 | 5.938 |
| | K311, P301 trans | 6924 | 0.068 | 5.105 | 8.242 | 0.069 | 2.709 | 4.729 | 0.072 | 3.425 | 4.991 | 0.096 | 7.207 | >10 |
| | SEQ ID NO: 136 | Avg. | 0.083 | 5.947 | 7.007 | 0.086 | 4.026 | 4.834 | 0.080 | 4.437 | 5.179 | 0.074 | 5.143 | 9.951 |
| 3 | p5183kb | 6925 | 0.086 | 5.834 | 7.915 | 0.085 | 4.944 | 5.068 | 0.071 | 4.975 | 5.195 | 0.081 | 5.985 | 7.945 |
| | UBITh1-εK-KKK-I297- | 6926 | 0.063 | 5.245 | 13.971 | 0.072 | 3.510 | 5.111 | 0.071 | 4.898 | 5.792 | 0.061 | 5.991 | 8.297 |
| | K311, P301 trans | 6927 | 0.077 | 5.446 | 6.285 | 0.069 | 4.525 | 4.792 | 0.063 | 4.829 | 5.118 | 0.059 | 5.307 | 13.885 |
| | SEQ ID NO: 140 | Avg. | 0.075 | 5.508 | 9.390 | 0.076 | 4.326 | 4.990 | 0.068 | 4.901 | 5.368 | 0.062 | 5.574 | 6.294 |
| 4 | p5184kb | 6928 | 0.071 | 3.613 | 5.096 | 0.089 | 2.818 | 3.646 | 0.074 | 1.703 | 4.023 | 0.060 | 5.624 | 9.492 |
| | I297-K311, P301 trans- | 6929 | 0.084 | 4.787 | 5.038 | 0.079 | 3.364 | 3.898 | 0.107 | 3.287 | 4.563 | 0.063 | 3.536 | 5.039 |
| | KKK-εK-UBITh1 | 6930 | 0.079 | 4.959 | 5.109 | 0.077 | 3.506 | 4.645 | 0.078 | 3.005 | 4.781 | 0.065 | 4.806 | 5.058 |
| | SEQ ID NO: 141 | Avg. | 0.078 | 4.453 | 5.081 | 0.082 | 3.229 | 4.063 | 0.086 | 2.665 | 4.456 | 0.070 | 4.787 | 5.091 |

TABLE 16

Localization of Immunogenic region within Tau 275-311 through fine epitope mapping

| | 275 | 311 | Hyperimmune serum (6w) p4603 kb, UBITh1-εK-KKK-(V275-K311, P301→S301) SEQ ID NO: 68 |
|---|---|---|---|
| SEQ ID NO: 19 | VQIINKKLDLSNVQSKCGSKDNIKHVPGGGSVQIVYK | | Abs (450 nm) |
| SEQ ID NO: 156 (281-311) | KLDLSNVQSKCGSKDNIKHVPGGGSVQMVYK | | 3.782 |
| SEQ ID NO: 157 (283-311) | DLSNVQSKCGSKDNIKITVPGGGSVQIVYK | | 3.802 |
| SEQ ID NO: 158 (285-311) | SNVQSKCGSYDNIKHVPGGGSVQIVYK | | 3.788 |
| SEQ ID NO: 159 (287-311) | VQSKCGSKDNIKHVPGGGSVQMVYK | | 3.836 |
| SEQ ID NO: 160 (289-311) | SKCGSYDNIKHVPGGGSVQIVYK | | 3.826 |
| SEQ ID NO: 161 (291-311) | CGSYDNIKHVPGGGSVQIVYK | | 3.781 |
| SEQ ID NO: 162 (293-311) | SKDNIKHVPGGGSVQMVYK | | 3.837 |
| SEQ ID NO: 163 (295-311) | DNIKHVPGGGSVQIVYK | | 3.732 |
| SEQ ID NO: 115 (297-311) | IKHVPGGGSVQIVYK | | 3.477 |
| SEQ ID NO: 164 (299-311) | HVPGGGSVQIVYK | | 0.221 |
| SEQ ID NO: 165 (301-311) | PGGGSVQIVYK | | 0.099 |
| SEQ ID NO: 166 (275-305) | VQIINKKLDLSNVQSKCGSKDNIKHVPGGGS | | 0.148 |
| SEQ ID NO: 167 (275-301) | VQIINKKLDLSNVQSKCGSKDNIKHVP | | 0.281 |
| SEQ ID NO: 168 (275-297) | VQIINKKLDLSNVQSKCGSYDNI | | 0.303 |
| SEQ ID NO: 169 (275-293) | VQIINKKLDLSNVQSKCGS | | 0.320 |
| SEQ ID NO: 170 (275-289) | VQIINKKLDLSNVQS | | 0.091 |
| SEQ ID NO: 171 (275-285) | VQIINKKLDLS | | 0.095 |
| SEQ ID NO: 19 (4604a, Tau V275-K311) | | | 3.994 |

The invention claimed is:

1. A Tau peptide immunogen construct can be represented by the formulae:

$$(Th)_m\text{-}(A)_n\text{-}(Tau\ fragment)\text{-}X$$

or $$(Tau\ fragment)\text{-}(A)_n\text{-}(Th)_m\text{-}X$$

wherein
Th is a heterologous T helper epitope;
A is a heterologous spacer;
(Tau fragment) comprises;
X is an α-COOH or α-CONH$_2$ of an amino acid;
m is from 1 to about 4; and
n is from 0 to about 10;
wherein the peptide immunogen construct comprises the amino acid sequence of SEO ID No: 69.

2. The Tau peptide immunogen construct according to claim 1, wherein the Tau fragment comprises the amino acid sequence of SEO ID No: 19.

3. The Tau peptide immunogen construct according to claim 1, wherein the Th epitope comprises the amino acid sequence of SEO ID No: 35.

4. A composition comprising the peptide immunogen construction according to claim 1.

5. A pharmaceutical composition comprising:
a. the peptide immunogen construct according to claim 1; and
b. and a pharmaceutically acceptable delivery vehicle and/or adjuvant.

6. A Tau peptide immunogen construct comprising:
a B cell epitope comprising amino acid sequence No: 19;
a T helper epitope comprising the amino acid sequence of SEQ ID No: 35; and
an optional heterologous spacer selected from the group consisting of an amino acid, Lys-, Gly-, Lys-Lys-Lys-, (α, ε-N)Lys, and ε-N-Lys-Lys-Lys-Lys (SEQ ID NO: 102),
wherein the B cell epitope is covalently linked to the T helper epitope directly or through the optional heterologous spacer.

7. The Tau peptide immunogen construct of claim 6, wherein the optional heterologous spacer is (α, ε-N)Lys or α-N-Lys-Lys-Lys-Lys (SEQ ID NO: 102).

8. The Tau peptide immunogen construct of claim 6, wherein the T helper epitope is covalently linked to the amino terminus of the B cell epitope.

9. The Tau peptide immunogen construct of claim 6, wherein the T helper epitope is covalently linked to the amino terminus of the B cell epitope through the optional heterologous spacer.

10. The pharmaceutical composition of claim 5, wherein
a. the Tau peptide immunogen construct comprises the amino acid sequence of SEQ ID No: 69; and
b. the Tau peptide immunogen construct is mixed with an CpG oligodeoxynucleotide (ODN) to form a stabilized immunostimulatory complex.

* * * * *

SEQUENCE LISTING

<160> NUMBER OF SEQ ID NOS: 171

<210> SEQ ID NO 1
<211> LENGTH: 16
<212> TYPE: PRT
<213> ORGANISM: Homo sapiens
<220> FEATURE:
<221> NAME/KEY: PEPTIDE
<222> LOCATION: (1)..(16)

```
<223> OTHER INFORMATION: pTau peptide - aa145-160 (pT149/pT153)
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 1

Ala Asp Gly Lys Thr Lys Ile Ala Thr Pro Arg Gly Ala Ala Pro Pro
1               5                   10                  15

<210> SEQ ID NO 2
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: Tau peptide - aa145-160

<400> SEQUENCE: 2

Ala Asp Gly Lys Thr Lys Ile Ala Thr Pro Arg Gly Ala Ala Pro Pro
1               5                   10                  15

<210> SEQ ID NO 3
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: pTau peptide - aa172-189 (pT175/pT181/pS185)
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION

<400> SEQUENCE: 3

Pro Ala Lys Thr Pro Pro Ala Pro Lys Thr Pro Pro Ser Ser Gly Glu
1               5                   10                  15

Pro Pro

<210> SEQ ID NO 4
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: Tau peptide - aa172-189

<400> SEQUENCE: 4

Pro Ala Lys Thr Pro Pro Ala Pro Lys Thr Pro Pro Ser Ser Gly Glu
1               5                   10                  15

Pro Pro

<210> SEQ ID NO 5
<211> LENGTH: 19
```

```
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: pTau peptide - aa182-200 (pS184/pY197)
<220> FEATURE:
<221> NAME/KEY: MOD_RES
<222> LOCATION: (3)..(3)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION

<400> SEQUENCE: 5

Pro Pro Ser Ser Gly Glu Pro Pro Lys Ser Gly Asp Arg Ser Gly Tyr
1               5                   10                  15

Ser Ser Pro

<210> SEQ ID NO 6
<211> LENGTH: 19
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: Tau peptide - aa182-200

<400> SEQUENCE: 6

Pro Pro Ser Ser Gly Glu Pro Pro Lys Ser Gly Asp Arg Ser Gly Tyr
1               5                   10                  15

Ser Ser Pro

<210> SEQ ID NO 7
<211> LENGTH: 19
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: pTau peptide - aa195-213 (pS198/pS208/pS210)
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (14)..(14)
<223> OTHER INFORMATION: PHOSPHORYLATION
<220> FEATURE:
<221> NAME/KEY: MOD_RES
<222> LOCATION: (16)..(16)
<223> OTHER INFORMATION: PHOSPHORYLATION

<400> SEQUENCE: 7

Ser Gly Tyr Ser Ser Pro Gly Ser Pro Gly Thr Pro Gly Ser Arg Ser
1               5                   10                  15

Arg Thr Pro

<210> SEQ ID NO 8
<211> LENGTH: 19
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: Tau peptide - aa195-213

<400> SEQUENCE: 8
```

Ser Gly Tyr Ser Ser Pro Gly Ser Pro Gly Thr Pro Gly Ser Arg Ser
1               5                   10                  15

Arg Thr Pro

<210> SEQ ID NO 9
<211> LENGTH: 19
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: pTau peptide - aa 195-213 (pS199/pS202/pT205)
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 9

Ser Gly Tyr Ser Ser Pro Gly Ser Pro Gly Thr Pro Gly Ser Arg Ser
1               5                   10                  15

Arg Thr Pro

<210> SEQ ID NO 10
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: pTau peptide - aa209-224 (pT212/pS214/pT217)
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 10

Arg Ser Arg Thr Pro Ser Leu Pro Thr Pro Pro Thr Arg Glu Pro Lys
1               5                   10                  15

<210> SEQ ID NO 11
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: Tau peptide - aa209-224

<400> SEQUENCE: 11

Arg Ser Arg Thr Pro Ser Leu Pro Thr Pro Pro Thr Arg Glu Pro Lys
1               5                   10                  15

<210> SEQ ID NO 12

```
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: pTau peptide - aa228-243 (pT231/pS235/pS238)
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (11)..(11)
<223> OTHER INFORMATION: PHOSPHORYLATION

<400> SEQUENCE: 12

Val Val Arg Thr Pro Pro Lys Ser Pro Ser Ser Ala Lys Ser Arg Leu
1               5                   10                  15

<210> SEQ ID NO 13
<211> LENGTH: 16
<212> TYPE: PRT
<213> ORGANISM: Homo sapiens
<220> FEATURE:
<221> NAME/KEY: PEPTIDE
<222> LOCATION: (1)..(16)
<223> OTHER INFORMATION: Tau peptide - aa228-243

<400> SEQUENCE: 13

Val Val Arg Thr Pro Pro Lys Ser Pro Ser Ser Ala Lys Ser Arg Leu
1               5                   10                  15

<210> SEQ ID NO 14
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: pTau peptide - aa257-274 (pS262)
<220> FEATURE:
<221> NAME/KEY: MOD_RES
<222> LOCATION: (6)..(6)
<223> OTHER INFORMATION: PHOSPHORYLATION

<400> SEQUENCE: 14

Lys Ser Lys Ile Gly Ser Thr Glu Asn Leu Lys His Gln Pro Gly Gly
1               5                   10                  15

Gly Lys

<210> SEQ ID NO 15
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: Tau peptide - aa257-274

<400> SEQUENCE: 15

Lys Ser Lys Ile Gly Ser Thr Glu Asn Leu Lys His Gln Pro Gly Gly
1               5                   10                  15

Gly Lys
```

-continued

```
<210> SEQ ID NO 16
<211> LENGTH: 30
<212> TYPE: PRT
<213> ORGANISM: Homo sapiens
<220> FEATURE:
<221> NAME/KEY: PEPTIDE
<222> LOCATION: (1)..(30)
<223> OTHER INFORMATION: pTau peptide - aa379-408 (pS396/pS404)
<220> FEATURE:
<221> NAME/KEY: MOD_RES
<222> LOCATION: (18)..(18)
<223> OTHER INFORMATION: PHOSPHORYLATION
<220> FEATURE:
<221> NAME/KEY: MOD_RES
<222> LOCATION: (26)..(26)
<223> OTHER INFORMATION: PHOSPHORYLATION

<400> SEQUENCE: 16

Arg Glu Asn Ala Lys Ala Lys Thr Asp His Gly Ala Glu Ile Val Tyr
 1               5                  10                  15

Lys Ser Pro Val Val Ser Gly Asp Thr Ser Pro Arg His Leu
            20                  25                  30

<210> SEQ ID NO 17
<211> LENGTH: 30
<212> TYPE: PRT
<213> ORGANISM: Homo sapiens
<220> FEATURE:
<221> NAME/KEY: PEPTIDE
<222> LOCATION: (1)..(30)
<223> OTHER INFORMATION: Tau peptide - aa379-408

<400> SEQUENCE: 17

Arg Glu Asn Ala Lys Ala Lys Thr Asp His Gly Ala Glu Ile Val Tyr
 1               5                  10                  15

Lys Ser Pro Val Val Ser Gly Asp Thr Ser Pro Arg His Leu
            20                  25                  30

<210> SEQ ID NO 18
<211> LENGTH: 37
<212> TYPE: PRT
<213> ORGANISM: Homo sapiens
<220> FEATURE:
<221> NAME/KEY: PEPTIDE
<222> LOCATION: (1)..(37)
<223> OTHER INFORMATION: pTau peptide - aa275-311; *P301->S;
      (pS293/pS301)
<220> FEATURE:
<221> NAME/KEY: MOD_RES
<222> LOCATION: (19)..(19)
<223> OTHER INFORMATION: PHOSPHORYLATION
<220> FEATURE:
<221> NAME/KEY: MOD_RES
<222> LOCATION: (27)..(27)
<223> OTHER INFORMATION: PHOSPHORYLATION

<400> SEQUENCE: 18

Val Gln Ile Ile Asn Lys Lys Leu Asp Leu Ser Asn Val Gln Ser Lys
 1               5                  10                  15

Cys Gly Ser Lys Asp Asn Ile Lys His Val Ser Gly Gly Gly Ser Val
            20                  25                  30

Gln Ile Val Tyr Lys
        35

<210> SEQ ID NO 19
<211> LENGTH: 37
<212> TYPE: PRT
<213> ORGANISM: Homo sapiens
<220> FEATURE:
```

```
<221> NAME/KEY: PEPTIDE
<222> LOCATION: (1)..(37)
<223> OTHER INFORMATION: Tau peptide - aa275-311

<400> SEQUENCE: 19

Val Gln Ile Ile Asn Lys Lys Leu Asp Leu Ser Asn Val Gln Ser Lys
1               5                   10                  15

Cys Gly Ser Lys Asp Asn Ile Lys His Val Pro Gly Gly Gly Ser Val
            20                  25                  30

Gln Ile Val Tyr Lys
        35

<210> SEQ ID NO 20
<211> LENGTH: 33
<212> TYPE: PRT
<213> ORGANISM: Homo sapiens
<220> FEATURE:
<221> NAME/KEY: PEPTIDE
<222> LOCATION: (1)..(33)
<223> OTHER INFORMATION: pTau peptide - aa393-425 (pS396/pS404/pS422)
<220> FEATURE:
<221> NAME/KEY: MOD_RES
<222> LOCATION: (4)..(4)
<223> OTHER INFORMATION: PHOSPHORYLATION
<220> FEATURE:
<221> NAME/KEY: MOD_RES
<222> LOCATION: (12)..(12)
<223> OTHER INFORMATION: PHOSPHORYLATION
<220> FEATURE:
<221> NAME/KEY: MOD_RES
<222> LOCATION: (30)..(30)
<223> OTHER INFORMATION: PHOSPHORYLATION

<400> SEQUENCE: 20

Val Tyr Lys Ser Pro Val Val Ser Gly Asp Thr Ser Pro Arg His Leu
1               5                   10                  15

Ser Asn Val Ser Ser Thr Gly Ser Ile Asp Met Val Asp Ser Pro Gln
            20                  25                  30

Leu

<210> SEQ ID NO 21
<211> LENGTH: 33
<212> TYPE: PRT
<213> ORGANISM: Homo sapiens
<220> FEATURE:
<221> NAME/KEY: PEPTIDE
<222> LOCATION: (1)..(33)
<223> OTHER INFORMATION: Tau peptide - aa393-425

<400> SEQUENCE: 21

Val Tyr Lys Ser Pro Val Val Ser Gly Asp Thr Ser Pro Arg His Leu
1               5                   10                  15

Ser Asn Val Ser Ser Thr Gly Ser Ile Asp Met Val Asp Ser Pro Gln
            20                  25                  30

Leu

<210> SEQ ID NO 22
<211> LENGTH: 17
<212> TYPE: PRT
<213> ORGANISM: Clostridium tetani
<220> FEATURE:
<221> NAME/KEY: PEPTIDE
<222> LOCATION: (1)..(17)
<223> OTHER INFORMATION: Clostridium tetani 1 Th

<400> SEQUENCE: 22
```

Lys Lys Gln Tyr Ile Lys Ala Asn Ser Lys Phe Ile Gly Ile Thr Glu
1               5                   10                  15

Leu

<210> SEQ ID NO 23
<211> LENGTH: 15
<212> TYPE: PRT
<213> ORGANISM: Measles virus
<220> FEATURE:
<221> NAME/KEY: PEPTIDE
<222> LOCATION: (1)..(15)
<223> OTHER INFORMATION: MvF1 Th

<400> SEQUENCE: 23

Leu Ser Glu Ile Lys Gly Val Ile Val His Arg Leu Glu Gly Val
1               5                   10                  15

<210> SEQ ID NO 24
<211> LENGTH: 24
<212> TYPE: PRT
<213> ORGANISM: Bordetella pertussis
<220> FEATURE:
<221> NAME/KEY: PEPTIDE
<222> LOCATION: (1)..(24)
<223> OTHER INFORMATION: Bordetella pertussis Th

<400> SEQUENCE: 24

Gly Ala Tyr Ala Arg Cys Pro Asn Gly Thr Arg Ala Leu Thr Val Ala
1               5                   10                  15

Glu Leu Arg Gly Asn Ala Glu Leu
            20

<210> SEQ ID NO 25
<211> LENGTH: 17
<212> TYPE: PRT
<213> ORGANISM: Clostridium tetani
<220> FEATURE:
<221> NAME/KEY: PEPTIDE
<222> LOCATION: (1)..(17)
<223> OTHER INFORMATION: Clostridium tetani 2 Th

<400> SEQUENCE: 25

Trp Val Arg Asp Ile Ile Asp Asp Phe Thr Asn Glu Ser Ser Gln Lys
1               5                   10                  15

Thr

<210> SEQ ID NO 26
<211> LENGTH: 23
<212> TYPE: PRT
<213> ORGANISM: Artificial Sequence
<220> FEATURE:
<223> OTHER INFORMATION: Synthetic peptide containing Diphtheria Th
      epitope
<220> FEATURE:
<221> NAME/KEY: PEPTIDE
<222> LOCATION: (1)..(23)
<223> OTHER INFORMATION: Diphtheria Th

<400> SEQUENCE: 26

Asp Ser Glu Thr Ala Asp Asn Leu Glu Lys Thr Val Ala Ala Leu Ser
1               5                   10                  15

Ile Leu Pro Gly His Gly Cys
            20

<210> SEQ ID NO 27
<211> LENGTH: 21

```
<212> TYPE: PRT
<213> ORGANISM: Plasmodium falciparum
<220> FEATURE:
<221> NAME/KEY: PEPTIDE
<222> LOCATION: (1)..(21)
<223> OTHER INFORMATION: Plasmodium falciparum Th

<400> SEQUENCE: 27

Asp His Glu Lys Lys His Ala Lys Met Glu Lys Ala Ser Ser Val Phe
1               5                   10                  15

Asn Val Val Asn Ser
            20

<210> SEQ ID NO 28
<211> LENGTH: 17
<212> TYPE: PRT
<213> ORGANISM: Schistosoma mansoni
<220> FEATURE:
<221> NAME/KEY: PEPTIDE
<222> LOCATION: (1)..(17)
<223> OTHER INFORMATION: Schistosoma mansoni Th

<400> SEQUENCE: 28

Lys Trp Phe Lys Thr Asn Ala Pro Asn Gly Val Asp Glu Lys His Arg
1               5                   10                  15

His

<210> SEQ ID NO 29
<211> LENGTH: 25
<212> TYPE: PRT
<213> ORGANISM: Artificial Sequence
<220> FEATURE:
<223> OTHER INFORMATION: Synthetic peptide containing Cholera Toxin Th
      epitope
<220> FEATURE:
<221> NAME/KEY: PEPTIDE
<222> LOCATION: (1)..(25)
<223> OTHER INFORMATION: Cholera Toxin Th

<400> SEQUENCE: 29

Ala Leu Asn Ile Trp Asp Arg Phe Asp Val Phe Cys Thr Leu Gly Ala
1               5                   10                  15

Thr Thr Gly Tyr Leu Lys Gly Asn Ser
            20                  25

<210> SEQ ID NO 30
<211> LENGTH: 15
<212> TYPE: PRT
<213> ORGANISM: Measles virus
<220> FEATURE:
<221> NAME/KEY: PEPTIDE
<222> LOCATION: (1)..(15)
<223> OTHER INFORMATION: MvF 2 Th

<400> SEQUENCE: 30

Ile Ser Glu Ile Lys Gly Val Ile Val His Lys Ile Glu Gly Ile
1               5                   10                  15

<210> SEQ ID NO 31
<211> LENGTH: 22
<212> TYPE: PRT
<213> ORGANISM: Measles virus
<220> FEATURE:
<221> NAME/KEY: PEPTIDE
<222> LOCATION: (1)..(22)
<223> OTHER INFORMATION: KKKMvF 3 Th
<220> FEATURE:
<221> NAME/KEY: SITE
```

```
<222> LOCATION: (7)..(7)
<223> OTHER INFORMATION: S or T
<220> FEATURE:
<221> NAME/KEY: SITE
<222> LOCATION: (10)..(10)
<223> OTHER INFORMATION: K or R
<220> FEATURE:
<221> NAME/KEY: SITE
<222> LOCATION: (11)..(11)
<223> OTHER INFORMATION: G or T
<220> FEATURE:
<221> NAME/KEY: SITE
<222> LOCATION: (15)..(15)
<223> OTHER INFORMATION: H or T
<220> FEATURE:
<221> NAME/KEY: SITE
<222> LOCATION: (16)..(16)
<223> OTHER INFORMATION: K or R
<220> FEATURE:
<221> NAME/KEY: SITE
<222> LOCATION: (19)..(19)
<223> OTHER INFORMATION: G or T

<400> SEQUENCE: 31

Lys Lys Lys Ile Ser Ile Xaa Glu Ile Xaa Xaa Val Ile Val Xaa Xaa
1               5                   10                  15

Ile Glu Xaa

```
<223> OTHER INFORMATION: L or I or V or F
<220> FEATURE:
<221> NAME/KEY: SITE
<222> LOCATION: (13)..(13)
<223> OTHER INFORMATION: L or I or V or F
<220> FEATURE:
<221> NAME/KEY: SITE
<222> LOCATION: (15)..(15)
<223> OTHER INFORMATION: Q or L or I or V or F
<220> FEATURE:
<221> NAME/KEY: SITE
<222> LOCATION: (17)..(17)
<223> OTHER INFORMATION: L or I or V or F
<220> FEATURE:
<221> NAME/KEY: SITE
<222> LOCATION: (18)..(18)
<223> OTHER INFORMATION: D or R

<400> SEQUENCE: 32

Xaa Xaa Xaa Xaa Xaa Xaa Xaa Thr Xaa Xaa Xaa Thr Xaa Pro Xaa Ser
1               5                   10                  15

Xaa Xaa

<210> SEQ ID NO 33
<211> LENGTH: 19
<212> TYPE: PRT
<213> ORGANISM: Measles virus
<220> FEATURE:
<221> NAME/KEY: PEPTIDE
<222> LOCATION: (1)..(19)
<223> OTHER INFORMATION: MvF 4 Th
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R

<400> SEQUENCE: 33

Ile Ser Ile Xaa Glu Ile Xaa Xaa Val Ile Val Xaa Xaa Ile Glu Thr
1               5                   10                  15

Ile Leu Phe

<210> SEQ ID NO 34
<211> LENGTH: 18
<212> TYPE: PRT
<213> ORGANISM: Hepatitis B virus
<220> FEATURE:
<221> NAME/KEY: PEPTIDE
<222> LOCATION: (1)..(18)
<223> OTHER INFORMATION: HBsAg 2 Th
<220> FEATURE:
<221> NAME/KEY: SITE
<222> LOCATION: (4)..(4)
<223> OTHER INFORMATION: I or F
<220> FEATURE:
<221> NAME/KEY: SITE
<222> LOCATION: (5)..(5)
<223> OTHER INFORMATION: I or F
```

```
<220> FEATURE:
<221> NAME/KEY: SITE
<222> LOCATION: (6)..(6)
<223> OTHER INFORMATION: T or L
<220> FEATURE:
<221> NAME/KEY: SITE
<222> LOCATION: (7)..(7)
<223> OTHER INFORMATION: I or L
<220> FEATURE:
<221> NAME/KEY: SITE
<222> LOCATION: (11)..(11)
<223> OTHER INFORMATION: I or L
<220> FEATURE:
<221> NAME/KEY: SITE
<222> LOCATION: (14)..(14)
<223> OTHER INFORMATION: P or I
<220> FEATURE:
<221> NAME/KEY: SITE
<222> LOCATION: (15)..(15)
<223> OTHER INFORMATION: Q or T
<220> FEATURE:
<221> NAME/KEY: SITE
<222> LOCATION: (16)..(16)
<223> OTHER INFORMATION: S or T
<220> FEATURE:
<221> NAME/KEY: SITE
<222> LOCATION: (17)..(17)
<223> OTHER INFORMATION: L or I

<400> SEQUENCE: 34

Lys Lys Lys Xaa Xaa Xaa Xaa Thr Arg Ile Xaa Thr Ile Xaa Xaa Xaa
1               5                   10                  15

Xaa Asp

<210> SEQ ID NO 35
<211> LENGTH: 19
<212> TYPE: PRT
<213> ORGANISM: Measles virus
<220> FEATURE:
<221> NAME/KEY: PEPTIDE
<222> LOCATION: (1)..(19)
<223> OTHER INFORMATION: MvF 5 Th

<400> SEQUENCE: 35

Ile Ser Ile Thr Glu Ile Lys Gly Val Ile Val His Arg Ile Glu Thr
1               5                   10                  15

Ile Leu Phe

<210> SEQ ID NO 36
<211> LENGTH: 18
<212> TYPE: PRT
<213> ORGANISM: Hepatitis B virus
<220> FEATURE:
<221> NAME/KEY: PEPTIDE
<222> LOCATION: (1)..(18)
<223> OTHER INFORMATION: HBsAg 3 Th

<400> SEQUENCE: 36

Lys Lys Lys Ile Ile Thr Ile Thr Arg Ile Ile Thr Ile Ile Thr Thr
1               5                   10                  15

Ile Asp

<210> SEQ ID NO 37
<211> LENGTH: 11
<212> TYPE: PRT
<213> ORGANISM: Influenza virus
<220> FEATURE:
<221> NAME/KEY: PEPTIDE
<222> LOCATION: (1)..(11)
<223> OTHER INFORMATION: Influenza Matrix protein 1 _1 Th
```

-continued

```
<220> FEATURE:
<221> NAME/KEY: PEPTIDE
<222> LOCATION: (1)..(11)
<223> OTHER INFORMATION: Influenza Matrix protein 1_1 Th

<400> SEQUENCE: 37

Phe Val Phe Thr Leu Thr Val Pro Ser Glu Arg
1               5                   10

<210> SEQ ID NO 38
<211> LENGTH: 15
<212> TYPE: PRT
<213> ORGANISM: Influenza virus
<220> FEATURE:
<221> NAME/KEY: PEPTIDE
<222> LOCATION: (1)..(15)
<223> OTHER INFORMATION: Influenza Matrix protein 1_2 Th

<400> SEQUENCE: 38

Ser Gly Pro Leu Lys Ala Glu Ile Ala Gln Arg Leu Glu Asp Val
1               5                   10                  15

<210> SEQ ID NO 39
<211> LENGTH: 9
<212> TYPE: PRT
<213> ORGANISM: Influenza virus
<220> FEATURE:
<221> NAME/KEY: PEPTIDE
<222> LOCATION: (1)..(9)
<223> OTHER INFORMATION: Influenza Non-structural protein 1 Th

<400> SEQUENCE: 39

Asp Arg Leu Arg Arg Asp Gln Lys Ser
1               5

<210> SEQ ID NO 40
<211> LENGTH: 19
<212> TYPE: PRT
<213> ORGANISM: Epstein-Barr virus
<220> FEATURE:
<221> NAME/KEY: PEPTIDE
<222> LOCATION: (1)..(19)
<223> OTHER INFORMATION: EBV BHRF1 Th

<400> SEQUENCE: 40

Ala Gly Leu Thr Leu Ser Leu Leu Val Ile Cys Ser Tyr Leu Phe Ile
1               5                   10                  15

Ser Arg Gly

<210> SEQ ID NO 41
<211> LENGTH: 15
<212> TYPE: PRT
<213> ORGANISM: Clostridium tetani
<220> FEATURE:
<221> NAME/KEY: PEPTIDE
<222> LOCATION: (1)..(15)
<223> OTHER INFORMATION: Clostridium tetani TT1 Th

<400> SEQUENCE: 41

Gln Tyr Ile Lys Ala Asn Ser Lys Phe Ile Gly Ile Thr Glu Leu
1               5                   10                  15

<210> SEQ ID NO 42
<211> LENGTH: 20
<212> TYPE: PRT
<213> ORGANISM: Epstein-Barr virus
<220> FEATURE:
<221> NAME/KEY: PEPTIDE
```

<222> LOCATION: (1)..(20)
<223> OTHER INFORMATION: EBV EBNA-1 Th

<400> SEQUENCE: 42

Pro Gly Pro Leu Arg Glu Ser Ile Val Cys Tyr Phe Met Val Phe Leu
1               5                   10                  15

Gln Thr His Ile
            20

<210> SEQ ID NO 43
<211> LENGTH: 21
<212> TYPE: PRT
<213> ORGANISM: Clostridium tetani
<220> FEATURE:
<221> NAME/KEY: PEPTIDE
<222> LOCATION: (1)..(21)
<223> OTHER INFORMATION: Clostridium tetani TT2 Th

<400> SEQUENCE: 43

Phe Asn Asn Phe Thr Val Ser Phe Trp Leu Arg Val Pro Lys Val Ser
1               5                   10                  15

Ala Ser His Leu Glu
            20

<210> SEQ ID NO 44
<211> LENGTH: 16
<212> TYPE: PRT
<213> ORGANISM: Clostridium tetani
<220> FEATURE:
<221> NAME/KEY: PEPTIDE
<222> LOCATION: (1)..(16)
<223> OTHER INFORMATION: Clostridium tetani TT3 Th

<400> SEQUENCE: 44

Lys Phe Ile Ile Lys Arg Tyr Thr Pro Asn Asn Glu Ile Asp Ser Phe
1               5                   10                  15

<210> SEQ ID NO 45
<211> LENGTH: 16
<212> TYPE: PRT
<213> ORGANISM: Clostridium tetani
<220> FEATURE:
<221> NAME/KEY: PEPTIDE
<222> LOCATION: (1)..(16)
<223> OTHER INFORMATION: Clostridium tetani TT4 Th

<400> SEQUENCE: 45

Val Ser Ile Asp Lys Phe Arg Ile Phe Cys Lys Ala Leu Asn Pro Lys
1               5                   10                  15

<210> SEQ ID NO 46
<211> LENGTH: 18
<212> TYPE: PRT
<213> ORGANISM: Epstein-Barr virus
<220> FEATURE:
<221> NAME/KEY: PEPTIDE
<222> LOCATION: (1)..(18)
<223> OTHER INFORMATION: EBV CP Th

<400> SEQUENCE: 46

Val Pro Gly Leu Tyr Ser Pro Cys Arg Ala Phe Phe Asn Lys Glu Glu
1               5                   10                  15

Leu Leu

<210> SEQ ID NO 47
<211> LENGTH: 14

```
<212> TYPE: PRT
<213> ORGANISM: Human cytomegalovirus
<220> FEATURE:
<221> NAME/KEY: PEPTIDE
<222> LOCATION: (1)..(14)
<223> OTHER INFORMATION: HCMV IE1 Th

<400> SEQUENCE: 47

Asp Lys Arg Glu Met Trp Met Ala Cys Ile Lys Glu Leu His
1               5                   10

<210> SEQ ID NO 48
<211> LENGTH: 15
<212> TYPE: PRT
<213> ORGANISM: Epstein-Barr virus
<220> FEATURE:
<221> NAME/KEY: PEPTIDE
<222> LOCATION: (1)..(15)
<223> OTHER INFORMATION: EBV GP340 Th

<400> SEQUENCE: 48

Thr Gly His Gly Ala Arg Thr Ser Thr Glu Pro Thr Thr Asp Tyr
1               5                   10                  15

<210> SEQ ID NO 49
<211> LENGTH: 13
<212> TYPE: PRT
<213> ORGANISM: Epstein-Barr virus
<220> FEATURE:
<221> NAME/KEY: PEPTIDE
<222> LOCATION: (1)..(13)
<223> OTHER INFORMATION: EBV BPLF1 Th

<400> SEQUENCE: 49

Lys Glu Leu Lys Arg Gln Tyr Glu Lys Lys Leu Arg Gln
1               5                   10

<210> SEQ ID NO 50
<211> LENGTH: 11
<212> TYPE: PRT
<213> ORGANISM: Epstein-Barr virus
<220> FEATURE:
<221> NAME/KEY: PEPTIDE
<222> LOCATION: (1)..(11)
<223> OTHER INFORMATION: EBV EBNA-2 Th

<400> SEQUENCE: 50

Thr Val Phe Tyr Asn Ile Pro Pro Met Pro Leu
1               5                   10

<210> SEQ ID NO 51
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(39)
```

<223> OTHER INFORMATION: pTau 145-P160 (pT149/pT153)
<220> FEATURE:
<221> NAME/KEY: MOD_RES
<222> LOCATION: (28)..(28)
<223> OTHER INFORMATION: PHOSPHORYLATION
<220> FEATURE:
<221> NAME/KEY: MOD_RES
<222> LOCATION: (32)..(32)
<223> OTHER INFORMATION: PHOSPHORYLATION

<400> SEQUENCE: 51

Ile Ser Ile Thr Glu Ile Lys Gly Val Ile Val His Arg Ile Glu Thr
1               5                   10                  15

Ile Leu Phe Lys Lys Lys Lys Ala Asp Gly Lys Thr Lys Ile Ala Thr
            20                  25                  30

Pro Arg Gly Ala Ala Pro Pro
        35

<210> SEQ ID NO 52
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(39)
<223> OTHER INFORMATION: Tau 145-160

<400> SEQUENCE: 52

Ile Ser Ile Thr Glu Ile Lys Gly Val Ile Val His Arg Ile Glu Thr
1               5                   10                  15

Ile Leu Phe Lys Lys Lys Lys Ala Asp Gly Lys Thr Lys Ile Ala Thr
            20                  25                  30

Pro Arg Gly Ala Ala Pro Pro
        35

<210> SEQ ID NO 53
<211> LENGTH: 41
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(41)
<223> OTHER INFORMATION: pTau 172-189 (pT175/pT181/pS185)

```
<220> FEATURE:
<221> NAME/KEY: MOD_RES
<222> LOCATION: (27)..(27)
<223> OTHER INFORMATION: PHOSPHORYLATION
<220> FEATURE:
<221> NAME/KEY: MOD_RES
<222> LOCATION: (33)..(33)
<223> OTHER INFORMATION: PHOSPHORYLATION
<220> FEATURE:
<221> NAME/KEY: MOD_RES
<222> LOCATION: (37)..(37)
<223> OTHER INFORMATION: PHOSPHORYLATION

<400> SEQUENCE: 53

Ile Ser Ile Thr Glu Ile Lys Gly Val Ile Val His Arg Ile Glu Thr
1               5                   10                  15

Ile Leu Phe Lys Lys Lys Lys Pro Ala Lys Thr Pro Pro Ala Pro Lys
            20                  25                  30

Thr Pro Pro Ser Ser Gly Glu Pro Pro
        35                  40

<210> SEQ ID NO 54
<211> LENGTH: 41
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(41)
<223> OTHER INFORMATION: Tau 172-189

<400> SEQUENCE: 54

Ile Ser Ile Thr Glu Ile Lys Gly Val Ile Val His Arg Ile Glu Thr
1               5                   10                  15

Ile Leu Phe Lys Lys Lys Lys Pro Ala Lys Thr Pro Pro Ala Pro Lys
            20                  25                  30

Thr Pro Pro Ser Ser Gly Glu Pro Pro
        35                  40

<210> SEQ ID NO 55
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
```

```
<221> NAME/KEY: PEPTIDE
<222> LOCATION: (24)..(42)
<223> OTHER INFORMATION: pTau 182-200 (pS184/pY197)
<220> FEATURE:
<221> NAME/KEY: MOD_RES
<222> LOCATION: (26)..(26)
<223> OTHER INFORMATION: PHOSPHORYLATION
<220> FEATURE:
<221> NAME/KEY: MOD_RES
<222> LOCATION: (39)..(39)
<223> OTHER INFORMATION: PHOSPHORYLATION

<400> SEQUENCE: 55

Ile Ser Ile Thr Glu Ile Lys Gly Val Ile Val His Arg Ile Glu Thr
1               5                   10                  15

Ile Leu Phe Lys Lys Lys Lys Pro Pro Ser Ser Gly Glu Pro Pro Lys
            20                  25                  30

Ser Gly Asp Arg Ser Gly Tyr Ser Ser Pro
        35                  40

<210> SEQ ID NO 56
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(42)
<223> OTHER INFORMATION: Tau 182-200

<400> SEQUENCE: 56

Ile Ser Ile Thr Glu Ile Lys Gly Val Ile Val His Arg Ile Glu Thr
1               5                   10                  15

Ile Leu Phe Lys Lys Lys Lys Pro Pro Ser Ser Gly Glu Pro Pro Lys
            20                  25                  30

Ser Gly Asp Arg Ser Gly Tyr Ser Ser Pro
        35                  40

<210> SEQ ID NO 57
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
```

```
<222> LOCATION: (24)..(42)
<223> OTHER INFORMATION: pTau 195-213  (pS199/pS202/pT205)
<220> FEATURE:
<221> NAME/KEY: MOD_RES
<222> LOCATION: (28)..(28)
<223> OTHER INFORMATION: PHOSPHORYLATION
<220> FEATURE:
<221> NAME/KEY: MOD_RES
<222> LOCATION: (31)..(31)
<223> OTHER INFORMATION: PHOSPHORYLATION
<220> FEATURE:
<221> NAME/KEY: MOD_RES
<222> LOCATION: (34)..(34)
<223> OTHER INFORMATION: PHOSPHORYLATION

<400> SEQUENCE: 57

Ile Ser Ile Thr Glu Ile Lys Gly Val Ile Val His Arg Ile Glu Thr
1               5                   10                  15

Ile Leu Phe Lys Lys Lys Lys Ser Gly Tyr Ser Ser Pro Gly Ser Pro
            20                  25                  30

Gly Thr Pro Gly Ser Arg Ser Arg Thr Pro
        35                  40

<210> SEQ ID NO 58
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(42)
<223> OTHER INFORMATION: Tau 195-213

<400> SEQUENCE: 58

Ile Ser Ile Thr Glu Ile Lys Gly Val Ile Val His Arg Ile Glu Thr
1               5                   10                  15

Ile Leu Phe Lys Lys Lys Lys Ser Gly Tyr Ser Ser Pro Gly Ser Pro
            20                  25                  30

Gly Thr Pro Gly Ser Arg Ser Arg Thr Pro
        35                  40

<210> SEQ ID NO 59
<211> LENGTH: 42
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF 5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
```

```
<223> OTHER INFORMATION: epsilon K-KKK as a spacer
<220> FEATURE:
<221> NAME/KEY: PEPTIDE
<222> LOCATION: (24)..(42)
<223> OTHER INFORMATION: pTau 195-213 (pS198/pS208/pS210)
<220> FEATURE:
<221> NAME/KEY: MOD_RES
<222> LOCATION: (27)..(27)
<223> OTHER INFORMATION: PHOSPHORYLATION
<220> FEATURE:
<221> NAME/KEY: MOD_RES
<222> LOCATION: (37)..(37)
<223> OTHER INFORMATION: PHOSPHORYLATION
<220> FEATURE:
<221> NAME/KEY: MOD_RES
<222> LOCATION: (39)..(39)
<223> OTHER INFORMATION: PHOSPHORYLATION

<400> SEQUENCE: 59

Ile Ser Ile Ser Glu Ile Lys Gly Val Ile Val His Lys Ile Glu Thr
1               5                   10                  15

Ile Leu Phe Lys Lys Lys Lys Ser Gly Tyr Ser Ser Pro Gly Ser Pro
            20                  25                  30

Gly Thr Pro Gly Ser Arg Ser Arg Thr Pro
            35                  40

<210> SEQ ID NO 60
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(39)
<223> OTHER INFORMATION: pTau 209-224 (pT212/pS214/pT217)
<220> FEATURE:
<221> NAME/KEY: MOD_RES
<222> LOCATION: (27)..(27)
<223> OTHER INFORMATION: PHOSPHORYLATION
<220> FEATURE:
<221> NAME/KEY: MOD_RES
<222> LOCATION: (29)..(29)
<223> OTHER INFORMATION: PHOSPHORYLATION
<220> FEATURE:
<221> NAME/KEY: MOD_RES
<222> LOCATION: (32)..(32)
<223> OTHER INFORMATION: PHOSPHORYLATION

<400> SEQUENCE: 60

Ile Ser Ile Thr Glu Ile Lys Gly Val Ile Val His Arg Ile Glu Thr
1               5                   10                  15

Ile Leu Phe Lys Lys Lys Lys Arg Ser Arg Thr Pro Thr Pro Gly Ser
            20                  25                  30

Arg Ser Arg Thr Pro Ser Leu
            35

<210> SEQ ID NO 61
<211> LENGTH: 39
```

-continued

```
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(39)
<223> OTHER INFORMATION: Tau 209-224

<400> SEQUENCE: 61

Ile Ser Ile Thr Glu Ile Lys Gly Val Ile Val His Arg Ile Glu Thr
1               5                   10                  15

Ile Leu Phe Lys Lys Lys Lys Arg Ser Arg Thr Pro Thr Pro Gly Ser
            20                  25                  30

Arg Ser Arg Thr Pro Ser Leu
        35

<210> SEQ ID NO 62
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(39)
<223> OTHER INFORMATION: pTau 228-243 (pT231/pS235/pS238)
<220> FEATURE:
<221> NAME/KEY: MOD_RES
<222> LOCATION: (27)..(27)
<223> OTHER INFORMATION: PHOSPHORYLATION
<220> FEATURE:
<221> NAME/KEY: MOD_RES
<222> LOCATION: (31)..(31)
<223> OTHER INFORMATION: PHOSPHORYLATION
<220> FEATURE:
<221> NAME/KEY: MOD_RES
<222> LOCATION: (34)..(34)
<223> OTHER INFORMATION: PHOSPHORYLATION

<400> SEQUENCE: 62

Ile Ser Ile Thr Glu Ile Lys Gly Val Ile Val His Arg Ile Glu Thr
1               5                   10                  15

Ile Leu Phe Lys Lys Lys Lys Val Val Arg Thr Pro Pro Lys Ser Pro
            20                  25                  30

Ser Ser Ala Lys Ser Arg Leu
        35
```

```
<210> SEQ ID NO 63
<211> LENGTH: 39
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(39)
<223> OTHER INFORMATION: Tau 228-243

<400> SEQUENCE: 63

Ile Ser Ile Thr Glu Ile Lys Gly Val Ile Val His Arg Ile Glu Thr
1               5                   10                  15

Ile Leu Phe Lys Lys Lys Lys Val Val Arg Thr Pro Pro Lys Ser Pro
            20                  25                  30

Ser Ser Ala Lys Ser Arg Leu
        35

<210> SEQ ID NO 64
<211> LENGTH: 41
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(41)
<223> OTHER INFORMATION: pTau 257-274 (pS262)
<220> FEATURE:
<221> NAME/KEY: MOD_RES
<222> LOCATION: (29)..(29)
<223> OTHER INFORMATION: PHOSPHORYLATION

<400> SEQUENCE: 64

Ile Ser Ile Thr Glu Ile Lys Gly Val Ile Val His Arg Ile Glu Thr
1               5                   10                  15

Ile Leu Phe Lys Lys Lys Lys Lys Ser Lys Ile Gly Ser Thr Glu Asn
            20                  25                  30

Leu Lys His Gln Pro Gly Gly Gly Lys
        35                  40

<210> SEQ ID NO 65
<211> LENGTH: 41
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(41)
<223> OTHER INFORMATION: Tau 257-274

<400> SEQUENCE: 65

Ile Ser Ile Thr Glu Ile Lys Gly Val Ile Val His Arg Ile Glu Thr
1               5                   10                  15

Ile Leu Phe Lys Lys Lys Lys Ser Lys Ile Gly Ser Thr Glu Asn
            20                  25                  30

Leu Lys His Gln Pro Gly Gly Gly Lys
        35                  40

<210> SEQ ID NO 66
<211> LENGTH: 53
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(53)
<223> OTHER INFORMATION: pTau 379-408 (pS396/pS404)
<220> FEATURE:
<221> NAME/KEY: MOD_RES
<222> LOCATION: (41)..(41)
<223> OTHER INFORMATION: PHOSPHORYLATION
<220> FEATURE:
<221> NAME/KEY: MOD_RES
<222> LOCATION: (49)..(49)
<223> OTHER INFORMATION: PHOSPHORYLATION

<400> SEQUENCE: 66

Ile Ser Ile Thr Glu Ile Lys Gly Val Ile Val His Arg Ile Glu Thr
1               5                   10                  15

Ile Leu Phe Lys Lys Lys Lys Arg Glu Asn Ala Lys Ala Lys Thr Asp
            20                  25                  30

His Gly Ala Glu Ile Val Tyr Lys Ser Pro Val Val Ser Gly Asp Thr
        35                  40                  45

Ser Pro Arg His Leu
    50

<210> SEQ ID NO 67
<211> LENGTH: 53
```

```
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(53)
<223> OTHER INFORMATION: Tau 379-408

<400> SEQUENCE: 67

Ile Ser Ile Thr Glu Ile Lys Gly Val Ile Val His Arg Ile Glu Thr
1               5                   10                  15

Ile Leu Phe Lys Lys Lys Lys Arg Glu Asn Ala Lys Ala Lys Thr Asp
            20                  25                  30

His Gly Ala Glu Ile Val Tyr Lys Ser Pro Val Val Ser Gly Asp Thr
        35                  40                  45

Ser Pro Arg His Leu
    50

<210> SEQ ID NO 68
<211> LENGTH: 60
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF 5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(60)
<223> OTHER INFORMATION: pTau 275-311 (*P301->S301; pS293/pS301)
<220> FEATURE:
<221> NAME/KEY: MOD_RES
<222> LOCATION: (42)..(42)
<223> OTHER INFORMATION: PHOSPHORYLATION
<220> FEATURE:
<221> NAME/KEY: MOD_RES
<222> LOCATION: (50)..(50)
<223> OTHER INFORMATION: PHOSPHORYLATION

<400> SEQUENCE: 68

Ile Ser Ile Ser Glu Ile Lys Gly Val Ile Val His Lys Ile Glu Thr
1               5                   10                  15

Ile Leu Phe Lys Lys Lys Lys Val Gln Ile Ile Asn Lys Lys Leu Asp
            20                  25                  30

Leu Ser Asn Val Gln Ser Lys Cys Gly Ser Lys Asp Asn Ile Lys His
        35                  40                  45

Val Ser Gly Gly Gly Ser Val Gln Ile Val Tyr Lys
```

-continued

```
                50              55              60

<210> SEQ ID NO 69
<211> LENGTH: 60
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(60)
<223> OTHER INFORMATION: Tau 275-311

<400> SEQUENCE: 69

Ile Ser Ile Thr Glu Ile Lys Gly Val Ile Val His Arg Ile Glu Thr
1               5                   10                  15

Ile Leu Phe Lys Lys Lys Lys Val Gln Ile Ile Asn Lys Lys Leu Asp
            20                  25                  30

Leu Ser Asn Val Gln Ser Lys Cys Gly Ser Lys Asp Asn Ile Lys His
        35                  40                  45

Val Pro Gly Gly Gly Ser Val Gln Ile Val Tyr Lys
    50                  55                  60

<210> SEQ ID NO 70
<211> LENGTH: 56
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(56)
<223> OTHER INFORMATION: pTau 393-425 (pS396/pS404/pS422)
<220> FEATURE:
<221> NAME/KEY: MOD_RES
<222> LOCATION: (27)..(27)
<223> OTHER INFORMATION: PHOSPHORYLATION
<220> FEATURE:
<221> NAME/KEY: MOD_RES
<222> LOCATION: (35)..(35)
<223> OTHER INFORMATION: PHOSPHORYLATION
<220> FEATURE:
<221> NAME/KEY: MOD_RES
<222> LOCATION: (53)..(53)
<223> OTHER INFORMATION: PHOSPHORYLATION

<400> SEQUENCE: 70

Ile Ser Ile Thr Glu Ile Lys Gly Val Ile Val His Arg Ile Glu Thr
```

```
                1               5                  10                  15
Ile Leu Phe Lys Lys Lys Lys Val Tyr Lys Ser Pro Val Val Ser Gly
                20                  25                  30

Asp Thr Ser Pro Arg His Leu Ser Asn Val Ser Ser Thr Gly Ser Ile
            35                  40                  45

Asp Met Val Asp Ser Pro Gln Leu
        50                  55

<210> SEQ ID NO 71
<211> LENGTH: 56
<212> TYPE: PRT
<213> ORGANISM: Artificial Sequence
<220> FEATURE:
<223> OTHER INFORMATION: Synthetic Peptide
<220> FEATURE:
<221> NAME/KEY: PEPTIDE
<222> LOCATION: (1)..(19)
<223> OTHER INFORMATION: MvF5 Th
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(56)
<223> OTHER INFORMATION: Tau 393-425

<400> SEQUENCE: 71

Ile Ser Ile Thr Glu Ile Lys Gly Val Ile Val His Arg Ile Glu Thr
1               5                   10                  15

Ile Leu Phe Lys Lys Lys Lys Val Tyr Lys Ser Pro Val Val Ser Gly
                20                  25                  30

Asp Thr Ser Pro Arg His Leu Ser Asn Val Ser Ser Thr Gly Ser Ile
            35                  40                  45

Asp Met Val Asp Ser Pro Gln Leu
        50                  55

<210> SEQ ID NO 72
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: Tau peptide, L215-V226

<400> SEQUENCE: 72

Leu Pro Thr Pro Pro Thr Arg Glu Pro Lys Lys Val
1               5                   10

<210> SEQ ID NO 73
<211> LENGTH: 22
<212> TYPE: PRT
<213> ORGANISM: Homo sapiens
<220> FEATURE:
<221> NAME/KEY: PEPTIDE
<222> LOCATION: (1)..(22)
<223> OTHER INFORMATION: Tau peptide, T205-V226

<400> SEQUENCE: 73

Thr Pro Gly Ser Arg Ser Arg Thr Pro Ser Leu Pro Thr Pro Pro Thr
1               5                   10                  15
```

```
Arg Glu Pro Lys Lys Val
            20

<210> SEQ ID NO 74
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Tau peptide, S195-V226

<400> SEQUENCE: 74

Ser Gly Tyr Ser Ser Pro Gly Ser Pro Gly Thr Pro Gly Ser Arg Ser
1               5                   10                  15

Arg Thr Pro Ser Leu Pro Thr Pro Pro Thr Arg Glu Pro Lys Lys Val
            20                  25                  30

<210> SEQ ID NO 75
<211> LENGTH: 42
<212> TYPE: PRT
<213> ORGANISM: Homo sapiens
<220> FEATURE:
<221> NAME/KEY: PEPTIDE
<222> LOCATION: (1)..(42)
<223> OTHER INFORMATION: Tau peptide, S185-V226

<400> SEQUENCE: 75

Ser Gly Glu Pro Pro Lys Ser Gly Asp Arg Ser Gly Tyr Ser Ser Pro
1               5                   10                  15

Gly Ser Pro Gly Thr Pro Gly Ser Arg Ser Arg Thr Pro Ser Leu Pro
            20                  25                  30

Thr Pro Pro Thr Arg Glu Pro Lys Lys Val
            35                  40

<210> SEQ ID NO 76
<211> LENGTH: 52
<212> TYPE: PRT
<213> ORGANISM: Homo sapiens
<220> FEATURE:
<221> NAME/KEY: PEPTIDE
<222> LOCATION: (1)..(52)
<223> OTHER INFORMATION: Tau peptide, T175-V226

<400> SEQUENCE: 76

Thr Pro Pro Ala Pro Lys Thr Pro Pro Ser Ser Gly Glu Pro Pro Lys
1               5                   10                  15

Ser Gly Asp Arg Ser Gly Tyr Ser Ser Pro Gly Ser Pro Gly Thr Pro
            20                  25                  30

Gly Ser Arg Ser Arg Thr Pro Ser Leu Pro Thr Pro Pro Thr Arg Glu
            35                  40                  45

Pro Lys Lys Val
    50

<210> SEQ ID NO 77
<211> LENGTH: 62
<212> TYPE: PRT
<213> ORGANISM: Homo sapiens
<220> FEATURE:
<221> NAME/KEY: PEPTIDE
<222> LOCATION: (1)..(62)
<223> OTHER INFORMATION: Tau peptide, Q165-V226

<400> SEQUENCE: 77

Gln Ala Asn Ala Thr Arg Ile Pro Ala Lys Thr Pro Pro Ala Pro Lys
```

-continued

```
                1               5                  10                  15
            Thr Pro Pro Ser Ser Gly Glu Pro Pro Lys Ser Gly Asp Arg Ser Gly
                        20                  25                  30
            Tyr Ser Ser Pro Gly Ser Pro Gly Thr Pro Gly Ser Arg Ser Arg Thr
                        35                  40                  45
            Pro Ser Leu Pro Thr Pro Pro Thr Arg Glu Pro Lys Lys Val
                        50                  55                  60

<210> SEQ ID NO 78
<211> LENGTH: 72
<212> TYPE: PRT
<213> ORGANISM: Homo sapiens
<220> FEATURE:
<221> NAME/KEY: PEPTIDE
<222> LOCATION: (1)..(72)
<223> OTHER INFORMATION: Tau peptide, R155-V226

<400> SEQUENCE: 78

Arg Gly Ala Ala Pro Pro Gly Gln Lys Gly Gln Ala Asn Ala Thr Arg
            1               5                  10                  15
            Ile Pro Ala Lys Thr Pro Pro Ala Pro Lys Thr Pro Pro Ser Ser Gly
                        20                  25                  30
            Glu Pro Pro Lys Ser Gly Asp Arg Ser Gly Tyr Ser Ser Pro Gly Ser
                        35                  40                  45
            Pro Gly Thr Pro Gly Ser Arg Ser Arg Thr Pro Ser Leu Pro Thr Pro
                        50                  55                  60
            Pro Thr Arg Glu Pro Lys Lys Val
            65                  70

<210> SEQ ID NO 79
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: Tau peptide, V287-K298

<400> SEQUENCE: 79

Val Gln Ser Lys Cys Gly Ser Lys Asp Asn Ile Lys
            1               5                  10

<210> SEQ ID NO 80
<211> LENGTH: 22
<212> TYPE: PRT
<213> ORGANISM: Homo sapiens
<220> FEATURE:
<221> NAME/KEY: PEPTIDE
<222> LOCATION: (1)..(22)
<223> OTHER INFORMATION: Tau peptide, I277-K298

<400> SEQUENCE: 80

Ile Ile Asn Lys Lys Leu Asp Leu Ser Asn Val Gln Ser Lys Cys Gly
            1               5                  10                  15
            Ser Lys Asp Asn Ile Lys
                        20

<210> SEQ ID NO 81
<211> LENGTH: 32
<212> TYPE: PRT
<213> ORGANISM: Homo sapiens
<220> FEATURE:
<221> NAME/KEY: PEPTIDE
<222> LOCATION: (1)..(32)
```

<223> OTHER INFORMATION: Tau peptide, K267-K298

<400> SEQUENCE: 81

Lys His Gln Pro Gly Gly Gly Lys Val Gln Ile Ile Asn Lys Lys Leu
1               5                   10                  15

Asp Leu Ser Asn Val Gln Ser Lys Cys Gly Ser Lys Asp Asn Ile Lys
            20                  25                  30

<210> SEQ ID NO 82
<211> LENGTH: 42
<212> TYPE: PRT
<213> ORGANISM: Homo sapiens
<220> FEATURE:
<221> NAME/KEY: PEPTIDE
<222> LOCATION: (1)..(42)
<223> OTHER INFORMATION: Tau peptide, K257-K298

<400> SEQUENCE: 82

Lys Ser Lys Ile Gly Ser Thr Glu Asn Leu Lys His Gln Pro Gly Gly
1               5                   10                  15

Gly Lys Val Gln Ile Ile Asn Lys Lys Leu Asp Leu Ser Asn Val Gln
            20                  25                  30

Ser Lys Cys Gly Ser Lys Asp Asn Ile Lys
            35                  40

<210> SEQ ID NO 83
<211> LENGTH: 52
<212> TYPE: PRT
<213> ORGANISM: Homo sapiens
<220> FEATURE:
<221> NAME/KEY: PEPTIDE
<222> LOCATION: (1)..(52)
<223> OTHER INFORMATION: Tau peptide, P247-K298

<400> SEQUENCE: 83

Pro Val Pro Met Pro Asp Leu Lys Asn Val Lys Ser Lys Ile Gly Ser
1               5                   10                  15

Thr Glu Asn Leu Lys His Gln Pro Gly Gly Gly Lys Val Gln Ile Ile
            20                  25                  30

Asn Lys Lys Leu Asp Leu Ser Asn Val Gln Ser Lys Cys Gly Ser Lys
        35                  40                  45

Asp Asn Ile Lys
    50

<210> SEQ ID NO 84
<211> LENGTH: 62
<212> TYPE: PRT
<213> ORGANISM: Homo sapiens
<220> FEATURE:
<221> NAME/KEY: PEPTIDE
<222> LOCATION: (1)..(62)
<223> OTHER INFORMATION: Tau peptide, S237-K298

<400> SEQUENCE: 84

Ser Ser Ala Lys Ser Arg Leu Gln Thr Ala Pro Val Pro Met Pro Asp
1               5                   10                  15

Leu Lys Asn Val Lys Ser Lys Ile Gly Ser Thr Glu Asn Leu Lys His
            20                  25                  30

Gln Pro Gly Gly Gly Lys Val Gln Ile Ile Asn Lys Lys Leu Asp Leu
        35                  40                  45

Ser Asn Val Gln Ser Lys Cys Gly Ser Lys Asp Asn Ile Lys
    50                  55                  60

<210> SEQ ID NO 85
<211> LENGTH: 72
<212> TYPE: PRT
<213> ORGANISM: Homo sapiens
<220> FEATURE:
<221> NAME/KEY: PEPTIDE
<222> LOCATION: (1)..(72)
<223> OTHER INFORMATION: Tau peptide, A227-K298

<400> SEQUENCE: 85

Ala Val Val Arg Thr Pro Pro Lys Ser Pro Ser Ser Ala Lys Ser Arg
1               5                   10                  15

Leu Gln Thr Ala Pro Val Pro Met Pro Asp Leu Lys Asn Val Lys Ser
            20                  25                  30

Lys Ile Gly Ser Thr Glu Asn Leu Lys His Gln Pro Gly Gly Gly Lys
        35                  40                  45

Val Gln Ile Ile Asn Lys Lys Leu Asp Leu Ser Asn Val Gln Ser Lys
    50                  55                  60

Cys Gly Ser Lys Asp Asn Ile Lys
65                  70

<210> SEQ ID NO 86
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: Tau peptide, N359-K370

<400> SEQUENCE: 86

Asn Ile Thr His Val Pro Gly Gly Gly Asn Lys Lys
1               5                   10

<210> SEQ ID NO 87
<211> LENGTH: 22
<212> TYPE: PRT
<213> ORGANISM: Homo sapiens
<220> FEATURE:
<221> NAME/KEY: PEPTIDE
<222> LOCATION: (1)..(22)
<223> OTHER INFORMATION: Tau peptide, R349-K370

<400> SEQUENCE: 87

Arg Val Gln Ser Lys Ile Gly Ser Leu Asp Asn Ile Thr His Val Pro
1               5                   10                  15

Gly Gly Gly Asn Lys Lys
            20

<210> SEQ ID NO 88
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Tau peptide, V339-K370

<400> SEQUENCE: 88

Val Lys Ser Glu Lys Leu Asp Phe Lys Asp Arg Val Gln Ser Lys Ile
1               5                   10                  15

Gly Ser Leu Asp Asn Ile Thr His Val Pro Gly Gly Gly Asn Lys Lys
            20                  25                  30

```
<210> SEQ ID NO 89
<211> LENGTH: 42
<212> TYPE: PRT
<213> ORGANISM: Homo sapiens
<220> FEATURE:
<221> NAME/KEY: PEPTIDE
<222> LOCATION: (1)..(42)
<223> OTHER INFORMATION: Tau peptide, H329-K370

<400> SEQUENCE: 89

His His Lys Pro Gly Gly Gly Gln Val Glu Val Lys Ser Glu Lys Leu
1               5                   10                  15

Asp Phe Lys Asp Arg Val Gln Ser Lys Ile Gly Ser Leu Asp Asn Ile
            20                  25                  30

Thr His Val Pro Gly Gly Gly Asn Lys Lys
            35                  40

<210> SEQ ID NO 90
<211> LENGTH: 52
<212> TYPE: PRT
<213> ORGANISM: Homo sapiens
<220> FEATURE:
<221> NAME/KEY: PEPTIDE
<222> LOCATION: (1)..(52)
<223> OTHER INFORMATION: Tau peptide, T319-K370

<400> SEQUENCE: 90

Thr Ser Lys Cys Gly Ser Leu Gly Asn Ile His His Lys Pro Gly Gly
1               5                   10                  15

Gly Gln Val Glu Val Lys Ser Glu Lys Leu Asp Phe Lys Asp Arg Val
            20                  25                  30

Gln Ser Lys Ile Gly Ser Leu Asp Asn Ile Thr His Val Pro Gly Gly
            35                  40                  45

Gly Asn Lys Lys
        50

<210> SEQ ID NO 91
<211> LENGTH: 62
<212> TYPE: PRT
<213> ORGANISM: Homo sapiens
<220> FEATURE:
<221> NAME/KEY: PEPTIDE
<222> LOCATION: (1)..(62)
<223> OTHER INFORMATION: Tau peptide, V309-K370

<400> SEQUENCE: 91

Val Tyr Lys Pro Val Asp Leu Ser Lys Val Thr Ser Lys Cys Gly Ser
1               5                   10                  15

Leu Gly Asn Ile His His Lys Pro Gly Gly Gly Gln Val Glu Val Lys
            20                  25                  30

Ser Glu Lys Leu Asp Phe Lys Asp Arg Val Gln Ser Lys Ile Gly Ser
            35                  40                  45

Leu Asp Asn Ile Thr His Val Pro Gly Gly Gly Asn Lys Lys
            50                  55                  60

<210> SEQ ID NO 92
<211> LENGTH: 72
<212> TYPE: PRT
<213> ORGANISM: Homo sapiens
<220> FEATURE:
<221> NAME/KEY: PEPTIDE
<222> LOCATION: (1)..(72)
<223> OTHER INFORMATION: Tau peptide, H299-K370

<400> SEQUENCE: 92
```

```
His Val Pro Gly Gly Ser Val Gln Ile Val Tyr Lys Pro Val Asp
1               5                   10                  15

Leu Ser Lys Val Thr Ser Lys Cys Gly Ser Leu Gly Asn Ile His His
                20                  25                  30

Lys Pro Gly Gly Gly Gln Val Glu Val Lys Ser Glu Lys Leu Asp Phe
            35                  40                  45

Lys Asp Arg Val Gln Ser Lys Ile Gly Ser Leu Asp Asn Ile Thr His
    50                  55                  60

Val Pro Gly Gly Gly Asn Lys Lys
65                  70

<210> SEQ ID NO 93
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: Tau peptide, E431-L441

<400> SEQUENCE: 93

Glu Val Ser Ala Ser Leu Ala Lys Gln Gly Leu
1               5                   10

<210> SEQ ID NO 94
<211> LENGTH: 21
<212> TYPE: PRT
<213> ORGANISM: Homo sapiens
<220> FEATURE:
<221> NAME/KEY: PEPTIDE
<222> LOCATION: (1)..(21)
<223> OTHER INFORMATION: Tau peptide, D421-L441

<400> SEQUENCE: 94

Asp Ser Pro Gln Leu Ala Thr Leu Ala Asp Glu Val Ser Ala Ser Leu
1               5                   10                  15

Ala Lys Gln Gly Leu
            20

<210> SEQ ID NO 95
<211> LENGTH: 31
<212> TYPE: PRT
<213> ORGANISM: Homo sapiens
<220> FEATURE:
<221> NAME/KEY: PEPTIDE
<222> LOCATION: (1)..(31)
<223> OTHER INFORMATION: Tau peptide, V411-L441

<400> SEQUENCE: 95

Val Ser Ser Thr Gly Ser Ile Asp Met Val Asp Ser Pro Gln Leu Ala
1               5                   10                  15

Thr Leu Ala Asp Glu Val Ser Ala Ser Leu Ala Lys Gln Gly Leu
                20                  25                  30

<210> SEQ ID NO 96
<211> LENGTH: 41
<212> TYPE: PRT
<213> ORGANISM: Homo sapiens
<220> FEATURE:
<221> NAME/KEY: PEPTIDE
<222> LOCATION: (1)..(41)
<223> OTHER INFORMATION: Tau peptide, G401-L441

<400> SEQUENCE: 96
```

```
Gly Asp Thr Ser Pro Arg His Leu Ser Asn Val Ser Thr Gly Ser
1               5                   10                  15

Ile Asp Met Val Asp Ser Pro Gln Leu Ala Thr Leu Ala Asp Glu Val
            20                  25                  30

Ser Ala Ser Leu Ala Lys Gln Gly Leu
        35                  40
```

<210> SEQ ID NO 97
<211> LENGTH: 51
<212> TYPE: PRT
<213> ORGANISM: Homo sapiens
<220> FEATURE:
<221> NAME/KEY: PEPTIDE
<222> LOCATION: (1)..(51)
<223> OTHER INFORMATION: Tau peptide, E391-L441

<400> SEQUENCE: 97

```
Glu Ile Val Tyr Lys Ser Pro Val Val Ser Gly Asp Thr Ser Pro Arg
1               5                   10                  15

His Leu Ser Asn Val Ser Ser Thr Gly Ser Ile Asp Met Val Asp Ser
            20                  25                  30

Pro Gln Leu Ala Thr Leu Ala Asp Glu Val Ser Ala Ser Leu Ala Lys
        35                  40                  45

Gln Gly Leu
    50
```

<210> SEQ ID NO 98
<211> LENGTH: 61
<212> TYPE: PRT
<213> ORGANISM: Homo sapiens
<220> FEATURE:
<221> NAME/KEY: PEPTIDE
<222> LOCATION: (1)..(61)
<223> OTHER INFORMATION: Tau peptide, N381-L441

<400> SEQUENCE: 98

```
Asn Ala Lys Ala Lys Thr Asp His Gly Ala Glu Ile Val Tyr Lys Ser
1               5                   10                  15

Pro Val Val Ser Gly Asp Thr Ser Pro Arg His Leu Ser Asn Val Ser
            20                  25                  30

Ser Thr Gly Ser Ile Asp Met Val Asp Ser Pro Gln Leu Ala Thr Leu
        35                  40                  45

Ala Asp Glu Val Ser Ala Ser Leu Ala Lys Gln Gly Leu
    50                  55                  60
```

<210> SEQ ID NO 99
<211> LENGTH: 71
<212> TYPE: PRT
<213> ORGANISM: Homo sapiens
<220> FEATURE:
<221> NAME/KEY: PEPTIDE
<222> LOCATION: (1)..(71)
<223> OTHER INFORMATION: Tau peptide, I371-L441

<400> SEQUENCE: 99

```
Ile Glu Thr His Lys Leu Thr Phe Arg Glu Asn Ala Lys Ala Lys Thr
1               5                   10                  15

Asp His Gly Ala Glu Ile Val Tyr Lys Ser Pro Val Val Ser Gly Asp
            20                  25                  30

Thr Ser Pro Arg His Leu Ser Asn Val Ser Ser Thr Gly Ser Ile Asp
        35                  40                  45

Met Val Asp Ser Pro Gln Leu Ala Thr Leu Ala Asp Glu Val Ser Ala
```

Ser Leu Ala Lys Gln Gly Leu
65                  70

<210> SEQ ID NO 100
<211> LENGTH: 441
<212> TYPE: PRT
<213> ORGANISM: Homo sapiens
<220> FEATURE:
<221> NAME/KEY: PEPTIDE
<222> LOCATION: (1)..(441)
<223> OTHER INFORMATION: Tau isoform with 4R and 2N (GenBank:
      AGF19246.1)

<400> SEQUENCE: 100

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln

```
                    325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
            435                 440

<210> SEQ ID NO 101
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: Tau peptide - aa131-141

<400> SEQUENCE: 101

Ser Lys Asp Gly Thr Gly Ser Asp Asp Lys Lys
1               5                   10

<210> SEQ ID NO 102
<211> LENGTH: 17
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: Tau peptide - aa241-257

<400> SEQUENCE: 102

Ser Arg Leu Gln Thr Ala Pro Val Pro Met Pro Asp Leu Lys Asn Val
1               5                   10                  15

Lys

<210> SEQ ID NO 103
<211> LENGTH: 17
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: Tau peptide - aa243-259

<400> SEQUENCE: 103

Leu Gln Thr Ala Pro Val Pro Met Pro Asp Leu Lys Asn Val Lys Ser
1               5                   10                  15

Lys

<210> SEQ ID NO 104
<211> LENGTH: 7
<212> TYPE: PRT
<213> ORGANISM: Homo sapiens
<220> FEATURE:
<221> NAME/KEY: PEPTIDE
```

```
<222> LOCATION: (1)..(7)
<223> OTHER INFORMATION: Tau peptide - aa275-281

<400> SEQUENCE: 104

Val Gln Ile Ile Asn Lys Lys
1               5

<210> SEQ ID NO 105
<211> LENGTH: 14
<212> TYPE: PRT
<213> ORGANISM: Homo sapiens
<220> FEATURE:
<221> NAME/KEY: PEPTIDE
<222> LOCATION: (1)..(14)
<223> OTHER INFORMATION: Tau peptide - aa281-294

<400> SEQUENCE: 105

Lys Leu Asp Leu Ser Asn Val Gln Ser Lys Cys Gly Ser Lys
1               5                  10

<210> SEQ ID NO 106
<211> LENGTH: 20
<212> TYPE: PRT
<213> ORGANISM: Homo sapiens
<220> FEATURE:
<221> NAME/KEY: PEPTIDE
<222> LOCATION: (1)..(20)
<223> OTHER INFORMATION: Tau peptide - aa275-294

<400> SEQUENCE: 106

Val Gln Ile Ile Asn Lys Lys Leu Asp Leu Ser Asn Val Gln Ser Lys
1               5                   10                  15

Cys Gly Ser Lys
            20

<210> SEQ ID NO 107
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: Tau peptide - aa294-311

<400> SEQUENCE: 107

Lys Asp Asn Ile Lys His Val Pro Gly Gly Gly Ser Val Gln Ile Val
1               5                   10                  15

Tyr Lys

<210> SEQ ID NO 108
<211> LENGTH: 18
<212> TYPE: PRT
<213> ORGANISM: Homo sapiens
<220> FEATURE:
<221> NAME/KEY: PEPTIDE
<222> LOCATION: (1)..(18)
<223> OTHER INFORMATION: Tau peptide - aa294-311, P301 to S301

<400> SEQUENCE: 108

Lys Asp Asn Ile Lys His Val Ser Gly Gly Gly Ser Val Gln Ile Val
1               5                   10                  15

Tyr Lys

<210> SEQ ID NO 109
<211> LENGTH: 18
<212> TYPE: PRT
```

```
<213> ORGANISM: Homo sapiens
<220> FEATURE:
<221> NAME/KEY: PEPTIDE
<222> LOCATION: (1)..(18)
<223> OTHER INFORMATION: Tau peptide - aa294-311, p301 trans

<400> SEQUENCE: 109

Lys Asp Asn Ile Lys His Val Pro Gly Gly Gly Ser Val Gln Ile Val
1               5                   10                  15

Tyr Lys

<210> SEQ ID NO 110
<211> LENGTH: 37
<212> TYPE: PRT
<213> ORGANISM: Homo sapiens
<220> FEATURE:
<221> NAME/KEY: PEPTIDE
<222> LOCATION: (1)..(37)
<223> OTHER INFORMATION: Tau peptide - aa275-311, p301 trans

<400> SEQUENCE: 110

Val Gln Ile Ile Asn Lys Lys Leu Asp Leu Ser Asn Val Gln Ser Lys
1               5                   10                  15

Cys Gly Ser Lys Asp Asn Ile Lys His Val Pro Gly Gly Gly Ser Val
            20                  25                  30

Gln Ile Val Tyr Lys
        35

<210> SEQ ID NO 111
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: Tau peptide - aa297-311, p301 trans

<400> SEQUENCE: 111

Ile Lys His Val Pro Gly Gly Gly Ser Val Gln Ile Val Tyr Lys
1               5                   10                  15

<210> SEQ ID NO 112
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: Tau peptide - aa22-34

<400> SEQUENCE: 112

Asp Arg Lys Asp Gln Gly Gly Tyr Thr Met His Gln Asp
1               5                   10

<210> SEQ ID NO 113
<211> LENGTH: 17
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: Tau peptide - aa18-34

<400> SEQUENCE: 113

Tyr Gly Leu Gly Asp Arg Lys Asp Gln Gly Gly Tyr Thr Met His Gln
1               5                   10                  15
```

-continued

Asp

```
<210> SEQ ID NO 114
<211> LENGTH: 17
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: Tau peptide - aa22-38

<400> SEQUENCE: 114
```

Asp Arg Lys Asp Gln Gly Gly Tyr Thr Met His Gln Asp Gln Glu Gly
1               5                   10                  15

Asp

```
<210> SEQ ID NO 115
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: Tau peptide - aa297-311

<400> SEQUENCE: 115
```

Ile Lys His Val Pro Gly Gly Gly Ser Val Gln Ile Val Tyr Lys
1               5                   10                  15

```
<210> SEQ ID NO 116
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: Tau peptide - aa359-370

<400> SEQUENCE: 116
```

Asn Ile Thr His Val Pro Gly Gly Gly Asn Lys Lys
1               5                   10

```
<210> SEQ ID NO 117
<211> LENGTH: 22
<212> TYPE: PRT
<213> ORGANISM: Homo sapiens
<220> FEATURE:
<221> NAME/KEY: PEPTIDE
<222> LOCATION: (1)..(22)
<223> OTHER INFORMATION: Tau peptide - aa349-370

<400> SEQUENCE: 117
```

Arg Val Gln Ser Lys Ile Gly Ser Leu Asp Asn Ile Thr His Val Pro
1               5                   10                  15

Gly Gly Gly Asn Lys Lys
            20

```
<210> SEQ ID NO 118
<211> LENGTH: 32
<212> TYPE: PRT
<213> ORGANISM: Homo sapiens
<220> FEATURE:
<221> NAME/KEY: PEPTIDE
<222> LOCATION: (1)..(32)
<223> OTHER INFORMATION: Tau peptide - aa339-370

<400> SEQUENCE: 118
```

Val Lys Ser Glu Lys Leu Asp Phe Lys Asp Arg Val Gln Ser Lys Ile
1               5                   10                  15

Gly Ser Leu Asp Asn Ile Thr His Val Pro Gly Gly Gly Asn Lys Lys
            20                  25                  30

<210> SEQ ID NO 119
<211> LENGTH: 42
<212> TYPE: PRT
<213> ORGANISM: Homo sapiens
<220> FEATURE:
<221> NAME/KEY: PEPTIDE
<222> LOCATION: (1)..(42)
<223> OTHER INFORMATION: Tau peptide - aa329-370

<400> SEQUENCE: 119

His His Lys Pro Gly Gly Gly Gln Val Glu Val Lys Ser Glu Lys Leu
1               5                   10                  15

Asp Phe Lys Asp Arg Val Gln Ser Lys Ile Gly Ser Leu Asp Asn Ile
            20                  25                  30

Thr His Val Pro Gly Gly Gly Asn Lys Lys
        35                  40

<210> SEQ ID NO 120
<211> LENGTH: 21
<212> TYPE: PRT
<213> ORGANISM: Homo sapiens
<220> FEATURE:
<221> NAME/KEY: PEPTIDE
<222> LOCATION: (1)..(21)
<223> OTHER INFORMATION: Tau peptide - aa329-349

<400> SEQUENCE: 120

His His Lys Pro Gly Gly Gly Gln Val Glu Val Lys Ser Glu Lys Leu
1               5                   10                  15

Asp Phe Lys Asp Arg
            20

<210> SEQ ID NO 121
<211> LENGTH: 40
<212> TYPE: PRT
<213> ORGANISM: Homo sapiens
<220> FEATURE:
<221> NAME/KEY: PEPTIDE
<222> LOCATION: (1)..(40)
<223> OTHER INFORMATION: Tau peptide - aa1-40

<400> SEQUENCE: 121

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp
        35                  40

<210> SEQ ID NO 122
<211> LENGTH: 40
<212> TYPE: PRT
<213> ORGANISM: Homo sapiens
<220> FEATURE:
<221> NAME/KEY: PEPTIDE
<222> LOCATION: (1)..(40)
<223> OTHER INFORMATION: Tau peptide - aa11-50

<400> SEQUENCE: 122

Met Glu Asp His Ala Gly Thr Tyr Gly Leu Gly Asp Arg Lys Asp Gln

```
                1               5                  10                  15
Gly Gly Tyr Thr Met His Gln Asp Gln Glu Gly Asp Thr Asp Ala Gly
                20                  25                  30

Leu Lys Glu Ser Pro Leu Gln Thr
        35                  40

<210> SEQ ID NO 123
<211> LENGTH: 34
<212> TYPE: PRT
<213> ORGANISM: Homo sapiens
<220> FEATURE:
<221> NAME/KEY: PEPTIDE
<222> LOCATION: (1)..(34)
<223> OTHER INFORMATION: Tau peptide - aa1-34

<400> SEQUENCE: 123

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp

<210> SEQ ID NO 124
<211> LENGTH: 22
<212> TYPE: PRT
<213> ORGANISM: Homo sapiens
<220> FEATURE:
<221> NAME/KEY: PEPTIDE
<222> LOCATION: (1)..(22)
<223> OTHER INFORMATION: Tau peptide - aa1-22

<400> SEQUENCE: 124

Met Ala Glu Pro Arg Gln Glu Phe Glu Val Met Glu Asp His Ala Gly
1               5                   10                  15

Thr Tyr Gly Leu Gly Asp
                20

<210> SEQ ID NO 125
<211> LENGTH: 34
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(34)
<223> OTHER INFORMATION: Tau S131-K141

<400> SEQUENCE: 125

Ile Ser Ile Thr Glu Ile Lys Gly Val Ile Val His Arg Ile Glu Thr
1               5                   10                  15

Ile Leu Phe Lys Lys Lys Lys Ser Lys Asp Gly Thr Gly Ser Asp Asp
                20                  25                  30

Lys Lys
```

```
<210> SEQ ID NO 126
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(40)
<223> OTHER INFORMATION: Tau S241-K257

<400> SEQUENCE: 126

Ile Ser Ile Thr Glu Ile Lys Gly Val Ile Val His Arg Ile Glu Thr
1               5                   10                  15

Ile Leu Phe Lys Lys Lys Lys Ser Arg Leu Gln Thr Ala Pro Val Pro
                20                  25                  30

Met Pro Asp Leu Lys Asn Val Lys
                35                  40

<210> SEQ ID NO 127
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(40)
<223> OTHER INFORMATION: Tau L243-K259

<400> SEQUENCE: 127

Ile Ser Ile Thr Glu Ile Lys Gly Val Ile Val His Arg Ile Glu Thr
1               5                   10                  15

Ile Leu Phe Lys Lys Lys Lys Leu Gln Thr Ala Pro Val Pro Met Pro
                20                  25                  30

Asp Leu Lys Asn Val Lys Ser Lys
                35                  40

<210> SEQ ID NO 128
<211> LENGTH: 30
<212> TYPE: PRT
<213> ORGANISM: Artificial Sequence
<220> FEATURE:
<223> OTHER INFORMATION: Synthetic peptide
<220> FEATURE:
```

```
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(30)
<223> OTHER INFORMATION: Tau V275-K281

<400> SEQUENCE: 128

Ile Ser Ile Thr Glu Ile Lys Gly Val Ile Val His Arg Ile Glu Thr
1               5                   10                  15
Ile Leu Phe Lys Lys Lys Lys Val Gln Ile Ile Asn Lys Lys
            20                  25                  30

<210> SEQ ID NO 129
<211> LENGTH: 37
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(37)
<223> OTHER INFORMATION: Tau K281-K294

<400> SEQUENCE: 129

Ile Ser Ile Thr Glu Ile Lys Gly Val Ile Val His Arg Ile Glu Thr
1               5                   10                  15
Ile Leu Phe Lys Lys Lys Lys Lys Leu Asp Leu Ser Asn Val Gln Ser
            20                  25                  30
Lys Cys Gly Ser Lys
        35

<210> SEQ ID NO 130
<211> LENGTH: 43
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
```

-continued

```
<221> NAME/KEY: PEPTIDE
<222> LOCATION: (24)..(43)
<223> OTHER INFORMATION: Tau V275-K294

<400> SEQUENCE: 130

Ile Ser Ile Thr Glu Ile Lys Gly Val Ile Val His Arg Ile Glu Thr
1               5                   10                  15

Ile Leu Phe Lys Lys Lys Lys Val Gln Ile Ile Asn Lys Lys Leu Asp
            20                  25                  30

Leu Ser Asn Val Gln Ser Lys Cys Gly Ser Lys
        35                  40

<210> SEQ ID NO 131
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(41)
<223> OTHER INFORMATION: Tau K294-K311

<400> SEQUENCE: 131

Ile Ser Ile Thr Glu Ile Lys Gly Val Ile Val His Arg Ile Glu Thr
1               5                   10                  15

Ile Leu Phe Lys Lys Lys Lys Lys Asp Asn Ile Lys His Val Pro Gly
            20                  25                  30

Gly Gly Ser Val Gln Ile Val Tyr Lys
        35                  40

<210> SEQ ID NO 132
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(41)
<223> OTHER INFORMATION: Tau K294-K311, P301 to S301

<400> SEQUENCE: 132

Ile Ser Ile Thr Glu Ile Lys Gly Val Ile Val His Arg Ile Glu Thr
1               5                   10                  15
```

```
Ile Leu Phe Lys Lys Lys Lys Lys Asp Asn Ile Lys His Val Ser Gly
            20                  25                  30

Gly Gly Ser Val Gln Ile Val Tyr Lys
            35                  40
```

<210> SEQ ID NO 133
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(41)
<223> OTHER INFORMATION: Tau K257-K274

<400> SEQUENCE: 133

```
Ile Ser Ile Xaa Glu Ile Xaa Xaa Val Ile Val Xaa Xaa Ile Glu Thr
1               5                   10                  15

Ile Leu Phe Lys Lys Lys Lys Lys Ser Lys Ile Gly Ser Thr Glu Asn
            20                  25                  30

Leu Lys His Gln Pro Gly Gly Gly Lys
            35                  40
```

<210> SEQ ID NO 134
<211> LENGTH: 53
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)

```
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(53)
<223> OTHER INFORMATION: Tau R379-L408

<400> SEQUENCE: 134

Ile Ser Ile Xaa Glu Ile Xaa Xaa Val Ile Val Xaa Xaa Ile Glu Thr
1               5                   10                  15

Ile Leu Phe Lys Lys Lys Lys Arg Glu Asn Ala Lys Ala Lys Thr Asp
            20                  25                  30

His Gly Ala Glu Ile Val Tyr Lys Ser Pro Val Val Ser Gly Asp Thr
        35                  40                  45

Ser Pro Arg His Leu
    50

<210> SEQ ID NO 135
<211> LENGTH: 41
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(41)
<223> OTHER INFORMATION: Tau K294-K311, p301 trans

<400> SEQUENCE: 135

Ile Ser Ile Thr Glu Ile Lys Gly Val Ile Val His Arg Ile Glu Thr
1               5                   10                  15

Ile Leu Phe Lys Lys Lys Lys Lys Asp Asn Ile Lys His Val Pro Gly
            20                  25                  30

Gly Gly Ser Val Gln Ile Val Tyr Lys
            35                  40

<210> SEQ ID NO 136
<211> LENGTH: 60
<212> TYPE: PRT
```

<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(60)
<223> OTHER INFORMATION: Tau V275-K311, p301 trans

<400> SEQUENCE: 136

Ile Ser Ile Thr Glu Ile Lys Gly Val Ile Val His Arg Ile Glu Thr
1               5                   10                  15

Ile Leu Phe Lys Lys Lys Lys Val Gln Ile Ile Asn Lys Lys Leu Asp
            20                  25                  30

Leu Ser Asn Val Gln Ser Lys Cys Gly Ser Lys Asp Asn Ile Lys His
        35                  40                  45

Val Pro Gly Gly Gly Ser Val Gln Ile Val Tyr Lys
    50                  55                  60

<210> SEQ ID NO 137
<211> LENGTH: 36
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(36)
<223> OTHER INFORMATION: Tau D22-D34

<400> SEQUENCE: 137

Ile Ser Ile Thr Glu Ile Lys Gly Val Ile Val His Arg Ile Glu Thr
1               5                   10                  15

Ile Leu Phe Lys Lys Lys Lys Asp Arg Lys Asp Gln Gly Gly Tyr Thr
            20                  25                  30

Met His Gln Asp
        35

<210> SEQ ID NO 138
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)

<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(40)
<223> OTHER INFORMATION: Tau Y18-D34

<400> SEQUENCE: 138

Ile Ser Ile Thr Glu Ile Lys Gly Val Ile Val His Arg Ile Glu Thr
1               5                   10                  15

Ile Leu Phe Lys Lys Lys Lys Tyr Gly Leu Gly Asp Arg Lys Asp Gln
            20                  25                  30

Gly Gly Tyr Thr Met His Gln Asp
        35                  40

<210> SEQ ID NO 139
<211> LENGTH: 40
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(40)
<223> OTHER INFORMATION: Tau D22-D38

<400> SEQUENCE: 139

Ile Ser Ile Thr Glu Ile Lys Gly Val Ile Val His Arg Ile Glu Thr
1               5                   10                  15

Ile Leu Phe Lys Lys Lys Lys Asp Arg Lys Asp Gln Gly Gly Tyr Thr
            20                  25                  30

Met His Gln Asp Gln Glu Gly Asp
        35                  40

<210> SEQ ID NO 140
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer

```
<220> FEATURE:
<221> NAME/KEY: PEPTIDE
<222> LOCATION: (24)..(38)
<223> OTHER INFORMATION: Tau I297-K311, p301 trans

<400> SEQUENCE: 140

Ile Ser Ile Thr Glu Ile Lys Gly Val Ile Val His Arg Ile Glu Thr
1               5                   10                  15

Ile Leu Phe Lys Lys Lys Lys Ile Lys His Val Pro Gly Gly Gly Ser
            20                  25                  30

Val Gln Ile Val Tyr Lys
            35

<210> SEQ ID NO 141
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(15)
<223> OTHER INFORMATION: Tau I297-K311
<220> FEATURE:
<221> NAME/KEY: SITE
<222> LOCATION: (16)..(16)
<223> OTHER INFORMATION: epsilon K
<220> FEATURE:
<221> NAME/KEY: PEPTIDE
<222> LOCATION: (16)..(19)
<223> OTHER INFORMATION: KKK-epsilon K as a spacer
<220> FEATURE:
<221> NAME/KEY: PEPTIDE
<222> LOCATION: (20)..(38)
<223> OTHER INFORMATION: MvF5 Th (UBITh1)

<400> SEQUENCE: 141

Ile Lys His Val Pro Gly Gly Gly Ser Val Gln Ile Val Tyr Lys Lys
1               5                   10                  15

Lys Lys Lys Ile Ser Ile Thr Glu Ile Lys Gly Val Ile Val His Arg
            20                  25                  30

Ile Glu Thr Ile Leu Phe
            35

<210> SEQ ID NO 142
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (21)..(38)
<223> OTHER INFORMATION: Tau K294-K311

<400> SEQUENCE: 142

Ile Ser Ile Thr Glu Ile Lys Gly Val Ile Val His Arg Ile Glu Thr
1               5                   10                  15

Ile Leu Phe Lys Lys Asp Asn Ile Lys His Val Pro Gly Gly Gly Ser
            20                  25                  30
```

```
Val Gln Ile Val Tyr Lys
        35

<210> SEQ ID NO 143
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (21)..(35)
<223> OTHER INFORMATION: Tau I297-K311

<400> SEQUENCE: 143

Ile Ser Ile Thr Glu Ile Lys Gly Val Ile Val His Arg Ile Glu Thr
1               5                   10                  15

Ile Leu Phe Lys Ile Lys His Val Pro Gly Gly Gly Ser Val Gln Ile
            20                  25                  30

Val Tyr Lys
        35

<210> SEQ ID NO 144
<211> LENGTH: 38
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(38)
<223> OTHER INFORMATION: Tau I297-K311

<400> SEQUENCE: 144

Ile Ser Ile Thr Glu Ile Lys Gly Val Ile Val His Arg Ile Glu Thr
1               5                   10                  15

Ile Leu Phe Lys Lys Lys Lys Ile Lys His Val Pro Gly Gly Gly Ser
            20                  25                  30

Val Gln Ile Val Tyr Lys
        35

<210> SEQ ID NO 145
<211> LENGTH: 39
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
```

```
<223> OTHER INFORMATION: MvF 4 Th (UBITH3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(39)
<223> OTHER INFORMATION: Tau A145-P160

<400> SEQUENCE: 145

Ile Ser Ile Xaa Glu Ile Xaa Xaa Val Ile Val Xaa Xaa Ile Glu Thr
1               5                   10                  15

Ile Leu Phe Lys Lys Lys Lys Ala Asp Gly Lys Thr Lys Ile Ala Thr
            20                  25                  30

Pro Arg Gly Ala Ala Pro Pro
        35

<210> SEQ ID NO 146
<211> LENGTH: 60
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF 4 Th (UBITh3)
<220> FEATURE:
<221> NAME/KEY: SITE
<222> LOCATION: (4)..(4)
<223> OTHER INFORMATION: S or T
<220> FEATURE:
<221> NAME/KEY: SITE
<222> LOCATION: (7)..(7)
<223> OTHER INFORMATION: K or R
<220> FEATURE:
<221> NAME/KEY: SITE
<222> LOCATION: (8)..(8)
<223> OTHER INFORMATION: G or T
<220> FEATURE:
<221> NAME/KEY: SITE
<222> LOCATION: (12)..(12)
<223> OTHER INFORMATION: H or T
<220> FEATURE:
<221> NAME/KEY: SITE
<222> LOCATION: (13)..(13)
<223> OTHER INFORMATION: K or R
<220> FEATURE:
<221> NAME/KEY: SITE
<222> LOCATION: (20)..(20)
```

<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(60)
<223> OTHER INFORMATION: Tau V275-K311

<400> SEQUENCE: 146

Ile Ser Ile Xaa Glu Ile Xaa Xaa Val Ile Val Xaa Xaa Ile Glu Thr
1               5                   10                  15

Ile Leu Phe Lys Lys Lys Lys Val Gln Ile Ile Asn Lys Lys Leu Asp
            20                  25                  30

Leu Ser Asn Val Gln Ser Lys Cys Gly Ser Lys Asp Asn Ile Lys His
        35                  40                  45

Val Pro Gly Gly Gly Ser Val Gln Ile Val Tyr Lys
    50                  55                  60

<210> SEQ ID NO 147
<211> LENGTH: 35
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(35)
<223> OTHER INFORMATION: Tau N359-K370

<400> SEQUENCE: 147

Ile Ser Ile Thr Glu Ile Lys Gly Val Ile Val His Arg Ile Glu Thr
1               5                   10                  15

Ile Leu Phe Lys Lys Lys Lys Asn Ile Thr His Val Pro Gly Gly Gly
            20                  25                  30

Asn Lys Lys
        35

<210> SEQ ID NO 148
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF 5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:

```
<221> NAME/KEY: PEPTIDE
<222> LOCATION: (24)..(45)
<223> OTHER INFORMATION: Tau R349-K370

<400> SEQUENCE: 148

Ile Ser Ile Ser Glu Ile Lys Gly Val Ile Val His Lys Ile Glu Thr
1               5                   10                  15

Ile Leu Phe Lys Lys Lys Lys Arg Val Gln Ser Lys Ile Gly Ser Leu
            20                  25                  30

Asp Asn Ile Thr His Val Pro Gly Gly Gly Asn Lys Lys
        35                  40                  45

<210> SEQ ID NO 149
<211> LENGTH: 55
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(55)
<223> OTHER INFORMATION: Tau V339-K370

<400> SEQUENCE: 149

Ile Ser Ile Thr Glu Ile Lys Gly Val Ile Val His Arg Ile Glu Thr
1               5                   10                  15

Ile Leu Phe Lys Lys Lys Lys Val Lys Ser Glu Lys Leu Asp Phe Lys
            20                  25                  30

Asp Arg Val Gln Ser Lys Ile Gly Ser Leu Asp Asn Ile Thr His Val
        35                  40                  45

Pro Gly Gly Gly Asn Lys Lys
        50                  55

<210> SEQ ID NO 150
<211> LENGTH: 65
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(65)
<223> OTHER INFORMATION: Tau H329-K370

<400> SEQUENCE: 150
```

```
Ile Ser Ile Thr Glu Ile Lys Gly Val Ile Val His Arg Ile Glu Thr
1               5                   10                  15

Ile Leu Phe Lys Lys Lys Lys His His Lys Pro Gly Gly Gly Gln Val
            20                  25                  30

Glu Val Lys Ser Glu Lys Leu Asp Phe Lys Asp Arg Val Gln Ser Lys
            35                  40                  45

Ile Gly Ser Leu Asp Asn Ile Thr His Val Pro Gly Gly Asn Lys
        50                  55                  60

Lys
65

<210> SEQ ID NO 151
<211> LENGTH: 44
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(19)
<223> OTHER INFORMATION: MvF5 Th (UBITh1)
<220> FEATURE:
<221> NAME/KEY: SITE
<222> LOCATION: (20)..(20)
<223> OTHER INFORMATION: epsilon-K
<220> FEATURE:
<221> NAME/KEY: PEPTIDE
<222> LOCATION: (20)..(23)
<223> OTHER INFORMATION: epsilon K-KKK as a spacer
<220> FEATURE:
<221> NAME/KEY: PEPTIDE
<222> LOCATION: (24)..(44)
<223> OTHER INFORMATION: Tau H329-R349

<400> SEQUENCE: 151

Ile Ser Ile Thr Glu Ile Lys Gly Val Ile Val His Arg Ile Glu Thr
1               5                   10                  15

Ile Leu Phe Lys Lys Lys Lys His His Lys Pro Gly Gly Gly Gln Val
            20                  25                  30

Glu Val Lys Ser Glu Lys Leu Asp Phe Lys Asp Arg
            35                  40

<210> SEQ ID NO 152
<211> LENGTH: 63
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(40)
<223> OTHER INFORMATION: Tau M1-D40
<220> FEATURE:
<221> NAME/KEY: SITE
<222> LOCATION: (41)..(41)
<223> OTHER INFORMATION: epsilon K
<220> FEATURE:
<221> NAME/KEY: PEPTIDE
<222> LOCATION: (41)..(44)
<223> OTHER INFORMATION: KKK-epsilon K as a spacer
<220> FEATURE:
<221> NAME/KEY: PEPTIDE
<222> LOCATION: (45)..(63)
<223> OTHER INFORMATION: MvF5 Th (UBITh1)

<400> SEQUENCE: 152

Met Ala Glu Pro Arg Gln Glu Phe Glu Val Met Glu Asp His Ala Gly
1               5                   10                  15
```

```
Thr Tyr Gly Leu Gly Asp Arg Lys Asp Gln Gly Gly Tyr Thr Met His
            20                  25                  30

Gln Asp Gln Glu Gly Asp Thr Asp Lys Lys Lys Ile Ser Ile Thr
        35                  40                  45

Glu Ile Lys Gly Val Ile Val His Arg Ile Glu Thr Ile Leu Phe
50                  55                  60

<210> SEQ ID NO 153
<211> LENGTH: 63
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(40)
<223> OTHER INFORMATION: Tau M11-T50
<220> FEATURE:
<221> NAME/KEY: SITE
<222> LOCATION: (41)..(41)
<223> OTHER INFORMATION: epsilon K
<220> FEATURE:
<221> NAME/KEY: PEPTIDE
<222> LOCATION: (41)..(44)
<223> OTHER INFORMATION: KKK-epsilon K as a spacer
<220> FEATURE:
<221> NAME/KEY: PEPTIDE
<222> LOCATION: (45)..(63)
<223> OTHER INFORMATION: MvF5 Th (UBITh1)

<400> SEQUENCE: 153

Met Glu Asp His Ala Gly Thr Tyr Gly Leu Gly Asp Arg Lys Asp Gln
1               5                   10                  15

Gly Gly Tyr Thr Met His Gln Asp Gln Glu Gly Asp Thr Asp Ala Gly
            20                  25                  30

Leu Lys Glu Ser Pro Leu Gln Thr Lys Lys Lys Ile Ser Ile Thr
        35                  40                  45

Glu Ile Lys Gly Val Ile Val His Arg Ile Glu Thr Ile Leu Phe
50                  55                  60

<210> SEQ ID NO 154
<211> LENGTH: 57
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(34)
<223> OTHER INFORMATION: Tau M1-D34
<220> FEATURE:
<221> NAME/KEY: SITE
<222> LOCATION: (35)..(35)
<223> OTHER INFORMATION: epsilon K
<220> FEATURE:
<221> NAME/KEY: PEPTIDE
<222> LOCATION: (35)..(38)
<223> OTHER INFORMATION: KKK-epsilon K as a spacer
<220> FEATURE:
<221> NAME/KEY: PEPTIDE
<222> LOCATION: (39)..(57)
<223> OTHER INFORMATION: MvF5 Th (UBITh1)

<400> SEQUENCE: 154

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30
```

```
Gln Asp Lys Lys Lys Ile Ser Ile Thr Glu Ile Lys Gly Val Ile
        35                  40                  45

Val His Arg Ile Glu Thr Ile Leu Phe
 50                  55

<210> SEQ ID NO 155
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(22)
<223> OTHER INFORMATION: Tau M1-D22
<220> FEATURE:
<221> NAME/KEY: SITE
<222> LOCATION: (23)..(23)
<223> OTHER INFORMATION: epsilon K
<220> FEATURE:
<221> NAME/KEY: PEPTIDE
<222> LOCATION: (23)..(26)
<223> OTHER INFORMATION: KKK-epsilon K as a spacer
<220> FEATURE:
<221> NAME/KEY: PEPTIDE
<222> LOCATION: (27)..(45)
<223> OTHER INFORMATION: MvF5 Th (UBITh1)

<400> SEQUENCE: 155

Met Ala Glu Pro Arg Gln Glu Phe Glu Val Met Glu Asp His Ala Gly
 1               5                  10                  15

Thr Tyr Gly Leu Gly Asp Lys Lys Lys Ile Ser Ile Thr Glu Ile
            20                  25                  30

Lys Gly Val Ile Val His Arg Ile Glu Thr Ile Leu Phe
        35                  40                  45

<210> SEQ ID NO 156
<211> LENGTH: 31
<212> TYPE: PRT
<213> ORGANISM: Homo sapiens
<220> FEATURE:
<221> NAME/KEY: PEPTIDE
<222> LOCATION: (1)..(31)
<223> OTHER INFORMATION: Tau peptide - aa281-311

<400> SEQUENCE: 156

Lys Leu Asp Leu Ser Asn Val Gln Ser Lys Cys Gly Ser Lys Asp Asn
 1               5                  10                  15

Ile Lys His Val Pro Gly Gly Gly Ser Val Gln Ile Val Tyr Lys
            20                  25                  30

<210> SEQ ID NO 157
<211> LENGTH: 29
<212> TYPE: PRT
<213> ORGANISM: Homo sapiens
<220> FEATURE:
<221> NAME/KEY: PEPTIDE
<222> LOCATION: (1)..(29)
<223> OTHER INFORMATION: Tau peptide - aa283-311

<400> SEQUENCE: 157

Asp Leu Ser Asn Val Gln Ser Lys Cys Gly Ser Lys Asp Asn Ile Lys
 1               5                  10                  15

His Val Pro Gly Gly Gly Ser Val Gln Ile Val Tyr Lys
            20                  25

<210> SEQ ID NO 158
```

```
<211> LENGTH: 27
<212> TYPE: PRT
<213> ORGANISM: Homo sapiens
<220> FEATURE:
<221> NAME/KEY: PEPTIDE
<222> LOCATION: (1)..(27)
<223> OTHER INFORMATION: Tau peptide - aa285-311

<400> SEQUENCE: 158

Ser Asn Val Gln Ser Lys Cys Gly Ser Lys Asp Asn Ile Lys His Val
1               5                   10                  15

Pro Gly Gly Gly Ser Val Gln Ile Val Tyr Lys
            20                  25

<210> SEQ ID NO 159
<211> LENGTH: 25
<212> TYPE: PRT
<213> ORGANISM: Homo sapiens
<220> FEATURE:
<221> NAME/KEY: PEPTIDE
<222> LOCATION: (1)..(25)
<223> OTHER INFORMATION: Tau peptide - aa287-311

<400> SEQUENCE: 159

Val Gln Ser Lys Cys Gly Ser Lys Asp Asn Ile Lys His Val Pro Gly
1               5                   10                  15

Gly Gly Ser Val Gln Ile Val Tyr Lys
            20                  25

<210> SEQ ID NO 160
<211> LENGTH: 23
<212> TYPE: PRT
<213> ORGANISM: Homo sapiens
<220> FEATURE:
<221> NAME/KEY: PEPTIDE
<222> LOCATION: (1)..(23)
<223> OTHER INFORMATION: Tau peptide - aa289-311

<400> SEQUENCE: 160

Ser Lys Cys Gly Ser Lys Asp Asn Ile Lys His Val Pro Gly Gly Gly
1               5                   10                  15

Ser Val Gln Ile Val Tyr Lys
            20

<210> SEQ ID NO 161
<211> LENGTH: 21
<212> TYPE: PRT
<213> ORGANISM: Homo sapiens
<220> FEATURE:
<221> NAME/KEY: PEPTIDE
<222> LOCATION: (1)..(21)
<223> OTHER INFORMATION: Tau peptide - aa291-311

<400> SEQUENCE: 161

Cys Gly Ser Lys Asp Asn Ile Lys His Val Pro Gly Gly Gly Ser Val
1               5                   10                  15

Gln Ile Val Tyr Lys
            20

<210> SEQ ID NO 162
<211> LENGTH: 19
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: Tau peptide - aa293-311
```

<400> SEQUENCE: 162

Ser Lys Asp Asn Ile Lys His Val Pro Gly Gly Gly Ser Val Gln Ile
1               5                   10                  15

Val Tyr Lys

<210> SEQ ID NO 163
<211> LENGTH: 17
<212> TYPE: PRT
<213> ORGANISM: Homo sapiens
<220> FEATURE:
<221> NAME/KEY: PEPTIDE
<222> LOCATION: (1)..(17)
<223> OTHER INFORMATION: Tau peptide - aa295-311

<400> SEQUENCE: 163

Asp Asn Ile Lys His Val Pro Gly Gly Gly Ser Val Gln Ile Val Tyr
1               5                   10                  15

Lys

<210> SEQ ID NO 164
<211> LENGTH: 13
<212> TYPE: PRT
<213> ORGANISM: Homo sapiens
<220> FEATURE:
<221> NAME/KEY: PEPTIDE
<222> LOCATION: (1)..(13)
<223> OTHER INFORMATION: Tau peptide - aa299-311

<400> SEQUENCE: 164

His Val Pro Gly Gly Gly Ser Val Gln Ile Val Tyr Lys
1               5                   10

<210> SEQ ID NO 165
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: Tau peptide - aa301-311

<400> SEQUENCE: 165

Pro Gly Gly Gly Ser Val Gln Ile Val Tyr Lys
1               5                   10

<210> SEQ ID NO 166
<211> LENGTH: 31
<212> TYPE: PRT
<213> ORGANISM: Homo sapiens
<220> FEATURE:
<221> NAME/KEY: PEPTIDE
<222> LOCATION: (1)..(31)
<223> OTHER INFORMATION: Tau peptide - aa275-305

<400> SEQUENCE: 166

Val Gln Ile Ile Asn Lys Lys Leu Asp Leu Ser Asn Val Gln Ser Lys
1               5                   10                  15

Cys Gly Ser Lys Asp Asn Ile Lys His Val Pro Gly Gly Gly Ser
            20                  25                  30

<210> SEQ ID NO 167
<211> LENGTH: 27
<212> TYPE: PRT
<213> ORGANISM: Homo sapiens
<220> FEATURE:

```
<221> NAME/KEY: PEPTIDE
<222> LOCATION: (1)..(27)
<223> OTHER INFORMATION: Tau peptide - aa275-301

<400> SEQUENCE: 167

Val Gln Ile Ile Asn Lys Lys Leu Asp Leu Ser Asn Val Gln Ser Lys
1               5                   10                  15

Cys Gly Ser Lys Asp Asn Ile Lys His Val Pro
            20                  25

<210> SEQ ID NO 168
<211> LENGTH: 23
<212> TYPE: PRT
<213> ORGANISM: Homo sapiens
<220> FEATURE:
<221> NAME/KEY: PEPTIDE
<222> LOCATION: (1)..(23)
<223> OTHER INFORMATION: Tau peptide - aa275-297

<400> SEQUENCE: 168

Val Gln Ile Ile Asn Lys Lys Leu Asp Leu Ser Asn Val Gln Ser Lys
1               5                   10                  15

Cys Gly Ser Lys Asp Asn Ile
            20

<210> SEQ ID NO 169
<211> LENGTH: 19
<212> TYPE: PRT
<213> ORGANISM: Homo sapiens
<220> FEATURE:
<221> NAME/KEY: PEPTIDE
<222> LOCATION: (1)..(19)
<223> OTHER INFORMATION: Tau peptide - aa275-293

<400> SEQUENCE: 169

Val Gln Ile Ile Asn Lys Lys Leu Asp Leu Ser Asn Val Gln Ser Lys
1               5                   10                  15

Cys Gly Ser

<210> SEQ ID NO 170
<211> LENGTH: 15
<212> TYPE: PRT
<213> ORGANISM: Homo sapiens
<220> FEATURE:
<221> NAME/KEY: PEPTIDE
<222> LOCATION: (1)..(15)
<223> OTHER INFORMATION: Tau peptide - aa275-289

<400> SEQUENCE: 170

Val Gln Ile Ile Asn Lys Lys Leu Asp Leu Ser Asn Val Gln Ser
1               5                   10                  15

<210> SEQ ID NO 171
<211> LENGTH: 11
<212> TYPE: PRT
<213> ORGANISM: Homo sapiens
<220> FEATURE:
<221> NAME/KEY: PEPTIDE
<222> LOCATION: (1)..(11)
<223> OTHER INFORMATION: Tau peptide - aa275-285

<400> SEQUENCE: 171

Val Gln Ile Ile Asn Lys Lys Leu Asp Leu Ser
1               5                   10
```